(12) United States Patent
McWhorter, Jr. et al.

(10) Patent No.: US 6,762,191 B2
(45) Date of Patent: Jul. 13, 2004

(54) THERAPEUTIC COMPOUNDS

(75) Inventors: William W. McWhorter, Jr., Parchment, MI (US); Valentina Badescu, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/179,585

(22) Filed: Jun. 25, 2002

(65) Prior Publication Data

US 2003/0050304 A1 Mar. 13, 2003

Related U.S. Application Data

(60) Provisional application No. 60/314,972, filed on Aug. 24, 2001, and provisional application No. 60/303,191, filed on Jul. 5, 2001.

(51) Int. Cl.$^7$ ............... A61K 31/4355; C07D 491/048
(52) U.S. Cl. ............... 514/291; 546/89; 546/80; 544/126; 544/361; 514/232.8; 514/254
(58) Field of Search ............... 514/291, 254, 514/232.8; 546/89, 80; 544/361, 126

(56) References Cited

U.S. PATENT DOCUMENTS

| 3,752,820 | A | * | 8/1973 | Suh ............... 546/80 |
| 5,616,575 | A | | 4/1997 | Efange et al. |
| 5,854,245 | A | | 12/1998 | Duggan et al. |
| 6,156,757 | A | | 12/2000 | Kennis et al. |
| 6,352,999 | B1 | | 3/2002 | Kennis et al. |

FOREIGN PATENT DOCUMENTS

| EP | 0 339 959 | | 11/1989 |
| JP | 63/149645 | | 6/1998 |
| WO | WO 92/16497 | | 10/1992 |
| WO | WO 96/03400 | | 2/1996 |
| WO | WO 98/45297 | | 10/1998 |
| WO | WO 99/54303 | | 10/1999 |
| WO | 00/20423 | * | 4/2000 ............... 546/80 |
| WO | WO 00/37466 | | 6/2000 |

OTHER PUBLICATIONS

*Preparation of 4a–Alkoxy–1,2,3,4,4a,9b–hexahydro– and –1,2,3,4–tetrahydro–benzofuro[3,2–c]pyridines,* by Cattanach et al, J. Chem. Soc. (C), 1971, pp 53–60.

"New Synthesis of Benzofuro [3,2–c] Pyridines", by N.F. Kucherova et al, Chem. Heterocycl. Compd. (1973), (9), 835–837.

"Reduction of 1,2,3,4–Tetrahydro–to 1,2,3,4,4a,9b–Hexahydrobenzofuro [3,2–c] Pyridines", by T.A. Kartashova et al, Chem. Heterocycl. Compd. (1979), (15), 957–959.

"Preparation and Pharmacological Examination of a Number of Derivatives of Tetrahydrobenzofuropyridine", by L.A. Aksanova et al, Pharm. Chem. J. (1975), (9(1)), 5–7.

"New 2–Substituted 1,2,3,4–Tetrahydrobenzofuro [3,2–c] pyridine Having Highly Active and Potent Central $\alpha_2$–Antagonistic Activity as Potential Antidepressants", by Ludo E.J. Kennis et al, Bioorganic & Medicinal Chemistry Letters (2000), (10), 71–74.

* cited by examiner

*Primary Examiner*—Charanjit S. Aulakh
(74) *Attorney, Agent, or Firm*—Mary J. Hosley

(57) ABSTRACT

The present invention provides compounds of formula (I):

(I)

wherein: $R_1$, $R_2$, $R_3$, $R_4$, $R_5$, $R_6$, X, - - -, m, and n have any of the values defined in the specification, as well as pharmaceutical compositions comprising the compounds or salts thereof. The invention also provides therapeutic methods as well as processes and intermediates useful for preparing compounds of formula (I). The compounds are useful as 5-HT ligands.

90 Claims, No Drawings

THERAPEUTIC COMPOUNDS

CROSS-REFERENCE TO RELATED APPLICATIONS

This application claims the benefit of U.S. provisional application Serial No. 60/303,191 filed Jul. 5, 2001, under 35 USC 119(e)(i), and U.S. provisional application Serial No. 60/314,972 filed Aug. 24, 2001, under 35 USC 119(e)(i), which are incorporated herein by reference in their entirety.

FIELD OF THE INVENTION

The present invention provides aryl or heteroaryl substituted benzofuran derivatives, and more specifically, provides compounds of formula (I) as described hereinbelow. These compounds are 5-HT ligands, and are useful for treating diseases wherein modulation of 5-HT activity is desired.

BACKGROUND OF THE INVENTION

Serotonin has been implicated in a number of diseases and conditions that originate in the central nervous system. These include diseases and conditions related to sleeping, eating, perceiving pain, controlling body temperature, controlling blood pressure, depression, anxiety, schizophrenia, and other bodily states. R. W. Fuller, Biology of Serotonergic Transmission, ed. Neville V. Osborne, John Wiley and Sons (1982), p 221; D. J. Boullin, Serotonin in Mental Abnormalities 1, John Wiley and Sons (1978), p. 316; J. Barchas, et al., Serotonin and Behavior, Academic Press, New York, N.Y. (1973). Serotonin also plays an important role in peripheral systems, such as the gastrointestinal system, where it has been found to mediate a variety of contractile, secretory, and electrophysiologic effects.

As a result of the broad distribution of serotonin within the body, there is a tremendous interest in drugs that affect serotonergic systems. In particular, receptor-specific agonists and antagonists are of interest for the treatment of a wide range of disorders, including anxiety, depression, hypertension, migraine, obesity, compulsive disorders, schizophrenia, autism, neurodegenerative disorders (e.g. Alzheimer's disease, Parkinsonism, and Huntington's chorea), and chemotherapy-induced vomiting. M. D. Gershon, et al., The Peripheral Actions of 5-Hydroxytryptamine, 246 (1989); P. R. Saxena, et al., Journal of Cardiovascular Pharmacology, 15:Supplement 7 (1990).

The major classes of serotonin receptors (5-HT$_{1-7}$) contain fourteen to eighteen separate receptors that have been formally classified. See Glennon, et al., Neuroscience and Behavioral Reviews, 1990, 14, 35; and D. Hoyer, et al. Pharmacol. Rev. 1994, 46, 157–203. Recently discovered information regarding subtype identity, distribution, structure, and function suggests that it is possible to identify novel, subtype specific agents, having improved therapeutic profiles (e.g. fewer side effects).

For example, the 5-HT$_2$ family of receptors is comprised of 5-HT$_{2A}$, 5-HT$_{2B}$, and 5-HT$_{2C}$ subtypes, which have been grouped together on the basis of primary structure, secondary messenger system, and operational profile. All three subtypes are G-protein coupled, activate phospholipase C as a principal transduction mechanism, and contain a seven-transmembrane domain structure. There are distinct differences in the distribution of the three 5-HT$_2$ subtypes. The 5-HT$_{2B}$ and 5-HT$_{2A}$ receptors are widely distributed in the periphery, while the 5-HT$_{2C}$ receptor has been found only in the central nervous system, being highly expressed in many regions of the human brain. See G. Baxter, et al. Trends in Pharmacol. Sci. 1995, 16, 105–110.

Subtype 5-HT$_{2A}$ has been associated with effects including vasoconstriction, platelet aggregation, and bronchoconstriction, while subtype 5-HT$_{2C}$ has been associated with diseases that include depression, anxiety, obsessive compulsive disorder, panic disorders, phobias, psychiatric syndromes, and obesity. Very little is known about the pharmacologic role of the 5-HT$_{2B}$ receptor. See F. Jenck, et al., Exp. Opin. Invest. Drugs, 1998, 7, 1587–1599; M. Bos, et al., J. Med. Chem., 1997, 40, 2762–2769; J. R. Martin, et al., The Journal of Pharmacology and Experimental Therapeutics, 1998, 286, 913–924; S. M. Bromidge, et al., J. Med. Chem., 1998, 41,1598–1612; G. A. Kennett, Drugs, 1998, 1, 4, 456–470; and A. Dekeyne, et al., Neuropharmacology, 1999, 38, 415–423.

Japanese Patent Application S63–149645 discusses a vast genus of compounds that are reported to be useful to prevent photochemical browning of organic pigments. The compounds specifically prepared in the application differ considerably in structure from the compounds of the invention. For example, they lack a benzofuran type ring system.

U.S. Pat. No. 5,616,575 relates to tricyclic ibogaine analogs of the following formula.

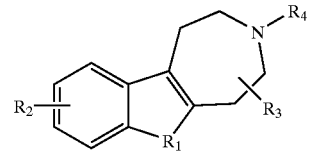

The compounds are reported to be useful to treat cocaine addiction and the use of other addictive substances. The compounds differ from the compounds of the invention at the groups R$_2$ and R$_3$ in the above formula.

There is currently a need for pharmaceutical agents that are useful to treat diseases and conditions associated with 5-HT receptors.

SUMMARY OF THE INVENTION

In accordance with the present invention, novel compounds that demonstrate useful biological activity, and particularly activity as 5-HT receptor ligands, are provided. Thus, the present invention provides a compound of formula (I):

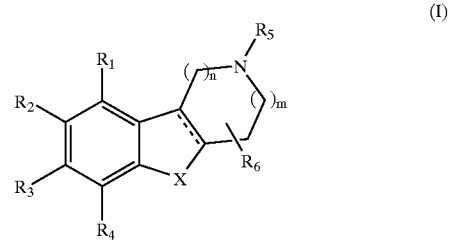

(I)

wherein:
R$_1$, R$_2$, R$_3$, and R$_4$ are independently hydrogen, halo, —CF$_3$, —OCF$_3$, —CN, —NO$_2$, —C$_{1-8}$alkyl, —C$_{3-8}$cycloalkyl, —OR$_8$, —NR$_8$R$_9$, —SR$_8$, —C(=O)aryl, aryl, —C$_{1-8}$alkylene(aryl), —C(=O)heteroaryl, heteroaryl, or —C$_{1-8}$alkylene(heteroaryl);
R$_5$ is hydrogen, C$_{1-8}$alkyl, haloC$_{1-8}$alkyl, C$_{3-8}$cycloalkyl, C$_{1-8}$alkanoyl, haloC$_{1-8}$alkanoyl, —C(=O)OR$^8$, —C(=O)aryl, aryl, —C$_{1-8}$alkylene(aryl), —C(=O)heteroaryl, heteroaryl, or —C$_{1-8}$alkylene(heteroaryl);

R$_6$ is hydrogen or C$_{1-4}$alkyl;

each R$_8$ and R$_9$ is independently hydrogen, C$_{1-8}$alkyl, haloC$_{1-8}$alkyl, C$_{3-8}$cycloalkyl, —C(=O)aryl, aryl, —C$_{1-8}$alkylene(aryl), —C(=O)heteroaryl, heteroaryl, —C$_{1-8}$alkylene(heteroaryl) or R$_8$ and R$_9$ together with the nitrogen to which they are attached form a pyrrolidino, piperidino, azepano, piperazino, morpholino, or thiomorpholino ring;

m is 0, 1, or 2;

n is 1 or 2;

X is oxy (—O—), thio (—S—) —S(=O)— or —SO$_2$—;

the bond represented by — is absent or present; and wherein any C$_{1-8}$alkyl, C$_{1-8}$alkylene, C$_{1-8}$alkoxy or C$_{3-8}$cycloalkyl of R$_1$, R$_2$, R$_3$, R$_4$, R$_5$, R$_6$, R$_8$ and R$_9$ is optionally partially unsaturated; and wherein any aryl or heteroaryl of R$_1$, R$_2$, R$_3$, R$_4$, R$_5$, R$_8$ or R$_9$ is optionally substituted with one or more (e.g., 1, 2, 3, or 4) substituents independently selected from halo, —CN, —NO$_2$, —CF$_3$, —OCF$_3$, C$_{1-8}$alkyl, C$_{2-8}$alkenyl, C$_{2-8}$alkynyl, C$_{3-8}$cycloalkyl, C$_{3-8}$cycloalkenyl, aryl, heteroaryl, —OR$_c$, —SR$_c$, —C(=O)R$_c$, —CO$_2$R$_c$, —C(=O)NR$_c$R$_d$, —NR$_c$C(=O)R$_d$, —NR$_c$R$_d$, —NR$_c$C(=O)NR$_c$R$_d$, —SO$_2$—NR$_c$R$_d$ or —SO$_2$R$_c$;

wherein each R$_c$ and R$_d$ is independently hydrogen, C$_{1-8}$alkyl, C$_{1-8}$alkanoyl, C$_{1-8}$alkoxycarbonyl, aryl, —C$_{1-8}$alkylene(aryl), —C(=O)aryl, —C(=O)oaryl, heteroaryl, —C$_{1-8}$alkylene(heteroaryl), —C(=O)heteroaryl, —C(=O)oheteroaryl or R$_c$ and R$_d$ together with the nitrogen to which they are attached form a pyrrolidino, piperidino, azepano, piperazino, morpholino, or thiomorpholino ring;

or a pharmaceutically acceptable salt thereof.

In another aspect, the present invention also provides:

a pharmaceutical composition comprising a compound of formula (I), or a pharmaceutically acceptable salt thereof, and a pharmaceutically acceptable excipient (the composition preferably comprises a therapeutically effective amount of the compound or salt), a method for treating a disease or condition in a mammal (e.g. a human) wherein a 5-HT receptor is implicated and modulation of a 5-HT function is desired comprising administering a therapeutically effective amount of a compound of formula (I), or a pharmaceutically acceptable salt thereof to the mammal, a method for treating or preventing a disease or disorder of the central nervous system in a mammal comprising administering a therapeutically effective amount of a compound of formula (I), or a pharmaceutically acceptable salt thereof to the mammal, a compound of formula (I) or a pharmaceutically acceptable salt thereof for use in medical diagnosis or therapy (e.g. the treatment or prevention of 5-HT related disease such as anxiety, obesity, depression, or a stress-related disease), the use of a compound of formula (I), or a pharmaceutically acceptable salt thereof to prepare a medicament useful for treating or preventing a disease or disorder of the central nervous system in a mammal, and a method for modulating the function of a 5-HT receptor, comprising contacting the receptor with an effective modulatory amount of a compound of formula (I), or a pharmaceutically acceptable salt thereof.

The invention also provides novel intermediates and processes disclosed herein that are useful for preparing compounds of formula (I).

DETAILED DESCRIPTION OF THE INVENTION

The present invention provides a compound of formula (I):

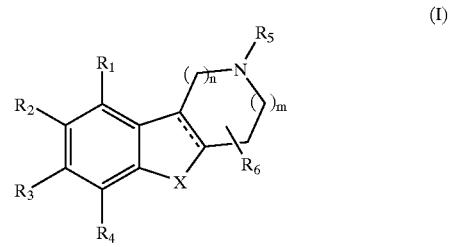

wherein:

R$_1$, R$_2$, R$_3$, and R$_4$ are independently hydrogen, halo, —CF$_3$, —OCF$_3$, —CN, —NO$_2$, —C$_{1-8}$alkyl, —C$_{3-8}$cycloalkyl, —OR$_8$, —NR$_8$R$_9$, —SR$_8$, —C(=O)aryl, aryl, —C$_{1-18}$alkylene(aryl), —C(=O)heteroaryl, heteroaryl, or —C$_{1-8}$alkylene(heteroaryl);

R$_5$ is hydrogen, C$_{1-8}$alkyl, haloC$_{1-8}$alkyl, C$_{3-8}$cycloalkyl, C$_{1-8}$alkanoyl, haloC$_{1-8}$alkanoyl, —C(=O)OR$^8$, —C(=O)aryl, aryl, —C$_{1-8}$alkylene(aryl), —C(=O)heteroaryl, heteroaryl, or —C$_{1-8}$alkylene(heteroaryl);

R$_6$ is hydrogen or C$_{1-4}$alkyl;

each R$_8$ and R$_9$ is independently hydrogen, C$_{1-8}$alkyl, haloC$_{1-8}$alkyl, C$_{3-8}$cycloalkyl, —C(=O)aryl, aryl, —C$_{1-8}$alkylene(aryl), —C(=O)heteroaryl, heteroaryl, —C$_{1-8}$alkylene(heteroaryl) or R$_8$ and R$_9$ together with the nitrogen to which they are attached form a pyrrolidino, piperidino, azepano, piperazino, morpholino, or thiomorpholino ring;

m is 0, 1, or 2;

n is 1 or 2;

X is oxy (—O—), thio (—S—) —S(=O)— or —SO$_2$—;

the bond represented by — is absent or present; and wherein any C$_{1-8}$alkyl, C$_{1-8}$alkylene, C$_{1-8}$alkoxy or C$_{3-8}$cycloalkyl of R$_1$, R$_2$, R$_3$, R$_4$, R$_5$, R$_6$, R$_8$ and R$_9$ is optionally partially unsaturated; and wherein any aryl or heteroaryl of R$_1$, R$_2$, R$_3$, R$_4$, R$_5$, R$_8$ or R$_9$ is optionally substituted with one or more (e.g., 1, 2, 3, or 4) substituents independently selected from halo, —CN, —NO$_2$, —CF$_3$, —OCF$_3$, C$_{1-8}$alkyl, C$_{2-8}$alkenyl, C$_{2-8}$alkynyl, C$_{3-8}$cycloalkyl, C$_{3-8}$cycloalkenyl, aryl, heteroaryl, —OR$_c$, —SR$_c$, —C(=O)R$_c$, —CO$_2$R$_c$, —C(=O)NR$_c$R$_d$, —NR$_c$C(=O)R$_d$, —NR$_c$R$_d$, —NR$_c$C(=O)NR$_c$R$_d$, —SO$_2$—NR$_c$R$_d$ or —SO$_2$R$_c$;

wherein each R$_c$ and R$_d$ is independently hydrogen, C$_{1-8}$alkyl, C$_{1-8}$alkanoyl, C$_{1-8}$alkoxycarbonyl, aryl, —C$_{1-8}$alkylene(aryl), —C(=O)aryl, —C(=O)aryl, heteroaryl, —C$_{1-8}$alkylene(heteroaryl), —C(=O)heteroaryl, —C(=O)heteroaryl or R$_c$ and R$_d$ together with the nitrogen to which they are attached form a pyrrolidino, piperidino, azepano, piperazino, morpholino, or thiomorpholino ring;

or a pharmaceutically acceptable salt thereof.

In another aspect, the present invention also provides:

a pharmaceutical composition comprising a compound of formula (I), or a pharmaceutically acceptable salt thereof, and a pharmaceutically acceptable excipient (the composition preferably comprises a therapeutically effective amount of the compound or salt), The compounds of the invention are useful for treating or preventing diseases or disorders of the central nervous system. Specific diseases or disorders of the central nervous system for which a compound of formula (I) may have activity include, but are not limited to: obesity, depression, schizophrenia, schizophreniform disorder, schizoaffective disorder, delusional disorder, a stress-related disease (e.g. general anxiety disorder), panic disorder, a phobia, obsessive compulsive disorder, post-traumatic-stress syndrome, immune system depression, a stress induced problem with the urinary, gastrointestinal or cardiovascular system (e.g., stress incontinence), neurodegenerative disorders, autism, chemotherapy-induced vomiting, hypertension, migraine, headaches, cluster headaches, sexual dysfunction in a mammal (e.g. a human), addictive disorder and withdrawal syndrome, an adjustment disorder, an age-associated learning and mental disorder, anorexia nervosa, apathy, an attention-deficit disorder due to general medical conditions, attention-deficit hyperactivity disorder, behavioral disturbance (including agitation in conditions associated with diminished cognition (e.g., dementia, mental retardation or delirium)), bipolar disorder, bulimia nervosa, chronic fatigue syndrome, conduct disorder, cyclothymic disorder, dysthymic disorder, fibromyalgia and other somatoform disorders, generalized anxiety disorder, an inhalation disorder, an intoxication disorder, movement disorder (e.g., Huntington's disease or Tardive Dyskinesia), oppositional defiant disorder, peripheral neuropathy, post-traumatic stress disorder, premenstrual dysphoric disorder, a psychotic disorder (brief and long duration disorders, psychotic disorder due to medical condition, psychotic disorder NOS), mood disorder (major depressive or bipolar disorder with psychotic features) seasonal affective disorder, a sleep disorder, a specific development disorder, agitation disorder, selective serotonin reuptake inhibition (SSRI) "poop out" syndrome or a Tic disorder (e.g., Tourette's syndrome).

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. When alkyl, alkylene or cycloalkyl can be partially unsaturated, the alkyl chain or cycloalkyl ring may comprise one or more (e.g., 1, 2, 3, or 4) double or triple bonds in the chain.

Aryl denotes a phenyl radical or an ortho-fused bicyclic carbocyclic radical having about nine to ten ring atoms in which at least one ring is aromatic. Heteroaryl denotes a radical of a monocyclic aromatic ring containing five or six ring atoms consisting of carbon and 1, 2, 3, or 4 heteroatoms each selected from the group consisting of non-peroxide oxygen, sulfur, and N(X) wherein X is absent or is H, O, $C_{1-4}$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine 5-HT activity using the standard tests which are well known in the art.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-6}$alkyl refers to alkyl of one to six carbon atoms, inclusive.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents.

Specifically, $C_{1-8}$alkyl can be methyl, ethyl, propyl, isopropyl, butyl, iso-butyl, sec-butyl, pentyl, 3-pentyl, hexyl, heptyl or octyl; $C_{1-3}$alkyl can be methyl, ethyl, propyl, isopropyl; halo$C_{1-3}$alkyl can be trifluoromethyl, chloromethyl, 2-chloroethyl, 2,2,2-trifluoroethyl, or perfluoroethyl; halo$C_{1-3}$alkoxy can be trifluoromethoxy, or 2,2,2-trifluoroethoxy; $C_{1-8}$alkoxy can be methoxy, ethoxy, propoxy, isopropoxy, butoxy, iso-butoxy, sec-butoxy, pentoxy, 3-pentoxy, hexyloxy, heptyloxy or octyloxy; $C_{1-8}$alkanoyl can be acetyl, propanoyl, butanoyl, pentanoyl, 4-methylpentanoyl, hexanoyl, heptanoyl or octanoyl; $C_{1-8}$alkoxycarbonyl can be methoxycarbonyl, ethoxycarbonyl, propoxycarbonyl, isopropoxycarbonyl, butoxycarbonyl, pentoxycarbonyl, or hexyloxycarbonyl, heptyloxycarbonyl or octyloxycarbonyl; $C_{1-8}$alkanoyloxy can be acetoxy, propanoyloxy, butanoyloxy, isobutanoyloxy, pentanoyloxy, hexanoyloxy, heptanoyloxy or octanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R_2$ is aryl, optionally substituted with one or more substituents independently selected from halo, hydroxy, cyano, nitro, trifluoromethyl, trifluoromethoxy, $C_{1-6}$alkyl, —$OR_c$, —$SR_c$, phenyl, —$NR_cR_d$, or —C(=O)$NR_cR_d$.

Another specific value for $R_2$ is phenyl, optionally substituted with one or more substituents independently selected from halo, cyano, nitro, trifluoromethyl, trifluoromethoxy, $C_{1-6}$alkyl, —$OR_c$, —$SR_c$, phenyl, —$NR_cR_d$, or —C(=O)$NR_cR_d$.

Another specific value for $R_2$ is phenyl, optionally substituted with one or more substituents independently selected from halo, cyano, trifluoromethyl, trifluoromethoxy, $C_{1-6}$alkyl, $C_{1-6}$alkoxy or thio$C_{1-6}$alkyl.

Another specific value for $R_2$ is phenyl, substituted with one or more substituents independently selected from halo, cyano, trifluoromethyl, trifluoromethoxy, $C_{1-6}$alkyl, $C_{1-6}$alkoxy or thio$C_{1-6}$alkyl.

Another specific value for $R_2$ is phenyl, substituted with one or more substituents independently selected from fluoro, chloro, bromo, trifluoromethyl, trifluoromethoxy, methoxy, ethoxy, propoxy, isopropoxy or thiomethyl.

Another specific value for $R_2$ is phenyl substituted at the 2- and the 6-position with halo independently selected from fluoro, chloro and bromo.

Another specific value for $R_2$ is phenyl substituted at the 2- or the 6-position with fluoro, chloro or bromo.

Another specific value for $R_2$ is phenyl substituted at the 2- and the 4-position with halo independently selected from fluoro, chloro and bromo.

Another specific value for $R_2$ is phenyl substituted at the 2- or the 4-position with fluoro, chloro or bromo.

Another specific value for $R_2$ is phenyl substituted at the 2-, 4- and 6-position with halo independently selected from fluoro, chloro and bromo.

Another specific value for $R_2$ is 2,4-dichlorophenyl, 2,4,6-trichlorophenyl or 2,6-difluoro-4-chlorophenyl.

Another specific value for $R_2$ is heteroaryl, optionally substituted with one or more substituents independently selected from halo, hydroxy, cyano, nitro, trifluoromethyl, trifluoromethoxy, $C_{1-6}$alkyl, —$OR_c$, —$SR_c$, phenyl, —$NR_cR_d$, or —$C(=O)NR_cR_d$.

Another specific value for $R_2$ is heteroaryl, optionally substituted with one or more substituents independently selected from halo, cyano, trifluoromethyl, trifluoromethoxy, $C_{1-6}$alkyl, —$OR_c$ or —$SR_c$.

Another specific value for $R_2$ is heteroaryl, optionally substituted with one or more substituents independently selected from fluoro, chloro, bromo, trifluoromethyl, trifluoromethoxy, methoxy, ethoxy, propoxy, or isopropoxy.

Another specific value for $R_2$ is heteroaryl, substituted with one or more substituents independently selected from fluoro, chloro, bromo, trifluoromethyl, trifluoromethoxy, methoxy, ethoxy, propoxy, or isopropoxy.

A specific value for $R_1$ is hydrogen, $C_{1-3}$alkyl, halo, halo$C_{1-3}$alkyl, $C_{1-3}$alkoxy, halo$C_{1-3}$alkoxy, or —$NR_8R_9$.

Another specific value for $R_1$ is hydrogen or $C_{1-3}$alkyl.

A specific value for $R_3$ is hydrogen, $C_{1-3}$alkyl, aryl, halo, halo$C_{1-3}$alkyl, $C_{1-3}$alkoxy, halo$C_{1-3}$alkoxy or —$NR_8R_9$.

A specific value for $R_3$ is hydrogen, $C_{1-3}$alkyl or aryl.

Another specific value for $R_3$ is hydrogen or $C_{1-3}$alkyl.

A specific value for $R_4$ is $C_{1-8}$alkyl, —$OR_8$, —$SR_8$, —$NR_8R_9$, aryl or —$C_{1-8}$alkylene(aryl), wherein the aryl groups are optionally substituted with one or more substituents independently selected from halo, hydroxy, cyano, nitro, trifluoromethyl, trifluoromethoxy, $C_{1-6}$alkyl, $C_{1-6}$alkoxy, phenyl, —$NR_cR_d$, or —$C(=O)NR_cR_d$.

A specific value for $R_4$ is $C_{1-8}$alkyl, —$OR_8$, —$SR_8$, —$NR_8R_9$, or aryl, wherein aryl is substituted with one or more substituents independently selected from halo, hydroxy, cyano, nitro, trifluoromethyl, trifluoromethoxy, $C_{1-6}$alkyl, $C_{1-6}$alkoxy, phenyl, —$NR_cR_d$, or —$C(=O)NR_cR_d$.

A specific value for $R_4$ is methyl, ethyl, propyl, isopropyl, butyl, ethylpropyl, cyclohexyl, phenyl, benzyl, methoxy, ethoxy, propoxy, isopropoxy, butoxy, (ethylpropyl)oxy, (cyclohexyl)oxy, phenoxy, (benzyl)oxy, methylthio, ethylthio, propylthio, isopropylthio, butylthio, (ethylpropyl)thio, (cyclohexyl)thio, phenylthio or (benzyl)thio or —$NR_8R_9$, wherein $R_8$ is hydrogen, methyl, ethyl, propyl or cyclohexyl and $R_9$ is methyl, ethyl, propyl, cyclohexyl or phenyl; or $R_8$ and $R_9$ together with the nitrogen to which they are attached form a pyrrolidino, piperidino, azepano, piperazino, morpholino, or thiomorpholino ring.

A specific value for $R_4$ is —$NR_8R_9$, wherein $R_8$ is hydrogen, methyl, ethyl, propyl or cyclohexyl and $R_9$ is methyl, ethyl, propyl, cyclohexyl or phenyl.

A specific value for $R_4$ is —$NR_8R_9$, wherein $R_8$ is hydrogen, methyl or ethyl and $R_9$ is methyl, ethyl, propyl, cyclohexyl or phenyl.

A specific value for $R_4$ is —$NR_8R_9$, wherein $R_8$ is hydrogen, methyl, ethyl or cyclohexyl and $R_9$ is methyl, ethyl, cyclohexyl or phenyl.

A specific value for $R_4$ is —$NR_8R_9$, wherein $R_8$ is methyl, ethyl or cyclohexyl and $R_9$ is methyl, ethyl or cyclohexyl.

A specific value for $R_4$ is pyrrolidino, piperidino, azepano, piperazino, morpholino, or thiomorpholino.

A specific value for $R_5$ is hydrogen, $C_{1-8}$alkyl, $C_{2-8}$alkenyl, $C_{2-8}$alkynyl, $C_{3-8}$cycloalkyl, or $C_{3-8}$cycloalkenyl, aryl, —$C_{1-8}$alkylene(aryl), heteroaryl or —$C_{1-8}$alkylene(heteroaryl).

A group of compounds of Formula I includes compounds where at least one of $R_1$, $R_3$, $R_2$, and $R_4$ is aryl optionally substituted with one or more substituents independently selected from halo, hydroxy, cyano, nitro, trifluoromethyl, trifluoromethoxy, $C_{1-6}$alkyl, —$OR_c$, —$SR_c$, phenyl, —$NR_cR_d$, or —$C(=O)NR_cR_d$.

A group of compounds of Formula I includes compounds where at least one of $R_1$, $R_3$, $R_2$, and $R_4$ is aryl optionally substituted with one or more substituents independently selected from halo, hydroxy, cyano, nitro, trifluoromethyl, trifluoromethoxy, $C_{1-6}$alkyl, —$OR_c$, —$SR_c$, phenyl, —$NR_cR_d$, or —$C(=O)NR_cR_d$, and at least two of $R_1$, $R_3$, $R_2$, and $R_4$ are other than hydrogen.

A specific value for $R_5$ is hydrogen or $C_{1-8}$alkyl

A specific value for $R_5$ is aryl, heteroaryl, —$C_{1-8}$alkylene (aryl) or —$C_{1-8}$alkylene(heteroaryl).

A specific value for $R_5$ is hydrogen, methyl, ethyl, benzyl, or phenethyl.

Another specific value for $R_5$ is hydrogen.

A specific value for $R_6$ is hydrogen.

A specific compound of formula (I) is a compound wherein m is 1 and n is 1.

A specific compound of formula (I) is a compound wherein m is 0; n is 1; and X is oxy.

A specific compound of formula (I) is a compound wherein m is 1; n is 1; and X is oxy.

A specific compound of formula (I) is a compound wherein m is 2; n is 1; and X is oxy.

A specific compound of formula (I) is a compound wherein m is 0; n is 2; and X is oxy.

A specific compound of formula (I) is a compound wherein m is 1; n is 2; and X is oxy.

A specific compound of formula (I) is a compound wherein m is 2; n is 2; and X is oxy.

A specific compound of formula (I) is a compound wherein m is 0; n is 1; and X is thio.

A specific compound of formula (I) is a compound wherein m is 1; n is 1; and X is thio.

A specific compound of formula (I) is a compound wherein m is 2; n is 1; and X is thio.

A specific compound of formula (I) is a compound wherein m is 0; n is 2; and X is thio.

A specific compound of formula (I) is a compound wherein m is 1; n is 2; and X is thio.

A specific compound of formula (I) is a compound wherein m is 2; n is 2; and X is thio.

A specific compound of formula (I) is a compound wherein the bond represented by—is absent, and $R_1$, $R_2$, $R_3$, $R_4$, $R_5$, $R_6$, m, and n have any of the values, specific values, more specific values, or preferred values described herein.

A specific compound of formula (I) is a compound having the formula (II):

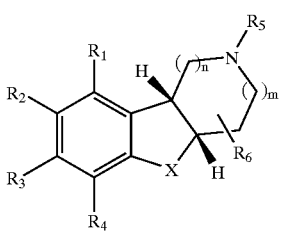

(II)

wherein $R_1$, $R_2$, $R_3$, $R_4$, $R_5$, $R_6$, m, and n have any of the values, specific values, more specific values, or preferred values described herein.

A specific compound of formula (I) is a compound wherein the bond represented by—is present, and $R_1$, $R_2$, $R_3$, $R_4$, $R_5$, $R_6$, m, and n have any of the values, specific values, more specific values, or preferred values described herein.

A specific compound of the present invention is a compound of formula (III):

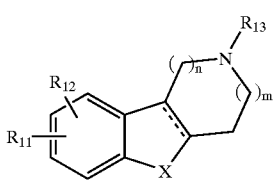

(III)

wherein:

$R_{11}$ is aryl or heteroaryl;

$R_{12}$ is hydrogen, halo, cyano, $C_{1-3}$alkyl, halo$C_{1-3}$alkyl, $C_{1-3}$alkoxy, halo$C_{1-3}$alkoxy, or —$NR_aR_b$;

$R_{13}$ is hydrogen, $C_{1-6}$alkyl, aryl$C_{1-6}$alkyl, or aryloxy$C_{1-6}$alkyl;

m is 0, 1, or 2;

n is 1 or 2;

X is oxy (—O—) or thio (—S—);

the bond represented by—is absent or present; and $R_a$ and $R_b$ are each independently hydrogen, $C_{1-6}$alkyl, aryl, (aryl)$C_{1-6}$alkyl, heteroaryl, or (heteroaryl)$C_{1-6}$alkyl; or $R_a$ and $R_b$ together with the nitrogen to which they are attached form a pyrrolidino, piperidino, morpholino, or thiomorpholino ring;

wherein any aryl or heteroaryl of $R_{11}$, $R_{12}$, $R_{13}$, $R_a$, or $R_b$ is optionally substituted with one or more (e.g. 1, 2, 3, or 4) substituents independently selected from halo, hydroxy, cyano, nitro, trifluoromethyl, trifluoromethoxy, $C_{1-6}$alkyl, $C_{1-6}$alkoxy, phenyl, —$NR_cR_d$, or —C(=O)$NR_cR_d$;

wherein each $R_c$ and $R_d$ is independently hydrogen, $C_{1-6}$alkyl, $C_{1-6}$alkanoyl, $C_{1-6}$alkoxycarbonyl, aryl, (aryl)$C_{1-6}$alkyl, arylcarbonyl, or aryloxycarbonyl; or $R_c$ and $R_d$ together with the nitrogen to which they are attached form a pyrrolidino, piperidino, morpholino, or thiomorpholino ring;

or a pharmaceutically acceptable salt thereof.

A specific compound of formula (III) is a compound wherein the bond represented by—is absent, and $R_{11}$, $R_{12}$, $R_{13}$, m, and n have any of the values, specific values, more specific values, or preferred values described herein.

A specific compound of formula (III) is a compound wherein the bond represented by — is present, and $R_{11}$, $R_{12}$, $R_{13}$, m, and n have any of the values, specific values, more specific values, or preferred values described herein.

A specific value for $R_{11}$ is aryl, optionally substituted with one or more substituents independently selected from halo, hydroxy, cyano, nitro, trifluoromethyl, trifluoromethoxy, $C_{1-6}$alkyl, $C_{1-6}$alkoxy, phenyl, —$NR_cR_d$, or —C(=O)$NR_cR_d$.

Another specific value for $R_{11}$ is phenyl, optionally substituted with one or more substituents independently selected from halo, hydroxy, cyano, nitro, trifluoromethyl, trifluoromethoxy, $C_{1-6}$alkyl, $C_{1-6}$alkoxy, phenyl, —$NR_cR_d$, or —C(=O)$NR_cR_d$.

Another specific value for $R_{11}$ is phenyl, optionally substituted with one or more substituents independently selected from halo, hydroxy, cyano, trifluoromethyl, trifluoromethoxy, $C_{1-6}$alkyl, or $C_{1-6}$alkoxy.

Another specific value for $R_{11}$ is phenyl, substituted with one or more substituents independently selected from halo, hydroxy, cyano, trifluoromethyl, trifluoromethoxy, $C_{1-6}$alkyl, or $C_{1-6}$alkoxy.

Another specific value for $R_{11}$ is phenyl, substituted with one or more substituents independently selected from fluoro, chloro, bromo, hydroxy, trifluoromethyl, trifluoromethoxy, methoxy, ethoxy, propoxy, or isopropoxy.

Another specific value for $R_{11}$ is heteroaryl, optionally substituted with one or more substituents independently selected from halo, hydroxy, cyano, nitro, trifluoromethyl, trifluoromethoxy, $C_{1-6}$alkyl, $C_{1-6}$alkoxy, phenyl, —$NR_cR_d$, or —C(=O)$NR_cR_d$.

Another specific value for $R_{11}$ is heteroaryl, optionally substituted with one or more substituents independently selected from halo, hydroxy, cyano, trifluoromethyl, trifluoromethoxy, $C_{1-6}$alkyl, or $C_{1-6}$alkoxy.

Another specific value for $R_{11}$ is heteroaryl, optionally substituted with one or more substituents independently selected from fluoro, chloro, bromo, hydroxy, trifluoromethyl, trifluoromethoxy, methoxy, ethoxy, propoxy, or isopropoxy.

Another specific value for $R_{11}$ is heteroaryl, substituted with one or more substituents independently selected from halo, hydroxy, cyano, trifluoromethyl, trifluoromethoxy, $C_{1-6}$alkyl, or $C_{1-6}$alkoxy.

Another specific value for $R_{1\ 1}$ is heteroaryl, substituted with one or more substituents independently selected from fluoro, chloro, bromo, hydroxy, trifluoromethyl, trifluoromethoxy, methoxy, ethoxy, propoxy, or isopropoxy.

A more specific value for $R_{11}$ is phenyl, optionally substituted with one or more substituents independently selected from fluoro, chloro, bromo, hydroxy, trifluoromethyl, trifluoromethoxy, methoxy, ethoxy, propoxy, or isopropoxy.

A specific value for $R_{12}$ is hydrogen or $C_{1-3}$alkyl.

Another specific value for $R_{12}$ is halo, halo$C_{1-3}$alkyl, $C_{1-3}$alkoxy, halo$C_{1-3}$alkoxy, or —$NR_aR_b$.

A specific value for $R_{13}$ is $C_{1-6}$alkyl, aryl$C_{1-6}$alkyl, or aryloxy$C_{1-6}$alkyl.

Another specific value for $R_{13}$ is hydrogen.

Another specific value for $R_{13}$ is $C_{1-6}$alkyl.

Another specific value for $R_{13}$ is aryl$C_{1-6}$alkyl or aryloxy$C_{1-6}$alkyl.

A more specific value for $R_{13}$ is hydrogen, methyl, ethyl, phenyl, or benzyl.

Specifically, the invention also provides a method for treating or preventing anxiety, obesity, depression, schizophrenia, a stress-related disease (e.g. general anxiety disorder), panic disorder, a phobia, obsessive compulsive disorder, post-traumatic-stress syndrome, immune system depression, a stress induced problem with the gastrointestinal or cardiovascular system, or sexual dysfunction in a mammal (e.g. a human) comprising administering a therapeutically effective amount of a compound of formula (I), or a pharmaceutically acceptable salt thereof to the mammal.

Specifically, the invention also provides a method of treating or preventing anxiety, obesity, depression, or a stress-related disease, comprising administering to a mammal (e.g. a human) in need of such treatment, a therapeutically effective amount of a compound of formula (I) or a pharmaceutically acceptable salt thereof.

Specifically, the invention also provides the use of a compound of formula (I) or a pharmaceutically acceptable salt thereof to prepare a medicament for treating or preventing anxiety, obesity, depression, schizophrenia, a stress-related disease (e.g. general anxiety disorder), panic disorder, a phobia, obsessive compulsive disorder, post-traumatic-stress syndrome, immune system depression, a stress induced problem with the gastrointestinal or cardiovascular system, or sexual dysfunction in a mammal (e.g. a human).

Specifically, the invention also provides the use of a compound of formula (I) or a pharmaceutically acceptable salt thereof to prepare a medicament for treating or preventing anxiety, obesity, depression, or a stress-related disease in a mammal (e.g. a human).

The invention also provides processes useful for preparing compounds of formula (I). Accordingly, the invention provides:

- a method for preparing a compound of formula (I) wherein the bond represented by—is absent comprising reducing a corresponding compound of formula (I) wherein the bond represented by—is present (as illustrated in Scheme 1 below);
- a method for preparing a compound of formula (I) wherein $R_1$ is hydrogen, comprising deprotecting a corresponding compound of formula (I) wherein $R_1$ is a suitable nitrogen protecting group (as illustrated in Scheme 2 below); and
- a method for preparing a compound of formula (I) wherein $R_1$ is other than hydrogen, comprising alkylating or acylating a corresponding compound of formula (I) wherein $R_1$ is hydrogen with the requisite alkylating or acylating agent.

Suitable nitrogen protecting groups, as well as methods for their preparation and removal are well known in the art, for example, see Greene, T. W.; Wutz, P. G. M. "Protecting Groups In Organic Synthesis" third edition, 1999, New York, John Wiley & sons, Inc. Preferred protecting groups include benzyloxycarbonyl (CBZ), tert-butoxycarbonyl (BOC), and benzoyl.

The invention also provides novel intermediates disclosed herein that are useful for preparing compounds of formula (I). For example, the invention provides an intermediate compound of formula (I) wherein $R_1$ is a suitable nitrogen protecting group.

Compounds of the invention can generally be prepared using synthetic techniques that are known in the art. They can also be prepared using the synthetic procedures illustrated in Schemes 1 and 2 below. Starting materials can be prepared by procedures described in these schemes or by procedures that would be well known to one of ordinary skill in organic chemistry. The variables used in the Schemes are as defined below or as in the claims. It is understood that other compounds of formula (I) can be prepared using procedures similar to those illustrated in the Schemes by modifying the starting materials or by performing additional steps to modify the products.

Compounds of formula (I) can be prepared by reactions outlined in Scheme 1.

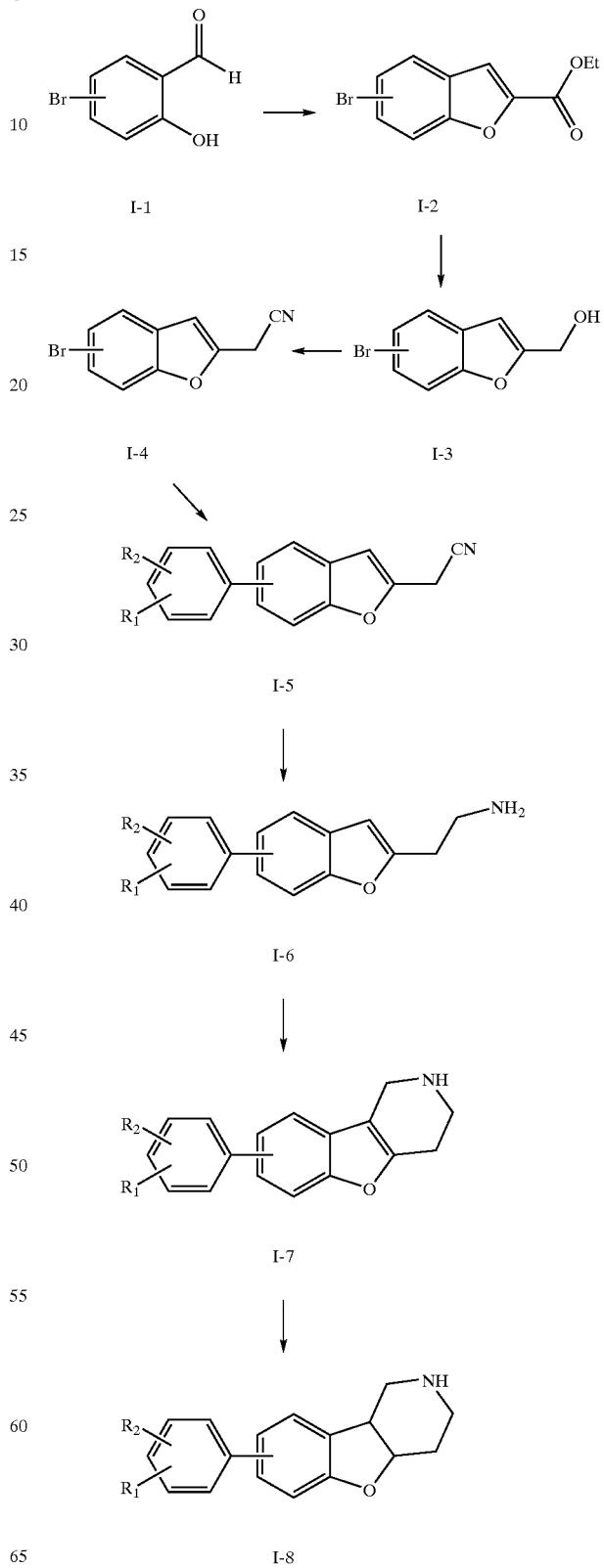

Bromosalicylaldehyde, I-1, is treated with ethyl bromoacetate in the presence of a base, such as potassium carbonate, in an appropriate solvent, such as dimethyl formamide, at elevated temperature to yield bromoindole-2-carboxylic acid ethyl ester, I-2. See for example A E Jakobs, L E Christiaens, M J Renson, *Tetrahedron* 50(31) 9315–24 (1994). The ethyl ester I-2 is treated with a reducing agent, such as $NaBH_4$, in an appropriate solvent, such as tetrahydrofuran, at room temperature to yield alcohol I-3. See for example International Patent Application Publication Number WO 9734885 A1. The alcohol I-3 is treated with an activating agent, such as methane sulfonyl chloride, in the presence of a base, such as triethylamine, in an appropriate solvent, such as methylene chloride at low temperature. The activated intermediate is treated with appropriate reagents, such as trimethylsilylcyanide and tetrabutylammonium fluoride, in an appropriate solvent, such as acetonitrile, at elevated temperature to yield the nitrile I-4. See for example E D Soli, A S Manoso, M C Patterson, P DeShong, D A Favor, R Hirschmann, A B Smith, *J. Org. Chem.* 64 3171–7 (1999). Nitrile I-4 is converted to aryl substituted benzofuran nitrile I-5 by means of an appropriate coupling reaction, such as the Suzuki coupling reaction. See for example N Miyaura, A Suzuki, *Chem. Rev.* 95 2457–83 (1995). The nitrile I-4 is reacted with an appropriately substituted phenylboronic acid in the presence of an appropriate catalyst, such as dichlorobis(triphenylphosphine)-palladium (II), and an appropriate base, such as aqueous sodium carbonate (2N), in an appropriate solvent, such as benzene, at elevated temperature to yield aryl substituted benzofuran nitrile I-5. Benzofuran nitrile I-5 is treated with a reducing agent, such as borane dimethylsulfide complex, in an appropriate solvent, such as tetrahydrofuran, at elevated temperature to yield amine I-6. See for example R Perrone, F Berardi, N A Colabufo, M Leopoldo, V Tortorella, *J. Med. Chem.* 43(2) 270–7 (2000). Amine I-6 is treated with formaldehyde or an equivalent under acidic conditions to yield the tetrahydrobenzofuropyridine I-7, which is a compound of the invention. See for example N Sotomayor, et. al., *Tetrahedron* 51 12159–68 (1995). Tetrahydrobenzofuropyridine I-7 is reduced with a reducing agent, such as potassium borohydride, in an appropriate solvent, such as trifluoroacetic acid, to yield hexahydrobenzofuropyridine I-8, which is also a compound of the invention. See for example L N Borisova, G S Rozenberg, N F Kucherova, V A Zagorevskii, *Chemistry of Heterocyclic Compounds* 17(9) 869–71 (1981).

Compounds of formula (I) can also be prepared by reactions outlined in Scheme 2.

Scheme 2

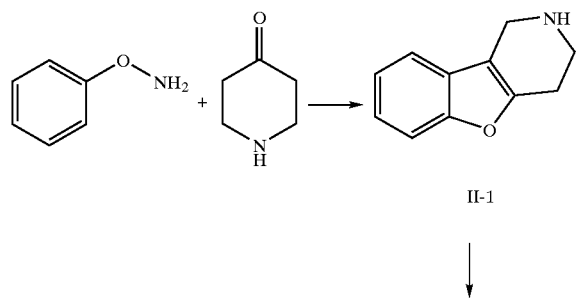

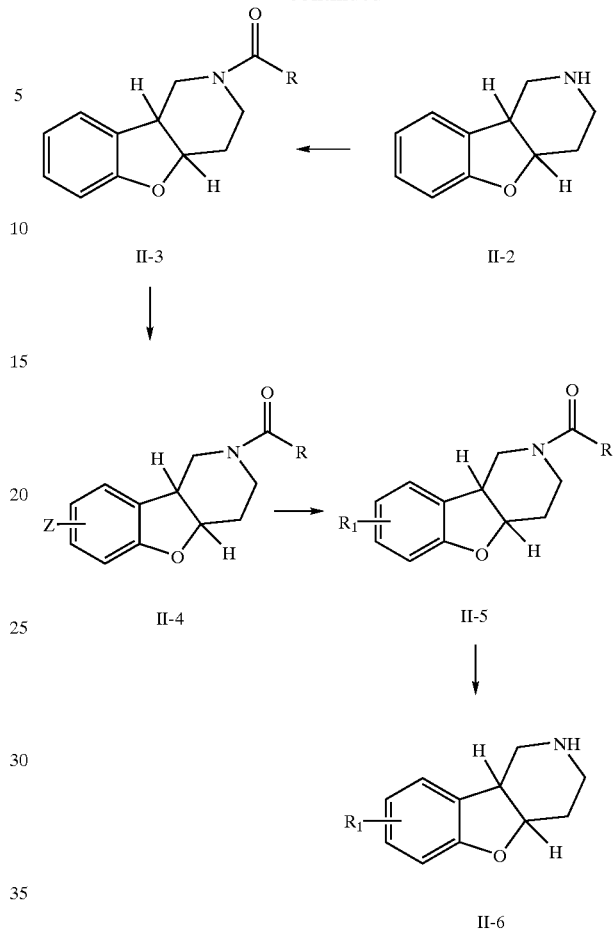

O-Phenylhydroxylamine is reacted with 4-piperidone in the presence of an acid catalyst, such as hydrochloric acid, in an appropriate solvent, such as 2-propanol, at elevated temperature to yield tetrahydrobenzofuropyridine II-1. See for example International Patent Application Publication Number WO 0037466 A1.

Tetrahydrobenzofuropyridine II-1 is treated with a reducing agent, such as $H_2$ and an appropriate catalyst, such as Pearlman's catalyst (20% $Pd(OH)_2$ on carbon), in an appropriate solvent, such as 1:1:1 acetic acid:ethanol:water at room temperature to yield hexahydrobenzofuropyridine II-2. See for example P. J. Coleman, et al., *Tetrahedron Lett.*, 2000, 41, 5803–5806. The amino nitrogen of compound II-2 is protected with a suitable protecting group, such as t-butyl carbamate (Boc), by reaction with di-tert-butyl dicarbonate in the presence of a base, such as potassium carbonate, in an appropriate solvent, such as a mixture of water and tetrahydrofuran at room temperature to yield hexahydrobenzofuran II-3 (R=tert-butoxy). Compound II-3 is halogenated with a halogenating agent, such as bromine, in an appropriate solvent, such as chloroform, at room temperature to yield halogenated hexahydrobenzofuran II-4 (Z=halo). Compound II-4 is converted to an aryl or heteroaryl substituted hexahydrobenzofuropyridine II-5 ($R_1$=aryl or heteroaryl) by means of an appropriate coupling reaction such as the Suzuki coupling reaction. See for example N Miyaura, A Suzuki, *Chem. Rev.* 95 2457–83 (1995). Compound II-4 is reacted with an appropriately substituted phenylboronic acid in the presence of an appropriate catalyst, such as dichlorobis(triphenylphosphine)palladium (II), and an appropriate base, such as aqueous sodium carbonate (2N), in an appropriate solvent, such as benzene, at elevated temperature to yield compound II-5. Compound II-5 is treated with an acid, such as trifluoroacetic acid, at room temperature to deprotect the nitrogen and provide amine II-6, which is a compound of the invention.

In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient. Such pharmaceutical compositions can be prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally (for example, by intravenous, intraperitoneal or intramuscular injection), topically, orally, or rectally.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula (I) can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing about 0.05 mg to about 500 mg, conveniently about 0.1 mg to about 250 mg, most conveniently, about 1 mg to about 150 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compositions can conveniently be administered orally, sublingually, transdermally, or parenterally at dose levels of about 0.01 to about 150 mg/kg, preferably about 0.1 to about 50 mg/kg, and more preferably about 0.1 to about 10 mg/kg of mammal body weight.

For parenteral administration the compounds are presented in aqueous solution in a concentration of from about 0.1 to about 10%, more preferably about 0.1 to about 7%. The solution may contain other ingredients, such as emulsifiers, antioxidants or buffers.

The exact regimen for administration of the compounds and compositions disclosed herein will necessarily be dependent upon the needs of the individual subject being treated, the type of treatment and, of course, the judgment of the attending practitioner.

The ability of a compound of the invention to act as a 5-HT receptor agonist or antagonist can also be determined using in vitro and in vivo assays that are known in the art. The invention provides compounds of formula (I) that act as either agonists or as antagonists of one or more 5-HT receptor subtypes. The compounds of the invention are 5-HT ligands, which typically displace >50% of a radiolabeled test ligand from one or more 5-HT receptor subtype at a concentration of 1 μM. The procedures used for testing such displacement are well known and would be readily available to one skilled in the art. For example, see L. W. Fitzgerald et al., *Mol. Pharmacol*, 2000, 57, 1, 75–81; and D. B. Wainscott, et al., *J. Pharmacol Exp Ther*, 1996, 276, 2, 720–727.

The invention will now be illustrated by the following non-limiting Examples.

DESCRIPTION OF PREFERRED EMBODIMENTS 8-(2,4-Dichlorophenyl)-3,4,4a,9b-tetrahydro[1]benzofuro[3,2-c]pyridine

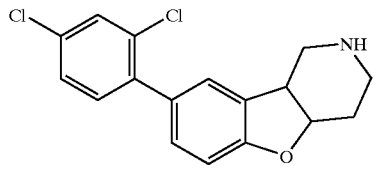

tert-Butyl 8-(2,4-dichlorophenyl)-3,4,4a,9b-tetrahydro[1]benzofuro[3,2-c]pyridine-2(1H)-carboxylate (0.221 g, 0.53 mmol) was dissolved in $CH_2Cl_2$ (7 mL). Trifluoroacetic acid (0.81 mL, 20 equiv.) was added, and the reaction mixture was stirred at rt under $N_2$ for 2 h. The reaction mixture was cooled to –5° C. and 2N aqueous NaOH (8 mL) was added. The reaction mixture was partitioned between $CH_2Cl_2$ and water. The water layer was extracted with $CH_2Cl_2$ (2x) and with 25:1 $CH_2Cl_2:CH_3OH$ (2x). The combined organic layers were dried over $Na_2SO_4$, filtered and concentrated under reduced pressure to provide the title compound (0.16 g, 98%). MS (ESI+) for $C_{17}H_{15}Cl_2NO$ m/z 320.1 $(M+H)^+$.

The intermediate tert-Butyl 8-(2,4-dichlorophenyl)-3,4,4a,9b-tetrahydro-[1]benzofuro[3,2-c]pyridine-2(1H)-carboxylate was prepared as follows.

a. 1,2,3,4-tetrahydro[1]benzofuro[3,2-c]pyridine hydrochloride. A mixture of O-phenylhydroxylamine hydrochloride (0.500 g, 3.43 mmol) and 4-piperidone monohydrate hydrochloride (0.575 g, 3.74 mmol) in 2-propanol (3.9 mL) was stirred at rt. Concentrated HCl (2 mL) was added dropwise. The reaction mixture was refluxed for 3 hours. The reaction mixture was cooled to room temperature. The precipitate was collected by filtration, washed with diethylether and air dried, to yield 1,2,3,4-tetrahydro[1]benzofuro[3,2-c]pyridine hydrochloride as a white solid (0.72 g, 100% yield). MS (ESI+) for $C_{11}H_{11}NO$ m/z 174.2 $(M+H)^+$. See for example International Patent Application Publication Number: WO 00/37466.

b. 1,2,3,4,4a,9b-hexahydro[1]benzofuro[3,2-c]pyridine hydrochloride. 1,2,3,4-Tetrahydro[1]benzofuro[3,2-c]pyridine hydrochlordide (1.0 g, 4.8 mmol) was dissolved in 1:1:1 $CH_3COOH:EtOH:H_2O$ (75 mL). Pearlman's catalyst (20% $Pd(OH)_2$ on carbon, 1.718 g) was added and the reaction mixture was stirred under $H_2$ (1 atm) at room temperature. After 10 hours, the starting material was consumed. The reaction mixture was filtered through a short pad of celite, the celite pad was rinsed with methanol and the filtrate was evaporated under reduced pressure. The acetic acid was removed by azeotropic distillation with toluene. After drying, 1,2,3,4,4a,9b-hexahydro[1]benzofuro[3,2-c]pyridine hydrochloride (1.02 g) was obtained as a white amorphous solid. MS (ESI+) for $C_{11}H_{13}NO$ m/z 176.1 $(M+H)^+$.

c. tert-Butyl 3,4,4a,9b-tetrahydro[1]benzofuro[3,2-c]pyridine -2(1H)-carboxylate. 1,2,3,4,4a,9b-Hexahydro[1]benzofuro[3,2-c]pyridine hydrochloride (1.02 g) was dissolved in THF (25 mL) and water (17 mL). $K_2CO_3$ (3.0 g) was added and the biphasic mixture was stirred at room temperature under $N_2$. Di-tert-butyl dicarbonate (1.04 g) was added in 3 equal portions over 1.5 hours. After 2 hours, the solvent was removed in vacuo at reduced pressure. The residue was partitioned between EtOAc and water. The aqueous layer was extracted with EtOAc (2x). The combined organic layers were washed with brine, dried over $MgSO_4$, filtered and concentrated. tert-Butyl 3,4,4a,9b-tetrahydro[1]benzofuro[3,2-c]pyridine-2(1H)-carboxylate (0.82 g, 63% yield) was obtained after purification by flash chromatography using 15% EtOAc/Hexane as the eluent. MS (ESI+) for $C_{16}H_{21}NO_3$ m/z 276.1 $(M+H)^+$.

d. tert-butyl 8-bromo-3,4,4a,9b-tetrahydro[1]benzofuro [3,2-c]pyridine-2(1H)-carboxylate. tert-Butyl 3,4,4a,9b-tetrahydro[1]benzofuro-[3,2-c]pyridine-2(1H)-carboxylate (0.82 g, 2.98 mmol) was dissolved in $CHCl_3$ (20 mL) and cooled to –5° C. Bromine (0.145 mL, 2.83 mmol, 1 equiv.) was dissolved in $CHCl_3$ (0.8 mL) and added dropwise to the cold reaction mixture over 4 hours. 5% aqueous $NaHCO_3$ (30 mL) was added to the reaction mixture (pH about 12). The reaction mixture was partitioned between $CHCl_3$ and water. The aqueous layer was extracted with $CHCl_3$ (2x). The combined organic layers were dried over $MgSO_4$, filtered and concentrated under reduced pressure to afford tert-butyl 8-bromo-3,4,4a,9b-tetrahydro[1]benzofuro[3,2-c]pyridine-2(1H)-carboxylate (0.6 g) in 50% yield. MS (ESI+) for $C_{16}H_{20}BrNO_3$ m/z 354.0 $(M+H)^+$.

e. tert-butyl 8-(2,4-dichlorophenyl)-3,4,4a,9b-tetrahydro[1]benzofuro[3,2-c]pyridine-2(1H)-carboxylate. tert-Butyl 8-bromo-3,4,4a,9b-tetrahydro[1]benzofuro[3,2-c]pyridine-2(1H)-carboxylate (0.250 g, 0.706 mmol) was dissolved in benzene (15 mL). 2,4-Dichlorobenzen-boronic acid (0.270 g, 1.41 mmol) was added. Bis(triphenylphosphine)-palladiumdichloride (0.035 g, 0.05 mmol) and 2M aqueous $Na_2CO_3$ (1.2 mL) were added to the reaction mixture. Ar was bubbled through the reaction mixture for 20 minutes. The reaction mixture was refluxed under $N_2$ for 22 hours. The solvent was evaporated at reduced pressure to yield a dark slurry. The crude material was partitioned between EtOAc and water. The aqueous layer was extracted with EtOAc (2×) and the combined organic layers were washed with brine, dried over $Na_2SO_4$, filtered and concentrated under reduced pressure. The crude product was purified by flash chromatography (15:1 toluene:EtOAc) and tert-butyl 8-(2,4-dichlorophenyl)-3,4,4a,9b-tetrahydro[1]benzofuro[3,2-c]pyridine-2(1H)-carboxylate (0.221 g) was obtained in 74% yield. MS (ESI+) for $C_{22}H_{23}Cl_2NO_3$ m/z 420.0 (M+H)$^+$.

Using synthetic procedures similar to those described herein, the following compounds of formula (I) can also be prepared:

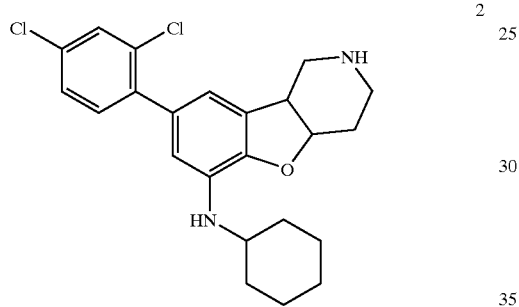

8-(2,4-dichlorophenyl)-N-cyclohexyl-1,2,3,4,4a,9b,-hexahydro[1]benzofuro[3,2-c]pyridin-6-amine, 2

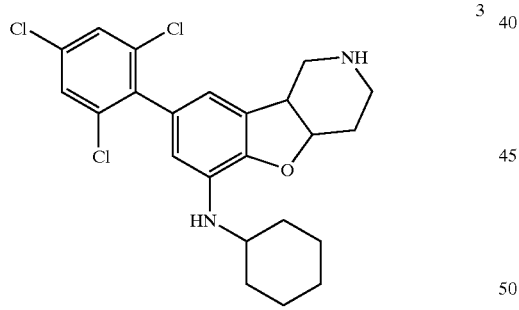

8-(2,4,6-trichlorophenyl)-N-cyclohexyl-1,2,3,4,4a,9b,-hexahydro[1]benzofuro[3,2-c]-pyridin-6-amine, 3

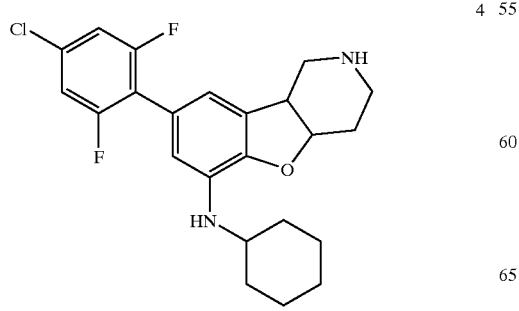

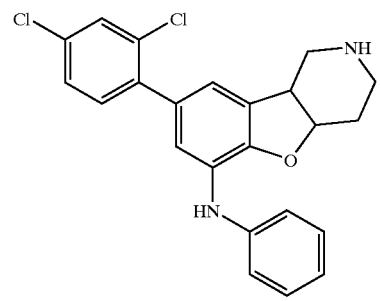

8-(2,6-difluoro-4-chlorophenyl)-N-cyclohexyl-1,2,3,4,4a,9b,-hexahydro[1]benzofuro-[3,2-c]pyridin-6-amine, 4

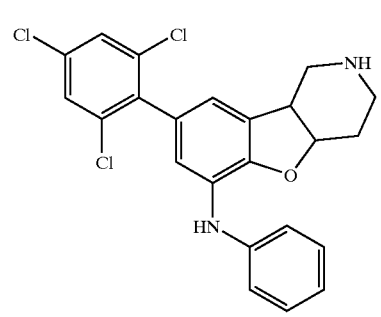

8-(2,4-dichlorophenyl)-N-phenyl-1,2,3,4,4a,9b,-hexahydro[1]benzofuro[3,2-c]pyridin-6-amine, 5

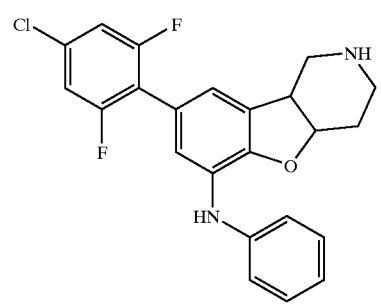

8-(2,4,6-trichlorophenyl)-N-phenyl-1,2,3,4,4a,9b,-hexahydro[1]benzofuro[3,2-c]-pyridin-6-amine, 6

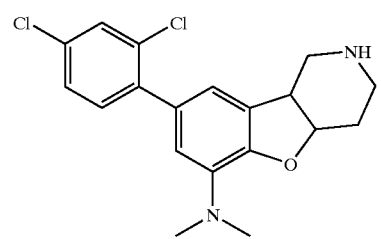

8-(2,6-difluoro-4-chlorophenyl)-N-phenyl-1,2,3,4,4a,9b,-hexahydro[1]benzofuro-[3,2-c]pyridin-6-amine, 7

8-(2,4-dichlorophenyl)-N,N-dimethyl-1,2,3,4,4a,9b,-hexahydro[1]benzofuro[3,2-c]-pyridin-6-amine, 8

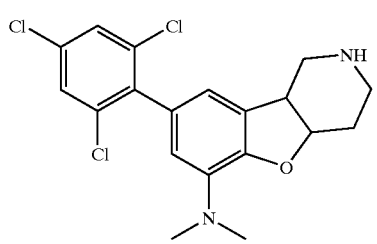

8-(2,4,6-trichlorophenyl)-N,N-dimethyl-1,2,3,4,4a,9b,-hexahydro[1]benzofuro[3,2-c]-pyridin-6-amine, 9

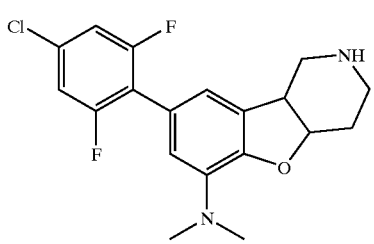

8-(2,6-difluoro-4-chlorophenyl)-N,N-dimethyl-1,2,3,4,4a,9b,-hexahydro[1]benzofuro-[3,2-c]pyridin-6-amine, 10

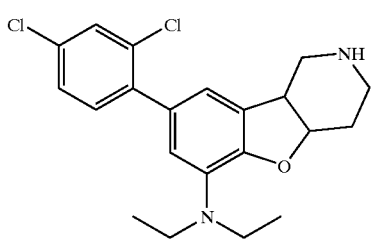

8-(2,4-dichlorophenyl)-N,N-diethyl-1,2,3,4,4a,9b,-hexahydro[1]benzofuro[3,2-c]-pyridin-6-amine, 11

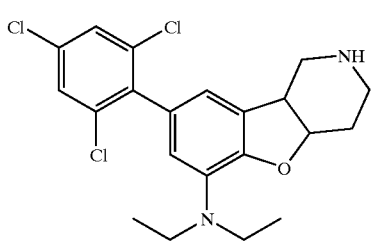

8-(2,4,6-trichlorophenyl)-N,N-diethyl-1,2,3,4,4a,9b,-hexahydro[1]benzofuro[3,2-c]-pyridin-6-amine, 12

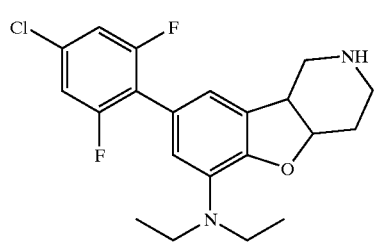

8-(2,6-difluoro-4-chlorophenyl)-N,N-diethyl-1,2,3,4,4a,9b,-hexahydro[1]benzofuro-[3,2-c]pyridin-6-amine, 13

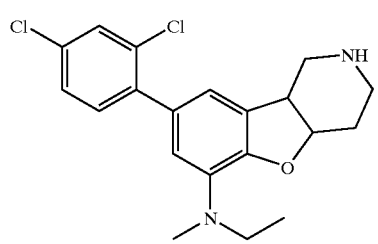

8-(2,4-dichlorophenyl)-N-methyl-N-ethyl-1,2,3,4,4a,9b,-hexahydro[1]benzofuro-[3,2-c]pyridin-6-amine, 14

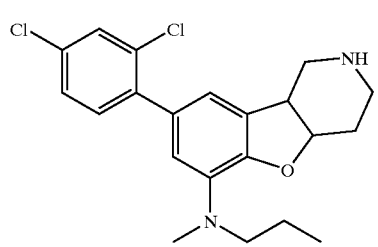

8-(2,4-dichlorophenyl)-N-methyl-N-propyl-1,2,3,4,4a,9b,-hexahydro[1]benzofuro-[3,2-c]pyridin-6-amine, 15

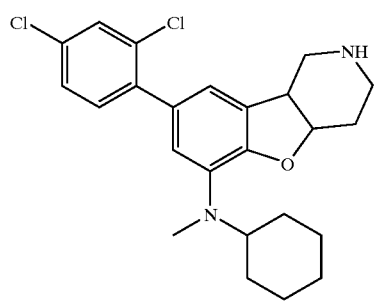

8-(2,4-dichlorophenyl)-N-methyl-N-cyclohexyl-1,2,
3,4,4a,9b,-hexahydro[1]benzofuro[3,2-c]pyridin-6-
amine, 16

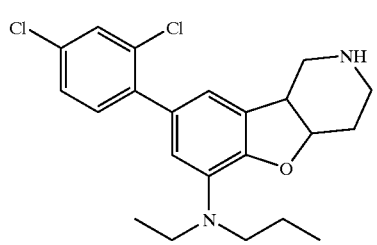

8-(2,4-dichlorophenyl)-N-ethyl-N-propyl-1,2,3,4,4a,
9b,-hexahydro[1]benzofuro-[3,2-c]pyridin-6-amine, 17

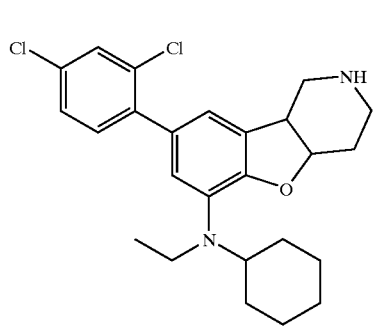

8-(2,4-dichlorophenyl)-N-ethyl-N-cyclohexyl-1,2,3,
4,4a,9b,-hexahydro[1]benzofuro[3,2-c]pyridin-6-
amine, 18

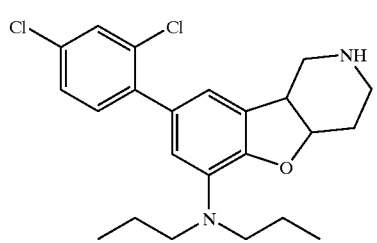

8-(2,4-dichlorophenyl)-N,N-dipropyl-1,2,3,4,4a,9b,-
hexahydro[1]benzofuro[3,2-c]-pyridin-6-amine, 19

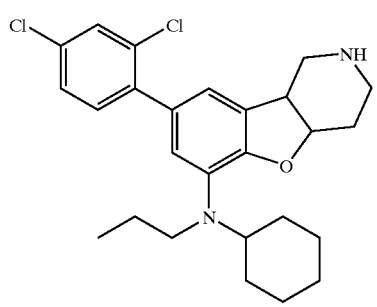

8-(2,4-dichlorophenyl)-N-propyl-N-cyclohexyl-1,2,
3,4,4a,9b,-hexahydro[1]benzofuro-[3,2-c]pyridin-6-
amine, 20

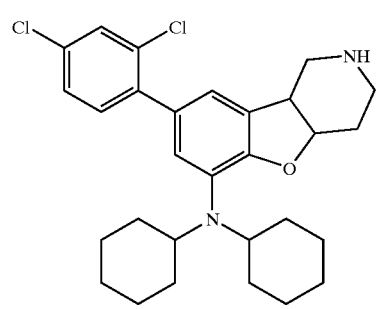

8-(2,4-dichlorophenyl)-N,N-dicyclohexyl-1,2,3,4,4a,
9b,-hexahydro[1]benzofuro-[3,2-c]pyridin-6-amine, 21

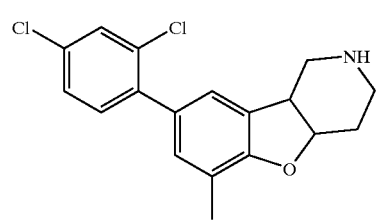

8-(2,4-dichlorophenyl)-6-methyl-1,2,3,4,4a,9b,-
hexahydro[1]benzofuro[3,2-c]-pyridine, 22

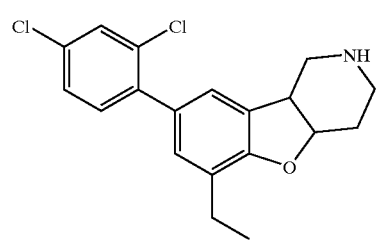

8-(2,4-dichlorophenyl)-6-ethyl-1,2,3,4,4a,9b,-
hexahydro[1]benzofuro[3,2-c]pyridine, 23

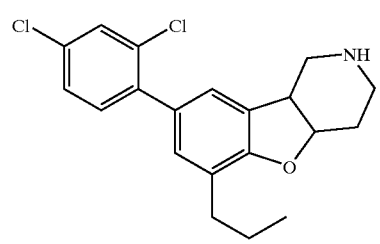

25

8-(2,4-dichlorophenyl)-6-propyl-1,2,3,4,4a,9b,-hexahydro[1]benzofuro[3,2-c]pyridine, 24

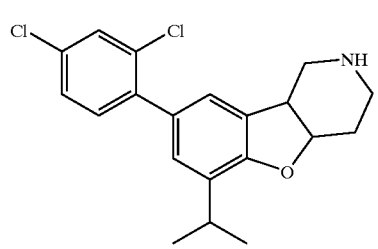

8-(2,4-dichlorophenyl)-6-isopropyl-1,2,3,4,4a,9b,-hexahydro[1]benzofuro[3,2-c]-pyridine, 25

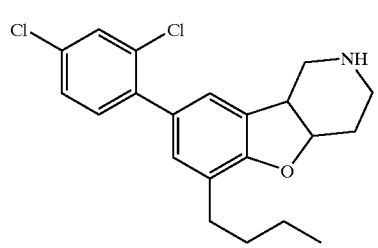

8-(2,4-dichlorophenyl)-6-butyl-1,2,3,4,4a,9b,-hexahydro[1]benzofuro[3,2-c]pyridine, 26

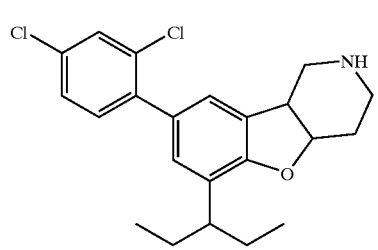

8-(2,4-dichlorophenyl)-6-(1-ethylpropyl)-1,2,3,4,4a,9b,-hexahydro[1]benzofuro-[3,2-c]pyridine, 27

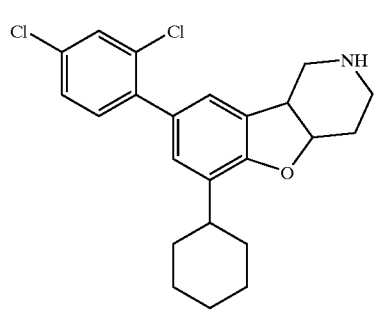

26

8-(2,4-dichlorophenyl)-6-cyclohexyl-1,2,3,4,4a,9b,-hexahydro[1]benzofuro[3,2-c]-pyridine, 28

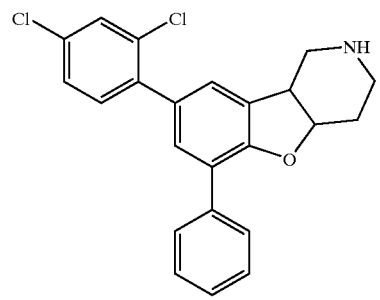

8-(2,4-dichlorophenyl)-6-phenyl-1,2,3,4,4a,9b,-hexahydro[1]benzofuro[3,2-c]-pyridine, 29

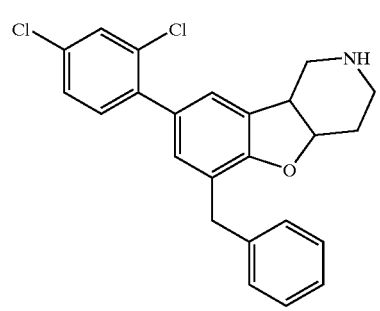

8-(2,4-dichlorophenyl)-6-benzyl-1,2,3,4,4a,9b,-hexahydro[1]benzofuro[3,2-c]-pyridine, 30

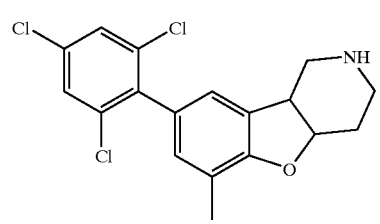

8-(2,4,6-trichlorophenyl)-6-methyl-1,2,3,4,4a,9b,-hexahydro[1]benzofuro[3,2-c]-pyridine, 31

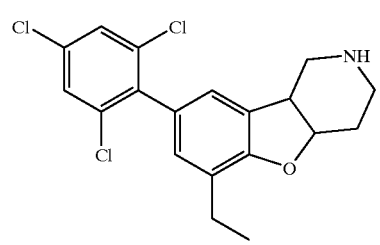

8-(2,4,6-trichlorophenyl)-6-ethyl-1,2,3,4,4a,9b,-
hexahydro[1]benzofuro[3,2-c]-pyridine, 32

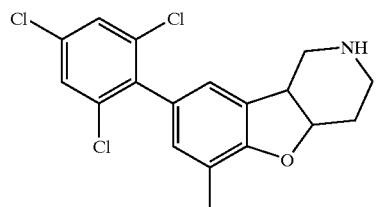

8-(2,4,6-trichlorophenyl)-6-propyl-1,2,3,4,4a,9b,-
hexahydro[1]benzofuro[3,2-c]-pyridine, 33

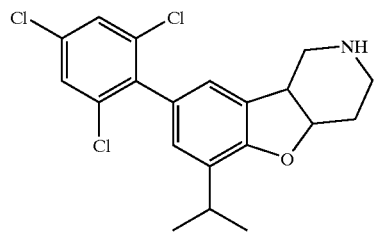

8-(2,4,6-trichlorophenyl)-6-isopropyl-1,2,3,4,4a,9b,-
hexahydro[1]benzofuro[3,2-c]-pyridine, 34

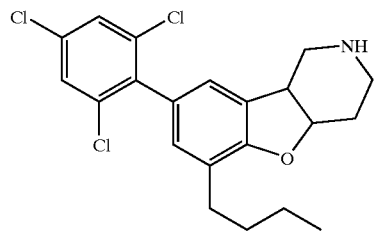

8-(2,4,6-trichlorophenyl)-6-butyl-1,2,3,4,4a,9b,-
hexahydro[1]benzofuro[3,2-c]-pyridine, 35

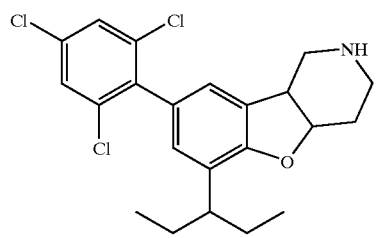

8-(2,4,6-trichlorophenyl)-6-(1-ethylpropyl)-1,2,3,4,
4a,9b,-hexahydro[1]benzofuro-[3,2-c]pyridine, 36

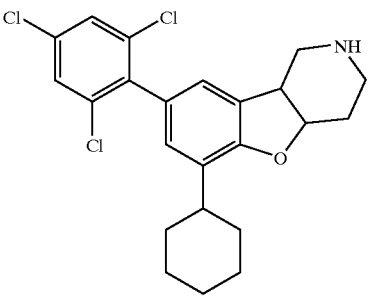

8-(2,4,6-trichlorophenyl)-6-cyclohexyl-1,2,3,4,4a,
9b,-hexahydro[1]benzofuro[3,2-c]-pyridine, 37

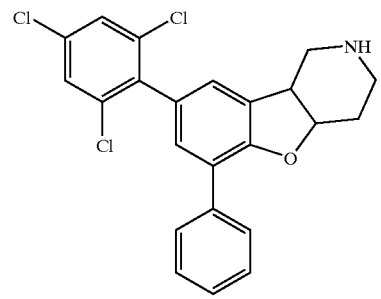

8-(2,4,6-trichlorophenyl)-6-phenyl-1,2,3,4,4a,9b,-
hexahydro[1]benzofuro[3,2-c]-pyridine, 38

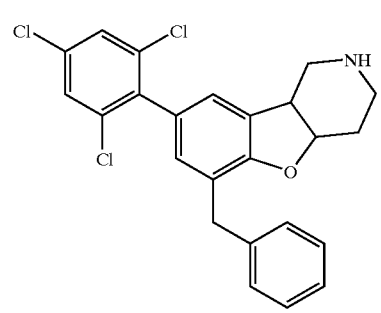

8-(2,4,6-trichlorophenyl)-6-benzyl-1,2,3,4,4a,9b,-
hexahydro[1]benzofuro[3,2-c]-pyridine, 39

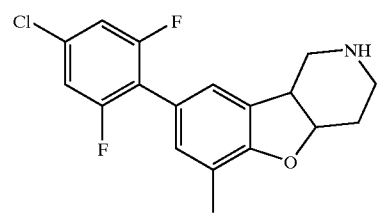

8-(2,6-difluoro-4-chlorophenyl)-6-methyl-1,2,3,4,4a,
9b,-hexahydro[1]benzofuro[3,2-c]pyridine, 40

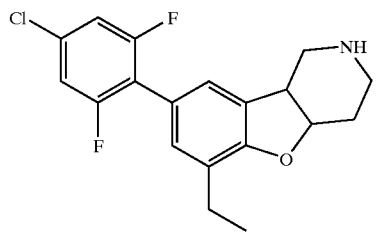

8-(2,6-difluoro-4-chlorophenyl)-6-ethyl-1,2,3,4,4a,
9b,-hexahydro[1]benzofuro[3,2-c]-pyridine, 41

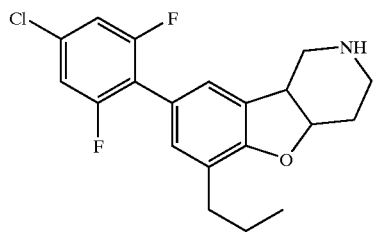

8-(2,6-difluoro-4-chlorophenyl)-6-propyl-1,2,3,4,4a,
9b,-hexahydro[1]benzofuro[3,2-c]pyridine, 42

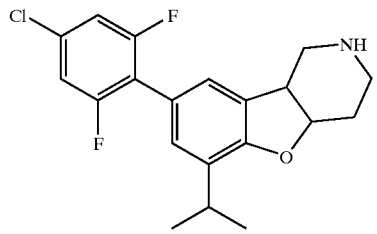

8-(2,6-difluoro-4-chlorophenyl)-6-isopropyl-1,2,3,4,
4a,9b,-hexahydro[1]benzofuro-[3,2-c]pyridine, 43

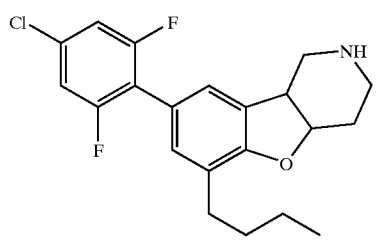

8-(2,6-difluoro-4-chlorophenyl)-6-butyl-1,2,3,4,4a,
9b,-hexahydro[1]benzofuro[3,2-c]-pyridine, 44

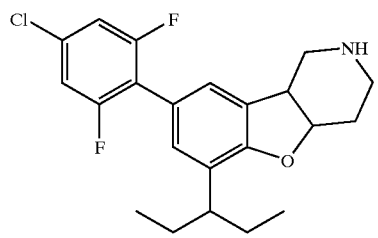

8-(2,6-difluoro-4-chlorophenyl)-6-(1-ethylpropyl)-1,2,
3,4,4a,9b,-hexahydro[1]-benzofuro[3,2-c]pyridine, 45

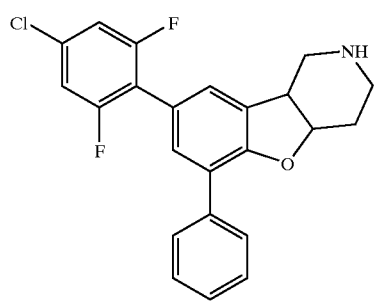

8-(2,6-difluoro-4-chlorophenyl)-6-cyclohexyl-1,2,3,
4,4a,9b,-hexahydro[1]benzofuro-[3,2-c]pyridine, 46

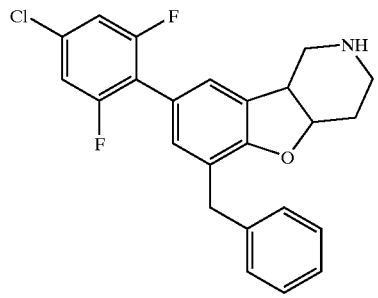

8-(2,6-difluoro-4-chlorophenyl)-6-phenyl-1,2,3,4,4a,
9b,-hexahydro[1]benzofuro-[3,2-c]pyridine, 47

8-(2,6-difluoro-4-chlorophenyl)-6-benzyl-1,2,3,4,4a,
9b,-hexahydro[1]benzofuro-[3,2-c]pyridine, 48

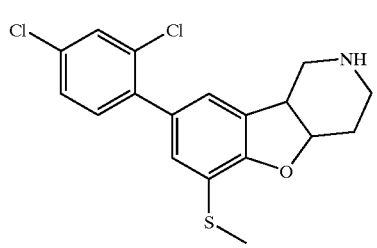

8-(2,4-dichlorophenyl)-6-(methylthio)-1,2,3,4,4a,
9b,-hexahydro[1]benzofuro[3,2-c]-pyridine, 49

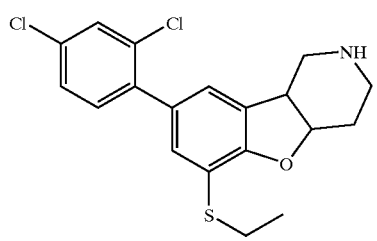

8-(2,4-dichlorophenyl)-6-(ethylthio)-1,2,3,4,4a,9b,-
hexahydro[1]benzofuro[3,2-c]-pyridine, 50

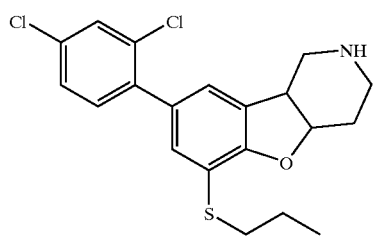

8-(2,4-dichlorophenyl)-6-(propylthio)-1,2,3,4,4a,9b,-
hexahydro[1]benzofuro[3,2-c]-pyridine, 51

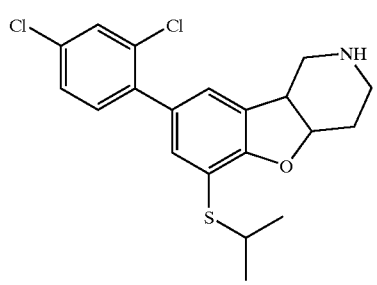

8-(2,4-dichlorophenyl)-6-(isopropylthio)-1,2,3,4,4a,
9b,-hexahydro[1]benzofuro-[3,2-c]pyridine, 52

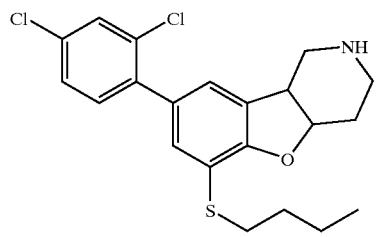

8-(2,4-dichlorophenyl)-6-(butylthio)-1,2,3,4,4a,9b,-
hexahydro[1]benzofuro[3,2-c]-pyridine, 53

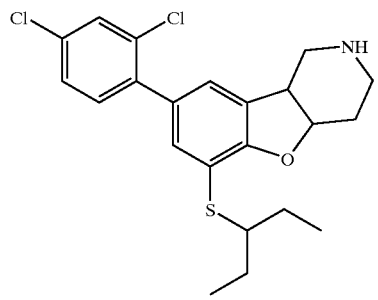

8-(2,4-dichlorophenyl)-6-[(1-ethylpropyl)thio]-1,2,3,
4,4a,9b,-hexahydro[1]benzofuro-[3,2-c]pyridine, 54

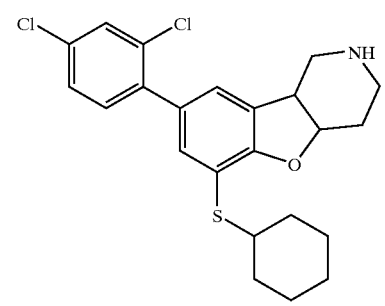

8-(2,4-dichlorophenyl)-6-(cyclohexylthio)-1,2,3,4,
4a,9b,-hexahydro[1]benzofuro-[3,2-c]pyridine, 55

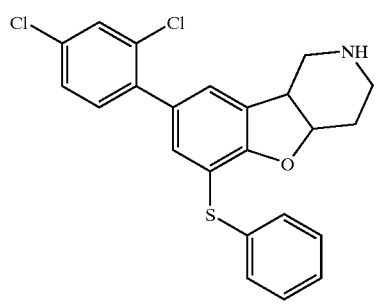

8-(2,4-dichlorophenyl)-6-(phenylthio)-1,2,3,4,4a,
9b,-hexahydro[1]benzofuro[3,2-c]-pyridine, 56

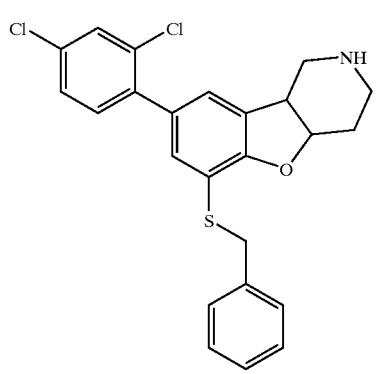

8-(2,4-dichlorophenyl)-6-(benzylthio)-1,2,3,4,4a,9b,-
hexahydro[1]benzofuro[3,2-c]-pyridine, 57

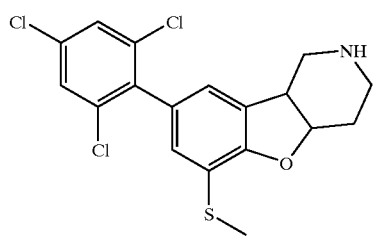

8-(2,4,6-trichlorophenyl)-6-(methylthio)-1,2,3,4,4a,
9b,-hexahydro[1]benzofuro-[3,2-c]pyridine, 58

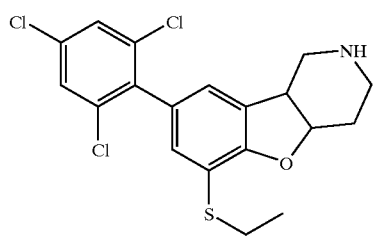

8-(2,4,6-trichlorophenyl)-6-(ethylthio)-1,2,3,4,4a,
9b,-hexahydro[1]benzofuro[3,2-c]-pyridine, 59

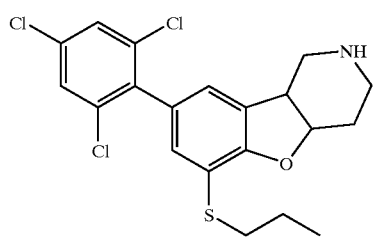

8-(2,4,6-trichlorophenyl)-6-(propylthio)-1,2,3,4,4a,
9b,-hexahydro[1]benzofuro[3,2-c]-pyridine, 60

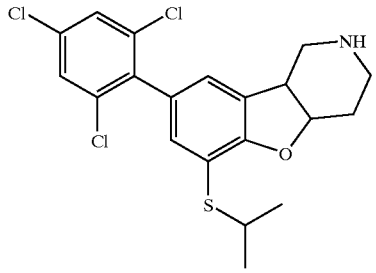

8-(2,4,6-trichlorophenyl)-6-(isopropylthio)-1,2,3,4,
4a,9b,-hexahydro[1]benzofuro-[3,2-c]pyridine, 61

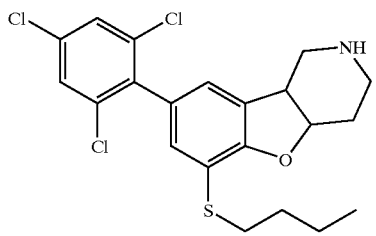

8-(2,4,6-trichlorophenyl)-6-(butylthio)-1,2,3,4,4a,
9b,-hexahydro[1]benzofuro[3,2-c]-pyridine, 62

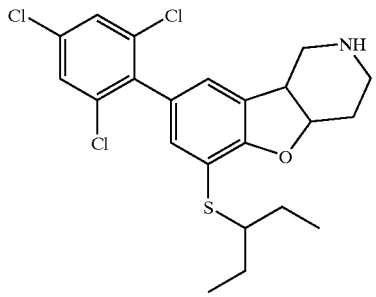

8-(2,4,6-trichlorophenyl)-6-[(1-ethylpropyl)thio]-1,2,
3,4,4a,9b,-hexahydro[1]benzofuro[3,2-c]pyridine, 63

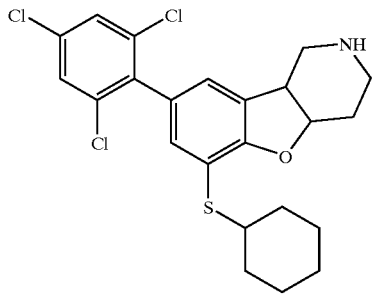

8-(2,4,6-trichlorophenyl)-6-(cyclohexylthio)-1,2,3,4,
4a,9b,-hexahydro[1]benzofuro-[3,2-c]pyridine, 64

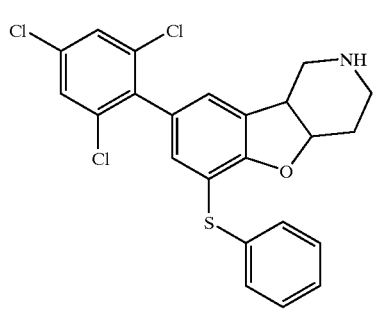

8-(2,4,6-trichlorophenyl)-6-(phenylthio)-1,2,3,4,4a,
9b,-hexahydro[1]benzofuro[3,2-c]-pyridine, 65

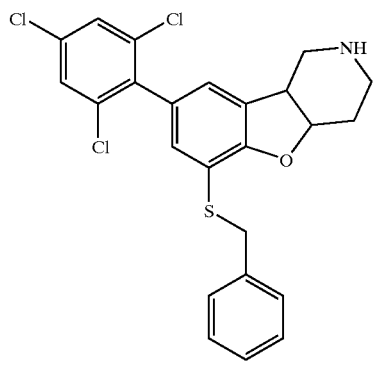

8-(2,4,6-trichlorophenyl)-6-(benzylthio)-1,2,3,4,4a,
9b,-hexahydro[1]benzofuro[3,2-c]-pyridine, 66

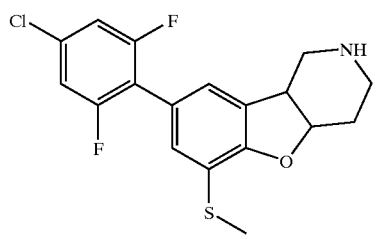

8-(2,6-difluoro-4-chlorophenyl)-6-(methylthio)-1,2,3,
4,4a,9b,-hexahydro[1]-benzofuro[3,2-c]pyridine, 67

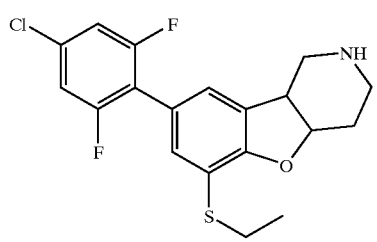

8-(2,6-difluoro-4-chlorophenyl)-6-(ethylthio)-1,2,3,
4,4a,9b,-hexahydro[1]benzofuro-[3,2-c]pyridine, 68

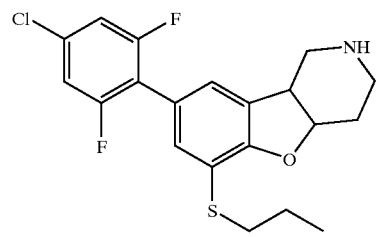

8-(2,6-difluoro-4-chlorophenyl)-6-(propylthio)-1,2,3,
4,4a,9b,-hexahydro[1]benzofuro-[3,2-c]pyridine, 69

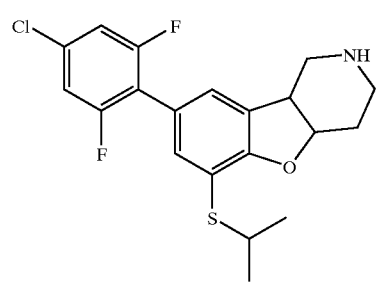

8-(2,6-difluoro-4-chlorophenyl)-6-(isopropylthio)-1,2,
3,4,4a,9b,-hexahydro[1]-benzofuro[3,2-c]pyridine, 70

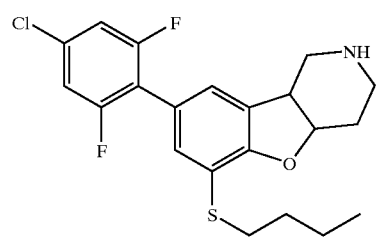

8-(2,6-difluoro-4-chlorophenyl)-6-(butylthio)-1,2,3,
4,4a,9b,-hexahydro[1]benzofuro-[3,2-c]pyridine, 71

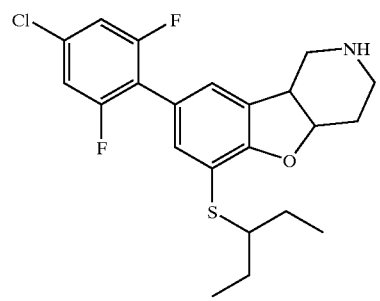

8-(2,6-difluoro-4-chlorophenyl)-6-[(1-ethylpropyl)thio]-1,2,3,4,4a,9b,-hexahydro[1]-benzofuro[3,2-c]pyridine, 72

8-(2,6-difluoro-4-chlorophenyl)-6-(benzylthio)-1,2,3,4,4a,9b,-hexahydro[1]benzofuro-[3,2-c]pyridine, 75

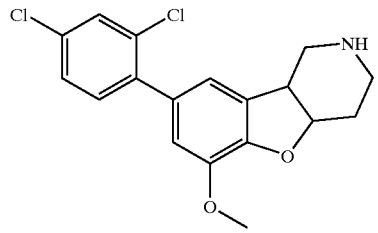

8-(2,4-dichlorophenyl)-6-methoxy-1,2,3,4,4a,9b,-hexahydro[1]benzofuro[3,2-c]-pyridine, 76

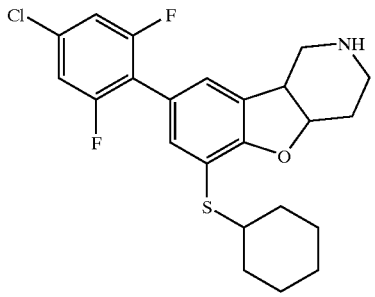

8-(2,6-difluoro-4-chlorophenyl)-6-(cyclohexylthio)-1,2,3,4,4a,9b,-hexahydro[1]-benzofuro[3,2-c]pyridine, 73

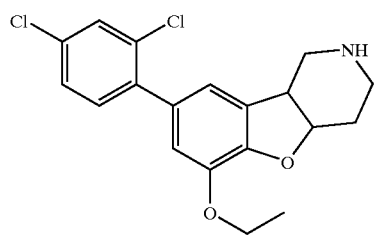

8-(2,4-dichlorophenyl)-6-ethoxy-1,2,3,4,4a,9b,-hexahydro[1]benzofuro[3,2-c]-pyridine, 77

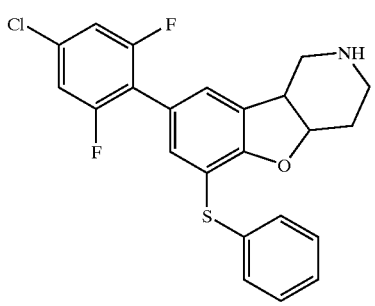

8-(2,6-difluoro-4-chlorophenyl)-6-(phenylthio)-1,2,3,4,4a,9b,-hexahydro[1]benzofuro-[3,2-c]pyridine, 74

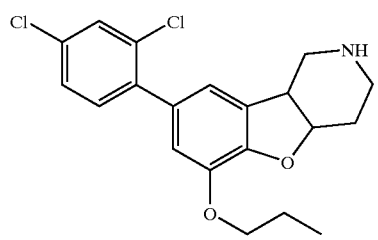

8-(2,4-dichlorophenyl)-6-propoxy-1,2,3,4,4a,9b,-hexahydro[1]benzofuro[3,2-c]-pyridine, 78

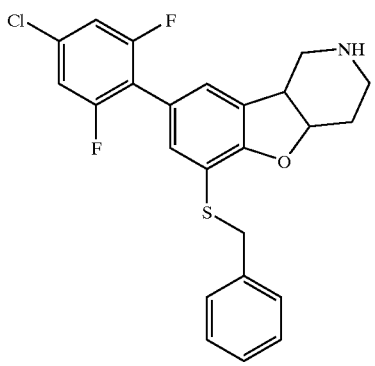

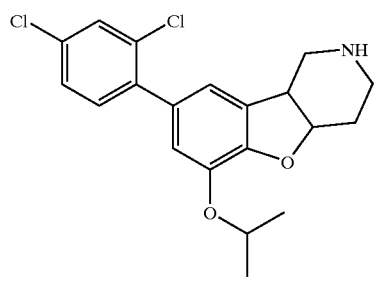

8-(2,4-dichlorophenyl)-6-isopropoxy-1,2,3,4,4a,9b,-
hexahydro[1]benzofuro[3,2-c]-pyridine, 79

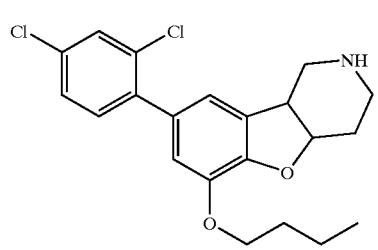

8-(2,4-dichlorophenyl)-6-butoxy-1,2,3,4,4a,9b,-
hexahydro[1]benzofuro[3,2-c]-pyridine, 80

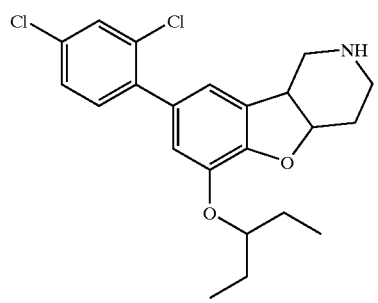

8-(2,4-dichlorophenyl)-6-[(1-ethylpropyl)oxy]-1,2,3,
4,4a,9b,-hexahydro[1]benzofuro-[3,2-c]pyridine, 81

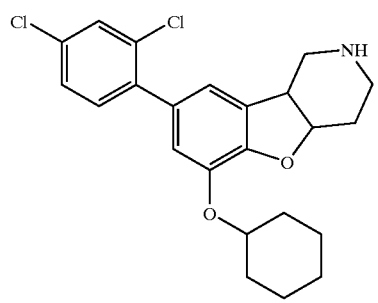

8-(2,4-dichlorophenyl)-6-(cyclohexyloxy)-1,2,3,4,
4a,9b,-hexahydro[1]benzofuro-[3,2-c]pyridine, 82

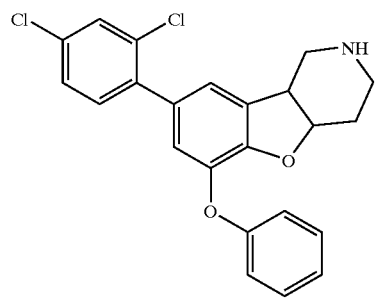

8-(2,4-dichlorophenyl)-6-phenoxy-1,2,3,4,4a,9b,-
hexahydro[1]benzofuro[3,2-c]-pyridine, 83

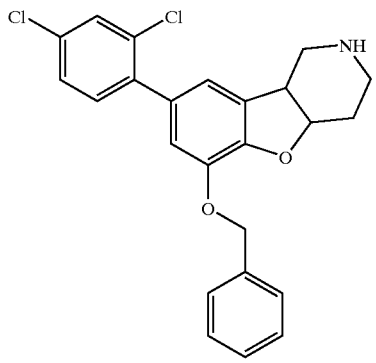

8-(2,4-dichlorophenyl)-6-(benzyloxy)-1,2,3,4,4a,9b,-
hexahydro[1]benzofuro[3,2-c]-pyridine, 84

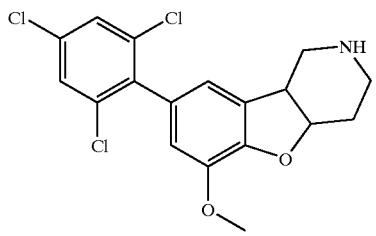

8-(2,4,6-trichlorophenyl)-6-methoxy-1,2,3,4,4a,9b,-
hexahydro[1]benzofuro[3,2-c]-pyridine, 85

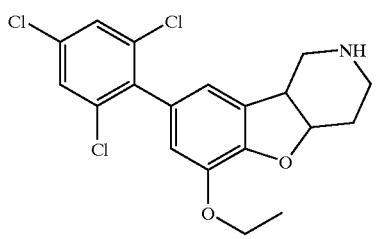

8-(2,4,6-trichlorophenyl)-6-ethoxy-1,2,3,4,4a,9b,-
hexahydro[1]benzofuro[3,2-c]-pyridine, 86

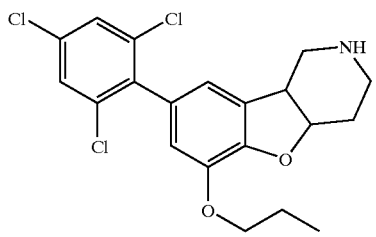

41

8-(2,4,6-trichlorophenyl)-6-propoxy-1,2,3,4,4a,9b,-hexahydro[1]benzofuro[3,2-c]-pyridine, 87

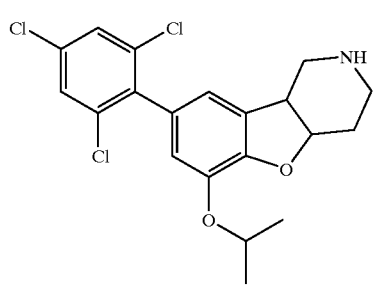

8-(2,4,6-trichlorophenyl)-6-isopropoxy-1,2,3,4,4a,9b,-hexahydro[1]benzofuro[3,2-c]-pyridine, 88

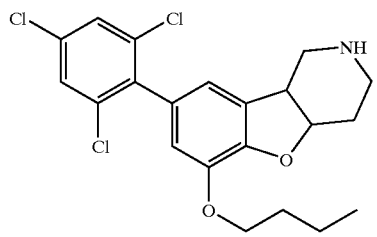

8-(2,4,6-trichlorophenyl)-6-butoxy-1,2,3,4,4a,9b,-hexahydro[1]benzofuro[3,2-c]-pyridine, 89

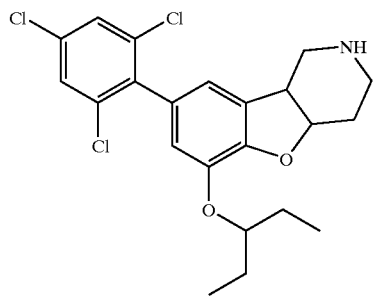

8-(2,4,6-trichlorophenyl)-6-[(1-ethylpropyl)oxy]-1,2,3,4,4a,9b,-hexahydro[1]-benzofuro[3,2-c]pyridine, 90

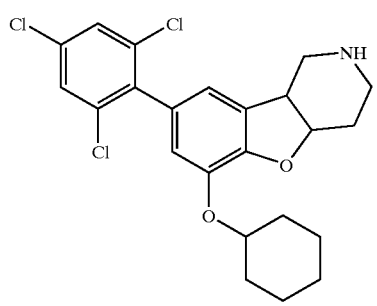

42

8-(2,4,6-trichlorophenyl)-6-(cyclohexyloxy)-1,2,3,4,4a,9b,-hexahydro[1]benzofuro-[3,2-c]pyridine, 91

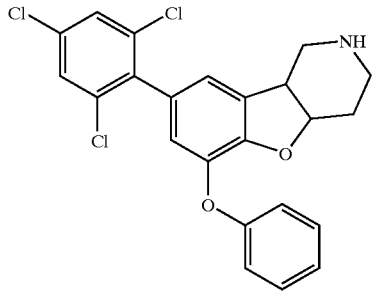

8-(2,4,6-trichlorophenyl)-6-phenoxy-1,2,3,4,4a,9b,-hexahydro[1]benzofuro[3,2-c]-pyridine, 92

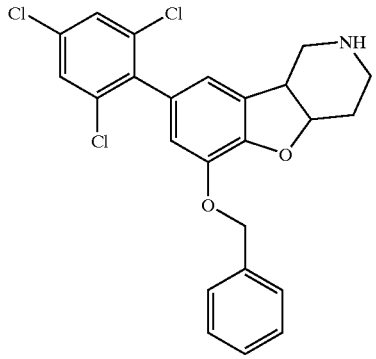

8-(2,4,6-trichlorophenyl)-6-(benzyloxy)-1,2,3,4,4a,9b,-hexahydro[1]benzofuro[3,2-c]-pyridine, 93

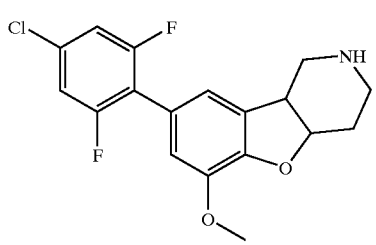

8-(2,6-difluoro-4-chlorophenyl)-6-methoxy-1,2,3,4,4a,9b,-hexahydro[1]benzofuro-[3,2-c]pyridine, 94

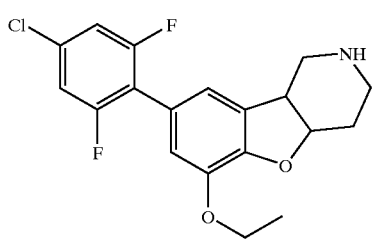

8-(2,6-difluoro-4-chlorophenyl)-6-ethoxy-1,2,3,4,4a, 9b,-hexahydro[1]benzofuro-[3,2-c]pyridine, 95

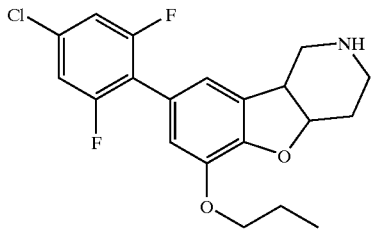

8-(2,6-difluoro-4-chlorophenyl)-6-propoxy-1,2,3,4, 4a,9b,-hexahydro[1]benzofuro-[3,2-c]pyridine, 96

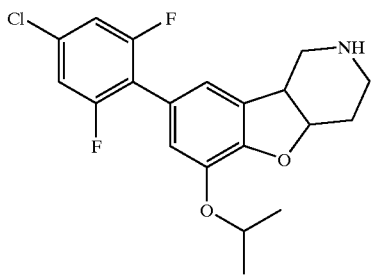

8-(2,6-difluoro-4-chlorophenyl)-6-(2-propoxy)-1,2,3, 4,4a,9b,-hexahydro[1]benzofuro-[3,2-c]pyridine, 97

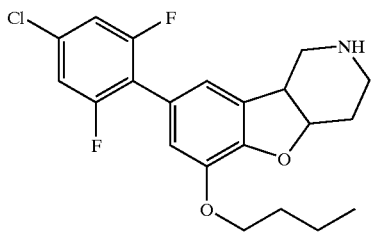

8-(2,6-difluoro-4-chlorophenyl)-6-butoxy-1,2,3,4,4a, 9b,-hexahydro[1]benzofuro-[3,2-c]pyridine, 98

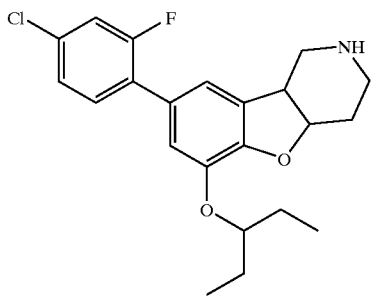

8-(2,6-difluoro-4-chlorophenyl)-6-[(1-ethylpropyl) oxy]-1,2,3,4,4a,9b,-hexahydro[1]-benzofuro[3,2-c] pyridine, 99

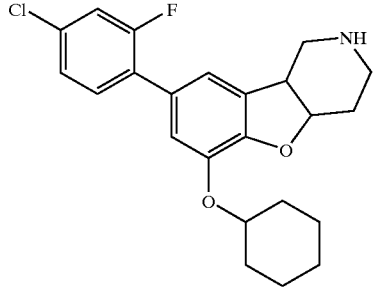

8-(2,6-difluoro-4-chlorophenyl)-6-(cyclohexyloxy)- 1,2,3,4,4a,9b,-hexahydro[1]-benzofuro[3,2-c] pyridine, 100

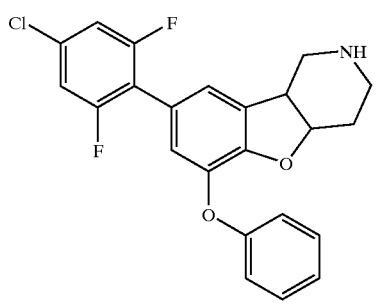

8-(2,6-difluoro-4-chlorophenyl)-6-phenoxy-1,2,3,4, 4a,9b,-hexahydro[1]benzofuro-[3,2-c]pyridine, 101

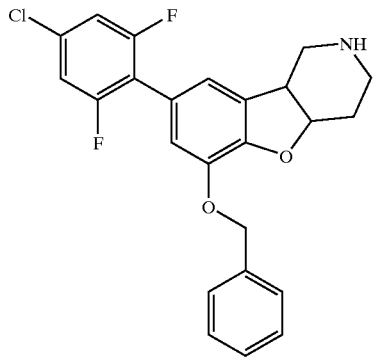

8-(2,6-difluoro-4-chlorophenyl)-6-(benzyloxy)-1,2,3, 4,4a,9b,-hexahydro[1]benzofuro-[3,2-c]pyridine, 102

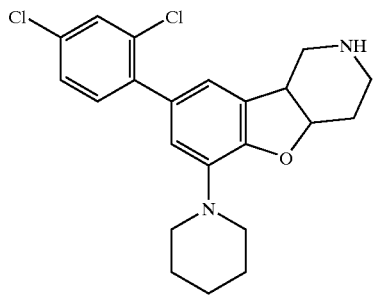

8-(2,4-dichlorophenyl)-6-piperidin-1-yl-1,2,3,4,4a,
9b-hexahydro[1]benzofuro-[3,2-c]pyridine, 103

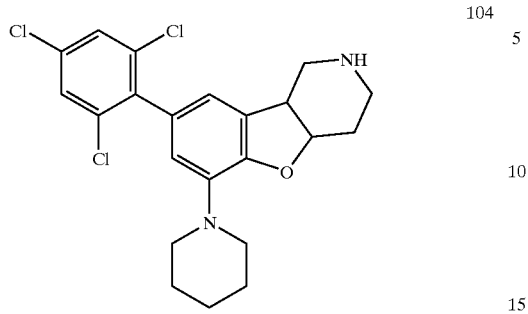

8-(2,4,6-trichlorophenyl)-6-piperidin-1-yl-1,2,3,4,4a,
9b-hexahydro[1]benzofuro[3,2-c]pyridine, 104

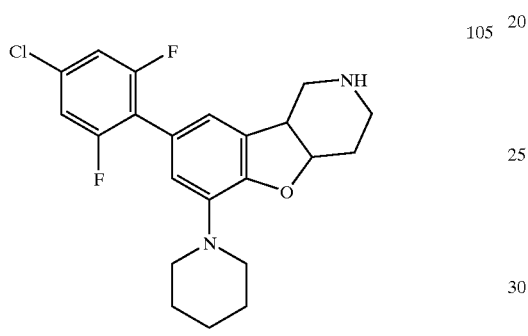

8-(2,6-difluoro-4-chlorophenyl)-6-piperidin-1-yl-1,2,
3,4,4a,9b-hexahydro[1]-benzofuro[3,2-c]pyridine,
105

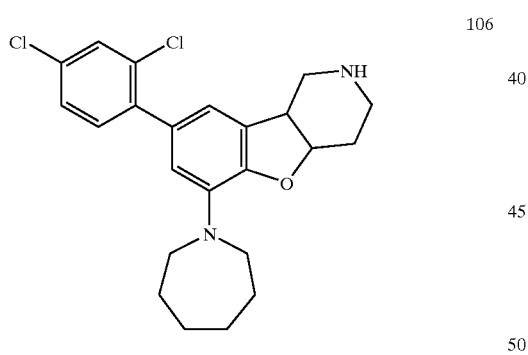

8-(2,4-dichlorophenyl)-6-azepano-1-yl-1,2,3,4,4a,
9b-hexahydro[1]benzofuro[3,2-c]pyridine, 106

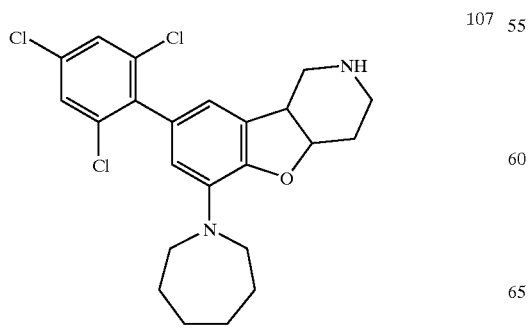

8-(2,4,6-trichlorophenyl)-6-azepano-1-yl-1,2,3,4,4a,
9b-hexahydro[1]benzofuro[3,2-c]pyridine, 107

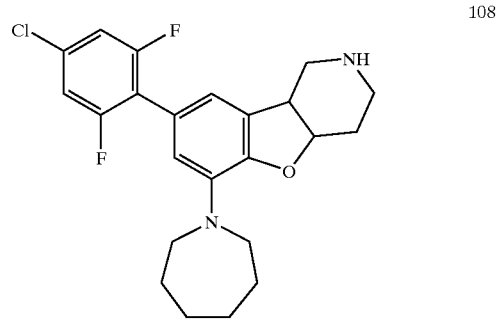

8-(2,6-difluoro-4-chlorophenyl)-6-azepano-1-yl-1,2,
3,4,4a,9b-hexahydro[1]benzofuro-[3,2-c]pyridine, 108

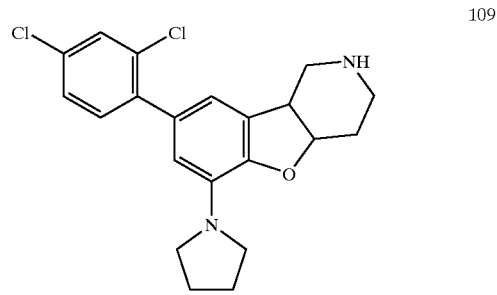

8-(2,4-dichlorophenyl)-6-pyrrolidin-1-yl-1,2,3,4,4a,
9b-hexahydro[1]benzofuro[3,2-c]pyridine, 109

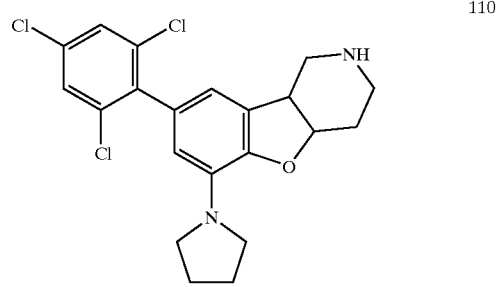

8-(2,4,6-trichlorophenyl)-6-pyrrolidin-1-yl-1,2,3,4,
4a,9b-hexahydro[1]benzofuro[3,2-c]pyridine, 110

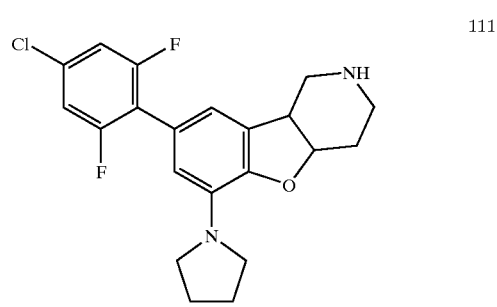

8-(2,6-difluoro-4-chlorophenyl)-6-pyrrolidin-1-yl-1,2,3,
4,4a,9b-hexahydro-[1]benzofuro[3,2-c]pyridine, 111

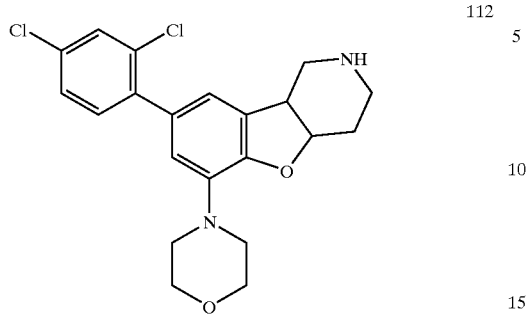

8-(2,4-dichlorophenyl)-5-morpholin-4-yl-1,2,3,4,4a,
9b-hexahydro[1]benzofuro[3,2-c]pyridine, 112

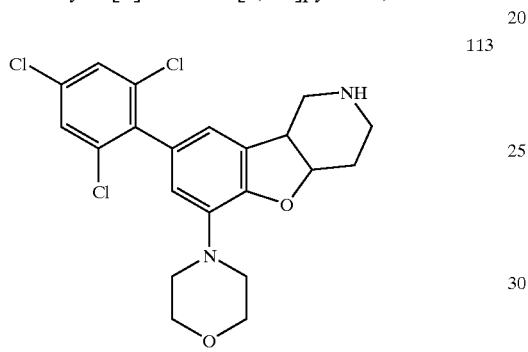

8-(2,4,6-trichlorophenyl)-5-morpholin-4-yl-1,2,3,4,
4a,9b-hexahydro[1]benzofuro[3,2-c]pyridine, 113

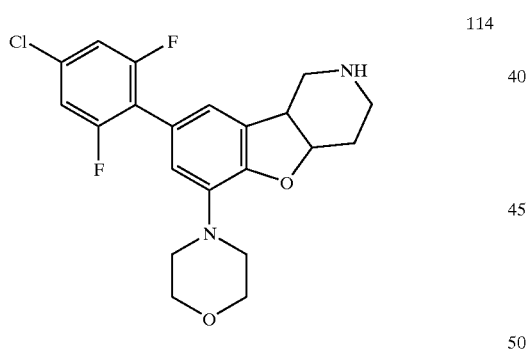

8-(2,6-difluoro-4-chlorophenyl)-5-morpholin-4-yl-1,2,3,
4,4a,9b-hexahydro-[1]benzofuro[3,2-c]pyridine, 114

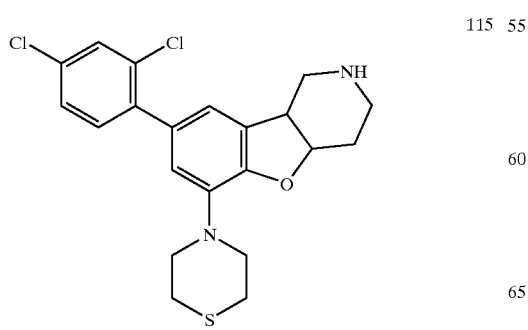

8-(2,4-dichlorophenyl)-6-thiomorpholin-4-yl-1,2,3,4,
4a,9b-hexahydro[1]benzofuro-[3,2-c]pyridine, 115

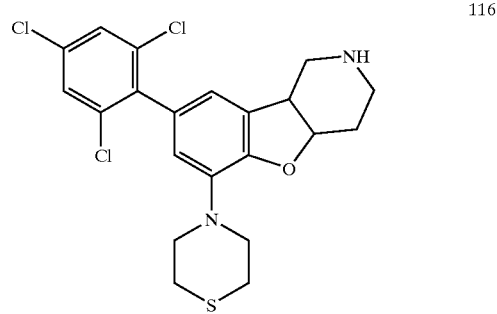

8-(2,4,6-trichlorophenyl)-6-thiomorpholin-4-yl-1,2,3,4,
4a,9b-hexahydro[1]benzofuro-[3,2-c]pyridine, 116

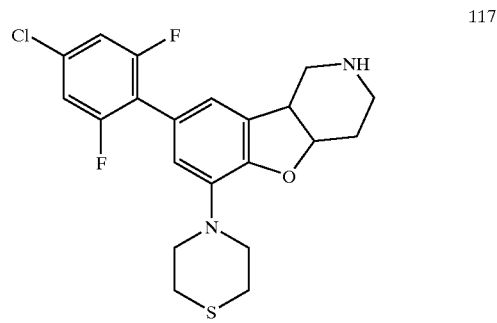

8-(2,6-difluoro-4-chlorophenyl)-6-thiomorpholin-4-
yl-1,2,3,4,4a,9b-hexahydro-[1]benzofuro[3,2-c]
pyridine, 117

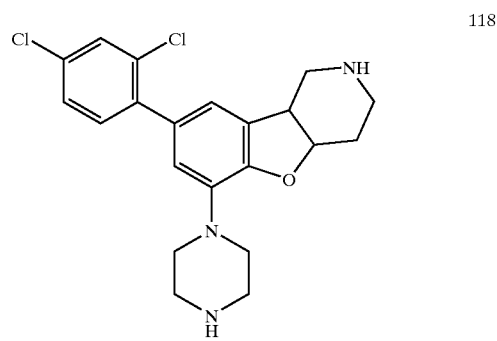

8-(2,4-dichlorophenyl)-6-piperazin-1-yl-1,2,3,4,4a,
9b-hexahydro[1]benzofuro[3,2-c]pyridine, 118

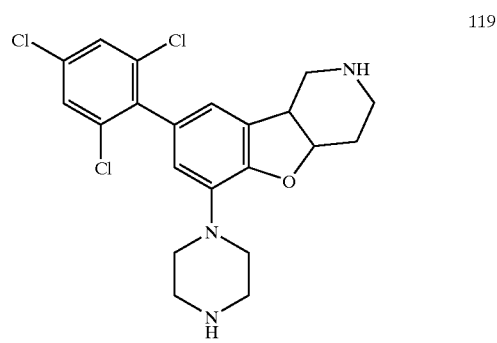

8-(2,4,6-trichlorophenyl)-6-piperazin-1-yl-1,2,3,4,
4a,9b-hexahydro[1]benzofuro[3,2-c]pyridine, 119

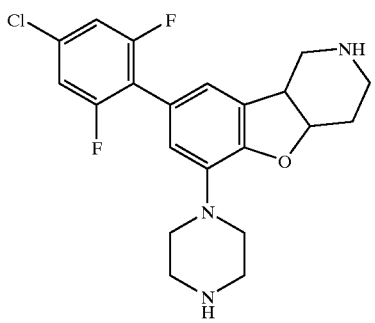

120

8-(2,6-difluoro-4-chlorophenyl)-6-piperazin-1-yl-1,2,3,
4,4a,9b-hexahydro-[1]benzofuro[3,2-c]pyridine, 120

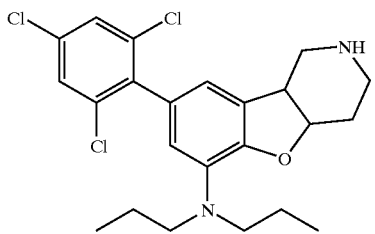

241

8-(2,4,6-trichlorophenyl)-N,N-dipropyl-1,2,3,4,4a,
9b,-hexahydro[1]benzofuro[3,2-c]-pyridin-6-amine,
241; and

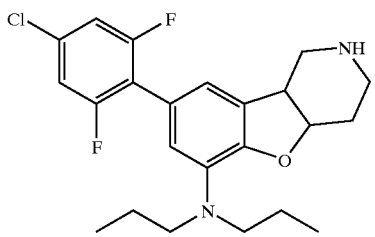

242

8-(2,6-difluoro-4-chlorophenyl)-N,N-dipropyl-1,2,3,
4,4a,9b,-hexahydro[1]benzofuro-[3,2-c]pyridin-6-
amine, 242

8-(2,4-Dichlorophenyl)-1,2,3,4,4a,9b-hexahydro[1]
benzofuro[3,2-c]pyridine, 245

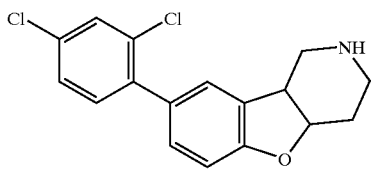

245 tert-Butyl 3,4,4a,9b-tetrahydro[1]benzofuro[3,2-c]-2-
(1H)-carboxylate (0.82 g, 2.98 mmol) was dissolved in
CHCl₃ (20 mL) and cooled to −5° C. Bromine (0.145 mL,
2.83 mmol, 1 equiv.) was dissolved in CHCl₃ (0.8 mL) and
added dropwise to the cold reaction mixture over 4 h. 5%
aqueous NaHCO₃ (30 mL) was added to the reaction mixture (pH~12). The reaction mixture was partitioned between
CHCl₃ and water. The aqueous layer was extracted with
CHCl₃ (2×). The combined organic layers were dried over
MgSO₄, filtered and concentrated under reduced pressure.
The crude product was treated with di-tert-butyl dicarbonate
and K₂CO₃ in 3:2 THF:H₂O and worked up as described
above. The crude product was recrystallized from hexane to
afford tert-butyl 8-bromo-3,4,4a,9b-tetrahydro[1]benzofuro
[3,2-c]pyridine-2(1H)-carboxylate (0.6 g) in 50% yield. MS
(ESI+) for $C_{16}H_{20}BrNO_3$ M/z 354.0 (M+H)⁺.

tert-Butyl 8-bromo-3,4,4a,9b-tetrahydro[1]benzofuro[3,
2-c]pyridine-2(1H)-carboxylate (0.250 g, 0.706 mmol) was
dissolved in benzene (15 mL). 2,4-Dichlorobenzenboronic
acid (0.270 g, 1.41 mmol) was added. Bis(triphenylphosphine)palladiumdichloride (0.035 g, 0.05 mmol) and 2M
aqueous Na₂CO₃ (1.2 mL) were added to the reaction
mixture. Ar was bubbled through the reaction mixture for 20
min. The reaction mixture was refluxed under N₂ for 22 h.
The solvent was evaporated at reduced pressure to yield a
dark slurry. The crude material was partitioned between
EtOAc and water. The aqueous layer was extracted with
EtOAc (2×) and the combined organic layers were washed
with brine, dried over Na₂SO₄, filtered and concentrated
under reduced pressure. The crude product was chromatographed (15:1 toluene:EtOAc) and tert-butyl 8-(2,4-
dichlorophenyl)-3,4,4a,9b-tetrahydro [1]benzofuro[3,2-c]
pyridine-2(1H)-carboxylate (0.221 g) was obtained in 74%
yield. MS (ESI+) for $C_{22}H_{23}Cl_2NO_3$ m/z 420.0 (M+H)⁺.

tert-Butyl 8-(2,4-dichlorophenyl)-3,4,4a,9b-tetrahydro[1]
benzofuro[3,2-c]pyridine-2(1H)-carboxylate (0.221 g, 0.53
mmol) was dissolved in CH₂Cl₂ (7 mL). Trifluoracetic acid
(0.81 mL, 20 equiv.) was added, and the reaction mixture
was stirred at rt under N₂ for 2 h. The reaction mixture was
cooled to −5° C. and 2N aqueous NaOH (8 mL) was added.
The reaction mixture was partitioned between CH₂Cl₂ and
water. The water layer was extracted with CH₂Cl₂ (2×) and
with 25:1 CH₂Cl₂:CH₃OH (2×). The combined organic
layers were dried over Na₂SO₄, filtered and concentrated
under reduced pressure. Example 245 (0.16 g) was obtained
in 98% yield. MS (ESI+) for $C_{17}H_{15}Cl_2NO$ m/z 320.1
(M+H)⁺.

1,2,3,4,4a,9b-Hexahydro[1]benzofuro[3,2-c]
pyridine, 246

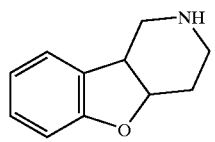

246

1,2,3,4-Tetrahydro[1]benzofuro[3,2-c]pyridine hydrochloride (1.0 g, 4.8 mmol) was dissolved in 1:1:1
CH₃COOH:EtOH:H₂O (75 mL). Pearlman's catalyst (20%
Pd(OH)₂ on carbon, 1.718 g) was added and the reaction
mixture was stirred under H₂ (1 atm) at rt. After 10 h, the
starting material was consumed. The reaction mixture was
filtered through a short pad of celite. The celite pad was
rinsed with methanol and the filtrate was evaporated under
reduced pressure. The acetic acid was removed azeotropically with toluene at reduced pressure. After drying, 1,2,3, 4,4a,9b-hexahydro[1]benzofuro[3,2-c]pyridine hydrochloride (1.02 g) was obtained as a white amorphous solid. MS (ESI+) for $C_{11}H_{13}NO$ m/z 176.1 (M+H)$^+$.

1,2,3,4,4a,9b-Hexahydro[1]benzofuro[3,2-c]pyridine hydrochloride (1.02 g) was dissolved in THF (25 mL) and water (17 mL). $K_2CO_3$ (3.0 g) was added and the biphasic mixture was stirred at rt under nitrogen. Di-tert-butyl dicarbonate (1.04 g) was added in 3 equal portions over 1.5 h. After 2 h, the solvent was removed in vacuo. The residue was partitioned between EtOAc and water. The aqueous layer was extracted with EtOAc (2×). The combined organic layers were washed with brine, dried over $MgSO_4$, filtered and concentrated. tert-Butyl 3,4,4a,9b-tetrahydro[1]benzofuro[3,2-c]-2-(1H)-carboxylate (0.82 g, 63% yield) was obtained after purification by chromatography using 15% EtOAc:Hexane as the eluent. MS (ESI+) for $C_{16}H_{21}NO_3$ m/z 276.1 (M+H)$^+$.

Obtained Example 246 in 40% yield for the removal of the protecting group according to the procedure used to prepare Example 245 making non-critical changes. MS (ESI+) for $C_{11}H_{13}NO$ m/z 176.2 (M+H)$^+$.

8-[2-(Trifluoromethyl)phenyl]-1,2,3,4,4a,9b-hexahydro[1]benzofuro[3,2-c]pyridine, 247

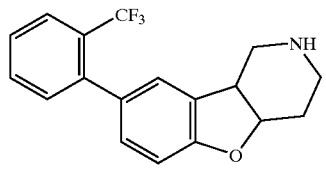

247

Obtained tert-butyl 8-(2-trifluoromethylphenyl)-3,4,4a,9b-tetrahydro[1]benzofuro[3,2-c]pyridine-2(1H)-carboxylate in 68% and Example 247 in 98% yield according to the procedure used to prepare Example 245 making non-critical changes. MS (ESI+) for $C_{18}H_{16}NO$ m/z 320.1 (M+H)$^+$.

8-[2-(Trifluoromethoxy)phenyl]-1,2,3,4,4a,9b-hexahydro[1]benzofuro[3,2-c]pyridine, 248

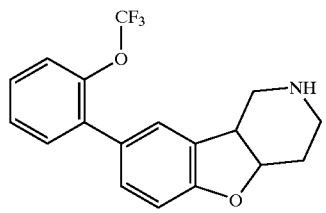

248

Obtained tert-butyl 8-[2-(trifluoromethoxy)phenyl]-3,4,4a,9b-tetrahydro[1]benzofuro[3,2-c]pyridine-2(1H)-carboxylate in 74% yield (MS (ESI+) for $C_{23}H_{24}O_4NF_3$ m/z 435.9 (M+H)$^+$) and Example 248 in 100% yield according to the procedure used to prepare Example 245 making non-critical changes. MS (ESI+) for $C_{18}H_{16}NO_2F_3$ m/z 336.1 (M+H)$^+$.

6-Bromo-8-(2,4-dichlorophenyl)-1,2,3,4,4a,9b-hexahydro[1]benzofuro[3,2-c]pyridine, 249

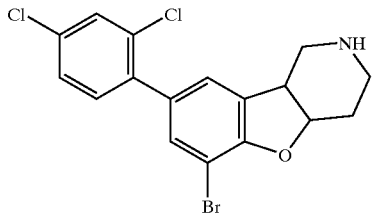

249

Example 249 as a racemic mixture was prepared according to the procedure used to prepare Example 245. Example 249 was obtained in 92% yield from tert-butyl 6-bromo-8-(2,4-dichlorophenyl)-3,4,4a,9b-tetrahydro[1]benzofuro[3,2-c]pyridine-2(1H)-carboxylate (racemic) which was obtained in 82% yield from tert-butyl 8-(2,4-dichlorophenyl)-3,4,4a,9b-tetrahydro[1]benzofuro[3,2-c]pyridine-2(1H)-carboxylate (MS (ESI+) for $C_{22}H_{22}BrCl_2NO_3$ m/z 499.8 (M+H)$^+$). HRMS (FAB) for Example 249, calcd for $C_{17}H_{14}BrCl_2NO+H_1$ 397.9714, found 397.9705.

(4aS,9bR) 6-Bromo-8-(2,4-dichlorophenyl)-1,2,3,4,4a,9b-hexahydro[1]benzofuro[3,2-c]pyridine & (4aR, 9bS) 6-Bromo-8-(2,4-dichlorophenyl)-1,2,3,4,4a,9b-hexahydro[1]benzofuro[3,2-c]pyridine:

tert-Butyl 8-(2,4-dichlorophenyl)-3,4,4a,9b-tetrahydro[1]benzofuro[3,2-c]pyridine-2(1H)-carboxylate (5.360 g, 12.750 mmol) was dissolved in 160 mL $CH_3COOH$. N-Bromosuccinimide (4.539 g, 25.500 mmol) was added. The reaction mixture was stirred under $N_2$ at rt for 27 h. The reaction mixture was poured into a mixture of 300 g ice and 100 mL water. The aqueous mixture was extracted with EtOAc (3×). The combined organic layers were washed with 5M NaOH (2×250 mL), 25% KOH (2×200 mL) and brine, dried over $Na_2SO_4$, filtered and concentrated under reduced pressure. The crude product was chromatographed ($SiO_2$, 15% EtOAc:hexane), and tert-butyl 6-bromo-8-(2,4-dichlorophenyl)-3,4,4a,9b-tetrahydro[1]benzofuro[3,2-c]pyridine-2(1H)-carboxylate was obtained in 82% yield (5.250 g, 10.516 mmol). MS (ESI+) for $C_{22}H_{22}BrCl_2NO_3$ m/z 499.8 (M+H)$^+$.

The enantiomers of tert-butyl 6-bromo-8-(2,4-dichlorophenyl)-3,4,4a,9b-tetrahydro[1]benzofuro[3,2-c]pyridine-2(1H)-carboxylate (253 mg) were separated using a 5×50 cm Chiralpak AD column eluting with 1:1 i-PrOH:heptane at a flowrate of 70 mL/min. with UV detection at 265 nm. The sample was dissolved in 15 mL of 3:1 i-PrOH:CHCl$_3$ for injection into the HPLC. Each pure enantiomer of tert-butyl 6-bromo-8-(2,4-dichlorophenyl)-3,4,4a,9b-tetrahydro[1]benzofuro[3,2-c]pyridine-2(1H)-carboxylate was separately converted to the respective pure enantiomer of 6-bromo-8-(2,4-dichlorophenyl)-1,2,3,4,4a,9b-hexahydro[1]benzofuro[3,2-c]pyridine according to the procedure used to prepare 8-(2,4-dichlorophenyl)-1,2,3,4,4a,9b-hexahydro[1]benzofuro[3,2-c]pyridine. The faster-eluting intermediate provided Example 249(a) and the slower-eluting enantiomer provided Example 249(b). MS for Example 249(a), (ESI+) for $C_{17}H_{14}BrCl_2NO$ m/z 399.8 (M+H)$^+$. MS for Example 249(b), (ESI+) for $C_{17}H_{14}BrCl_2NO$ m/z 399.8 (M+H)$^+$.

6-Benzyl-8-(2,4-dichlorophenyl)-1,2,3,4,4a,9b-hexahydro[1]benzofuro[3,2-c]pyridine, 250

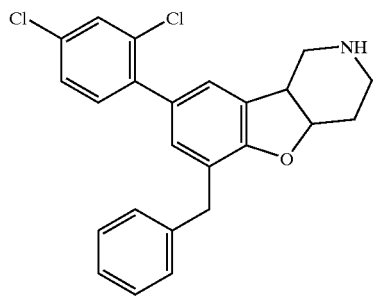

B-Benzyl-9-BBN (1.3 mL 0.5 M sol in THF, 0.650 mmol) was added to degassed DMF (3 mL), followed by sequential addition of tert-butyl 6-bromo-8-(2,4-dichlorophenyl)-3,4,4a,9b-tetrahydro[1]benzofuro[3,2-c]pyridine-2(1H)-carboxylate (0.255 g, 0.511 mmol), catalyst Cl$_2$PdDPPF (0.018 g, 0.022 mmol) and K$_2$CO$_3$ (0.220 g, 1.592 mmol). The reaction mixture was stirred under N$_2$ at 65° C. for 6 h. The reaction mixture was poured into water and extracted with EtOAc (2×). The combined organic layers were washed with brine, dried over Na$_2$SO$_4$, filtered and concentrated under reduced pressure. The crude was purified by chromatography (14% EtOAc/Hexane) and tert-butyl 6-benzyl-8-(2,4-dichlorophenyl)-3,4,4a,9b-tetrahydro[1]benzofuro[3,2-c]pyridine-2(1H)-carboxylate was obtained in 77% yield (0.200 g, 0.392 mmol). MS (ESI+) for C$_{29}$H$_{29}$Cl$_2$NO$_3$ m/z 510.1 (M+H)$^+$.

tert-Butyl 6-benzyl-8-(2,4-dichlorophenyl)-3,4,4a,9b-tetrahydro[1]benzofuro[3,2-c]pyridine-2(1H)-carboxylate (0.137 g, 0.270 mmol) was dissolved in CH$_2$Cl$_2$ (5 mL). Trifluoroacetic acid (0.44 mL, 5.670 mmol) was added and the reaction mixture was stirred at rt under N$_2$ for 4 h. The reaction mixture was cooled to 0° C. and 25% aqueous NaOH (15 mL) was added. The reaction mixture was partitioned between CH$_2$Cl$_2$ and water. The water layer was extracted with CH$_2$Cl$_2$ (2×). The combined organic layers were dried over Na$_2$SO$_4$, filtered and concentrated under reduced pressure. The crude was purified by chromatography (1% NH$_4$OH, 5.95% CH$_3$OH, 93.05% CH$_2$Cl$_2$), and Example 250 was obtained in 86% yield. MS (ESI+) for C$_{24}$H$_{21}$Cl$_2$NO m/z 410.0 (M+H)$^+$.

6-Butyl-8-(2,4-dichlorophenyl)-1,2,3,4,4a,9b-hexahydro[1]benzofuro[3,2-c]pyridine, 251

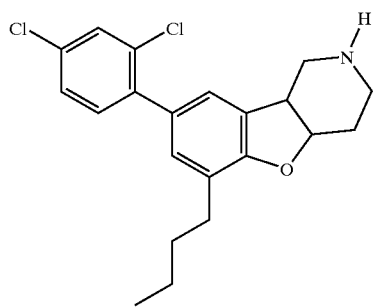

Obtained tert-butyl 6-butyl-8-(2,4-dichlorophenyl)-3,4,4a,9b-tetrahydro[1]benzofuro[3,2-c]pyridine-2(1H)-carboxylate in 63% yield based on recovered starting material (MS (ESI+) for C$_{26}$H$_{31}$Cl$_2$NO$_3$ m/z 475.9 (M+H)$^+$) and Example 251 in 93% yield according to the procedure used to prepare Example 250 making non-critical changes. HRMS (FAB) calcd for C$_{21}$H$_{23}$Cl$_2$NO+H$_1$ 376.1235, found 376.1243.

8-(2,4-Dichlorophenyl)-6-(propylthio)-1,2,3,4,4a,9b-hexahydro[1]benzofuro[3,2-c]pyridine, 252

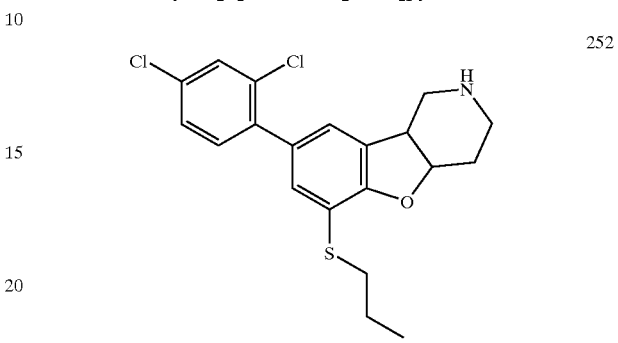

tert-Butyl 6-bromo-8-(2,4-dichlorophenyl)-3,4,4a,9b-tetrahydro[1]benzofuro[3,2-c]pyridine-(1H)-carboxylate (3.30 g, 6.62 mmol, 1 equiv.), potassium triisopropylsilanethiolate (1.51 g, 6.62 mmol, 1 equiv.) and tetrakis(triphenylphosphine)palladium (0.772 g, 0.668 mmol, 0.1 equiv.) were combined in a dry flask under N$_2$. Benzene (66 mL) and THF (26 mL) were added to the flask and Ar was bubbled through the reaction mixture for 15 min. The reaction mixture was heated to 80° C. for 26.5 hr. under N$_2$. Upon cooling, the reaction mixture was partitioned between 4:1 toluene:EtOAc (100 mL) and H$_2$O (100 mL). The layers were separated and the aqueous layer was extracted with 4:1 toluene:EtOAc (100 μL). The combined organic layers were dried over MgSO$_4$, filtered and concentrated. The crude product (6.27 g) was chromatographed (SiO$_2$ 250 g, eluted with 2:1 heptane:Et$_2$O followed by 1:1 heptane:Et$_2$O) to yield tert-Butyl 8-(2,4-dichlorophenyl)-6-[(triisopropylsilyl)thio]-3,4,4a,9b-tetrahydro[1]benzofuro[3,2-c]pyridine-2(1H)-carboxylate (2.49 g) in 62% yield. MS (ESI+) for C$_{26}$H$_{35}$Cl$_2$NOSSi m/z 508.1 (M+H)$^+$.

tert-Butyl 8-(2,4-dichlorophenyl)-6-[(triisopropylsilyl)thio]-3,4,4a,9b-tetrahydro[1]benzofuro[3,2-c]pyridine-2(1H)-carboxylate (0.111 g, 0.182 mmol) was dissolved in DMF (3 mL). 1-Iodopropane (0.2 mL) and cesium fluoride (0.060 g) were added to the reaction mixture. The reaction mixture was stirred at rt under N$_2$ for 2.5 h. The reaction mixture was partitioned between EtOAc (30 mL) and 2:3 water:brine (25 mL). The aqueous layer was back extracted with EtOAc (30 mL). The combined organic layers were washed with water (20 mL), with brine (20 mL), dried over Na$_2$SO$_4$, filtered and concentrated under reduced pressure. tert-Butyl 8-(2,4-dichlorophenyl)-6-(propylthio)-3,4,4a,9b-tetrahydro[1]benzofuro[3,2-c]pyridine-2(1H)-carboxylate was obtained in quantitative yield (0.090 g). MS (ESI+) for C$_{25}$H$_{29}$Cl$_2$NO$_3$S m/z 517.0 (M+23)$^+$.

tert-Butyl 8-(2,4-dichlorophenyl)-6-(propylthio)-3,4,4a,9b-tetrahydro[1]benzofuro[3,2-c]pyridine-2(1H)-carboxylate (0.090 g, 0.182 mmol) was dissolved in CH$_2$Cl$_2$ (5 mL). Trifluoroacetic acid (0.3 mL, 0.182 mmol) was added and the reaction mixture was stirred at rt under N$_2$ for 2.5 h when all the starting material was consumed. The reaction mixture was cooled to 0° C. and 5M NaOH (10 mL) was added. The reaction mixture was partitioned between CH₂Cl₂ and water. The aqueous layer was extracted with CH₂Cl₂ (2×). The combined organic layers were dried over Na₂SO₄, filtered and concentrated under reduced pressure. The crude was purified by chromatography (first eluting with 3:1 Hexane:EtOAc, and then eluting with 2:6:92 conc. NH₄OH:CH₃OH:CH₂Cl₂ to elute the product). Example 252 (0.070 g) was obtained in 97% yield. HRMS (FAB) calcd for $C_{20}H_{21}CL2NOS +H_1$ 394.0799, found 394.0797.

8-(2,4-Dichlorophenyl)-6-(isopropylthio)-1,2,3,4,4a,9b-hexahydro[1]benzofuro[3,2-c]pyridine, 253

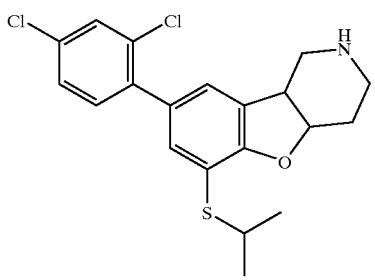

253

Example 253 is obtained using the procedures to obtain Example 252, making non-critical changes. tert-Butyl 8-(2,4-dichlorophenyl)-6-(isopropylthio)-3,4,4a,9b-tetrahydro[1]benzofuro[3,2-c]pyridine-2(1H)-carboxylate was obtained 90% yield from tert-Butyl 8-(2,4-dichlorophenyl)-6-[(triisopropylsilyl)thio]-3,4,4a,9b-tetrahydro[1]benzofuro[3,2-c]pyridine-2(1H)-carboxylate using 2-iodopropane as the alkylating agent. MS (ESI+) for $C_{25}H_{29}Cl_2NO_3S$ m/z 493.9 (M+H)⁺. Example 253 is obtained in 91% yield. HRMS (FAB) calcd for $C_{20}H_{21}Cl_2NOS +H_1$ 394.0799, found 394.0797.

8-(2,4-Dichlorophenyl)-6-(isobutylthio)-1,2,3,4,4a,9b-hexahydro[1]benzofuro[3,2-c]pyridine, 254

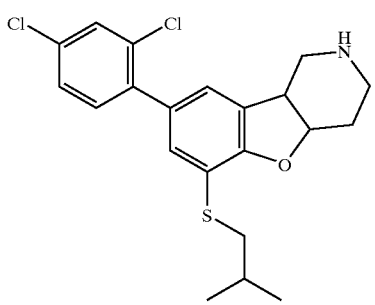

254 tert-Butyl 8-(2,4-dichlorophenyl)-6-(isopropylthio)-3,4,4a,9b-tetrahydro[1]benzofuro[3,2-c]pyridine-2(1H)-carboxylate is obtained in 93% yield (MS (ESI+) for $C_{26}H_{31}Cl_2NO_3S$ m/z 529.8 (M+Na)⁺) and Example 254 is obtained in 75% yield according to the procedures used to prepare Example 252, making non-critical changes. HRMS (FAB) calcd for $C_{21}H_{23}Cl_2NOS+H_1$ 408.0956, found 408.0959.

8-(2,4-Dichlorophenyl)-6-(methylthio)-1,2,3,4,4a,9b-hexahydro[1]benzofuro[3,2-c]pyridine, 255

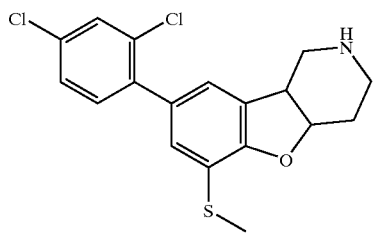

255 tert-Butyl 8-(2,4-dichlorophenyl)-6-(methylthio)-3,4,4a,9b-tetrahydro[1]benzofuro[3,2-c]pyridine-2(1H)-carboxylate is obtained 61% yield (MS (ESI+) for $C_{23}H_{25}Cl_2NO_3S$ m/z 465.8 (M+H)⁺) and Example 255 is obtained in 99% yield according to the procedures used to prepare Example 252, making non-critical changes. HRMS (FAB) calcd for $C_{18}H_{17}Cl_2NOS+H_1$ 366.0486, found 366.0483.

6-(Cyclopentylthio)-8-(2,4-dichlorophenyl)-1,2,3,4,4a,9b-hexahydro[1]benzofuro[3,2-c]pyridine, 256

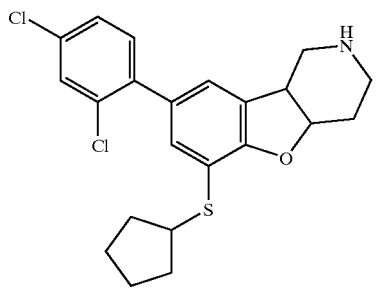

256 tert-Butyl 6-(cyclopentylthio)-8-(2,4-dichlorophenyl)-3,4,4a,9b-tetrahydro[1]benzofuro[3,2-c]pyridine-2(1H)-carboxylate is obtained in 92% yield (MS (ESI+) 464.1 ($C_{27}H_{31}Cl_2NO_3S+H—C_4H_8$, rel. intensity 16%), 446.1 (16), 420.1 (44), 396.1 (100), 378.1 (78), 352.1 (44)) and Example 256 is obtained according to Example 252, making non-critical changes. MS (ESI+) 420.2; HRMS (FAB) calcd for $C_{22}H_{23}CL2NOS+H_1$ 420.0956, found 420.0953.

6-(Cyclobutylthio)-8-(2,4-dichlorophenyl)-1,2,3,4,4a,9b-hexahydro[1]benzofuro[3,2-c]pyridine, 257

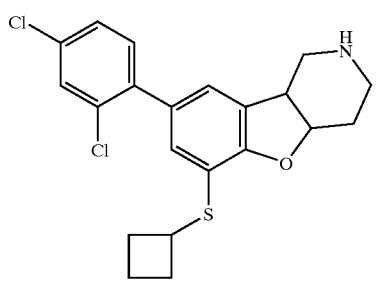

257 tert-Butyl 6-(cyclobutylthio)-8-(2,4-dichlorophenyl)-3,4,4a,9b-tetrahydro[1]benzofuro[3,2-c]pyridine-2(1H)-carboxylate is obtained in 42% yield (MS (ESI+) 450.1

($C_{26}H_{29}Cl_2NO_3S+H—C_4H_8$, rel. intensity 100%), 432 (55), 406.1 (70), 396 (49), 378.1 (31), 352 (16)) and Example 257 is obtained according to Example 252. OAMS supporting ions at: ESI+406.2; HRMS (FAB) calcd for $C_{21}H_{21}CL_2NOS+H_1$ 406.0799, found 406.0797.

8-(2,4-Dichlorophenyl)-6-morpholin-4-yl-1,2,3,4,4a, 9b-hexahydro[1]benzofuro[3,2-c]pyridine, 258

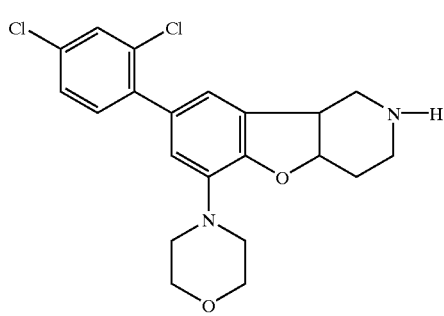

A 7 mL vial with a Teflon lined cap was charged with $Pd(OAc)_2$ (3.4 mg, 0.015 mmol), 2-(di-t-butylphosphino)biphenyl (17.9 mg, 0.06 mmol), and NaOtBu (67.2 mg (0.7 mmol) under an argon blanket. A solution of the bromide (250 mg, 0.5 mmol) in toluene (1 mL) was added followed by the morpholine (0.052 mL, 0.6 mmol). The reaction was placed on an orbital shaker and heated to 50° C. for 18 hours. The reaction was cooled to RT and diluted with ethyl ether (25 mL), filtered through a pad of celite and concentrated to give 308 mg of a crude orange oil. The crude was purified on silica gel using 25% EtOAc in heptane as the eluent to give 181 mg (72%) of tert-butyl 8-(2,4-dichlorophenyl)-6-morpholin-4-yl-3,4,4a,9b-tetrahydro[1]benzofuro[3,2-c]pyridine-2(1H)-carboxylate as a pale yellow oil. OAMS supporting ions at: ESI+ 504.9.

The carboxylate was diluted in a solution of $CH_2Cl_2$ (5 mL) cooled to 0° C. TFA (5 mL) was added to the cooled solution and the ice bath was removed. The reaction turned from pale yellow to pale green within 10 minutes. After stirring at ambient temperature for 1.5 hours, the reaction was concentrated in vacuo, partioned between 5N NaOH and EtOAc (2 times). The organics were combined, dried with $MgSO_4$, filtered and concentrated to 160 mg of a crude clear oil. The crude was purified on silica gel using 5% methanol in $CH_2Cl_2$ as the eluent to give 124 mg (87%) of 8-(2,4-dichlorophenyl)-6-morpholin-4-yl-1,2,3,4,4a,9b-hexahydro[1]benzofuro[3,2-c]pyridine as a yellow oil. OAMS supporting ions at: ESI+404.8. HRMS (FAB) calcd for $C_{21}H_{22}CL_2N_2O_2+H_1$ 405.1136, found 405.1122.

N-Benzyl-8-(2,4-dichlorophenyl)-1,2,3,4,4a,9b-hexahydro[1]benzofuro[3,2-c]pyridin-6-amine, 259

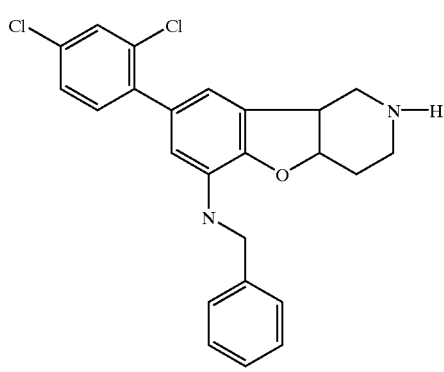

Following the general procedure of Example 258, making non-critical variations (substituting morpholine with benzylamine), gave 230 mg of a crude solid. This material was purified by eluting with 5% methanol in $CH_2Cl_2$ to afford 90 mg (40%) of Example 259 as a yellow oil. HRMS (FAB) calcd for $C_{24}H_{22}CL_2N_2O+H_1$ 425.1187, found 425.1199.

8-(2,4-Dichlorophenyl)-6-pyrrolidin-1-yl-1,2,3,4,4a, 9b-hexahydro[1]benzofuro[3,2-c]pyridine, 260

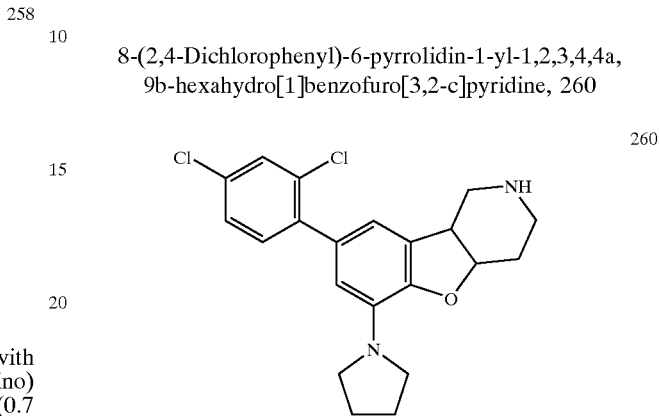

Prepared using the general procedure for Example 258, making non-critical variations (substituting morpholine with pyrrolidine) to give 85 mg off white foam (44%).

8-(2,4-Dichlorophenyl)-6-methoxy-1,2,3,4,4a,9b-hexahydro[1]benzofuro[3,2-c]pyridine, 261

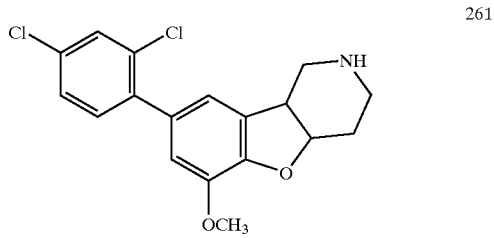

In a 7 mL vial, copper (I) bromide (0.15 mmol, 22 mg) was diluted with 0.1 mL EtOAc and 0.6 mL of sodium methoxide in methanol (25 wt %). tert-Butyl 6-bromo-8-(2,4-dichlorophenyl)-3,4,4a,9b-tetrahydro[1]benzofuro[3,2-c]pyridine-2(1H)-carboxylate (0.5 mmol, 250 mg) was added to the thick slurry and heated to 85° C. on the orbit shaker. An additional 0.1 mL of EtOAc was added. After 4.5 hr, the solvent was removed in vacuo. The resulting material was diluted with water and extracted three times with EtOAc. The combined organics were washed with brine, dried over $NaSO_4$, decanted and concentrated to give crude yellow-brown oil. This material was diluted with 4 mL $CH_2Cl_2$ and cooled to 0° C. with an ice bath. After 15 min, 4 ml trifluoroacetic acid was added and the reaction was stirred at rt. After 2 hr the solvent was removed in vacuo to give crude oil after a NaOH workup. The crude material was purified by column chromatography (0.5/3.5/96 $NH_4OH/CH_3OH/CH_2Cl_2$) to give 105 mg colorless oil (60%).

Using synthetic procedures similar to those described herein, the following compounds of formula (II) can also be prepared:

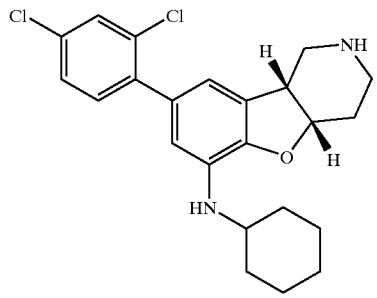

121

(4aS,9bR)-8-(2,4-dichlorophenyl)-N-cyclohexyl-1,2,3,4,4a,9b,-hexahydro[1]benzofuro[3,2-c]pyridin-6-amine, 121

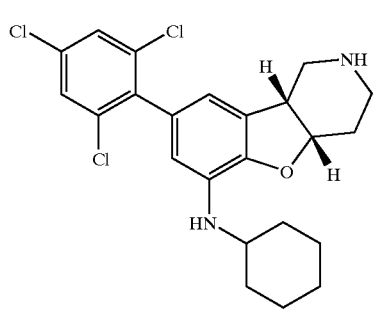

122

(4aS,9bR)-8-(2,4,6-trichlorophenyl)-N-cyclohexyl-1,2,3,4,4a,9b,-hexahydro[1]benzofuro[3,2-c]pyridin-6-amine, 122

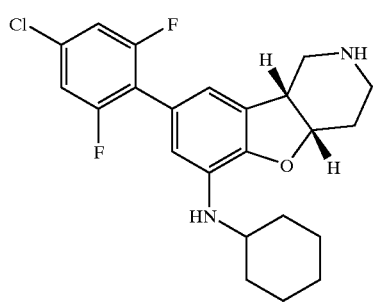

123

(4aS,9bR)-8-(2,6-difluoro-4-chlorophenyl)-N-cyclohexyl-1,2,3,4,4a,9b,-hexahydro[1]-benzofuro[3,2-c]pyridin-6-amine, 123

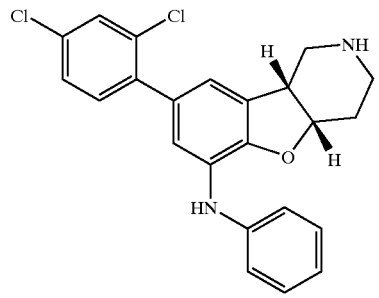

124

(4aS,9bR)-8-(2,4-dichlorophenyl)-N-phenyl-1,2,3,4,4a,9b,-hexahydro[1]benzofuro-[3,2-c]pyridin-6-amine, 124

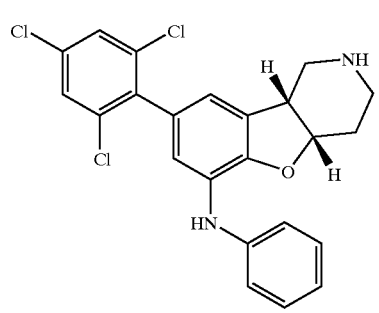

125

(4aS,9bR)-8-(2,4,6-trichlorophenyl)-N-phenyl-1,2,3,4,4a,9b,-hexahydro[1]benzofuro-[3,2-c]pyridin-6-amine, 125

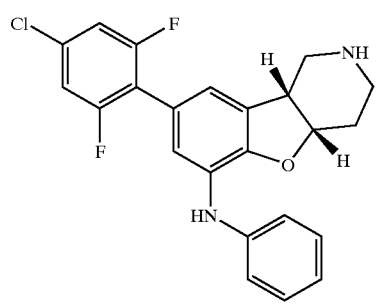

126

61

(4aS,9bR)-8-(2,6-difluoro-4-chlorophenyl)-N-phenyl-1,2,3,4,4a,9b,-hexahydro[1]-benzofuro[3,2-c]pyridin-6-amine, 126

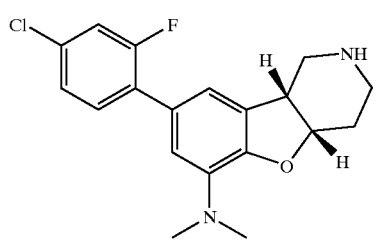

(4aS,9bR)-8-(2,4-dichlorophenyl)-N,N-dimethyl-1,2,3,4,4a,9b,-hexahydro[1]-benzofuro[3,2-c]pyridin-6-amine, 127

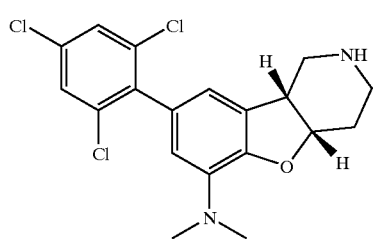

(4aS,9bR)-8-(2,4,6-trichlorophenyl)-N,N-dimethyl-1,2,3,4,4a,9b,-hexahydro[1]-benzofuro[3,2-c]pyridin-6-amine, 128

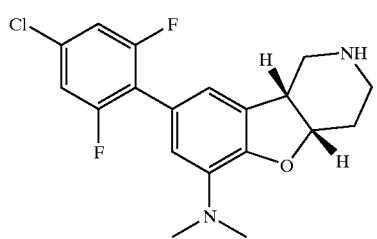

(4aS,9bR)-8-(2,6-difluoro-4-chlorophenyl)-N,N-dimethyl-1,2,3,4,4a,9b,-hexahydro-[1]benzofuro[3,2-c]pyridin-6-amine, 129

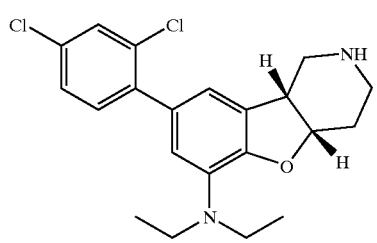

62

(4aS,9bR)-8-(2,4-dichlorophenyl)-N,N-diethyl-1,2,3,4,4a,9b,-hexahydro[1]benzofuro-[3,2-c]pyridin-6-amine, 130

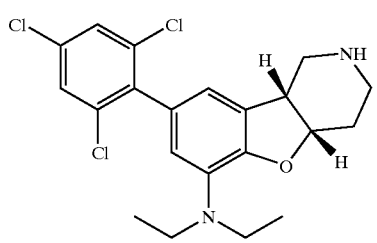

(4aS,9bR)-8-(2,4,6-trichlorophenyl)-N,N-diethyl-1,2,3,4,4a,9b,-hexahydro[1]benzofuro[3,2-c]pyridin-6-amine, 131

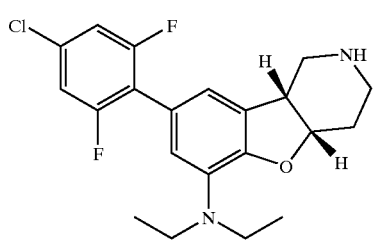

(4aS,9bR)-8-(2,6-difluoro-4-chlorophenyl)-N,N-diethyl-1,2,3,4,4a,9b,-hexahydro[1]benzofuro[3,2-c]pyridin-6-amine, 132

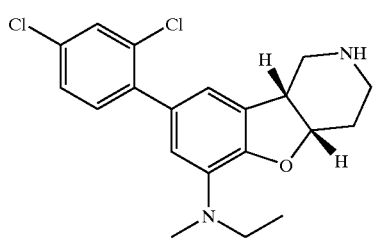

(4aS,9bR)-8-(2,4-dichlorophenyl)-N-methyl-N-ethyl-1,2,3,4,4a,9b,-hexahydro[1]-benzofuro[3,2-c]pyridin-6-amine, 133

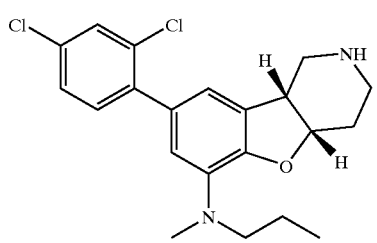

(4aS,9bR)-8-(2,4-dichlorophenyl)-N-methyl-N-propyl-1,2,3,4,4a,9b,-hexahydro[1]-benzofuro[3,2-c]pyridin-6-amine, 134

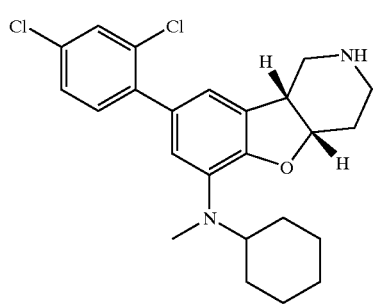

(4aS,9bR)-8-(2,4-dichlorophenyl)-N-methyl-N-cyclohexyl-1,2,3,4,4a,9b,-hexahydro[1]benzofuro[3,2-c]pyridin-6-amine, 135

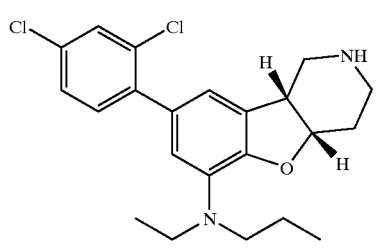

(4aS,9bR)-8-(2,4-dichlorophenyl)-N-ethyl-N-propyl-1,2,3,4,4a,9b,-hexahydro[1]-benzofuro[3,2-c]pyridin-6-amine, 136

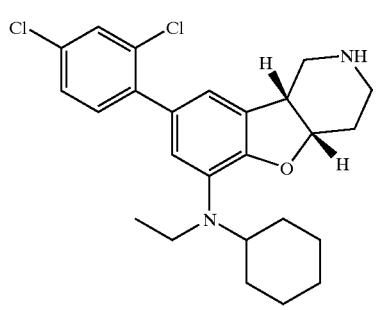

(4aS,9bR)-8-(2,4-dichlorophenyl)-N-ethyl-N-cyclohexyl-1,2,3,4,4a,9b,-hexahydro[1]-benzofuro[3,2-c]pyridin-6-amine, 137

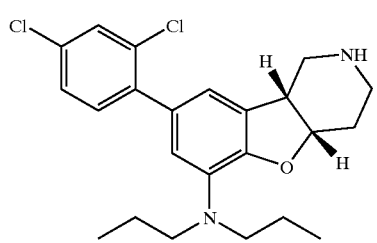

(4aS,9bR)-8-(2,4-dichlorophenyl)-N,N-dipropyl-1,2,3,4,4a,9b,-hexahydro[1]benzofuro[3,2-c]pyridin-6-amine, 138

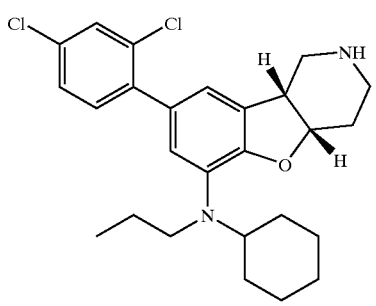

(4aS,9bR)-8-(2,4-dichlorophenyl)-N-propyl-N-cyclohexyl-1,2,3,4,4a,9b,-hexahydro[1]benzofuro[3,2-c]pyridin-6-amine, 139

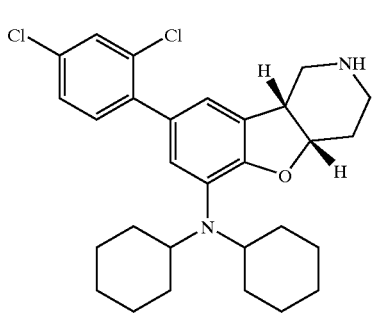

(4aS,9bR)-8-(2,4-dichlorophenyl)-N,N-dicyclohexyl-1,2,3,4,4a,9b,-hexahydro[1]-benzofuro[3,2-c]pyridin-6-amine, 140

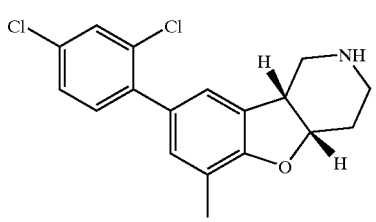

(4aS,9bR)-8-(2,4-dichlorophenyl)-6-methyl-1,2,3,4,4a,9b,-hexahydro[1]benzofuro-[3,2-c]pyridine, 141

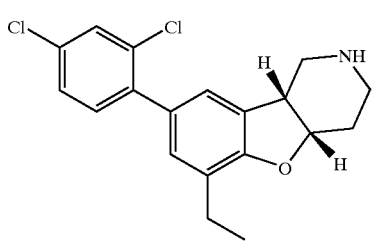

65

(4aS,9bR)-8-(2,4-dichlorophenyl)-6-ethyl-1,2,3,4,4a,9b,-hexahydro[1]benzofuro-[3,2-c]pyridine, 142

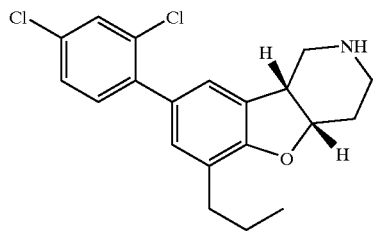

(4aS,9bR)-8-(2,4-dichlorophenyl)-6-propyl-1,2,3,4,4a,9b,-hexahydro[1]benzofuro-[3,2-c]pyridine, 143

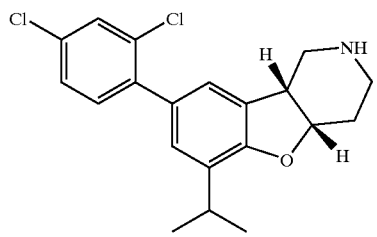

(4aS,9bR)-8-(2,4-dichlorophenyl)-6-(isopropyl)-1,2,3,4,4a,9b,-hexahydro[1]-benzofuro[3,2-c]pyridine, 144

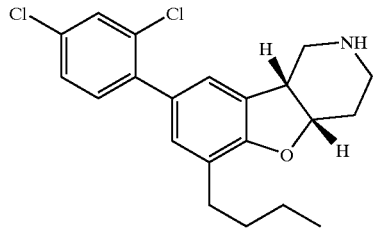

(4aS,9bR)-8-(2,4-dichlorophenyl)-6-butyl-1,2,3,4,4a,9b,-hexahydro[1]benzofuro-[3,2-c]pyridine, 145

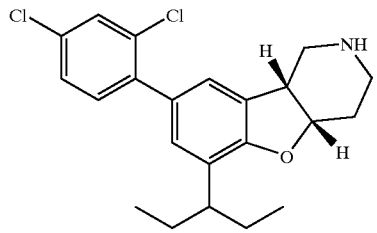

66

(4aS,9bR)-8-(2,4-dichlorophenyl)-6-(1-ethylpropyl)-1,2,3,4,4a,9b,-hexahydro[1]-benzofuro[3,2-c]pyridine, 146

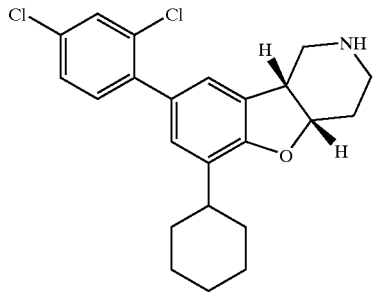

(4aS,9bR)-8-(2,4-dichlorophenyl)-6-cyclohexyl-1,2,3,4,4a,9b,-hexahydro[1]benzofuro[3,2-c]pyridine, 147

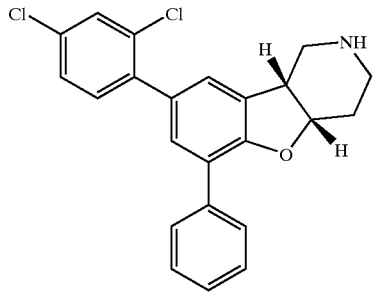

(4aS,9bR)-8-(2,4-dichlorophenyl)-6-phenyl-1,2,3,4,4a,9b,-hexahydro[1]benzofuro-[3,2-c]pyridine, 148

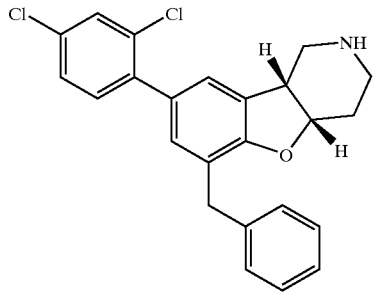

(4aS,9bR)-8-(2,4-dichlorophenyl)-6-benzyl-1,2,3,4,4a,9b,-hexahydro[1]benzofuro-[3,2-c]pyridine, 149

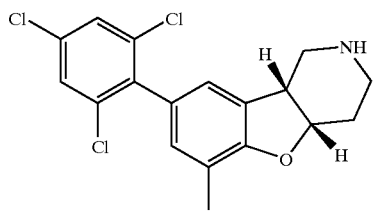

(4aS,9bR)-8-(2,4,6-trichlorophenyl)-6-methyl-1,2,3,4,
4a,9b,-hexahydro[1]benzofuro-[3,2-c]pyridine, 150

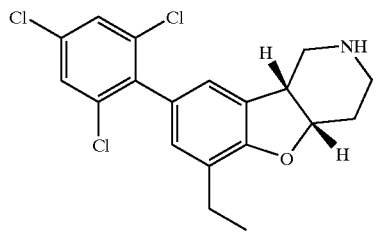

(4aS,9bR)-8-(2,4,6-trichlorophenyl)-6-ethyl-1,2,3,4,
4a,9b,-hexahydro[1]benzofuro-[3,2-c]pyridine, 151

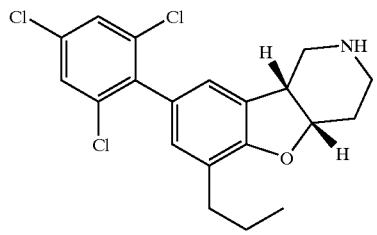

(4aS,9bR)-8-(2,4,6-trichlorophenyl)-6-propyl-1,2,3,4,
4a,9b,-hexahydro[1]benzofuro-[3,2-c]pyridine, 152

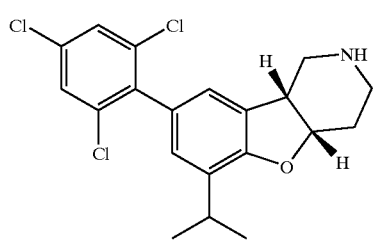

(4aS,9bR)-8-(2,4,6-trichlorophenyl)-6-(isopropyl)-1,2,
3,4,4a,9b,-hexahydro[1]-benzofuro[3,2-c]pyridine, 153

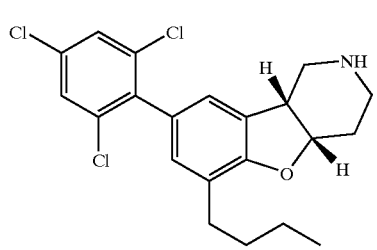

(4aS,9bR)-8-(2,4,6-trichlorophenyl)-6-butyl-1,2,3,4,
4a,9b,-hexahydro[1]benzofuro-[3,2-c]pyridine, 154

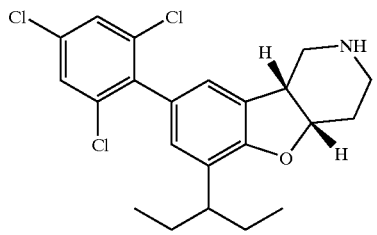

(4aS,9bR)-8-(2,4,6-trichlorophenyl)-6-(1-
ethylpropyl)-1,2,3,4,4a,9b,-hexahydro[1]-benzofuro
[3,2-c]pyridine, 155

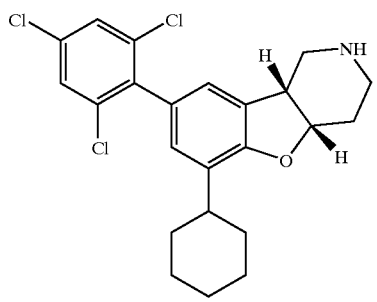

(4aS,9bR)-8-(2,4,6-trichlorophenyl)-6-cyclohexyl-1,2,
3,4,4a,9b,-hexahydro[1]-benzofuro[3,2-c]pyridine, 156

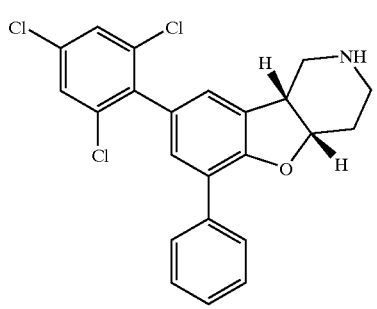

(4aS,9bR)-8-(2,4,6-trichlorophenyl)-6-phenyl-1,2,3,4,
4a,9b,-hexahydro[1]benzofuro-[3,2-c]pyridine, 157

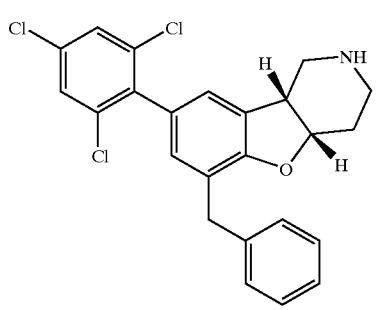

(4aS,9bR)-8-(2,4,6-trichlorophenyl)-6-benzyl-1,2,3,4,4a,9b,-hexahydro[1]benzofuro-[3,2-c]pyridine, 159

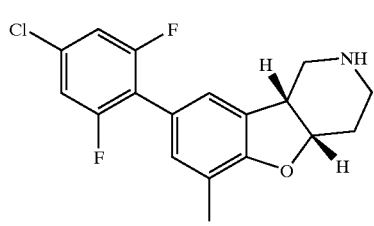

(4aS,9bR)-8-(2,6-difluoro-4-chlorophenyl)-6-methyl-1,2,3,4,4a,9b,-hexahydro[1]-benzofuro[3,2-c]pyridine, 160

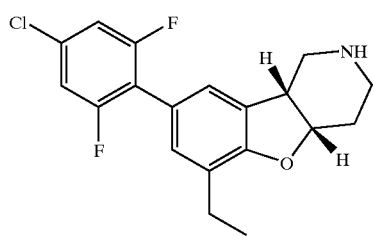

(4aS,9bR)-8-(2,6-difluoro-4-chlorophenyl)-6-ethyl-1,2,3,4,4a,9b,-hexahydro[1]benzofuro[3,2-c]pyridine, 161

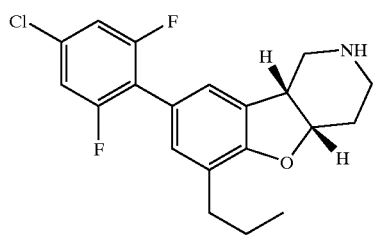

(4aS,9bR)-8-(2,6-difluoro-4-chlorophenyl)-6-propyl-1,2,3,4,4a,9b,-hexahydro[1]-benzofuro[3,2-c]pyridine, 162

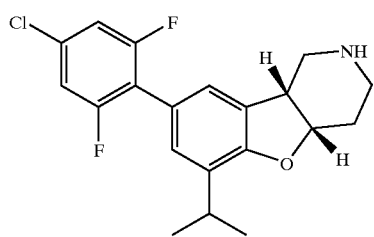

(4aS,9bR)-8-(2,6-difluoro-4-chlorophenyl)-6-(isopropyl)-1,2,3,4,4a,9b,-hexahydro[1]-benzofuro[3,2-c]pyridine, 163

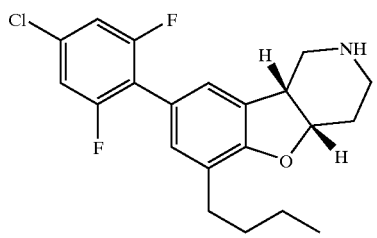

(4aS,9bR)-8-(2,6-difluoro-4-chlorophenyl)-6-butyl-1,2,3,4,4a,9b,-hexahydro[1]-benzofuro[3,2-c]pyridine, 164

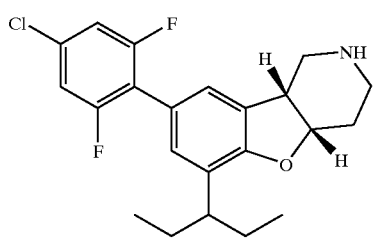

(4aS,9bR)-8-(2,6-difluoro-4-chlorophenyl)-6-(1-ethylpropyl)-1,2,3,4,4a,9b,-hexahydro[1]benzofuro[3,2-c]pyridine, 165

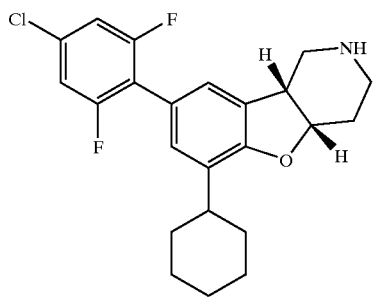

(4aS,9bR)-8-(2,6-difluoro-4-chlorophenyl)-6-cyclohexyl-1,2,3,4,4a,9b,-hexahydro[1]benzofuro[3,2-c]pyridine, 166

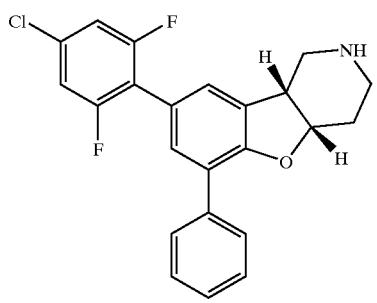

(4aS,9bR)-8-(2,6-difluoro-4-chlorophenyl)-6-phenyl-1,2,3,4,4a,9b,-hexahydro[1]-benzofuro[3,2-c]pyridine, 167

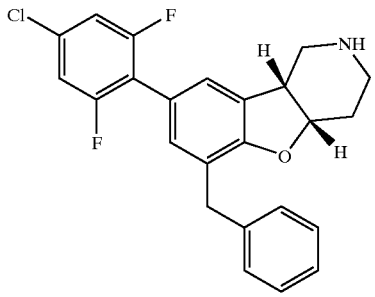

(4aS,9bR)-8-(2,6-difluoro-4-chlorophenyl)-6-benzyl-1,2,3,4,4a,9b,-hexahydro[1]-benzofuro[3,2-c]pyridine, 168

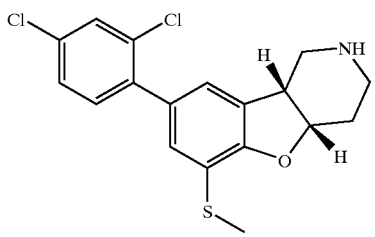

(4aS,9bR)-8-(2,4-dichlorophenyl)-6-(methylthio)-1,2,3,4,4a,9b,-hexahydro[1]-benzofuro[3,2-c]pyridine, 169

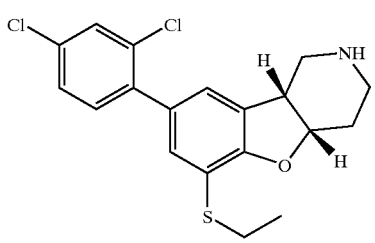

(4aS,9bR)-8-(2,4-dichlorophenyl)-6-(ethylthio)-1,2,3,4,4a,9b,-hexahydro[1]-benzofuro[3,2-c]pyridine, 170

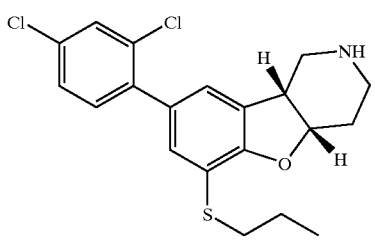

(4aS,9bR)-8-(2,4-dichlorophenyl)-6-(propylthio)-1,2,3,4,4a,9b,-hexahydro[1]-benzofuro[3,2-c]pyridine, 171

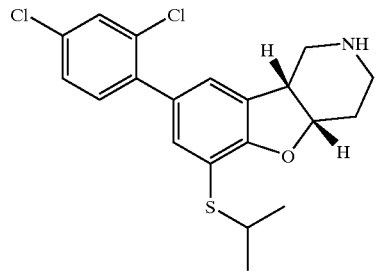

(4aS,9bR)-8-(2,4-dichlorophenyl)-6-(2-propylthio)-1,2,3,4,4a,9b,-hexahydro[1]-benzofuro[3,2-c]pyridine, 172

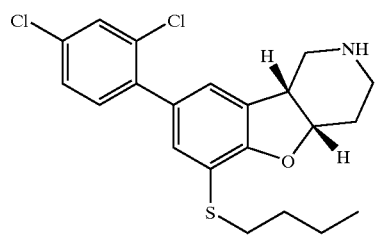

(4aS,9bR)-8-(2,4-dichlorophenyl)-6-(butylthio)-1,2,3,4,4a,9b,-hexahydro[1]-benzofuro[3,2-c]pyridine, 173

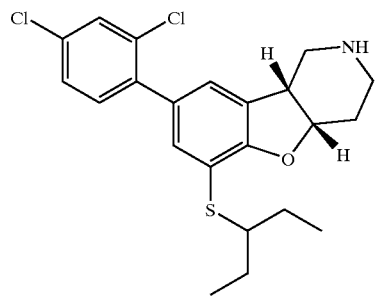

(4aS,9bR)-8-(2,4-dichlorophenyl)-6-[(1-ethylpropyl)thio]-1,2,3,4,4a,9b,-hexahydro[1]-benzofuro[3,2-c]pyridine, 174

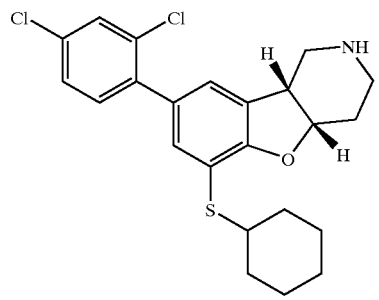

(4aS,9bR)-8-(2,4-dichlorophenyl)-6-(cyclohexylthio)-1,2,3,4,4a,9b,-hexahydro[1]-benzofuro[3,2-c]pyridine, 175

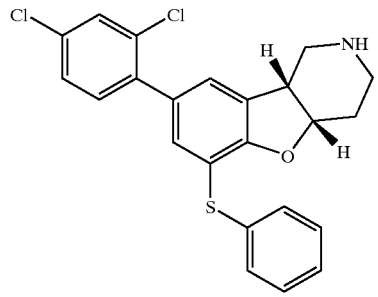

(4aS,9bR)-8-(2,4-dichlorophenyl)-6-(phenylthio)-1,2,3,4,4a,9b,-hexahydro[1]-benzofuro[3,2-c]pyridine, 176

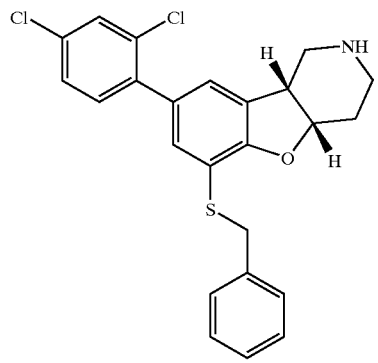

(4aS,9bR)-8-(2,4-dichlorophenyl)-6-(benzylthio)-1,2,3,4,4a,9b,-hexahydro[1]-benzofuro[3,2-c]pyridine, 177

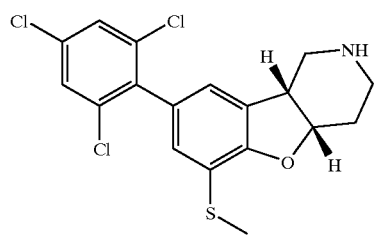

(4aS,9bR)-8-(2,4,6-trichlorophenyl)-6-(methylthio)-1,2,3,4,4a,9b,-hexahydro[1]-benzofuro[3,2-c]pyridine, 178

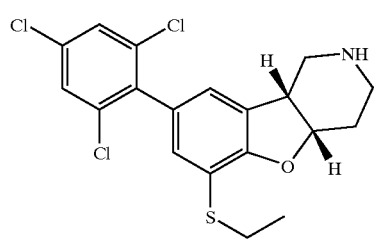

(4aS,9bR)-8-(2,4,6-trichlorophenyl)-6-(ethylthio)-1,2,3,4,4a,9b,-hexahydro[1]-benzofuro[3,2-c]pyridine, 179

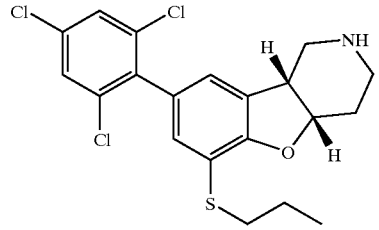

(4aS,9bR)-8-(2,4,6-trichlorophenyl)-6-(propylthio)-1,2,3,4,4a,9b,-hexahydro[1]-benzofuro[3,2-c]pyridine, 180

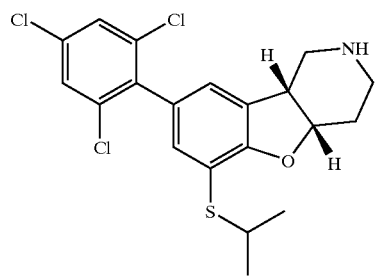

(4aS,9bR)-8-(2,4,6-trichlorophenyl)-6-(2-propylthio)-1,2,3,4,4a,9b,-hexahydro[1]-benzofuro[3,2-c]pyridine, 181

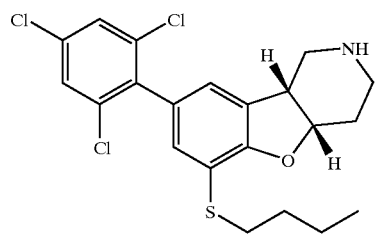

(4aS,9bR)-8-(2,4,6-trichlorophenyl)-6-(butylthio)-1,2,3,4,4a,9b,-hexahydro[1]-benzofuro[3,2-c]pyridine, 182

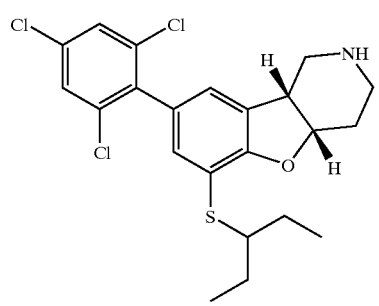

75

(4aS,9bR)-8-(2,4,6-trichlorophenyl)-6-[(1-ethylpropyl)thio]-1,2,3,4,4a,9b,-hexahydro[1]benzofuro[3,2-c]pyridine, 183

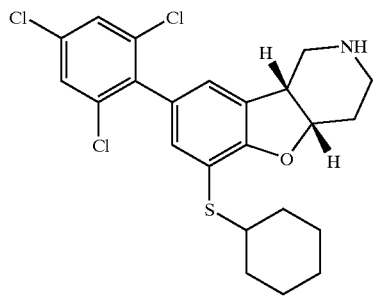

(4aS,9bR)-8-(2,4,6-trichlorophenyl)-6-(cyclohexylthio)-1,2,3,4,4a,9b,-hexahydro[1]-benzofuro[3,2-c]pyridine, 184

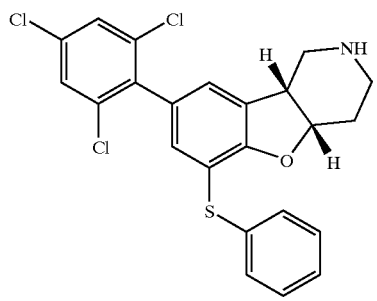

(4aS,9bR)-8-(2,4,6-trichlorophenyl)-6-(phenylthio)-1,2,3,4,4a,9b,-hexahydro[1]-benzofuro[3,2-c]pyridine, 185

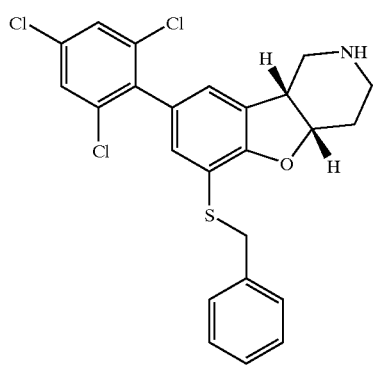

76

(4aS,9bR)-8-(2,4,6-trichlorophenyl)-6-(benzylthio)-1,2,3,4,4a,9b,-hexahydro[1]-benzofuro[3,2-c]pyridine, 186

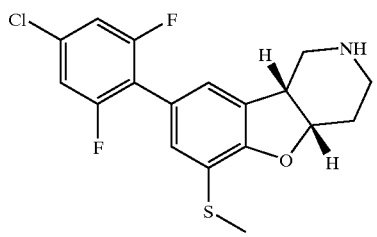

(4aS,9bR)-8-(2,6-difluoro-4-chlorophenyl)-6-(methylthio)-1,2,3,4,4a,9b,-hexahydro[1]benzofuro[3,2-c]pyridine, 187

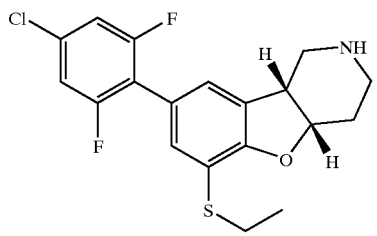

(4aS,9bR)-8-(2,6-difluoro-4-chlorophenyl)-6-(ethylthio)-1,2,3,4,4a,9b,-hexahydro[1]-benzofuro[3,2-c]pyridine, 188

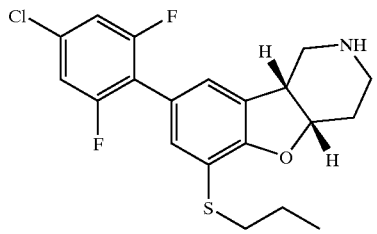

(4aS,9bR)-8-(2,6-difluoro-4-chlorophenyl)-6-(propylthio)-1,2,3,4,4a,9b,-hexahydro-[1]benzofuro[3,2-c]pyridine, 189

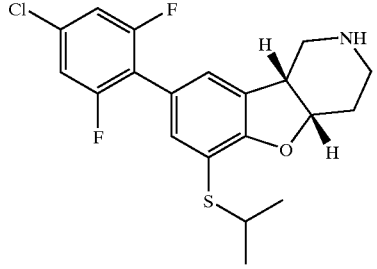

(4aS,9bR)-8-(2,6-difluoro-4-chlorophenyl)-6-(isopropyl)-1,2,3,4,4a,9b,-hexahydro[1]-benzofuro[3,2-c]pyridine, 190

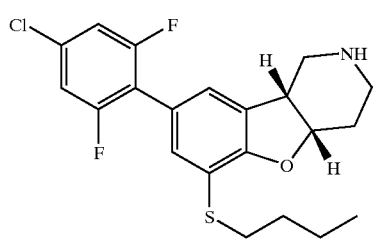

(4aS,9bR)-8-(2,6-difluoro-4-chlorophenyl)-6-(butylthio)-1,2,3,4,4a,9b,-hexahydro[1]benzofuro[3,2-c]pyridine, 191

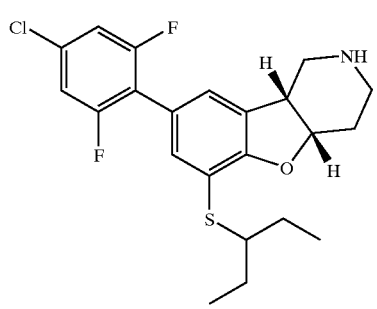

(4aS,9bR)-8-(2,6-difluoro-4-chlorophenyl)-6-[(1-ethylpropyl)thio]-1,2,3,4,4a,9b,-hexahydro[1]benzofuro[3,2-c]pyridine, 192

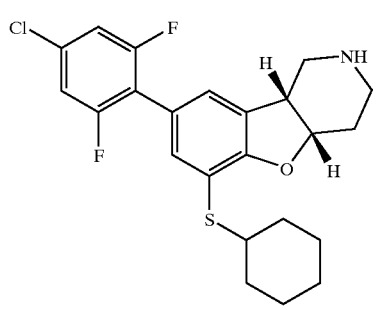

(4aS,9bR)-8-(2,6-difluoro-4-chlorophenyl)-6-(cyclohexylthio)-1,2,3,4,4a,9b,-hexahydro[1]benzofuro[3,2-c]pyridine, 193

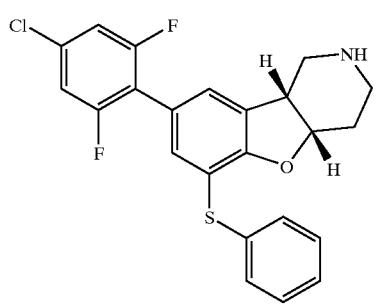

(4aS,9bR)-8-(2,6-difluoro-4-chlorophenyl)-6-(phenylthio)-1,2,3,4,4a,9b,-hexahydro[1]benzofuro[3,2-c]pyridine, 194

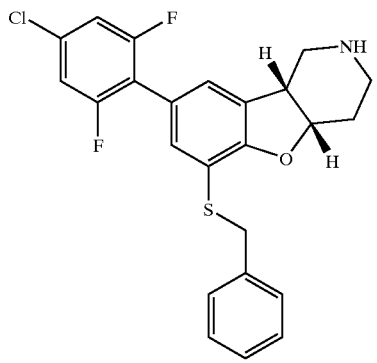

(4aS,9bR)-8-(2,6-difluoro-4-chlorophenyl)-6-(benzylthio)-1,2,3,4,4a,9b,-hexahydro[1]benzofuro[3,2-c]pyridine, 195

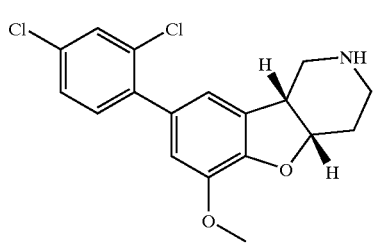

(4aS,9bR)-8-(2,4-dichlorophenyl)-6-methoxy-1,2,3,4,4a,9b,-hexahydro[1]benzofuro-[3,2-c]pyridine, 196

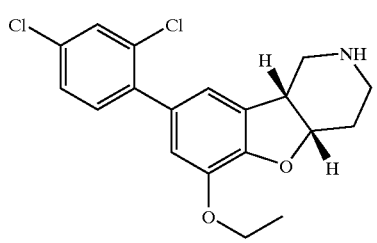

(4aS,9bR)-8-(2,4-dichlorophenyl)-6-ethoxy-1,2,3,4,4a,9b,-hexahydro[1]benzofuro-[3,2-c]pyridine, 197

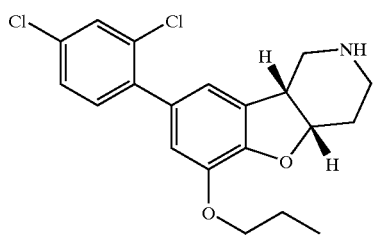

79

(4aS,9bR)-8-(2,4-dichlorophenyl)-6-propoxy-1,2,3,4,
4a,9b,-hexahydro[1]benzofuro-[3,2-c]pyridine, 198

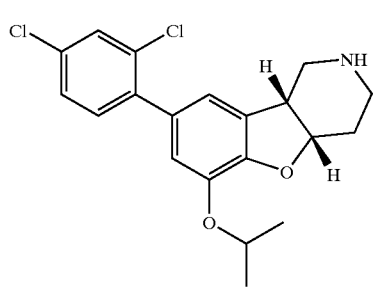

(4aS,9bR)-8-(2,4-dichlorophenyl)-6-isopropoxy-1,2,3,
4,4a,9b,-hexahydro[1]-benzofuro[3,2-c]pyridine, 199

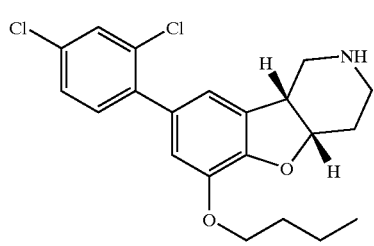

(4aS,9bR)-8-(2,4-dichlorophenyl)-6-butoxy-1,2,3,4,
4a,9b,-hexahydro[1]benzofuro-[3,2-c]pyridine, 200

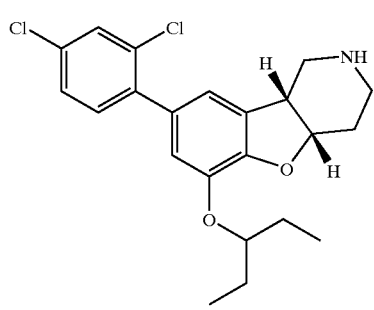

(4aS,9bR)-8-(2,4-dichlorophenyl)-6-[(1-ethylpropyl)
oxy]-1,2,3,4,4a,9b,-hexahydro[1]benzofuro[3,2-c]
pyridine, 201

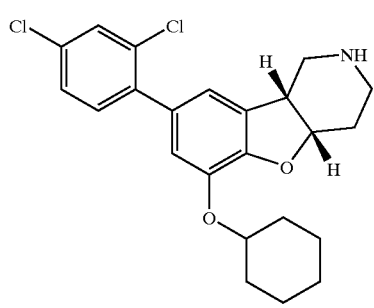

80

(4aS,9bR)-8-(2,4-dichlorophenyl)-6-
(cyclohexyloxy)-1,2,3,4,4a,9b,-hexahydro[1]-
benzofuro[3,2-c]pyridine, 202

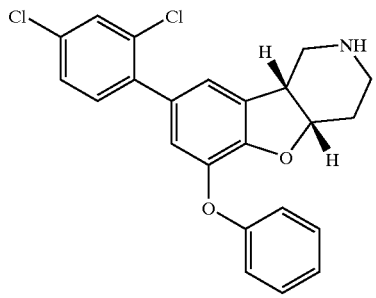

(4aS,9bR)-8-(2,4-dichlorophenyl)-6-phenoxy-1,2,3,4,
4a,9b,-hexahydro[1]benzofuro-[3,2-c]pyridine, 203

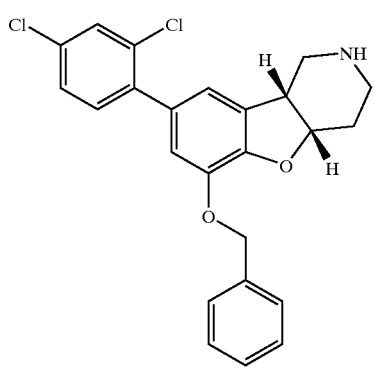

(4aS,9bR)-8-(2,4-dichlorophenyl)-6-(benzyloxy)-1,2,
3,4,4a,9b,-hexahydro[1]-benzofuro[3,2-c]pyridine, 204

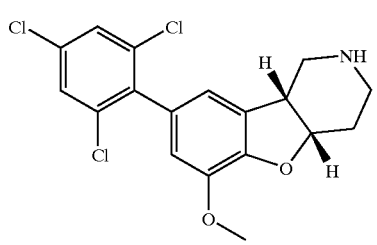

(4aS,9bR)-8-(2,4,6-trichlorophenyl)-6-methoxy-1,2,3,
4,4a,9b,-hexahydro[1]-benzofuro[3,2-c]pyridine, 205

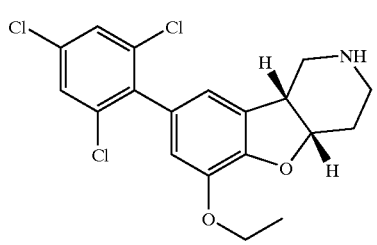

(4aS,9bR)-8-(2,4,6-trichlorophenyl)-6-ethoxy-1,2,3,4,
4a,9b,-hexahydro[1]benzofuro-[3,2-c]pyridine, 206

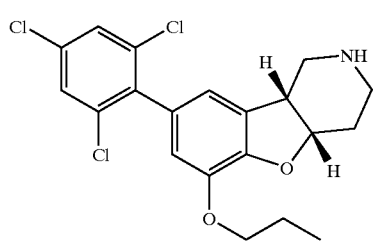

(4aS,9bR)-8-(2,4,6-trichlorophenyl)-6-propoxy-1,2,3,
4,4a,9b,-hexahydro[1]-benzofuro[3,2-c]pyridine, 207

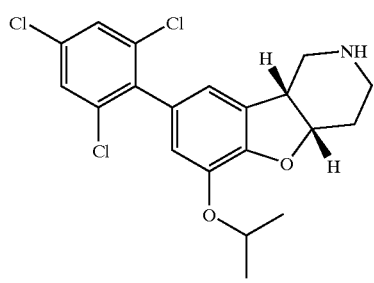

(4aS,9bR)-8-(2,4,6-trichlorophenyl)-6-isopropoxy-1,2,
3,4,4a,9b,-hexahydro[1]-benzofuro[3,2-c]pyridine, 208

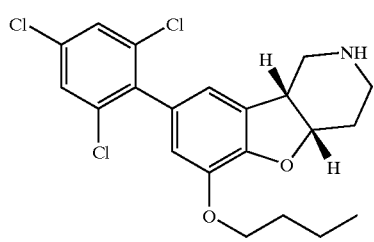

(4aS,9bR)-8-(2,4,6-trichlorophenyl)-6-butoxy-1,2,3,4,
4a,9b,-hexahydro[1]benzofuro-[3,2-c]pyridine, 209

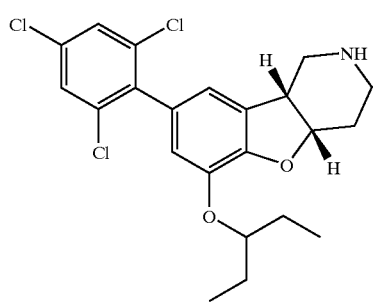

(4aS,9bR)-8-(2,4,6-trichlorophenyl)-6-[(1-
ethylpropyl)oxy]-1,2,3,4,4a,9b,-hexahydro[1]
benzofuro[3,2-c]pyridine, 210

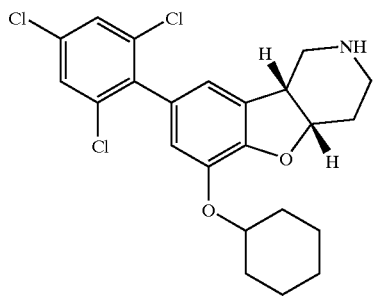

(4aS,9bR)-8-(2,4,6-trichlorophenyl)-6-
(cyclohexyloxy)-1,2,3,4,4a,9b,-hexahydro[1]-
benzofuro[3,2-c]pyridine, 211

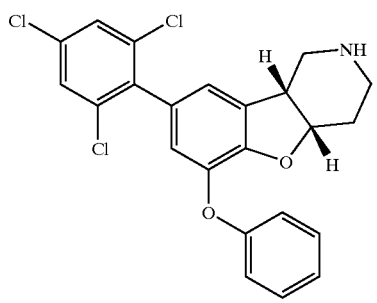

(4aS,9bR)-8-(2,4,6-trichlorophenyl)-6-phenoxy-1,2,3,
4,4a,9b,-hexahydro[1]-benzofuro[3,2-c]pyridine, 212

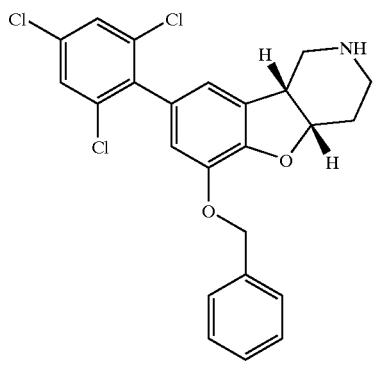

(4aS,9bR)-8-(2,4,6-trichlorophenyl)-6-(benzyloxy)-
1,2,3,4,4a,9b,-hexahydro[1]-benzofuro[3,2-c]
pyridine, 213

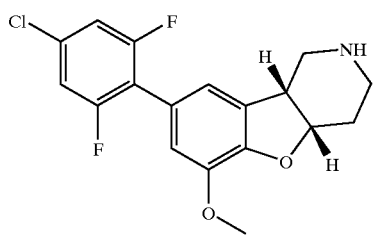

(4aS,9bR)-8-(2,6-difluoro-4-chlorophenyl)-6-methoxy-1,2,3,4,4a,9b,-hexahydro[1]-benzofuro[3,2-c]pyridine, 214

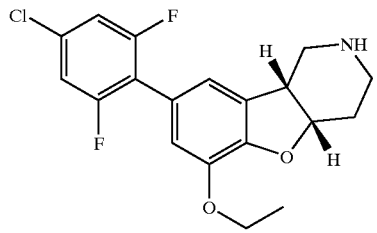

(4aS,9bR)-8-(2,6-difluoro-4-chlorophenyl)-6-ethoxy-1,2,3,4,4a,9b,-hexahydro[1]-benzofuro[3,2-c]pyridine, 215

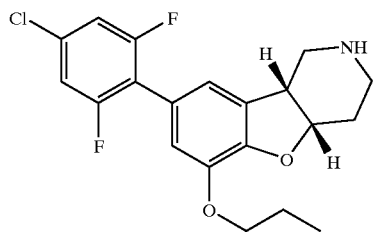

(4aS,9bR)-8-(2,6-difluoro-4-chlorophenyl)-6-propoxy-1,2,3,4,4a,9b,-hexahydro[1]-benzofuro[3,2-c]pyridine, 216

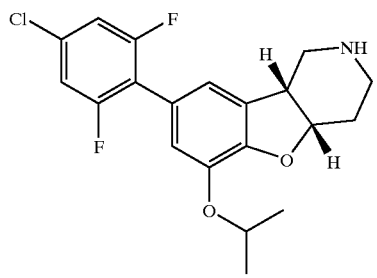

(4aS,9bR)-8-(2,6-difluoro-4-chlorophenyl)-6-(2-propoxy)-1,2,3,4,4a,9b,-hexahydro[1]benzofuro[3,2-c]pyridine, 217

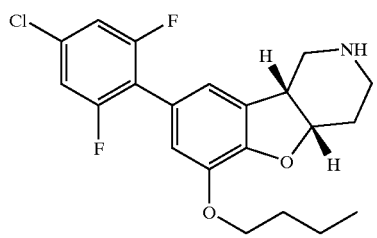

(4aS,9bR)-8-(2,6-difluoro-4-chlorophenyl)-6-butoxy-1,2,3,4,4a,9b,-hexahydro[1]-benzofuro[3,2-c]pyridine, 218

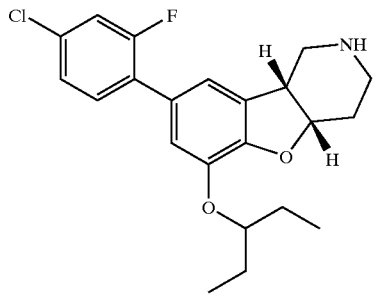

(4aS,9bR)-8-(2,6-difluoro-4-chlorophenyl)-6-[(1-ethylpropyl)oxy]-1,2,3,4,4a,9b,-hexahydro[1]benzofuro[3,2-c]pyridine, 219

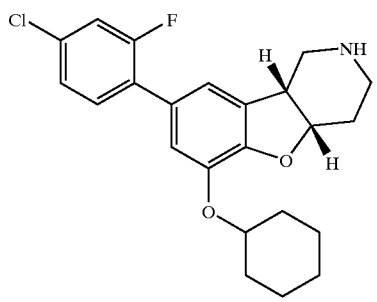

(4aS,9bR)-8-(2,6-difluoro-4-chlorophenyl)-6-(cyclohexyloxy)-1,2,3,4,4a,9b,-hexahydro[1]benzofuro[3,2-c]pyridine, 220

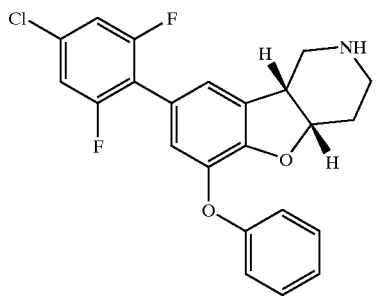

(4aS,9bR)-8-(2,6-difluoro-4-chlorophenyl)-6-phenoxy-1,2,3,4,4a,9b,-hexahydro[1]0-benzofuro[3,2-c]pyridine, 221

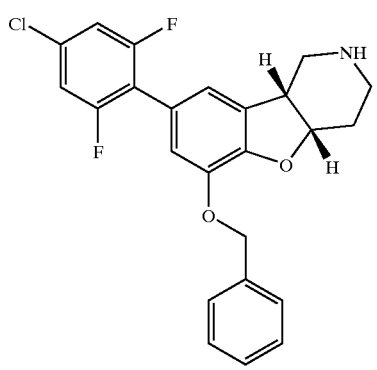

| 85 | 86 |
|---|---|
| (4aS,9bR)-8-(2,6-difluoro-4-chlorophenyl)-6-(benzyloxy)-1,2,3,4,4a,9b,-hexahydro[1]benzofuro[3,2-c]pyridine, 222 | (4aS,9bR)-8-(2,6-difluoro-4-chlorophenyl)-6-piperidin-1-yl-1,2,3,4,4a,9b-hexahydro[1]benzofuro[3,2-c]pyridine, 225 |

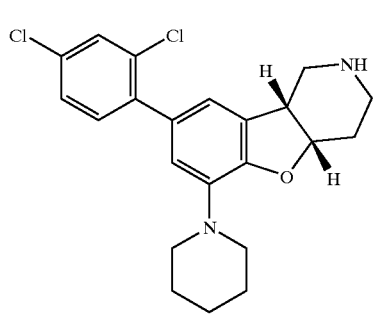

223

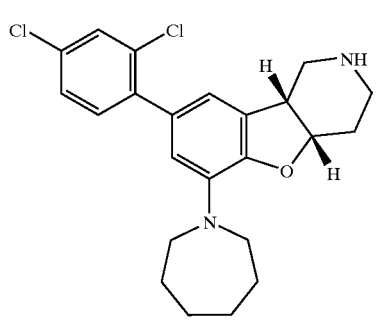

226

(4aS,9bR)-8-(2,4-dichlorophenyl)-6-piperidin-1-yl-1,2,3,4,4a,9b-hexahydro[1]benzofuro[3,2-c]pyridine, 223

(4aS,9bR)-8-(2,4-dichlorophenyl)-6-azepano-1-yl-1,2,3,4,4a,9b-hexahydro[1]benzofuro[3,2-c]pyridine, 226

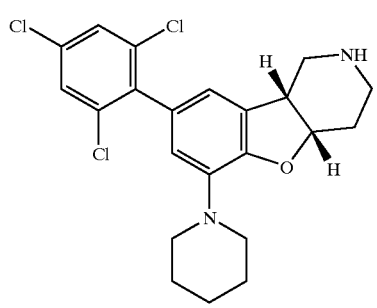

224

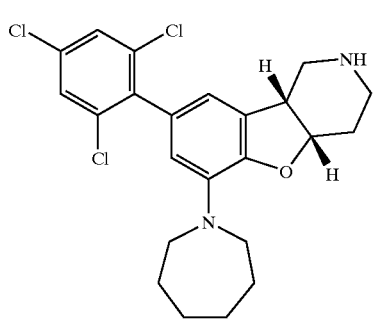

227

(4aS,9bR)-8-(2,4,6-trichlorophenyl)-6-piperidin-1-yl-1,2,3,4,4a,9b-hexahydro[1]benzofuro[3,2-c]pyridine, 224

(4aS,9bR)-8-(2,4,6-trichlorophenyl)-6-azepano-1-yl-1,2,3,4,4a,9b-hexahydro[1]benzofuro[3,2-c]pyridine, 227

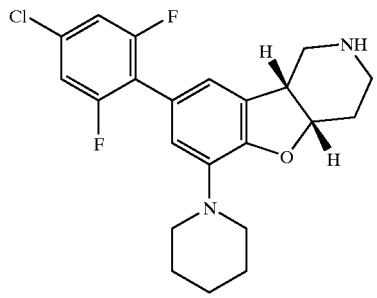

225

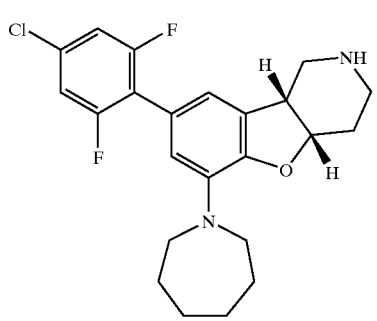

228

87

(4aS,9bR)-8-(2,6-difluoro-4-chlorophenyl)-6-azepano-1-yl-1,2,3,4,4a,9b-hexahydro[1]benzofuro[3,2-c]pyridine, 228

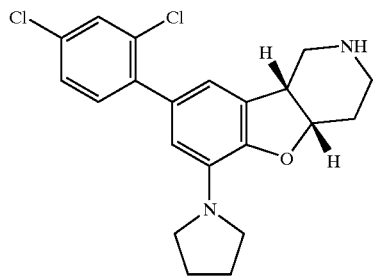

(4aS,9bR)-8-(2,4-dichlorophenyl)-6-pyrrolidin-1-yl-1,2,3,4,4a,9b-hexahydro[1]benzofuro[3,2-c]pyridine, 229

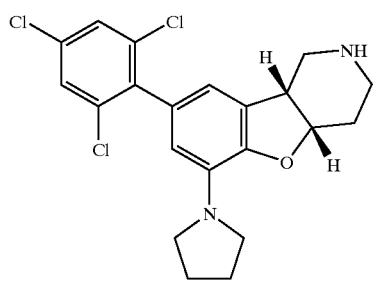

(4aS,9bR)-8-(2,4,6-trichlorophenyl)-6-pyrrolidin-1-yl-1,2,3,4,4a,9b-hexahydro[1]benzofuro[3,2-c]pyridine, 230

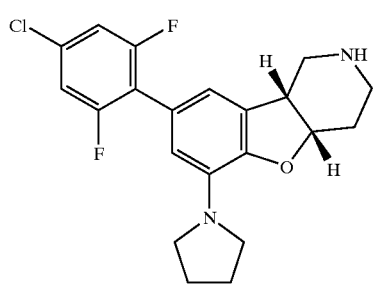

88

(4aS,9bR)-8-(2,6-difluoro-4-chlorophenyl)-6-pyrrolidin-1-yl-1,2,3,4,4a,9b-hexahydro[1]benzofuro[3,2-c]pyridine, 231

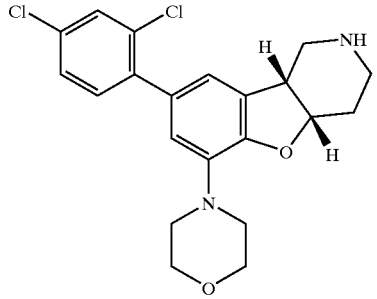

(4aS,9bR)-8-(2,4-dichlorophenyl)-5-morpholin-4-yl-1,2,3,4,4a,9b-hexahydro-[1]benzofuro[3,2-c]pyridine, 232

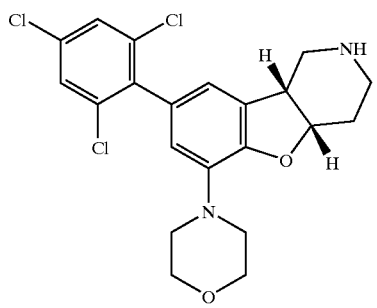

(4aS,9bR)-8-(2,4,6-trichlorophenyl)-5-morpholin-4-yl-1,2,3,4,4a,9b-hexahydro[1]benzofuro[3,2-c]pyridine, 233

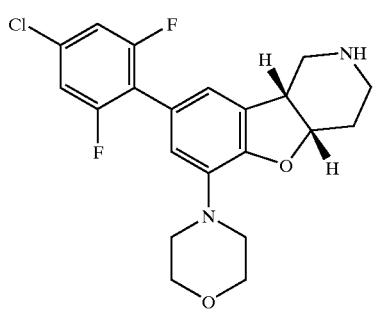

(4aS,9bR)-8-(2,6-difluoro-4-chlorophenyl)-5-
morpholin-4-yl-1,2,3,4,4a,9b-hexahydro[1]
benzofuro[3,2-c]pyridine, 234

(4aS,9bR)-8-(2,6-difluoro-4-chlorophenyl)-6-
thiomorpholin-4-yl-1,2,3,4,4a,9b-hexahydro[1]
benzofuro[3,2-c]pyridine, 237

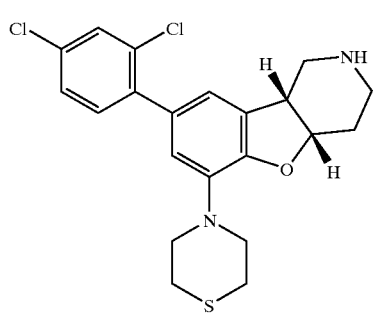

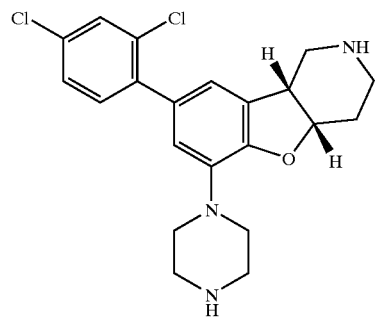

(4aS,9bR)-8-(2,4-dichlorophenyl)-6-thiomorpholin-
4-yl-1,2,3,4,4a,9b-hexahydro[1]benzofuro[3,2-c]
pyridine, 235

(4aS,9bR)-8-(2,4-dichlorophenyl)-6-piperazin-1-yl-1,
2,3,4,4a,9b-hexahydro[1]benzofuro[3,2-c]pyridine, 238

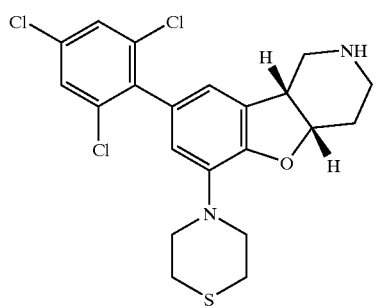

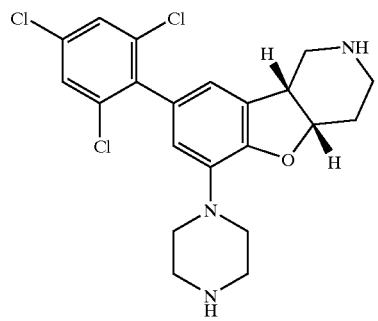

(4aS,9bR)-8-(2,4,6-trichlorophenyl)-6-
thiomorpholin-4-yl-1,2,3,4,4a,9b-hexahydro[1]
benzofuro[3,2-c]pyridine, 236

(4aS,9bR)-8-(2,4,6-trichlorophenyl)-6-piperazin-1-
yl-1,2,3,4,4a,9b-hexahydro[1]benzofuro[3,2-c]
pyridine, 239

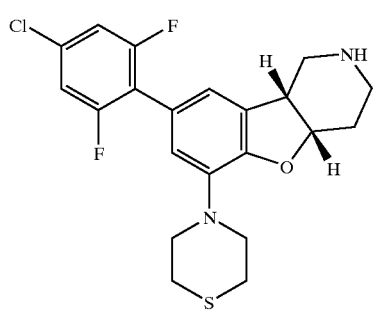

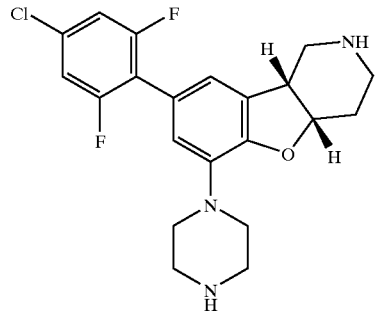

(4aS,9bR)-8-(2,6-difluoro-4-chlorophenyl)-6-piperazin-1-yl-1,2,3,4,4a,9b-hexahydro[1]benzofuro[3,2-c]pyridine, 240

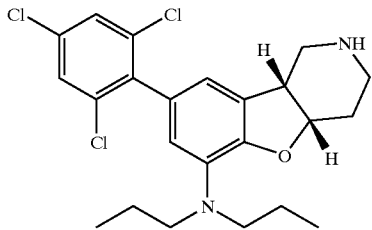

(4aS,9bR)-8-(2,4,6-trichlorophenyl)-N,N-dipropyl-1,2,3,4,4a,9b,-hexahydro[1]benzofuro[3,2-c]pyridin-6-amine, 243; and

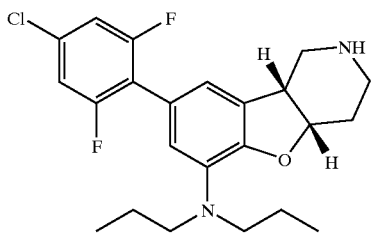

(4aS,9bR)-8-(2,6-difluoro-4-chlorophenyl)-N,N-dipropyl-1,2,3,4,4a,9b,-hexahydro[1]benzofuro[3,2-c]pyridin-6-amine, 244

All cited publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed:

1. A compound of formula (I):

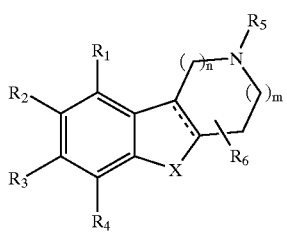

wherein:
$R_1$, $R_3$, and $R_4$ are independently hydrogen, halo, —$CF_3$, —$OCF_3$, —CN, —$NO_2$, —$C_{1-8}$alkyl, —$C_{3-8}$cycloalkyl, —$OR_8$, —$NR_8R_9$, —$SR_8$, —C(=O)aryl, aryl, —$C_{1-8}$alkylene(aryl), —C(=O)heteroaryl, heteroaryl, or —$C_{1-8}$alkylene(heteroaryl);
$R_2$ is —$OCF_3$, —CN, —$C_{3-8}$cycloalkyl, —$NR_8R_9$, —$SR_8$, —C(=O)aryl, aryl, —$C_{1-8}$alkylene (aryl), —C(=O) heteroaryl, heteoaryl, or —$C_{1-8}$alkylene (heteroaryl);
$R_5$ is hydrogen, $C_{1-8}$alkyl, halo$C_{1-8}$alkyl, $C_{3-8}$cycloalkyl, $C_{1-8}$alkanoyl, halo$C_{1-8}$alkanoyl; —C(=O)O$R_8$, —C(=)aryl, aryl, —$C_{1-8}$alkylene (aryl), —C(=O) heteroaryl, heteoaryl, or —$C_{1-8}$alkylene(heteroaryl);
$R_6$ is hydrogen or $C_{1-4}$alkyl;
each $R_8$ and $R_9$ is independently hydrogen, $C_{1-8}$alkyl, halo$C_{1-8}$alkyl, $C_{3-8}$cycloalkyl, —C(=O)aryl, aryl, —$C_{1-8}$alkylene(aryl), —C(=O)heteroaryl, heteroaryl, —$C_8$alkylene(heteroaryl) or $R_8$ and $R_9$ together with the nitrogen to which they are attached form a pyrrolidino, piperidino, azepano, piperazino, morpholino, or thiomorpholino ring;
m is 1;
n is 1;
X is oxy (—O—), thio (—S—) —S(=O)— or —$SO_2$—; and
the bond represented by—is absent or present;
wherein any $C_{1-8}$alkyl, $C_{1-8}$alkylene, $C_{1-8}$alkoxy or $C_{3-8}$cycloalkyl of $R_1$, $R_2$, $R_3$, $R_4$, $R_5$, $R_6$, $R_8$ and $R_9$ is optionally partially unsaturated; and
wherein heteroaryl of $R_1$, $R_2$, $R_3$, $R_4$, $R_5$, $R_8$ or $R_9$ is optionally substituted with one or more substituents independently selected from halo, —CN, —$NO_2$, —$CF_3$, —$OCF_3$, $C_{1-8}$alkyl, $C_{2-8}$alkenyl, $C_{2-8}$alkynyl, $C_{3-8}$cycloalkyl, $C_{3-8}$cycloalkenyl, aryl, heteroaryl, —$OR_c$, —$SR_c$, —C(=O)$R_c$, —$CO_2R_c$, —C(=O)$NR_cR_d$, —$NR_cC(=O)R_d$, —C(=O)$NR_cR_d$, —$NR_cR_d$, —$NR_cC(=O)NR_cR_d$, —$SO_2NR_cR_d$ or —$SO_2R_c$;
wherein each $R_c$ and $R_d$ is independently hydrogen, $C_{1-8}$alkyl, $C_{1-8}$alkanoyl, $C_{1-8}$alkoxycarbonyl, aryl, —$C_{1-8}$alkylene(aryl), —C(=O)aryl, —C(=O)Oaryl, heteroaryl, —$C_{1-8}$alkylene(heteroaryl),
—C(=O)heteroaryl, —C(=O)Oheteroaryl or $R_c$ and $R_d$ together with the nitrogen to which they are attached form a pyrrolidino, piperidino, azepano, piperazino, morpholino, or thiomorpholino ring;
or a pharmaceutically acceptable salt thereof.

2. The compound of claim 1, wherein the bond represented by—is absent.

3. The compound of claim 1, wherein the bond represented by—is present.

4. The compound of claim 1, wherein X is oxy.

5. The compound of claim 1, wherein X is thio.

6. The compound of claim 1, wherein $R_2$ is aryl, optionally substituted with one or more substituents independently selected from halo, hydroxy, cyano, nitro, trifluoromethyl, trifluoromethoxy, $C_{1-6}$alkyl, —$OR_c$, —$SR_c$, phenyl, —$NR_cR_d$, and —C(=O)$NR_cR_d$.

7. The compound of claim 1, wherein $R_2$ is phenyl, optionally substituted with one or more substituents independently selected from halo, cyano, nitro, trifluoromethyl, trifluoromethoxy, $C_{1-6}$alkyl, —$OR_c$, —$SR_c$, phenyl, —$NR_cR_d$, and —C(=O)$NR_cR_d$.

8. The compound of claim 7, wherein $R_2$ is phenyl, optionally substituted with one or more substituents independently selected from halo, cyano, trifluoromethyl, trifluoromethoxy, $C_{1-6}$alkyl, $C_{1-6}$alkoxy and thio$C_{1-6}$alkyl.

9. The compound of claim 8, wherein $R_2$ is phenyl, substituted with one or more substituents independently selected from halo, cyano, trifluoromethyl, trifluoromethoxy, $C_{1-6}$alkyl, $C_{1-6}$alkoxy and thio$C_{1-6}$alkyl.

10. The compound of claim 9, wherein $R_2$ is phenyl, substituted with one or more substituents independently selected from fluoro, chloro, bromo, trifluoromethyl, trifluoromethoxy, methoxy, ethoxy, propoxy, isopropoxy and thiomethyl.

11. The compound of claim 10, wherein $R_2$ is phenyl substituted at the 2- or 6-position with fluoro, chloro or bromo.

12. The compound of claim 10, wherein $R_2$ is phenyl independently substituted at the 2- and 6-position with fluoro, chloro or bromo.

13. The compound of claim 10, wherein $R_2$ is phenyl substituted at the 2- or 4-position with fluoro, chloro or bromo.

14. The compound of claim 10, wherein $R_2$ is phenyl independently substituted at the 2- and 4-position with fluoro, chloro or bromo.

15. The compound of claim 10, wherein $R_2$ is phenyl independently substituted at the 2-, 4- and 6-position with fluoro, chloro or bromo.

16. The compound of claim 10, wherein $R_2$ is 2,4-dichlorophenyl, 2,4,6-trichlorophenyl or 2,6-difluoro-4-chlorophenyl.

17. The compound of claim 1, wherein $R_2$ is heteroaryl, optionally substituted with one or more substituents independently selected from halo, hydroxy, cyano, nitro, trifluoromethyl, trifluoromethoxy, $C_{1-6}$alkyl, $-OR_c$, $-SR_c$, phenyl, $-NR_cR_d$, and $-C(=O)NR_cR_d$.

18. The compound of claim 17, wherein $R_2$ is heteroaryl, optionally substituted with one or more substituents independently selected from halo, cyano, trifluoromethyl, trifluoromethoxy, $C_{1-6}$alkyl, $-OR_c$ and $-SR_c$.

19. The compound of claim 18, wherein $R_2$ is heteroaryl, optionally substituted with one or more substituents independently selected from fluoro, chloro, bromo, trifluoromethyl, trifluoromethoxy, methoxy, ethoxy, propoxy, and isopropoxy.

20. The compound of claim 1, wherein $R_1$ is hydrogen, $C_{1-3}$alkyl, halo, halo$C_{1-3}$alkyl, $C_{1-3}$alkoxy, halo$C_{1-3}$alkoxy, or $-NR_8R_9$.

21. The compound of claim 20, wherein $R_1$ is hydrogen or $C_{1-3}$alkyl.

22. The compound of claim 1, wherein $R_3$ is hydrogen, $C_{1-3}$alkyl, aryl, halo, halo$C_{1-3}$alkyl, $C_{1-3}$alkoxy, halo$C_{1-3}$alkoxy or $-NR_8R_9$.

23. The compound of claim 22, wherein $R_3$ is hydrogen, $C_{1-3}$alkyl, or aryl.

24. The compound of claim 23, wherein $R_3$ is hydrogen or $C_{1-3}$alkyl.

25. The compound of claim 1, wherein $R_4$ is $C_{1-8}$alkyl, $-OR_8$, $-SR_8$, $-NR_8R_9$, aryl or $-C_{1-8}$alkylene(aryl), wherein the aryl groups are optionally substituted with one or more substituents independently selected from halo, hydroxy, cyano, nitro, trifluoromethyl, trifluoromethoxy, $C_{1-6}$alkyl, $C_{1-6}$alkoxy, phenyl, $-NR_cR_d$, and $-C(=O)NR_cR_d$.

26. The compound of claim 25, wherein $R_4$ is $C_{1-8}$alkyl, $-OR_8$, $-SR_8$, $-NR_8R_9$ or aryl, wherein the aryl group is substituted with one or more substituents independently selected from halo, hydroxy, cyano, nitro, trifluoromethyl, trifluoromethoxy, $C_{1-6}$alkyl, $C_{1-6}$alkoxy, phenyl, $-NR_cR_d$, and $-C(=O)NR_cR_d$.

27. The compound of claim 25, wherein $R_4$ is methyl, ethyl, propyl, isopropyl, butyl, ethylpropyl, cyclohexyl, phenyl, benzyl, methoxy, ethoxy, propoxy, isopropoxy, butoxy, (ethylpropyl)oxy, (cyclohexyl)oxy, phenoxy, (benzyl)oxy, methylthio, ethylthio, propylthio, isopropylthio, butylthio, (ethylpropyl)thio, (cyclohexyl)thio, phenylthio, (benzyl)thio, or $-NR_8R_9$, wherein $R_8$ is hydrogen, methyl, ethyl, propyl or cyclohexyl; and $R_9$ is methyl, ethyl, propyl, cyclohexyl or phenyl; or $R_8$ and $R_9$ together with the nitrogen to which they are attached form a pyrrolidino, piperidino, azepano, piperazino, morpholino, or thiomorpholino ring.

28. The compound of claim 27, wherein $R_4$ is $-NR_8R_9$, wherein $R_8$ is hydrogen, methyl, ethyl, propyl or cyclohexyl and $R_9$ is methyl, ethyl, propyl, cyclohexyl or phenyl.

29. The compound of claim 28, wherein $R_4$ is $-NR_8R_9$, wherein $R_8$ is hydrogen, methyl or ethyl and $R_9$ is methyl, ethyl, propyl, cyclohexyl or phenyl.

30. The compound of claim 29, wherein $R_4$ is $-NR_8R_9$, wherein $R_8$ is hydrogen, methyl or ethyl and $R_9$ is methyl, ethyl, cyclohexyl or phenyl.

31. The compound of claim 30, wherein $R_4$ is $-NR_8R_9$, wherein $R_8$ is methyl or ethyl and $R_9$ is methyl, ethyl or cyclohexyl.

32. The compound of claim 27, wherein $R_4$ is pyrrolidino, piperidino, azepano, piperazino, morpholino, or thiomorpholino.

33. The compound of claim 1, wherein $R_5$ is hydrogen, $C_{1-8}$alkyl, $C_{2-8}$alkenyl, $C_{2-8}$alkynyl, $C_{3-8}$cycloalkyl, $C_{3-8}$cycloalkenyl, aryl, $-C_{1-8}$alkylene(aryl), heteroaryl, or $-C_{1-8}$alkylene(heteroaryl).

34. The compound of claim 33, wherein $R_5$ is hydrogen or $C_{1-8}$alkyl.

35. The compound of claim 33, wherein $R_5$ is hydrogen, methyl, ethyl, benzyl, or phenethyl.

36. The compound of claim 33, wherein $R_5$ is aryl, $-C_{1-8}$alkylene(aryl), heteroaryl, or $-C_{1-8}$akylene(heteroaryl).

37. The compound of claim 34, wherein $R_5$ is hydrogen.

38. The compound of claim 1, wherein m is 1; n is 1; and X is oxy.

39. The compound of claim 1, wherein the compound is:

8-(2,4-dichlorophenyl)-3,4,4a,9b-tetrahydro[1]benzofuro[3,2-c]-pyridine;

8-(2,4-dichlorophenyl)-N-cyclohexyl-1,2,3,4,4a,9b,-hexahydro[1]benzofuro[3,2-c]pyridin-6-amine;

8-(2,4,6-trichlorophenyl)-N-cyclohexyl-1,2,3,4,4a,9b,-hexahydro[1]benzofuro[3,2-c]pyridin-6-amine;

8-(2,6-difluoro-4-chlorophenyl)-N-cyclohexyl-1,2,3,4,4a,9b,-hexahydro[1]benzofuro[3,2-c]pyridin-6-amine;

8-(2,4-dichlorophenyl)-N-phenyl-1,2,3,4,4a,9b,-hexahydro[1]benzofuro[3,2-c]pyridin-6-amine;

8-(2,4,6-trichlorophenyl)-N-phenyl-1,2,3,4,4a,9b,-hexahydro[1]benzofuro[3,2-c]pyridin-6-amine;

8-(2,6-difluoro-4-chlorophenyl)-N-phenyl-1,2,3,4,4a,9b,-hexahydro[1]benzofuro[3,2-c]pyridin-6-amine;

8-(2,4-dichlorophenyl)-N,N-dimethyl-1,2,3,4,4a,9b,-hexahydro[1]benzofuro[3,2-c]pyridin-6-amine;

8-(2,4,6-trichlorophenyl)-N,N-dimethyl-1,2,3,4,4a,9b,-hexahydro[1]benzofuro[3,2-c]pyridin-6-amine;

8-(2,6-difluoro-4-chlorophenyl)-N,N-dimethyl-1,2,3,4,4a,9b,-hexahydro[1]benzofuro[3,2-c]pyridin-6-amine;

8-(2,4-dichlorophenyl)-N,N-diethyl-1,2,3,4,4a,9b,-hexahydro[1]benzofuro[3,2-c]pyridin-6-amine;

8-(2,4,6-trichlorophenyl)-N,N-diethyl-1,2,3,4,4a,9b,-hexahydro[1]benzofuro[3,2-c]pyridin-6-amine;

8-(2,6-difluoro-4-chlorophenyl)-N,N-diethyl-1,2,3,4,4a,9b,-hexahydro[1]benzofuro[3,2-c]pyridin-6-amine;

8-(2,4-dichlorophenyl)-N-methyl-N-ethyl-1,2,3,4,4a,9b,-hexahydro[1]benzofuro[3,2-c]pyridin-6-amine;

8-(2,4-dichlorophenyl)-N-methyl-N-propyl-1,2,3,4,4a,9b,-hexahydro[1]benzofuro[3,2-c]pyridin-6-amine;

8-(2,4-dichlorophenyl)-N-methyl-N-cyclohexyl-1,2,3,4,4a,9b,-hexahydro[1]benzofuro[3,2-c]pyridin-6-amine;

8-(2,4-dichlorophenyl)-N-ethyl-N-propyl-1,2,3,4,4a,9b,-hexahydro[1]benzofuro[3,2-c]pyridin-6-amine;

8-(2,4-dichlorophenyl)-N-ethyl-N-cyclohexyl-1,2,3,4,4a,9b,-hexahydro[1]benzofuro[3,2-c]pyridin-6-amine;

8-(2,4-dichlorophenyl)-N,N-dipropyl-1,2,3,4,4a,9b,-hexahydro[1]benzofuro[3,2-c]pyridin-6-amine;

8-(2,4-dichlorophenyl)-N-propyl-N-cyclohexyl-1,2,3,4,4a,9b,-hexahydro[1]benzofuro[3,2-c]pyridin-6-amine;

8-(2,4-dichlorophenyl)-N,N-dicyclohexyl-1,2,3,4,4a,9b,-hexahydro[1]benzofuro[3,2-c]pyridin-6-amine;

8-(2,4-dichlorophenyl)-6-methyl-1,2,3,4,4a,9b,-hexahydro[1]benzofuro[3,2-c]pyridine;

8-(2,4-dichlorophenyl)-6-ethyl-1,2,3,4,4a,9b,-hexahydro[1]benzofuro[3,2-c]pyridine;

8-(2,4-dichlorophenyl)-6-propyl-1,2,3,4,4a,9b,-hexahydro[1]benzofuro[3,2-c]pyridine;

8-(2,4-dichlorophenyl)-6-isopropyl-1,2,3,4,4a,9b,-hexahydro[1]benzofuro[3,2-c]pyridine;

8-(2,4-dichlorophenyl)-6-butyl-1,2,3,4,4a,9b,-hexahydro[1]benzofuro[3,2-c]pyridine;

8-(2,4-dichlorophenyl)-6-(1-ethylpropyl)-1,2,3,4,4a,9b,-hexahydro[1]benzofuro[3,2-c]pyridine;

8-(2,4-dichlorophenyl)-6-cyclohexyl-1,2,3,4,4a,9b,-hexahydro[1]benzofuro[3,2-c]pyridine;

8-(2,4-dichlorophenyl)-6-phenyl-1,2,3,4,4a,9b,-hexahydro[1]benzofuro[3,2-c]pyridine;

8-(2,4-dichlorophenyl)-6-benzyl-1,2,3,4,4a,9b,-hexahydro[1]benzofuro[3,2-c]pyridine;

8-(2,4,6-trichlorophenyl)-6-methyl-1,2,3,4,4a,9b,-hexahydro[1]benzofuro[3,2-c]pyridine;

8-(2,4,6-trichlorophenyl)-6-ethyl-1,2,3,4,4a,9b,-hexahydro[1]benzofuro[3,2-c]pyridine;

8-(2,4,6-trichlorophenyl)-6-propyl-1,2,3,4,4a,9b,-hexahydro[1]benzofuro[3,2-c]pyridine;

8-(2,4,6-trichlorophenyl)-6-isopropyl-1,2,3,4,4a,9b,-hexahydro[1]benzofuro[3,2-c]pyridine;

8-(2,4,6-trichlorophenyl)-6-butyl-1,2,3,4,4a,9b,-hexahydro[1]benzofuro[3,2-c]pyridine;

8-(2,4,6-trichlorophenyl)-6-(1-ethylpropyl)-1,2,3,4,4a,9b,-hexahydro[1]benzofuro[3,2-c]pyridine;

8-(2,4,6-trichlorophenyl)-6-cyclohexyl-1,2,3,4,4a,9b,-hexahydro[1]benzofuro[3,2-c]pyridine;

8-(2,4,6-trichlorophenyl)-6-phenyl-1,2,3,4,4a,9b,-hexahydro[1]benzofuro[3,2-c]pyridine;

8-(2,4,6-trichlorophenyl)-6-benzyl-1,2,3,4,4a,9b,-hexahydro[1]benzofuro[3,2-c]pyridine;

8-(2,6-difluoro-4-chlorophenyl)-6-methyl-1,2,3,4,4a,9b,-hexahydro[1]benzofuro[3,2-c]pyridine;

8-(2,6-difluoro-4-chlorophenyl)-6-ethyl-1,2,3,4,4a,9b,-hexahydro[1]benzofuro[3,2-c]pyridine;

8-(2,6-difluoro-4-chlorophenyl)-6-propyl-1,2,3,4,4a,9b,-hexahydro[1]benzofuro[3,2-c]pyridine;

8-(2,6-difluoro-4-chlorophenyl)-6-isopropyl-1,2,3,4,4a,9b,-hexahydro[1]benzofuro[3,2-c]pyridine;

8-(2,6-difluoro-4-chlorophenyl)-6-butyl-1,2,3,4,4a,9b,-hexahydro[1]benzofuro[3,2-c]pyridine;

8-(2,6-difluoro-4-chlorophenyl)-6-(1-ethylpropyl)-1,2,3,4,4a,9b,-hexahydro[1]benzofuro[3,2-c]pyridine;

8-(2,6-difluoro-4-chlorophenyl)-6-cyclohexyl-1,2,3,4,4a,9b,-hexahydro[1]benzofuro[3,2-c]pyridine;

8-(2,6-difluoro-4-chlorophenyl)-6-phenyl-1,2,3,4,4a,9b,-hexahydro[1]benzofuro[3,2-c]pyridine;

8-(2,6-difluoro-4-chlorophenyl)-6-benzyl-1,2,3,4,4a,9b,-hexahydro[1]benzofuro[3,2-c]pyridine;

8-(2,4-dichlorophenyl)-6-(methylthio)-1,2,3,4,4a,9b,-hexahydro[1]benzofuro[3,2-c]pyridine;

8-(2,4-dichlorophenyl)-6-(ethylthio)-1,2,3,4,4a,9b,-hexahydro[1]benzofuro[3,2-c]pyridine;

8-(2,4-dichlorophenyl)-6-(propylthio)-1,2,3,4,4a,9b,-hexahydro[1]benzofuro[3,2-c]pyridine;

8-(2,4-dichlorophenyl)-6-(isopropylthio)-1,2,3,4,4a,9b,-hexahydro[1]benzofuro[3,2-c]pyridine;

8-(2,4-dichlorophenyl)-6-(butylthio)-1,2,3,4,4a,9b,-hexahydro[1]benzofuro[3,2-c]pyridine;

8-(2,4-dichlorophenyl)-6-[(1-ethylpropyl)thio]-1,2,3,4,4a,9b,-hexahydro[1]benzofuro[3,2-c]pyridine;

8-(2,4-dichlorophenyl)-6-(cyclohexylthio)-1,2,3,4,4a,9b,-hexahydro[1]benzofuro[3,2-c]pyridine;

8-(2,4-dichlorophenyl)-6-(phenylthio)-1,2,3,4,4a,9b,-hexahydro[1]benzofuro[3,2-c]pyridine;

8-(2,4-dichlorophenyl)-6-(benzylthio)-1,2,3,4,4a,9b,-hexahydro[1]benzofuro[3,2-c]pyridine;

8-(2,4,6-trichlorophenyl)-6-(methylthio)-1,2,3,4,4a,9b,-hexahydro[1]benzofuro[3,2-c]pyridine;

8-(2,4,6-trichlorophenyl)-6-(ethylthio)-1,2,3,4,4a,9b,-hexahydro[1]benzofuro[3,2-c]pyridine;

8-(2,4,6-trichlorophenyl)-6-(propylthio)-1,2,3,4,4a,9b,-hexahydro[1]benzofuro[3,2-c]pyridine;

8-(2,4,6-trichlorophenyl)-6-(isopropylthio)-1,2,3,4,4a,9b,-hexahydro[1]benzofuro[3,2-c]pyridin;

8-(2,4,6-trichlorophenyl)-6-(butylthio)-1,2,3,4,4a,9b,-hexahydro[1]benzofuro[3,2-c]pyridine;

8-(2,4,6-trichlorophenyl)-6-[(1-ethylpropyl)thio]-1,2,3,4,4a,9b,-hexahydro[1]benzofuro[3,2-c]pyridine;

8-(2,4,6-trichlorophenyl)-6-(cyclohexylthio)-1,2,3,4,4a,9b,-hexahydro[1]benzofuro[3,2-c]pyridine;

8-(2,4,6-trichlorophenyl)-6-(phenylthio)-1,2,3,4,4a,9b,-hexahydro[1]benzofuro[3,2-c]pyridine;

8-(2,4,6-trichlorophenyl)-6-(benzylthio)-1,2,3,4,4a,9b,-hexahydro[1]benzofuro[3,2-c]pyridine;

8-(2,6-difluoro-4-chlorophenyl)-6-(methylthio)-1,2,3,4,4a,9b,-hexahydro[1]benzofuro[3,2-c]pyridine;

8-(2,6-difluoro-4-chlorophenyl)-6-(ethylthio)-1,2,3,4,4a,9b,-hexahydro[1]benzofuro[3,2-c]pyridine;

8-(2,6-difluoro-4-chlorophenyl)-6-(propylthio)-1,2,3,4,4a,9b,-hexahydro[1]benzofuro[3,2-c]pyridine;

8-(2,6-difluoro-4-chlorophenyl)-6-(isopropylthio)-1,2,3,4,4a,9b,-hexahydro[1]benzofuro[3,2-c]pyridine;

8-(2,6-difluoro-4-chlorophenyl)-6-(butylthio)-1,2,3,4,4a,9b,-hexahydro[1]benzofuro[3,2-c]pyridine;

8-(2,6-difluoro-4-chlorophenyl)-6-[(1-ethylpropyl)thio]-1,2,3,4,4a,9b,-hexahydro[1]benzofuro[3,2-c]pyridine;

8-(2,6-difluoro-4-chlorophenyl)-6-(cyclohexylthio)-1,2,3,4,4a,9b,-hexahydro[1]benzofuro[3,2-c]pyridine;

8-(2,6-difluoro-4-chlorophenyl)-6-(phenylthio)-1,2,3,4,4a,9b,-hexahydro[1]benzofuro[3,2-c]pyridine;

8-(2,6-difluoro-4-chlorophenyl)-6-(benzylthio)-1,2,3,4,4a,9b,-hexahydro[1]benzofuro[3,2-c]pyridine;

8-(2,4-dichlorophenyl)-6-methoxy-1,2,3,4,4a,9b,-hexahydro[1]benzofuro[3,2-c]pyridine;

8-(2,4-dichlorophenyl)-6-ethoxy-1,2,3,4,4a,9b,-hexahydro[1]benzofuro[3,2-c]pyridine;

8-(2,4-dichlorophenyl)-6-propoxy-1,2,3,4,4a,9b,-hexahydro[1]benzofuro[3,2-c]pyridine;

8-(2,4-dichlorophenyl)-6-isopropoxy-1,2,3,4,4a,9b,-hexahydro[1]benzofuro[3,2-c]pyridine;

8-(2,4-dichlorophenyl)-6-butoxy-1,2,3,4,4a,9b,-hexahydro[1]benzofuro[3,2-c]pyridine;

8-(2,4-dichlorophenyl)-6-[(1-ethylpropyl)oxy]-1,2,3,4,4a,9b,-hexahydro[1]benzofuro[3,2-c]pyridine;

8-(2,4-dichlorophenyl)-6-(cyclohexyloxy)-1,2,3,4,4a,9b,-hexahydro[1]benzofuro[3,2-c]pyridine;

8-(2,4-dichlorophenyl)-6-phenoxy-1,2,3,4,4a,9b,-hexahydro[1]benzofuro[3,2-c]pyridine;

8-(2,4-dichlorophenyl)-6-(benzyloxy)-1,2,3,4,4a,9b,-hexahydro[1]benzofuro[3,2-c]pyridine;

8-(2,4,6-trichlorophenyl)-6-methoxy-1,2,3,4,4a,9b,-hexahydro[1]benzofuro[3,2-c]pyridine;

8-(2,4,6-trichlorophenyl)-6-ethoxy-1,2,3,4,4a,9b,-hexahydro[1]benzofuro[3,2-c]pyridine;

8-(2,4,6-trichlorophenyl)-6-propoxy-1,2,3,4,4a,9b,-hexahydro[1]benzofuro[3,2-c]pyridine;

8-(2,4,6-trichlorophenyl)-6-isopropoxy-1,2,3,4,4a,9b,-hexahydro[1]benzofuro[3,2-c]pyridine;

8-(2,4,6-trichlorophenyl)-6-butoxy-1,2,3,4,4a,9b,-hexahydro[1]benzofuro[3,2-c]pyridine;

8-(2,4,6-trichlorophenyl)-6-[(1-ethylpropyl)oxy]-1,2,3,4,4a,9b,-hexahydro[1]benzofuro[3,2-c]pyridine;

8-(2,4,6-trichlorophenyl)-6-(cyclohexyloxy)-1,2,3,4,4a,9b,-hexahydro[1]benzofuro[3,2-c]pyridine;

8-(2,4,6-trichlorophenyl)-6-phenoxy-1,2,3,4,4a,9b,-hexahydro[1]benzofuro[3,2-c]pyridine;

8-(2,4,6-trichlorophenyl)-6-(benzyloxy)-1,2,3,4,4a,9b,-hexahydro[1]benzofuro[3,2-c]pyridine;

8-(2,6-difluoro-4-chlorophenyl)-6-methoxy-1,2,3,4,4a,9b,-hexahydro[1]benzofuro[3,2-c]pyridine;

8-(2,6-difluoro-4-chlorophenyl)-6-ethoxy-1,2,3,4,4a,9b,-hexahydro[1]benzofuro[3,2-c]pyridine;

8-(2,6-difluoro-4-chlorophenyl)-6-propoxy-1,2,3,4,4a,9b,-hexahydro[1]benzofuro[3,2-c]pyridine;

8-(2,6-difluoro-4-chlorophenyl)-6-(2-propoxy)-1,2,3,4,4a,9b,-hexahydro[1]benzofuro[3,2-c]pyridine;

8-(2,6-difluoro-4-chlorophenyl)-6-butoxy-1,2,3,4,4a,9b,-hexahydro[1]benzofuro[3,2-c]pyridine;

8-(2,6-difluoro-4-chlorophenyl)-6-[(1-ethylpropyl)oxy]-1,2,3,4,4a,9b,-hexahydro[1]benzofuro[3,2-c]pyridine;

8-(2,6-difluoro-4-chlorophenyl)-6-(cyclohexyloxy)-1,2,3,4,4a,9b,-hexahydro[1]benzofuro[3,2-c]pyridine;

8-(2,6-difluoro-4-chlorophenyl)-6-phenoxy-1,2,3,4,4a,9b,-hexahydro[1]benzofuro[3,2-c]pyridine;

8-(2,6-difluoro-4-chlorophenyl)-6-(benzyloxy)-1,2,3,4,4a,9b,-hexahydro[1]benzofuro[3,2-c]pyridine;

8-(2,4-dichlorophenyl)-6-piperidin-1-yl-1,2,3,4,4a,9b-hexahydro[1]benzofuro[3,2-c]pyridine;

8-(2,4,6-trichlorophenyl)-6-piperidin-1-yl-1,2,3,4,4a,9b-hexahydro[1]benzofuro[3,2-c]pyridine;

8-(2,6-difluoro-4-chlorophenyl)-6-piperidin-1-yl-1,2,3,4,4a,9b-hexahydro[1]benzofuro[3,2-c]pyridine;

8-(2,4-dichlorophenyl)-6-azepano-1-yl-1,2,3,4,4a,9b-hexahydro[1]benzofuro[3,2-c]pyridine;

8-(2,4,6-trichlorophenyl)-6-azepano-1-yl-1,2,3,4,4a,9b-hexahydro[1]benzofuro[3,2-c]pyridine;

8-(2,6-difluoro-4-chlorophenyl)-6-azepano-1-yl-1,2,3,4,4a,9b-hexahydro[1]benzofuro[3,2-c]pyridine;

8-(2,4-dichlorophenyl)-6-pyrrolidin-1-yl-1,2,3,4,4a,9b-hexahydro[1]benzofuro[3,2-c]pyridine;

8-(2,4,6-trichlorophenyl)-6-pyrrolidin-1-yl-1,2,3,4,4a,9b-hexahydro[1]benzofuro[3,2-c]pyridine;

8-(2,6-difluoro-4-chlorophenyl)-6-pyrrolidin-1-yl-1,2,3,4,4a,9b-hexahydro[1]benzofuro[3,2-c]pyridine;

8-(2,4-dichlorophenyl)-5-morpholin-4-yl-1,2,3,4,4a,9b-hexahydro[1]benzofuro[3,2-c]pyridine;

8-(2,4,6-trichlorophenyl)-5-morpholin-4-yl-1,2,3,4,4a,9b-hexahydro[1]benzofuro[3,2-c]pyridine;

8-(2,6-difluoro-4-chlorophenyl)-5-morpholin-4-yl-1,2,3,4,4a,9b-hexahydro[1]benzofuro[3,2-c]pyridine;

8-(2,4-dichlorophenyl)-6-thiomorpholin-4-yl-1,2,3,4,4a,9b-hexahydro-[1]benzofuro[3,2-c]pyridine;

8-(2,4,6-trichlorophenyl)-6-thiomorpholin-4-yl-1,2,3,4,4a,9b-hexahydro[1]benzofuro[3,2-c]pyridine;

8-(2,6-difluoro-4-chlorophenyl)-6-thiomorpholin-4-yl-1,2,3,4,4a,9b-hexahydro[1]benzofuro[3,2-c]pyridine;

8-(2,4-dichlorophenyl)-6-piperazin-1-yl-1,2,3,4,4a,9b-hexahydro[1]benzofuro[3,2-c]pyridine;

8-(2,4,6-trichlorophenyl)-6-piperazin-1-yl-1,2,3,4,4a,9b-hexahydro[1]benzofuro[3,2-c]pyridine;

8-(2,6-difluoro-4-chlorophenyl)-6-piperazin-1-yl-1,2,3,4,4a,9b-hexahydro[1]benzofuro[3,2-c]pyridine;

8-(2,4,6-trichlorophenyl)-N,N-dipropyl-1,2,3,4,4a,9b,-hexahydro[1]benzofuro[3,2-c]pyridin-6-amine;

8-(2,6-difluoro-4-chlorophenyl)-N,N-dipropyl-1,2,3,4,4a,9b,-hexahydro[1]benzofuro[3,2-c]pyridin-6-amine;

8-(2,4-Dichlorophenyl)-1,2,3,4,4a,9b-hexahydro[1]benzofuro[3,2-c]pyridine;

1,2,3,4,4a,9b-Hexahydro[1]benzofuro[3,2-c]pyridine;

8-[2-(Trifluoromethyl)phenyl]-1,2,3,4,4a,9b-hexahydro[1]benzofuro[3,2-c]pyridine;

8-[2-(Trifluoromethoxy)phenyl]-1,2,3,4,4a,9b-hexahydro[1]benzofuro[3,2-c]pyridine;

6-Bromo-8-(2,4-dichlorophenyl)-1,2,3,4,4a,9b-hexahydro[1]benzofuro[3,2-c]pyridine;

6-Benzyl-8-(2,4-dichlorophenyl)-1,2,3,4,4a,9b-hexahydro[1]benzofuro[3,2-c]pyridine;

6-Butyl-8-(2,4-dichlorophenyl)-1,2,3,4,4a,9b-hexahydro[1]benzofuro[3,2-c]pyridine;

8-(2,4-Dichlorophenyl)-6-(propylthio)-1,2,3,4,4a,9b,-hexahydro[1]benzofuro[3,2-c]pyridine;

8-(2,4-Dichlorophenyl)-6-(isopropylthio)-1,2,3,4,4a,9b,-hexahydro[1]benzofuro[3,2-c]pyridine;

8-(2,4-Dichlorophenyl)-6-(isobutylthio)-1,2,3,4,4a,9b,-hexahydro[1]benzofuro[3,2-c]pyridine;

8-(2,4-Dichlorophenyl)-6-(methylthio)-1,2,3,4,4a,9b,-hexahydro[1]benzofuro[3,2-c]pyridine;

6-(Cyclopentylthio)-8-(2,4-dichlorophenyl)-1,2,3,4,4a,9b-hexahydro[1]benzofuro[3,2-c]pyridine;

6-(Cyclobutylthio)-8-(2,4-dichlorophenyl)-1,2,3,4,4a,9b,-hexahydro[1]benzofuro[3,2-c]pyridine;

8-(2,4-dichlorophenyl)-6-morpholin-4-yl-1,2,3,4,4a,9b-hexahydro[1]benzofuro[3,2-c]pyridine;

N-Benzyl-8-(2,4-dichlorophenyl)-1,2,3,4,4a,9b-hexahydro[1]benzofuro[3,2-c]pyridin-6-amine;

8-(2,4-Dichlorophenyl)-6-pyrrolidin-1-yl-1,2,3,4,4a,9b-hexahydro[1]benzofuro[3,2-c]pyridine;

8-(2,4-Dichlorophenyl)-6-methoxy-1,2,3,4,4a,9b-hexahydro[1]benzofuro[3,2-c]pyridine;

or a pharmaceutically acceptable salt thereof.

40. The compound of claim 1, wherein the compound is:

(4aS,9bR)-8-(2,4-dichlorophenyl)-N-cyclohexyl-1,2,3,4,4a,9b,-hexahydro[1]benzofuro[3,2-c]pyridin-6-amine;

(4aS,9bR)-8-(2,4,6-trichlorophenyl)-N-cyclohexyl-1,2,3,4,4a,9b,-hexahydro[1]benzofuro[3,2-c]pyridin-6-amine;

(4aS,9bR)-8-(2,6-difluoro-4-chlorophenyl)-N-cyclohexyl-1,2,3,4,4a,9b,-hexahydro[1]benzofuro[3,2-c]pyridin-6-amine;

(4aS,9bR)-8-(2,4-dichlorophenyl)-N-phenyl-1,2,3,4,4a,9b,-hexahydro[1]benzofuro[3,2-c]pyridin-6-amine;

(4aS,9bR)-8-(2,4,6-trichlorophenyl)-N-phenyl-1,2,3,4,4a,9b,-hexahydro[1]benzofuro[3,2-c]pyridin-6-amine;

(4aS,9bR)-8-(2,6-difluoro-4-chlorophenyl)-N-phenyl-1,2,3,4,4a,9b,-hexahydro[1]benzofuro[3,2-c]pyridin-6-amine;

(4aS,9bR)-8-(2,4-dichlorophenyl)-N,N-dimethyl-1,2,3,4,4a,9b,-hexahydro[1]benzofuro[3,2-c]pyridin-6-amine;

(4aS,9bR)-8-(2,4,6-trichlorophenyl)-N,N-dimethyl-1,2,3,4,4a,9b,-hexahydro[1]benzofuro[3,2-c]pyridin-6-amine;

(4aS,9bR)-8-(2,6-difluoro-4-chlorophenyl)-N,N-dimethyl-1,2,3,4,4a,9b,-hexahydro[1]benzofuro[3,2-c]pyridin-6-amine;

(4aS,9bR)-8-(2,4-dichlorophenyl)-N,N-diethyl-1,2,3,4,4a,9b,-hexahydro[1]benzofuro[3,2-c]pyridin-6-amine;

(4aS,9bR)-8-(2,4,6-trichlorophenyl)-N,N-diethyl-1,2,3,4,4a,9b,-hexahydro[1]benzofuro[3,2-c]pyridin-6-amine;

(4aS,9bR)-8-(2,6-difluoro-4-chlorophenyl)-N,N-diethyl-1,2,3,4,4a,9b,-hexahydro[1]benzofuro[3,2-c]pyridin-6-amine;

(4aS,9bR)-8-(2,4-dichlorophenyl)-N-methyl-N-ethyl-1,2,3,4,4a,9b,-hexahydro[1]benzofuro[3,2-c]pyridin-6-amine;

(4aS,9bR)-8-(2,4-dichlorophenyl)-N-methyl-N-propyl-1,2,3,4,4a,9b,-hexahydro[1]benzofuro[3,2-c]pyridin-6-amine;

(4aS,9bR)-8-(2,4-dichlorophenyl)-N-methyl-N-cyclohexyl-1,2,3,4,4a,9b,-hexahydro[1]benzofuro[3,2-c]pyridin-6-amine;

(4aS,9bR)-8-(2,4-dichlorophenyl)-N-ethyl-N-propyl-1,2,3,4,4a,9b,-hexahydro[1]benzofuro[3,2-c]pyridin-6-amine;

(4aS,9bR)-8-(2,4-dichlorophenyl)-N-ethyl-N-cyclohexyl-1,2,3,4,4a,9b,-hexahydro[1]benzofuro[3,2-c]pyridin-6-amine;

(4aS,9bR)-8-(2,4-dichlorophenyl)-N,N-dipropyl-1,2,3,4,4a,9b,-hexahydro[1]benzofuro[3,2-c]pyridin-6-amine;

(4aS,9bR)-8-(2,4-dichlorophenyl)-N-propyl-N-cyclohexyl-1,2,3,4,4a,9b,-hexahydro[1]benzofuro[3,2-c]pyridin-6-amine;

(4aS,9bR)-8-(2,4-dichlorophenyl)-N,N-dicyclohexyl-1,2,3,4,4a,9b,-hexahydro[1]benzofuro[3,2-c]pyridin-6-amine;

(4aS,9bR)-8-(2,4-dichlorophenyl)-6-methyl-1,2,3,4,4a,9b,-hexahydro[1]benzofuro[3,2-c]pyridine;

(4aS,9bR)-8-(2,4-dichlorophenyl)-6-ethyl-1,2,3,4,4a,9b,-hexahydro[1]benzofuro[3,2-c]pyridine;

(4aS,9bR)-8-(2,4-dichlorophenyl)-6-propyl-1,2,3,4,4a,9b,-hexahydro[1]benzofuro[3,2-c]pyridine;

(4aS,9bR)-8-(2,4-dichlorophenyl)-6-(isopropyl)-1,2,3,4,4a,9b,-hexahydro[1]benzofuro[3,2-c]pyridine;

(4aS,9bR)-8-(2,4-dichlorophenyl)-6-butyl-1,2,3,4,4a,9b,-hexahydro[1]benzofuro[3,2-c]pyridine;

(4aS,9bR)-8-(2,4-dichlorophenyl)-6-(1-ethylpropyl)-1,2,3,4,4a,9b,-hexahydro[1]benzofuro[3,2-c]pyridine;

(4aS,9bR)-8-(2,4-dichlorophenyl)-6-cyclohexyl-1,2,3,4,4a,9b,-hexahydro[1]benzofuro[3,2-c]pyridine;

(4aS,9bR)-8-(2,4-dichlorophenyl)-6-phenyl-1,2,3,4,4a,9b,-hexahydro[1]benzofuro[3,2-c]pyridine;

(4aS,9bR)-8-(2,4-dichlorophenyl)-6-benzyl-1,2,3,4,4a,9b,-hexahydro[1]benzofuro[3,2-c]pyridine;

(4aS,9bR)-8-(2,4,6-trichlorophenyl)-6-methyl-1,2,3,4,4a,9b,-hexahydro[1]benzofuro[3,2-c]pyridine;

(4aS,9bR)-8-(2,4,6-trichlorophenyl)-6-ethyl-1,2,3,4,4a,9b,-hexahydro[1]benzofuro[3,2-c]pyridine;

(4aS,9bR)-8-(2,4,6-trichlorophenyl)-6-propyl-1,2,3,4,4a,9b,-hexahydro[1]benzofuro[3,2-c]pyridine;

(4aS,9bR)-8-(2,4,6-trichlorophenyl)-6-(isopropyl)-1,2,3,4,4a,9b,-hexahydro[1]benzofuro[3,2-c]pyridine;

(4aS,9bR)-8-(2,4,6-trichlorophenyl)-6-butyl-1,2,3,4,4a,9b,-hexahydro[1]benzofuro[3,2-c]pyridine;

(4aS,9bR)-8-(2,4,6-trichlorophenyl)-6-(1-ethylpropyl)-1,2,3,4,4a,9b,-hexahydro[1]benzofuro[3,2-c]pyridine;

(4aS,9bR)-8-(2,4,6-trichlorophenyl)-6-cyclohexyl-1,2,3,4,4a,9b,-hexahydro[1]benzofuro[3,2-c]pyridine;

(4aS,9bR)-8-(2,4,6-trichlorophenyl)-6-phenyl-1,2,3,4,4a,9b,-hexahydro[1]benzofuro[3,2-c]pyridine;

(4aS,9bR)-8-(2,4,6-trichlorophenyl)-6-benzyl-1,2,3,4,4a,9b,-hexahydro[1]benzofuro[3,2-c]pyridine;

(4aS,9bR)-8-(2,6-difluoro-4-chlorophenyl)-6-methyl-1,2,3,4,4a,9b,-hexahydro[1]benzofuro[3,2-c]pyridine;

(4aS,9bR)-8-(2,6-difluoro-4-chlorophenyl)-6-ethyl-1,2,3,4,4a,9b,-hexahydro[1]benzofuro[3,2-c]pyridine;

(4aS,9bR)-8-(2,6-difluoro-4-chlorophenyl)-6-propyl-1,2,3,4,4a,9b,-hexahydro[1]benzofuro[3,2-c]pyridine;

(4aS,9bR)-8-(2,6-difluoro-4-chlorophenyl)-6-(isopropyl)-1,2,3,4,4a,9b,-hexahydro[1]benzofuro[3,2-c]pyridine;

(4aS,9bR)-8-(2,6-difluoro-4-chlorophenyl)-6-butyl-1,2,3,4,4a,9b,-hexahydro[1]benzofuro[3,2-c]pyridine;

(4aS,9bR)-8-(2,6-difluoro-4-chlorophenyl)-6-(1-ethylpropyl)-1,2,3,4,4a,9b,-hexahydro[1]benzofuro[3,2-c]pyridine;

(4aS,9bR)-8-(2,6-difluoro-4-chlorophenyl)-6-cyclohexyl-1,2,3,4,4a,9b,-hexahydro[1]benzofuro[3,2-c]pyridine;

(4aS,9bR)-8-(2,6-difluoro-4-chlorophenyl)-6-phenyl-1,2,3,4,4a,9b,-hexahydro[1]benzofuro[3,2-c]pyridine;

(4aS,9bR)-8-(2,6-difluoro-4-chlorophenyl)-6-benzyl-1,2,3,4,4a,9b,-hexahydro[1]benzofuro[3,2-c]pyridine;

(4aS,9bR)-8-(2,4-dichlorophenyl)-6-(methylthio)-1,2,3,4,4a,9b,-hexahydro[1]benzofuro[3,2-c]pyridine;

(4aS,9bR)-8-(2,4-dichlorophenyl)-6-(ethylthio)-1,2,3,4,4a,9b,-hexahydro[1]benzofuro[3,2-c]pyridine;

(4aS,9bR)-8-(2,4-dichlorophenyl)-6-(propylthio)-1,2,3,4,4a,9b,-hexahydro[1]benzofuro[3,2-c]pyridine;

(4aS,9bR)-8-(2,4-dichlorophenyl)-6-(2-propylthio)-1,2,3,4,4a,9b,-hexahydro[1]benzofuro[3,2-c]pyridine;

(4aS,9bR)-8-(2,4-dichlorophenyl)-6-(butylthio)-1,2,3,4,4a,9b,-hexahydro[1]benzofuro[3,2-c]pyridine;

(4aS,9bR)-8-(2,4-dichlorophenyl)-6-[(1-ethylpropyl)thio]-1,2,3,4,4a,9b,-hexahydro[1]benzofuro[3,2-c]pyridine;

(4aS,9bR)-8-(2,4-dichlorophenyl)-6-(cyclohexylthio)-1,2,3,4,4a,9b,-hexahydro[1]benzofuro[3,2-c]pyridine;

(4aS,9bR)-8-(2,4-dichlorophenyl)-6-(phenylthio)-1,2,3,4,4a,9b,-hexahydro[1]benzofuro[3,2-c]pyridine;

(4aS,9bR)-8-(2,4-dichlorophenyl)-6-(benzylthio)-1,2,3,4,4a,9b,-hexahydro[1]benzofuro[3,2-c]pyridine;

(4aS,9bR)-8-(2,4,6-trichlorophenyl)-6-(methylthio)-1,2,3,4,4a,9b,-hexahydro[1]benzofuro[3,2-c]pyridine;

(4aS,9bR)-8-(2,4,6-trichlorophenyl)-6-(ethylthio)-1,2,3,4,4a,9b,-hexahydro[1]benzofuro[3,2-c]pyridine;

(4aS,9bR)-8-(2,4,6-trichlorophenyl)-6-(propylthio)-1,2,3,4,4a,9b,-hexahydro[1]benzofuro[3,2-c]pyridine;

(4aS,9bR)-8-(2,4,6-trichlorophenyl)-6-(2-propylthio)-1,2,3,4,4a,9b,-hexahydro[1]benzofuro[3,2-c]pyridine;

(4aS,9bR)-8-(2,4,6-trichlorophenyl)-6-(butylthio)-1,2,3,4,4a,9b,-hexahydro[1]benzofuro[3,2-c]pyridine;

(4aS,9bR)-8-(2,4,6-trichlorophenyl)-6-[(1-ethylpropyl)thio]-1,2,3,4,4a,9b,-hexahydro[1]benzofuro[3,2-c]pyridine;

(4aS,9bR)-8-(2,4,6-trichlorophenyl)-6-(cyclohexylthio)-1,2,3,4,4a,9b,-hexahydro[1]benzofuro[3,2-c]pyridine;

(4aS,9bR)-8-(2,4,6-trichlorophenyl)-6-(phenylthio)-1,2,3,4,4a,9b,-hexahydro[1]benzofuro[3,2-c]pyridine;

(4aS,9bR)-8-(2,4,6-trichlorophenyl)-6-(benzylthio)-1,2,3,4,4a,9b,-hexahydro[1]benzofuro[3,2-c]pyridine;

(4aS,9bR)-8-(2,6-difluoro-4-chlorophenyl)-6-(methylthio)-1,2,3,4,4a,9b,-hexahydro[1]benzofuro[3,2-c]pyridine;

(4aS,9bR)-8-(2,6-difluoro-4-chlorophenyl)-6-(ethylthio)-1,2,3,4,4a,9b,-hexahydro[1]benzofuro[3,2-c]pyridine;

(4aS,9bR)-8-(2,6-difluoro-4-chlorophenyl)-6-(propylthio)-1,2,3,4,4a,9b,-hexahydro[1]benzofuro[3,2-c]pyridine;

(4aS,9bR)-8-(2,6-difluoro-4-chlorophenyl)-6-(isopropyl)-1,2,3,4,4a,9b,-hexahydro[1]benzofuro[3,2-c]pyridine;

(4aS,9bR)-8-(2,6-difluoro-4-chlorophenyl)-6-(butylthio)-1,2,3,4,4a,9b,-hexahydro[1]benzofuro[3,2-c]pyridine;

(4aS,9bR)-8-(2,6-difluoro-4-chlorophenyl)-6-[(1-ethylpropyl)thio]-1,2,3,4,4a,9b,-hexahydro[1]benzofuro[3,2-c]pyridine;

(4aS,9bR)-8-(2,6-difluoro-4-chlorophenyl)-6-(cyclohexylthio)-1,2,3,4,4a,9b,-hexahydro[1]benzofuro[3,2-c]pyridine;

(4aS,9bR)-8-(2,6-difluoro-4-chlorophenyl)-6-(phenylthio)-1,2,3,4,4a,9b,-hexahydro[1]benzofuro[3,2-c]pyridine;

(4aS,9bR)-8-(2,6-difluoro-4-chlorophenyl)-6-(benzylthio)-1,2,3,4,4a,9b,-hexahydro[1]benzofuro[3,2-c]pyridine;

(4aS,9bR)-8-(2,4-dichlorophenyl)-6-methoxy-1,2,3,4,4a,9b,-hexahydro[1]benzofuro[3,2-c]pyridine;

(4aS,9bR)-8-(2,4-dichlorophenyl)-6-ethoxy-1,2,3,4,4a,9b,-hexahydro[1]benzofuro[3,2-c]pyridine;

(4aS,9bR)-8-(2,4-dichlorophenyl)-6-propoxy-1,2,3,4,4a,9b,-hexahydro[1]benzofuro[3,2-c]pyridine;

(4aS,9bR)-8-(2,4-dichlorophenyl)-6-isopropoxy-1,2,3,4,4a,9b,-hexahydro[1]benzofuro[3,2-c]pyridine;

(4aS,9bR)-8-(2,4-dichlorophenyl)-6-butoxy-1,2,3,4,4a,9b,-hexahydro[1]benzofuro[3,2-c]pyridine;

(4aS,9bR)-8-(2,4-dichlorophenyl)-6-[(1-ethylpropyl)oxy]-1,2,3,4,4a,9b,-hexahydro[1]benzofuro[3,2-c]pyridine;

(4aS,9bR)-8-(2,4-dichlorophenyl)-6-(cyclohexyloxy)-1,2,3,4,4a,9b,-hexahydro[1]benzofuro[3,2-c]pyridine;

(4aS,9bR)-8-(2,4-dichlorophenyl)-6-phenoxy-1,2,3,4,4a,9b,-hexahydro[1]benzofuro[3,2-c]pyridine;

(4aS,9bR)-8-(2,4-dichlorophenyl)-6-(benzyloxy)-1,2,3,4,4a,9b,-hexahydro[1]benzofuro[3,2-c]pyridine;

(4aS,9bR)-8-(2,4,6-trichlorophenyl)-6-methoxy-1,2,3,4,4a,9b,-hexahydro[1]benzofuro[3,2-c]pyridine;

(4aS,9bR)-8-(2,4,6-trichlorophenyl)-6-ethoxy-1,2,3,4,4a,9b,-hexahydro[1]benzofuro[3,2-c]pyridine;

(4aS,9bR)-8-(2,4,6-trichlorophenyl)-6-propoxy-1,2,3,4,4a,9b,-hexahydro[1]benzofuro[3,2-c]pyridine;

(4aS,9bR)-8-(2,4,6-trichlorophenyl)-6-isopropoxy-1,2,3,4,4a,9b,-hexahydro[1]benzofuro[3,2-c]pyridine;

(4aS,9bR)-8-(2,4,6-trichlorophenyl)-6-butoxy-1,2,3,4,4a,9b,-hexahydro[1]benzofuro[3,2-c]pyridine;

(4aS,9bR)-8-(2,4,6-trichlorophenyl)-6-[(1-ethylpropyl)oxy]-1,2,3,4,4a,9b,-hexahydro[1]benzofuro[3,2-c]pyridine;

(4aS,9bR)-8-(2,4,6-trichlorophenyl)-6-(cyclohexyloxy)-1,2,3,4,4a,9b,-hexahydro[1]benzofuro[3,2-c]pyridine;

(4aS,9bR)-8-(2,4,6-trichlorophenyl)-6-phenoxy-1,2,3,4,4a,9b,-hexahydro[1]benzofuro[3,2-c]pyridine;

(4aS,9bR)-8-(2,4,6-trichlorophenyl)-6-(benzyloxy)-1,2,3,4,4a,9b,-hexahydro[1]benzofuro[3,2-c]pyridine;

(4aS,9bR)-8-(2,6-difluoro-4-chlorophenyl)-6-methoxy-1,2,3,4,4a,9b,-hexahydro[1]benzofuro[3,2-c]pyridine;

(4aS,9bR)-8-(2,6-difluoro-4-chlorophenyl)-6-ethoxy-1,2,3,4,4a,9b,-hexahydro[1]benzofuro[3,2-c]pyridine;

(4aS,9bR)-8-(2,6-difluoro-4-chlorophenyl)-6-propoxy-1,2,3,4,4a,9b,-hexahydro[1]benzofuro[3,2-c]pyridine;

(4aS,9bR)-8-(2,6-difluoro-4-chlorophenyl)-6-(2-propoxy)-1,2,3,4,4a,9b,-hexahydro[1]benzofuro[3,2-c]pyridine;

(4aS,9bR)-8-(2,6-difluoro-4-chlorophenyl)-6-butoxy-1,2,3,4,4a,9b,-hexahydro[1]benzofuro[3,2-c]pyridine;

(4aS,9bR)-8-(2,6-difluoro-4-chlorophenyl)-6-[(1-ethylpropyl)oxy]-1,2,3,4,4a,9b,-hexahydro[1]benzofuro[3,2-c]pyridine;

(4aS,9bR)-8-(2,6-difluoro-4-chlorophenyl)-6-(cyclohexyloxy)-1,2,3,4,4a,9b,-hexahydro[1]benzofuro[3,2-c]pyridine;

(4aS,9bR)-8-(2,6-difluoro-4-chlorophenyl)-6-phenoxy-1,2,3,4,4a,9b,-hexahydro[1]benzofuro[3,2-c]pyridine;

(4aS,9bR)-8-(2,6-difluoro-4-chlorophenyl)-6-(benzyloxy)-1,2,3,4,4a,9b,-hexahydro[1]benzofuro[3,2-c]pyridine;

(4aS,9bR)-8-(2,4-dichlorophenyl)-6-piperidin-1-yl-1,2,3,4,4a,9b-hexahydro[1]benzofuro[3,2-c]pyridine;

(4aS,9bR)-8-(2,4,6-trichlorophenyl)-6-piperidin-1-yl-1,2,3,4,4a,9b-hexahydro[1]benzofuro[3,2-c]pyridine;

(4aS,9bR)-8-(2,6-difluoro-4-chlorophenyl)-6-piperidin-1-yl-1,2,3,4,4a,9b-hexahydro[1]benzofuro[3,2-c]pyridine;

(4aS,9bR)-8-(2,4-dichlorophenyl)-6-azepan-1-yl-1,2,3,4,4a,9b-hexahydro[1]benzofuro[3,2-c]pyridine;

(4aS,9bR)-8-(2,4,6-trichlorophenyl)-6-hexahydroazepin-1-yl-1,2,3,4,4a,9b-hexahydro[1]benzofuro[3,2-c]pyridine;

(4aS,9bR)-8-(2,6-difluoro-4-chlorophenyl)-6-hexahydroazepin-1-yl-1,2,3,4,4a,9b-hexahydro[1]benzofuro[3,2-c]pyridine;

(4aS,9bR)-8-(2,4-dichlorophenyl)-6-pyrrolidin-1-yl-1,2,3,4,4a,9b-hexahydro[1]benzofuro[3,2-c]pyridine;

(4aS,9bR)-8-(2,4,6-trichlorophenyl)-6-pyrrolidin-1-yl-1,2,3,4,4a,9b-hexahydro[1]benzofuro[3,2-c]pyridine;

(4aS,9bR)-8-(2,6-difluoro-4-chlorophenyl)-6-pyrrolidin-1-yl-1,2,3,4,4a,9b-hexahydro[1]benzofuro[3,2-c]pyridine;

(4aS,9bR)-8-(2,4-dichlorophenyl)-5-morpholin-4-yl-1,2,3,4,4a,9b-hexahydro-[1]benzofuro[3,2-c]pyridine;

(4aS,9bR)-8-(2,4,6-trichlorophenyl)-5-morpholin-4-yl-1,2,3,4,4a,9b-hexahydro[1]benzofuro[3,2-c]pyridine;

(4aS,9bR)-8-(2,6-difluoro-4-chlorophenyl)-5-morpholin-4-yl-1,2,3,4,4a,9b-hexahydro[1]benzofuro[3,2-c]pyridine;

(4aS,9bR)-8-(2,4-dichlorophenyl)-6-thiomorpholin-4-yl-1,2,3,4,4a,9b-hexahydro[1]benzofuro[3,2-c]pyridine;

(4aS,9bR)-8-(2,4,6-trichlorophenyl)-6-thiomorpholin-4-yl-1,2,3,4,4a,9b-hexahydro[1]benzofuro[3,2-c]pyridine;

(4aS,9bR)-8-(2,6-difluoro-4-chlorophenyl)-6-thiomorpholin-4-yl-1,2,3,4,4a,9b-hexahydro[1]benzofuro[3,2-c]pyridine;

(4aS,9bR)-8-(2,4-dichlorophenyl)-6-piperazin-1-yl-1,2,3,4,4a,9b-hexahydro[1]benzofuro[3,2-c]pyridine;

(4aS,9bR)-8-(2,4,6-trichlorophenyl)-6-piperazin-1-yl-1,2,3,4,4a,9b-hexahydro[1]benzofuro[3,2-c]pyridine;

(4aS,9bR)-8-(2,6-difluoro-4-chlorophenyl)-6-piperazin-1-yl-1,2,3,4,4a,9b-hexahydro[1]benzofuro[3,2-c]pyridine;

(4aS,9bR)-8-(2,4,6-trichlorophenyl)-N,N-dipropyl-1,2,3,4,4a,9b,-hexahydro[1]benzofuro[3,2-c]pyridin-6-amine;

(4aS,9bR)-8-(2,6-difluoro-4-chlorophenyl)-N,N-dipropyl-1,2,3,4,4a,9b,-hexahydro[1]benzofuro[3,2-c]pyridin-6-amine;

(4aS,9bR) 6-Bromo-8-(2,4-dichlorophenyl)-1,2,3,4,4a,9b-hexahydro[1]benzofuro[3,2-c]pyridine;

(4aR,9bS) 6-Bromo-8-(2,4-dichlorophenyl)-1,2,3,4,4a,9b-hexahydro[1]benzofuro[3,2-c]pyridine;

or a pharmaceutically acceptable salt thereof.

41. A pharmaceutical composition comprising a compound of claim 1 and a pharmaceutically acceptable excipient.

42. A method for treating a central nervous system disease or condition in a mammal in need thereof wherein the 5-HT$_{2C}$ receptor is implicated and modulation of 5-HT$_{2C}$ function is desired comprising administering a therapeutically effective amount of a compound of Formula (I) to the mammal, wherein the disease or condition is selected from the group consisting of anxiety, obesity, migraine, depression, schizophrenia, a stress-related disease, psychiatric syndrome, phobias, obsessive compulsive disorder, post-traumatic-stress syndrome, immune system depression, panic disorder, a stress inducted problem with gastrointestinal or cardiovascular system, or sexual dysfunction.

43. The method of claim 42, wherein the disease is anxiety, obesity, depression, or a stress-related disease or panic disorder.

44. A compound of formula (I):

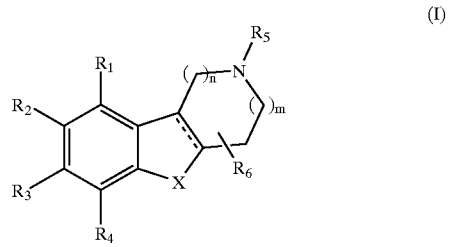

wherein:

$R_1$, $R_3$, and $R_4$ are independently hydrogen, halo, —CF$_3$, —OCF$_3$, —CN, —NO$_2$, —C$_{1-8}$alkyl, —C$_{3-8}$cycloalkyl, —OR$_8$, —NR$_8$R$_9$, —SR$_8$, —C(=O)aryl, aryl, —C$_{1-8}$alkylene(aryl), —C(=O)heteroaryl, heteroaryl, or —C$_{1-8}$alkylene(heteroaryl);

$R_2$ is aryl, optionally substituted with one or more substituents independently selected from halo, hydroxy, cyano, nitro, trifluoromethyl, trifluoromethoxy, C$_{1-6}$alkyl, —OR$_c$, —SR$_c$, phenyl, —NR$_c$R$_d$, or —C(=O)NR$_c$R$_d$;

$R_5$ is hydrogen, C$_{1-8}$alkyl, haloC$_{1-8}$alkyl, C$_{3-8}$cycloalkyl, C$_{1-8}$alkanoyl, haloC$_{1-8}$alkanoyl, —C(=O)OR$_8$, —C(=O)aryl, aryl, —C$_{1-8}$alkylene(aryl), —C(=O)heteroaryl, heteroaryl, or —C$_{1-8}$alkylene(heteroaryl);

$R_6$ is hydrogen or C$_{1-4}$alkyl;

each $R_8$ and $R_9$ is independently hydrogen, C$_{1-8}$alkyl, haloC$_{1-8}$alkyl, C$_{3-8}$cycloalkyl, —C(=O)aryl, aryl, —C$_{1-8}$alkylene(aryl), —C(=O)heteroaryl, heteroaryl, —C$_{1-8}$alkylene(heteroaryl) or $R_8$ and $R_9$ together with the nitrogen to which they are attached form a pyrrolidino, piperidino, azepano, piperazino, morpholino, or thiomorpholino ring;

m is 1;

n is 1;

X is oxy (—O—), thio (—S—) —S(=O)— or —SO$_2$—; and the bond represented by—is absent or present;

wherein any C$_{1-8}$alkyl, C$_{1-8}$alkylene, C$_{1-8}$alkoxy or C$_{3-8}$cycloalkyl of $R_1$, $R_3$, $R_4$, $R_5$, $R_6$, $R_8$ and $R_9$ is optionally partially unsaturated; and wherein any aryl or heteroaryl of $R_1$, $R_2$, $R_3$, $R_4$, $R_5$, $R_8$ or $R_9$ is optionally substituted with one or more substituents independently selected from halo, —CN, —NO$_2$, —CF$_3$, —OCF$_3$, C$_{1-8}$alkyl, C$_{2-8}$alkenyl, C$_{2-8}$alkynyl, C$_{3-8}$cycloalkyl, C$_{3-8}$cycloalkenyl, aryl, heteroaryl, —OR$_c$, —SR$_c$, —C(=O)R$_c$, —CO$_2$R$_c$, —C(=O)NR$_c$R$_d$, NR$_c$C(=O)R$_d$, —C(=O)NR$_c$R$_d$, —NR$_c$R$_d$, —NR$_c$C(=O)NR$_c$R$_d$, —SO$_2$NR$_c$R$_d$ or —SO$_2$R$_c$;

wherein each $R_c$ and $R_d$ is independently hydrogen, C$_{1-8}$alkyl, C$_{1-8}$alkanoyl, C$_{1-8}$alkoxycarbonyl, aryl, —C$_{1-8}$alkylene(aryl), —C(=O)aryl, —C(=O)Oaryl, heteroaryl, —C$_{1-8}$alkylene(heteroaryl), —C(=O)heteroaryl, —C(=O)Oheteroaryl or $R_c$ and $R_d$ together with the nitrogen to which they are attached form a pyrrolidino, piperidino, azepano, piperazino, morpholino, or thiomorpholino ring; or a pharmaceutically acceptable salt thereof.

45. The compound of claim 44, wherein—is absent.

46. The compound of claim 44, wherein $R_2$ is phenyl optionally substituted with one or more substituents independently selected from halo, cyano, nitro, trifluoromethyl, trifluoromethoxy, $C_{1-6}$alkyl, —$OR_c$, —$SR_c$, phenyl, —$NR_cR_d$, or —$C(=O)NR_cR_d$.

47. The compound of claim 46, wherein $R_2$ is phenyl optionally substituted with one or more halo.

48. The compound of claim 47, wherein $R_2$ is phenyl substituted at the 2- or 6-position with fluoro, chloro, or bromo.

49. The compound of claim 47, wherein $R_2$ is phenyl substituted at the 2- and 6-position with halo independently selected from fluoro, chloro, and bromo.

50. The compound of claim 47, wherein $R_2$ is phenyl substituted at the 2- or 4-position with fluoro, chloro, or bromo.

51. The compound of claim 47, wherein $R_2$ is phenyl substituted at the 2- and 4-position with halo independently selected from fluoro, chloro, and bromo.

52. The compound of claim 47, wherein $R_2$ is phenyl substituted at the 2-, 4- and 6-position with halo independently selected from fluoro, chloro, and bromo.

53. The compound of claim 47, wherein $R_2$ is 2,4-dichlorophenyl, 2,4,6-trichlorophenyl, or 2,6-difluoro-4-chlorophenyl.

54. The compound of claim 47, wherein $R_4$ is halo, —$CF_3$, $C_{1-8}$alkyl, —$OR_8$, —$SR_8$, —$NR_8R_9$, aryl, or —$C_{1-8}$alkylene(aryl), wherein aryl is optionally substituted with one or more substituents independently selected from halo, hydroxy, cyano, nitro, trifluoromethyl, trifluoromethoxy, $C_{1-6}$alkyl, $C_{1-6}$alkoxy, phenyl, —$NR_cR_d$, and —$C(=O)NR_cR_d$.

55. The compound of claim 54, wherein $R_4$ is halo, —$CF_3$, $C_{1-8}$alkyl, —$NR_8R_9$, aryl, or —$C_{1-8}$alkylene(aryl), wherein aryl is optionally substituted with one or more substituents independently selected from halo, hydroxy, cyano, nitro, trifluoromethyl, trifluoromethoxy, $C_{1-6}$alkyl, $C_{1-6}$alkoxy, phenyl, —$NR_cR_d$, and —$C(=O)NR_cR_d$.

56. The compound of claim 55, wherein $R_4$ is aryl, —$C_{1-8}$alkylene(aryl), wherein aryl is optionally substituted with one or more substituents independently selected from halo, hydroxy, cyano, nitro, trifluoromethyl, trifluoromethoxy, $C_{1-6}$alkyl, $C_{1-6}$alkoxy, phenyl, —$NR_cR_d$, and —$C(=O)NR_cR_d$, or —$NR_8R_9$, wherein $R_8$ is hydrogen, methyl, ethyl, propyl or cyclohexyl and $R_9$ is methyl, ethyl, propyl, cyclohexyl or phenyl.

57. The compound of claim 55, wherein $R_4$ is halo, —$CF_3$, or —$CH_3$.

58. The compound of claim 44, wherein the compound is:
8-(2,4-dichlorophenyl)-3,4,4a,9b-tetrahydro[1]benzofuro[3,2-c]pyridine;
8-(2,4-dichlorophenyl)-N-cyclohexyl-1,2,3,4,4a,9b,-hexahydro[1]benzofuro[3,2-c]pyridin-6-amine;
8-(2,4,6-trichlorophenyl)-N-cyclohexyl-1,2,3,4,4a,9b,-hexahydro[1]benzofuro[3,2-c]pyridin-6-amine;
8-(2,6-difluoro-4-chlorophenyl)-N-cyclohexyl-1,2,3,4,4a,9b,-hexahydro[1]benzofuro[3,2-c]pyridin-6-amine;
8-(2,4-dichlorophenyl)-N-phenyl-1,2,3,4,4a,9b,-hexahydro[1]benzofuro[3,2-c]pyridin-6-amine;
8-(2,4,6-trichlorophenyl)-N-phenyl-1,2,3,4,4a,9b,-hexahydro[1]benzofuro[3,2-c]pyridin-6-amine;
8-(2,6-difluoro-4-chlorophenyl)-N-phenyl-1,2,3,4,4a,9b,-hexahydro[1]benzofuro[3,2-c]pyridin-6-amine;
8-(2,4-dichlorophenyl)-N,N-dimethyl-1,2,3,4,4a,9b,-hexahydro[1]benzofuro[3,2-c]pyridin-6-amine;
8-(2,4,6-trichlorophenyl)-N,N-dimethyl-1,2,3,4,4a,9b,-hexahydro[1]benzofuro[3,2-c]pyridin-6-amine;
8-(2,6-difluoro-4-chlorophenyl)-N,N-dimethyl-1,2,3,4,4a,9b,-hexahydro[1]benzofuro[3,2-c]pyridin-6-amine;
8-(2,4-dichlorophenyl)-N,N-diethyl-1,2,3,4,4a,9b,-hexahydro[1]benzofuro[3,2-c]pyridin-6-amine;
8-(2,4,6-trichlorophenyl)-N,N-diethyl-1,2,3,4,4a,9b,-hexahydro[1]benzofuro[3,2-c]pyridin-6-amine;
8-(2,6-difluoro-4-chlorophenyl)-N,N-diethyl-1,2,3,4,4a,9b,-hexahydro[1]benzofuro[3,2-c]pyridin-6-amine;
8-(2,4-dichlorophenyl)-N-methyl-N-ethyl-1,2,3,4,4a,9b,-hexahydro[1]benzofuro[3,2-c]pyridin-6-amine;
8-(2,4-dichlorophenyl)-N-methyl-N-propyl-1,2,3,4,4a,9b,-hexahydro[1]benzofuro[3,2-c]pyridin-6-amine;
8-(2,4-dichlorophenyl)-N-methyl-N-cyclohexyl-1,2,3,4,4a,9b,-hexahydro[1]benzofuro[3,2-c]pyridin-6-amine;
8-(2,4-dichlorophenyl)-N-ethyl-N-propyl-1,2,3,4,4a,9b,-hexahydro[1]benzofuro[3,2-c]pyridin-6-amine;
8-(2,4-dichlorophenyl)-N-ethyl-N-cyclohexyl-1,2,3,4,4a,9b,-hexahydro[1]benzofuro[3,2-c]pyridin-6-amine;
8-(2,4-dichlorophenyl)-N,N-dipropyl-1,2,3,4,4a,9b,-hexahydro[1]benzofuro[3,2-c]pyridin-6-amine;
8-(2,4-dichlorophenyl)-N-propyl-N-cyclohexyl-1,2,3,4,4a,9b,-hexahydro[1]benzofuro[3,2-c]pyridin-6-amine;
8-(2,4-dichlorophenyl)-N,N-dicyclohexyl-1,2,3,4,4a,9b,-hexahydro[1]benzofuro[3,2-c]pyridin-6-amine;
8-(2,4-dichlorophenyl)-6-methyl-1,2,3,4,4a,9b,-hexahydro[1]benzofuro[3,2-c]-pyridine;
8-(2,4-dichlorophenyl)-6-ethyl-1,2,3,4,4a,9b,-hexahydro[1]benzofuro[3,2-c]-pyridine;
8-(2,4-dichlorophenyl)-6-propyl-1,2,3,4,4a,9b,-hexahydro[1]benzofuro[3,2-c]-pyridine;
8-(2,4-dichlorophenyl)-6-isopropyl-1,2,3,4,4a,9b,-hexahydro[1]benzofuro[3,2-c]-pyridine;
8-(2,4-dichlorophenyl)-6-butyl-1,2,3,4,4a,9b,-hexahydro[1]benzofuro[3,2-c]-pyridine;
8-(2,4-dichlorophenyl)-6-(1-ethylpropyl)-1,2,3,4,4a,9b,-hexahydro[1]benzofuro[3,2-c]pyridine;
8-(2,4-dichlorophenyl)-6-cyclohexyl-1,2,3,4,4a,9b,-hexahydro[1]benzofuro[3,2-c]pyridine;
8-(2,4-dichlorophenyl)-6-phenyl-1,2,3,4,4a,9b,-hexahydro[1]benzofuro[3,2-c]pyridine;
8-(2,4-dichlorophenyl)-6-benzyl-1,2,3,4,4a,9b,-hexahydro[1]benzofuro[3,2-c]pyridine;
8-(2,4,6-trichlorophenyl)-6-methyl-1,2,3,4,4a,9b,-hexahydro[1]benzofuro[3,2-c]pyridine;
8-(2,4,6-trichlorophenyl)-6-ethyl-1,2,3,4,4a,9b,-hexahydro[1]benzofuro[3,2-c]pyridine;
8-(2,4,6-trichlorophenyl)-6-propyl-1,2,3,4,4a,9b,-hexahydro[1]benzofuro[3,2-c]pyridine;
8-(2,4,6-trichlorophenyl)-6-isopropyl-1,2,3,4,4a,9b,-hexahydro[1]benzofuro[3,2-c]pyridine;
8-(2,4,6-trichlorophenyl)-6-butyl-1,2,3,4,4a,9b,-hexahydro[1]benzofuro[3,2-c]pyridine;
8-(2,4,6-trichlorophenyl)-6-(1-ethylpropyl)-1,2,3,4,4a,9b,-hexahydro[1]benzofuro[3,2-c]pyridine;
8-(2,4,6-trichlorophenyl)-6-cyclohexyl-1,2,3,4,4a,9b,-hexahydro[1]benzofuro[3,2-c]pyridine;
8-(2,4,6-trichlorophenyl)-6-phenyl-1,2,3,4,4a,9b,-hexahydro[1]benzofuro[3,2-c]pyridine;
8-(2,4,6-trichlorophenyl)-6-benzyl-1,2,3,4,4a,9b,-hexahydro[1]benzofuro[3,2-c]pyridine;
8-(2,6-difluoro-4-chlorophenyl)-6-methyl-1,2,3,4,4a,9b,-hexahydro[1]benzofuro[3,2-c]pyridine;
8-(2,6-difluoro-4-chlorophenyl)-6-ethyl-1,2,3,4,4a,9b,-hexahydro[1]benzofuro[3,2-c]pyridine;

8-(2,6-difluoro-4-chlorophenyl)-6-propyl-1,2,3,4,4a,9b,-hexahydro[1]benzofuro[3,2-c]pyridine;

8-(2,6-difluoro-4-chlorophenyl)-6-isopropyl-1,2,3,4,4a,9b,-hexahydro[1]benzofuro[3,2-c]pyridine;

8-(2,6-difluoro-4-chlorophenyl)-6-butyl-1,2,3,4,4a,9b,-hexahydro[1]benzofuro[3,2-c]pyridine;

8-(2,6-difluoro-4-chlorophenyl)-6-(1-ethylpropyl)-1,2,3,4,4a,9b,-hexahydro[1]benzofuro[3,2-c]pyridine;

8-(2,6-difluoro-4-chlorophenyl)-6-cyclohexyl-1,2,3,4,4a,9b,-hexahydro[1]benzofuro[3,2-c]pyridine;

8-(2,6-difluoro-4-chlorophenyl)-6-phenyl-1,2,3,4,4a,9b,-hexahydro[1]benzofuro[3,2-c]pyridine;

8-(2,6-difluoro-4-chlorophenyl)-6-benzyl-1,2,3,4,4a,9b,-hexahydro[1]benzofuro[3,2-c]pyridine;

8-(2,4-dichlorophenyl)-6-(methylthio)-1,2,3,4,4a,9b,-hexahydro[1]benzofuro[3,2-c]pyridine;

8-(2,4-dichlorophenyl)-6-(ethylthio)-1,2,3,4,4a,9b,-hexahydro[1]benzofuro[3,2-c]pyridine;

8-(2,4-dichlorophenyl)-6-(propylthio)-1,2,3,4,4a,9b,-hexahydro[1]benzofuro[3,2-c]pyridine;

8-(2,4-dichlorophenyl)-6-(isopropylthio)-1,2,3,4,4a,9b,-hexahydro[1]benzofuro[3,2-c]pyridine;

8-(2,4-dichlorophenyl)-6-(butylthio)-1,2,3,4,4a,9b,-hexahydro[1]benzofuro[3,2-c]pyridine;

8-(2,4-dichlorophenyl)-6-[(1-ethylpropyl)thio]-1,2,3,4,4a,9b,-hexahydro[1]benzofuro[3,2-c]pyridine;

8-(2,4-dichlorophenyl)-6-(cyclohexylthio)-1,2,3,4,4a,9b,-hexahydro[1]benzofuro[3,2-c]pyridine;

8-(2,4-dichlorophenyl)-6-(phenylthio)-1,2,3,4,4a,9b,-hexahydro[1]benzofuro[3,2-c]pyridine;

8-(2,4-dichlorophenyl)-6-(benzylthio)-1,2,3,4,4a,9b,-hexahydro[1]benzofuro[3,2-c]pyridine;

8-(2,4,6-trichlorophenyl)-6-(methylthio)-1,2,3,4,4a,9b,-hexahydro[1]benzofuro[3,2-c]pyridine;

8-(2,4,6-trichlorophenyl)-6-(ethylthio)-1,2,3,4,4a,9b,-hexahydro[1]benzofuro[3,2-c]pyridine;

8-(2,4,6-trichlorophenyl)-6-(propylthio)-1,2,3,4,4a,9b,-hexahydro[1]benzofuro[3,2-c]pyridine;

8-(2,4,6-trichlorophenyl)-6-(isopropylthio)-1,2,3,4,4a,9b,-hexahydro[1]benzofuro[3,2-c]pyridine;

8-(2,4,6-trichlorophenyl)-6-(butylthio)-1,2,3,4,4a,9b,-hexahydro[1]benzofuro[3,2-c]pyridine;

8-(2,4,6-trichlorophenyl)-6-[(1-ethylpropyl)thio]-1,2,3,4,4a,9b,-hexahydro[1]benzofuro[3,2-c]pyridine;

8-(2,4,6-trichlorophenyl)-6-(cyclohexylthio)-1,2,3,4,4a,9b,-hexahydro[1]benzofuro[3,2-c]pyridine;

8-(2,4,6-trichlorophenyl)-6-(phenylthio)-1,2,3,4,4a,9b,-hexahydro[1]benzofuro[3,2-c]pyridine;

8-(2,4,6-trichlorophenyl)-6-(benzylthio)-1,2,3,4,4a,9b,-hexahydro[1]benzofuro[3,2-c]pyridine;

8-(2,6-difluoro-4-chlorophenyl)-6-(methylthio)-1,2,3,4,4a,9b,-hexahydro[1]benzofuro[3,2-c]pyridine;

8-(2,6-difluoro-4-chlorophenyl)-6-(ethylthio)-1,2,3,4,4a,9b,-hexahydro[1]benzofuro[3,2-c]pyridine;

8-(2,6-difluoro-4-chlorophenyl)-6-(propylthio)-1,2,3,4,4a,9b,-hexahydro[1]benzofuro[3,2-c]pyridine;

8-(2,6-difluoro-4-chlorophenyl)-6-(isopropylthio)-1,2,3,4,4a,9b,-hexahydro[1]benzofuro[3,2-c]pyridine;

8-(2,6-difluoro-4-chlorophenyl)-6-(butylthio)-1,2,3,4,4a,9b,-hexahydro[1]benzofuro[3,2-c]pyridine;

8-(2,6-difluoro-4-chlorophenyl)-6-[(1-ethylpropyl)thio]-1,2,3,4,4a,9b,-hexahydro[1]benzofuro[3,2-c]pyridine;

8-(2,6-difluoro-4-chlorophenyl)-6-(cyclohexylthio)-1,2,3,4,4a,9b,-hexahydro[1]benzofuro[3,2-c]pyridine;

8-(2,6-difluoro-4-chlorophenyl)-6-(phenylthio)-1,2,3,4,4a,9b,-hexahydro[1]benzofuro[3,2-c]pyridine;

8-(2,6-difluoro-4-chlorophenyl)-6-(benzylthio)-1,2,3,4,4a,9b,-hexahydro[1]benzofuro[3,2-c]pyridine;

8-(2,4-dichlorophenyl)-6-methoxy-1,2,3,4,4a,9b,-hexahydro[1]benzofuro[3,2-c]pyridine;

8-(2,4-dichlorophenyl)-6-ethoxy-1,2,3,4,4a,9b,-hexahydro[1]benzofuro[3,2-c]-pyridine;

8-(2,4-dichlorophenyl)-6-propoxy-1,2,3,4,4a,9b,-hexahydro[1]benzofuro[3,2-c]pyridine;

8-(2,4-dichlorophenyl)-6-isopropoxy-1,2,3,4,4a,9b,-hexahydro[1]benzofuro[3,2-c]pyridine;

8-(2,4-dichlorophenyl)-6-butoxy-1,2,3,4,4a,9b,-hexahydro[1]benzofuro[3,2-c]-pyridine;

8-(2,4-dichlorophenyl)-6-[(1-ethylpropyl)oxy]-1,2,3,4,4a,9b,-hexahydro[1]benzofuro[3,2-c]pyridine;

8-(2,4-dichlorophenyl)-6-(cyclohexyloxy)-1,2,3,4,4a,9b,-hexahydro[1]benzofuro[3,2-c]pyridine;

8-(2,4-dichlorophenyl)-6-phenoxy-1,2,3,4,4a,9b,-hexahydro[1]benzofuro[3,2-c]pyridine;

8-(2,4-dichlorophenyl)-6-(benzyloxy)-1,2,3,4,4a,9b,-hexahydro[1]benzofuro[3,2-c]pyridine;

8-(2,4,6-trichlorophenyl)-6-methoxy-1,2,3,4,4a,9b,-hexahydro[1]benzofuro[3,2-c]pyridine;

8-(2,4,6-trichlorophenyl)-6-ethoxy-1,2,3,4,4a,9b,-hexahydro[1]benzofuro[3,2-c]pyridine;

8-(2,4,6-trichlorophenyl)-6-propoxy-1,2,3,4,4a,9b,-hexahydro[1]benzofuro[3,2-c]pyridine;

8-(2,4,6-trichlorophenyl)-6-isopropoxy-1,2,3,4,4a,9b,-hexahydro[1]benzofuro[3,2-c]pyridine;

8-(2,4,6-trichlorophenyl)-6-butoxy-1,2,3,4,4a,9b,-hexahydro[1]benzofuro[3,2-c]pyridine;

8-(2,4,6-trichlorophenyl)-6-[(1-ethylpropyl)oxy]-1,2,3,4,4a,9b,-hexahydro[1]benzofuro[3,2-c]pyridine;

8-(2,4,6-trichlorophenyl)-6-(cyclohexyloxy)-1,2,3,4,4a,9b,-hexahydro[1]benzofuro[3,2-c]pyridine;

8-(2,4,6-trichlorophenyl)-6-phenoxy-1,2,3,4,4a,9b,-hexahydro[1]benzofuro[3,2-c]pyridine;

8-(2,4,6-trichlorophenyl)-6-(benzyloxy)-1,2,3,4,4a,9b,-hexahydro[1]benzofuro[3,2-c]pyridine;

8-(2,6-difluoro-4-chlorophenyl)-6-methoxy-1,2,3,4,4a,9b,-hexahydro[1]benzofuro[3,2-c]pyridine;

8-(2,6-difluoro-4-chlorophenyl)-6-ethoxy-1,2,3,4,4a,9b,-hexahydro[1]benzofuro[3,2-c]pyridine;

8-(2,6-difluoro-4-chlorophenyl)-6-propoxy-1,2,3,4,4a,9b,-hexahydro[1]benzofuro[3,2-c]pyridine;

8-(2,6-difluoro-4-chlorophenyl)-6-(2-propoxy)-1,2,3,4,4a,9b,-hexahydro[1]benzofuro[3,2-c]pyridine;

8-(2,6-difluoro-4-chlorophenyl)-6-butoxy-1,2,3,4,4a,9b,-hexahydro[1]benzofuro[3,2-c]pyridine;

8-(2,6-difluoro-4-chlorophenyl)-6-[(1-ethylpropyl)oxy]-1,2,3,4,4a,9b,-hexahydro[1]benzofuro[3,2-c]pyridine;

8-(2,6-difluoro-4-chlorophenyl)-6-(cyclohexyloxy)-1,2,3,4,4a,9b,-hexahydro[1]benzofuro[3,2-c]pyridine;

8-(2,6-difluoro-4-chlorophenyl)-6-phenoxy-1,2,3,4,4a,9b,-hexahydro[1]benzofuro[3,2-c]pyridine;

8-(2,6-difluoro-4-chlorophenyl)-6-(benzyloxy)-1,2,3,4,4a,9b,-hexahydro[1]benzofuro[3,2-c]pyridine;

8-(2,4-dichlorophenyl)-6-piperidin-1-yl-1,2,3,4,4a,9b-hexahydro[1]benzofuro[3,2-c]pyridine;

8-(2,4,6-trichlorophenyl)-6-piperidin-1-yl-1,2,3,4,4a,9b-hexahydro[1]benzofuro[3,2-c]pyridine;

8-(2,6-difluoro-4-chlorophenyl)-6-piperidin-1-yl-1,2,3,4,4a,9b-hexahydro[1]benzofuro[3,2-c]pyridine;

8-(2,4-dichlorophenyl)-6-azepano-1-yl-1,2,3,4,4a,9b-hexahydro[1]benzofuro[3,2-c]pyridine;

8-(2,4,6-trichlorophenyl)-6-azepano-1-yl-1,2,3,4,4a,9b-hexahydro[1]benzofuro[3,2-c]pyridine;

8-(2,6-difluoro-4-chlorophenyl)-6-azepano-1-yl-1,2,3,4,4a,9b-hexahydro-[1]benzofuro[3,2-c]pyridine;

8-(2,4-dichlorophenyl)-6-pyrrolidin-1-yl-1,2,3,4,4a,9b-hexahydro[1]benzofuro[3,2-c]pyridine;

8-(2,4,6-trichlorophenyl)-6-pyrrolidin-1-yl-1,2,3,4,4a,9b-hexahydro[1]benzofuro[3,2-c]pyridine;

8-(2,6-difluoro-4-chlorophenyl)-6-pyrrolidin-1-yl-1,2,3,4,4a,9b-hexahydro[1]benzofuro[3,2-c]pyridine;

8-(2,4-dichlorophenyl)-5-morpholin-4-yl-1,2,3,4,4a,9b-hexahydro[1]benzofuro[3,2-c]pyridine;

8-(2,4,6-trichlorophenyl)-5-morpholin-4-yl-1,2,3,4,4a,9b-hexahydro[1]benzofuro[3,2-c]pyridine;

8-(2,6-difluoro-4-chlorophenyl)-5-morpholin-4-yl-1,2,3,4,4a,9b-hexahydro[1]benzofuro[3,2-c]pyridine;

8-(2,4-dichlorophenyl)-6-thiomorpholin-4-yl-1,2,3,4,4a,9b-hexahydro[1]benzofuro[3,2-c]pyridine;

8-(2,4,6-trichlorophenyl)-6-thiomorpholin-4-yl-1,2,3,4,4a,9b-hexahydro[1]benzofuro[3,2-c]pyridine;

8-(2,6-difluoro-4-chlorophenyl)-6-thiomorpholin-4-yl-1,2,3,4,4a,9b-hexahydro[1]benzofuro[3,2-c]pyridine;

8-(2,4-dichlorophenyl)-6-piperazin-1-yl-1,2,3,4,4a,9b-hexahydro[1]benzofuro[3,2-c]pyridine;

8-(2,4,6-trichlorophenyl)-6-piperazin-1-yl-1,2,3,4,4a,9b-hexahydro[1]benzofuro[3,2-c]pyridine;

8-(2,6-difluoro-4-chlorophenyl)-6-piperazin-1-yl-1,2,3,4,4a,9b-hexahydro[1]benzofuro[3,2-c]pyridine;

8-(2,4,6-trichlorophenyl)-N,N-dipropyl-1,2,3,4,4a,9b,-hexahydro[1]benzofuro[3,2-c]pyridin-6-amine;

8-(2,6-difluoro-4-chlorophenyl)-N,N-dipropyl-1,2,3,4,4a,9b,-hexahydro[1]benzofuro[3,2-c]pyridin-6-amine;

8-(2,4-Dichlorophenyl)-1,2,3,4,4a,9b-hexahydro[1]benzofuro[3,2-c]pyridine;

1,2,3,4,4a,9b-Hexahydro[1]benzofuro[3,2-c]pyridine;

8-[2-(Trifluoromethyl)phenyl]-1,2,3,4,4a,9b-hexahydro[1]benzofuro[3,2-c]pyridine;

8-[2-(Trifluoromethoxy)phenyl]-1,2,3,4,4a,9b-hexahydro[1]benzofuro[3,2-c]pyridine;

6-Bromo-8-(2,4-dichlorophenyl)-1,2,3,4,4a,9b-hexahydro[1]benzofuro[3,2-c]pyridine;

6-Benzyl-8-(2,4-dichlorophenyl)-1,2,3,4,4a,9b-hexahydro[1]benzofuro[3,2-c]pyridine;

6-Butyl-8-(2,4-dichlorophenyl)-1,2,3,4,4a,9b-hexahydro[1]benzofuro[3,2-c]pyridine;

8-(2,4-Dichlorophenyl)-6-(propylthio)-1,2,3,4,4a,9b-hexahydro[1]benzofuro[3,2-c]pyridine;

8-(2,4-Dichlorophenyl)-6-(isopropylthio)-1,2,3,4,4a,9b-hexahydro[1]benzofuro[3,2-c]pyridine;

8-(2,4-Dichlorophenyl)-6-(isobutylthio)-1,2,3,4,4a,9b-hexahydro[1]benzofuro[3,2-c]pyridine;

8-(2,4-Dichlorophenyl)-6-(methylthio)-1,2,3,4,4a,9b-hexahydro[1]benzofuro[3,2-c]pyridine;

6-(Cyclopentylthio)-8-(2,4-dichlorophenyl)-1,2,3,4,4a,9b-hexahydro[1]benzofuro[3,2-c]pyridine;

6-(Cyclobutylthio)-8-(2,4-dichlorophenyl)-1,2,3,4,4a,9b-hexahydro[1]benzofuro[3,2-c]pyridine;

8-(2,4-dichlorophenyl)-6-morpholin-4-yl-1,2,3,4,4a,9b-hexahydro[1]benzofuro[3,2-c]pyridine;

N-Benzyl-8-(2,4-dichlorophenyl)-1,2,3,4,4a,9b-hexahydro[1]benzofuro[3,2-c]pyridin-6-amine;

8-(2,4-Dichlorophenyl)-6-pyrrolidin-1-yl-1,2,3,4,4a,9b-hexahydro[1]benzofuro[3,2-c]pyridine;

8-(2,4-Dichlorophenyl)-6-methoxy-1,2,3,4,4a,9b-hexahydro[1]benzofuro[3,2-c]pyridine;

or a pharmaceutically acceptable salt thereof.

59. The compound of claim 44, wherein the compound is:

(4aS,9bR)-8-(2,4-dichlorophenyl)-N-cyclohexyl-1,2,3,4,4a,9b,-hexahydro[1]benzofuro[3,2-c]pyridin-6-amine;

(4aS,9bR)-8-(2,4,6-trichlorophenyl)-N-cyclohexyl-1,2,3,4,4a,9b,-hexahydro[1]benzofuro[3,2-c]pyridin-6-amine;

(4aS,9bR)-8-(2,6-difluoro-4-chlorophenyl)-N-cyclohexyl-1,2,3,4,4a,9b,-hexahydro[1]benzofuro[3,2-c]pyridin-6-amine;

(4aS,9bR)-8-(2,4-dichlorophenyl)-N-phenyl-1,2,3,4,4a,9b,-hexahydro[1]benzofuro[3,2-c]pyridin-6-amine;

(4aS,9bR)-8-(2,4,6-trichlorophenyl)-N-phenyl-1,2,3,4,4a,9b,-hexahydro[1]benzofuro[3,2-c]pyridin-6-amine;

(4aS,9bR)-8-(2,6-difluoro-4-chlorophenyl)-N-phenyl-1,2,3,4,4a,9b,-hexahydro[1]benzofuro[3,2-c]pyridin-6-amine;

(4aS,9bR)-8-(2,4-dichlorophenyl)-N,N-dimethyl-1,2,3,4,4a,9b,-hexahydro[1]benzofuro[3,2-c]pyridin-6-amine;

(4aS,9bR)-8-(2,4,6-trichlorophenyl)-N,N-dimethyl-1,2,3,4,4a,9b,-hexahydro[1]benzofuro[3,2-c]pyridin-6-amine;

(4aS,9bR)-8-(2,6-difluoro-4-chlorophenyl)-N,N-dimethyl-1,2,3,4,4a,9b,-hexahydro[1]benzofuro[3,2-c]pyridin-6-amine;

(4aS,9bR)-8-(2,4-dichlorophenyl)-N,N-diethyl-1,2,3,4,4a,9b,-hexahydro[1]benzofuro[3,2-c]pyridin-6-amine;

(4aS,9bR)-8-(2,4,6-trichlorophenyl)-N,N-diethyl-1,2,3,4,4a,9b,-hexahydro[1]benzofuro[3,2-c]pyridin-6-amine;

(4aS,9bR)-8-(2,6-difluoro-4-chlorophenyl)-N,N-diethyl-1,2,3,4,4a,9b,-hexahydro[1]benzofuro[3,2-c]pyridin-6-amine;

(4aS,9bR)-8-(2,4-dichlorophenyl)-N-methyl-N-ethyl-1,2,3,4,4a,9b,-hexahydro[1]benzofuro[3,2-c]pyridin-6-amine;

(4aS,9bR)-8-(2,4-dichlorophenyl)-N-methyl-N-propyl-1,2,3,4,4a,9b,-hexahydro[1]benzofuro[3,2-c]pyridin-6-amine;

(4aS,9bR)-8-(2,4-dichlorophenyl)-N-methyl-N-cyclohexyl-1,2,3,4,4a,9b,-hexahydro[1]benzofuro[3,2-c]pyridin-6-amine;

(4aS,9bR)-8-(2,4-dichlorophenyl)-N-ethyl-N-propyl-1,2,3,4,4a,9b,-hexahydro[1]benzofuro[3,2-c]pyridin-6-amine;

(4aS,9bR)-8-(2,4-dichlorophenyl)-N-ethyl-N-cyclohexyl-1,2,3,4,4a,9b,-hexahydro[1]benzofuro[3,2-c]pyridin-6-amine;

(4aS,9bR)-8-(2,4-dichlorophenyl)-N,N-dipropyl-1,2,3,4,4a,9b,-hexahydro[1]benzofuro[3,2-c]pyridin-6-amine;

(4aS,9bR)-8-(2,4-dichlorophenyl)-N-propyl-N-cyclohexyl-1,2,3,4,4a,9b,-hexahydro[1]benzofuro[3,2-c]pyridin-6-amine;

(4aS,9bR)-8-(2,4-dichlorophenyl)-N,N-dicyclohexyl-1,2,3,4,4a,9b,-hexahydro[1]benzofuro[3,2-c]pyridin-6-amine;

(4aS,9bR)-8-(2,4-dichlorophenyl)-6-methyl-1,2,3,4,4a,9b,-hexahydro[1]benzofuro[3,2-c]pyridine;
(4aS,9bR)-8-(2,4-dichlorophenyl)-6-ethyl-1,2,3,4,4a,9b,-hexahydro[1]benzofuro[3,2-c]pyridine;
(4aS,9bR)-8-(2,4-dichlorophenyl)-6-propyl-1,2,3,4,4a,9b,-hexahydro[1]benzofuro[3,2-c]pyridine;
(4aS,9bR)-8-(2,4-dichlorophenyl)-6-(isopropyl)-1,2,3,4,4a,9b,-hexahydro[1]benzofuro[3,2-c]pyridine;
(4aS,9bR)-8-(2,4-dichlorophenyl)-6-butyl-1,2,3,4,4a,9b,-hexahydro[1]benzofuro[3,2-c]pyridine;
(4aS,9bR)-8-(2,4-dichlorophenyl)-6-(1-ethylpropyl)-1,2,3,4,4a,9b,-hexahydro[1]benzofuro[3,2-c]pyridine;
(4aS,9bR)-8-(2,4-dichlorophenyl)-6-cyclohexyl-1,2,3,4,4a,9b,-hexahydro[1]benzofuro[3,2-c]pyridine;
(4aS,9bR)-8-(2,4-dichlorophenyl)-6-phenyl-1,2,3,4,4a,9b,-hexahydro[1]benzofuro[3,2-c]pyridine;
(4aS,9bR)-8-(2,4-dichlorophenyl)-6-benzyl-1,2,3,4,4a,9b,-hexahydro[1]benzofuro[3,2-c]pyridine;
(4aS,9bR)-8-(2,4,6-trichlorophenyl)-6-methyl-1,2,3,4,4a,9b,-hexahydro[1]benzofuro[3,2-c]pyridine;
(4aS,9bR)-8-(2,4,6-trichlorophenyl)-6-ethyl-1,2,3,4,4a,9b,-hexahydro[1]benzofuro[3,2-c]pyridine;
(4aS,9bR)-8-(2,4,6-trichlorophenyl)-6-propyl-1,2,3,4,4a,9b,-hexahydro[1]benzofuro[3,2-c]pyridine;
(4aS,9bR)-8-(2,4,6-trichlorophenyl)-6-(isopropyl)-1,2,3,4,4a,9b,-hexahydro[1]benzofuro[3,2-c]pyridine;
(4aS,9bR)-8-(2,4,6-trichlorophenyl)-6-butyl-1,2,3,4,4a,9b,-hexahydro[1]benzofuro[3,2-c]pyridine;
(4aS,9bR)-8-(2,4,6-trichlorophenyl)-6-(1-ethylpropyl)-1,2,3,4,4a,9b,-hexahydro[1]benzofuro[3,2-c]pyridine;
(4aS,9bR)-8-(2,4,6-trichlorophenyl)-6-cyclohexyl-1,2,3,4,4a,9b,-hexahydro[1]benzofuro[3,2-c]pyridine;
(4aS,9bR)-8-(2,4,6-trichlorophenyl)-6-phenyl-1,2,3,4,4a,9b,-hexahydro[1]benzofuro[3,2-c]pyridine;
(4aS,9bR)-8-(2,4,6-trichlorophenyl)-6-benzyl-1,2,3,4,4a,9b,-hexahydro[1]benzofuro[3,2-c]pyridine;
(4aS,9bR)-8-(2,6-difluoro-4-chlorophenyl)-6-methyl-1,2,3,4,4a,9b,-hexahydro[1]benzofuro[3,2-c]pyridine;
(4aS,9bR)-8-(2,6-difluoro-4-chlorophenyl)-6-ethyl-1,2,3,4,4a,9b,-hexahydro[1]benzofuro[3,2-c]pyridine;
(4aS,9bR)-8-(2,6-difluoro-4-chlorophenyl)-6-propyl-1,2,3,4,4a,9b,-hexahydro[1]benzofuro[3,2-c]pyridine;
(4aS,9bR)-8-(2,6-difluoro-4-chlorophenyl)-6-(isopropyl)-1,2,3,4,4a,9b,-hexahydro[1]benzofuro[3,2-c]pyridine;
(4aS,9bR)-8-(2,6-difluoro-4-chlorophenyl)-6-butyl-1,2,3,4,4a,9b,-hexahydro[1]benzofuro[3,2-c]pyridine;
(4aS,9bR)-8-(2,6-difluoro-4-chlorophenyl)-6-(1-ethylpropyl)-1,2,3,4,4a,9b,-hexahydro[1]benzofuro[3,2-c]pyridine;
(4aS,9bR)-8-(2,6-difluoro-4-chlorophenyl)-6-cyclohexyl-1,2,3,4,4a,9b,-hexahydro[1]benzofuro[3,2-c]pyridine;
(4aS,9bR)-8-(2,6-difluoro-4-chlorophenyl)-6-phenyl-1,2,3,4,4a,9b,-hexahydro[1]benzofuro[3,2-c]pyridine;
(4aS,9bR)-8-(2,6-difluoro-4-chlorophenyl)-6-benzyl-1,2,3,4,4a,9b,-hexahydro[1]benzofuro[3,2-c]pyridine;
(4aS,9bR)-8-(2,4-dichlorophenyl)-6-(methylthio)-1,2,3,4,4a,9b,-hexahydro[1]benzofuro[3,2-c]pyridine;
(4aS,9bR)-8-(2,4-dichlorophenyl)-6-(ethylthio)-1,2,3,4,4a,9b,-hexahydro[1]benzofuro[3,2-c]pyridine;
(4aS,9bR)-8-(2,4-dichlorophenyl)-6-(propylthio)-1,2,3,4,4a,9b,-hexahydro[1]benzofuro[3,2-c]pyridine;
(4aS,9bR)-8-(2,4-dichlorophenyl)-6-(2-propylthio)-1,2,3,4,4a,9b,-hexahydro[1]benzofuro[3,2-c]pyridine;
(4aS,9bR)-8-(2,4-dichlorophenyl)-6-(butylthio)-1,2,3,4,4a,9b,-hexahydro[1]benzofuro[3,2-c]pyridine;
(4aS,9bR)-8-(2,4-dichlorophenyl)-6-[(1-ethylpropyl)thio]-1,2,3,4,4a,9b,-hexahydro[1]benzofuro[3,2-c]pyridine;
(4aS,9bR)-8-(2,4-dichlorophenyl)-6-(cyclohexylthio)-1,2,3,4,4a,9b,-hexahydro[1]benzofuro[3,2-c]pyridine;
(4aS,9bR)-8-(2,4-dichlorophenyl)-6-(phenylthio)-1,2,3,4,4a,9b,-hexahydro[1]benzofuro[3,2-c]pyridine;
(4aS,9bR)-8-(2,4-dichlorophenyl)-6-(benzylthio)-1,2,3,4,4a,9b,-hexahydro[1]benzofuro[3,2-c]pyridine;
(4aS,9bR)-8-(2,4,6-trichlorophenyl)-6-(methylthio)-1,2,3,4,4a,9b,-hexahydro[1]benzofuro[3,2-c]pyridine;
(4aS,9bR)-8-(2,4,6-trichlorophenyl)-6-(ethylthio)-1,2,3,4,4a,9b,-hexahydro[1]benzofuro[3,2-c]pyridine;
(4aS,9bR)-8-(2,4,6-trichlorophenyl)-6-(propylthio)-1,2,3,4,4a,9b,-hexahydro[1]benzofuro[3,2-c]pyridine;
(4aS,9bR)-8-(2,4,6-trichlorophenyl)-6-(2-propylthio)-1,2,3,4,4a,9b,-hexahydro[1]benzofuro[3,2-c]pyridine;
(4aS,9bR)-8-(2,4,6-trichlorophenyl)-6-(butylthio)-1,2,3,4,4a,9b,-hexahydro[1]benzofuro[3,2-c]pyridine;
(4aS,9bR)-8-(2,4,6-trichlorophenyl)-6-[(1-ethylpropyl)thio]-1,2,3,4,4a,9b,-hexahydro[1]benzofuro[3,2-c]pyridine;
(4aS,9bR)-8-(2,4,6-trichlorophenyl)-6-(cyclohexylthio)-1,2,3,4,4a,9b,-hexahydro[1]benzofuro[3,2-c]pyridine;
(4aS,9bR)-8-(2,4,6-trichlorophenyl)-6-(phenylthio)-1,2,3,4,4a,9b,-hexahydro[1]benzofuro[3,2-c]pyridine;
(4aS,9bR)-8-(2,4,6-trichlorophenyl)-6-(benzylthio)-1,2,3,4,4a,9b,-hexahydro[1]benzofuro[3,2-c]pyridine;
(4aS,9bR)-8-(2,6-difluoro-4-chlorophenyl)-6-(methylthio)-1,2,3,4,4a,9b,-hexahydro[1]benzofuro[3,2-c]pyridine;
(4aS,9bR)-8-(2,6-difluoro-4-chlorophenyl)-6-(ethylthio)-1,2,3,4,4a,9b,-hexahydro[1]benzofuro[3,2-c]pyridine;
(4aS,9bR)-8-(2,6-difluoro-4-chlorophenyl)-6-(propylthio)-1,2,3,4,4a,9b,-hexahydro[1]benzofuro[3,2-c]pyridine;
(4aS,9bR)-8-(2,6-difluoro-4-chlorophenyl)-6-(isopropyl)-1,2,3,4,4a,9b,-hexahydro[1]benzofuro[3,2-c]pyridine;
(4aS,9bR)-8-(2,6-difluoro-4-chlorophenyl)-6-(butylthio)-1,2,3,4,4a,9b,-hexahydro[1]benzofuro[3,2-c]pyridine;
(4aS,9bR)-8-(2,6-difluoro-4-chlorophenyl)-6-[(1-ethylpropyl)thio]-1,2,3,4,4a,9b,-hexahydro[1]benzofuro[3,2-c]pyridine;
(4aS,9bR)-8-(2,6-difluoro-4-chlorophenyl)-6-(cyclohexylthio)-1,2,3,4,4a,9b,-hexahydro[1]benzofuro[3,2-c]pyridine;
(4aS,9bR)-8-(2,6-difluoro-4-chlorophenyl)-6-(phenylthio)-1,2,3,4,4a,9b,-hexahydro[1]benzofuro[3,2-c]pyridine;
(4aS,9bR)-8-(2,6-difluoro-4-chlorophenyl)-6-(benzylthio)-1,2,3,4,4a,9b,-hexahydro[1]benzofuro[3,2-c]pyridine;
(4aS,9bR)-8-(2,4-dichlorophenyl)-6-methoxy-1,2,3,4,4a,9b,-hexahydro[1]benzofuro[3,2-c]pyridine;
(4aS,9bR)-8-(2,4-dichlorophenyl)-6-ethoxy-1,2,3,4,4a,9b,-hexahydro[1]benzofuro[3,2-c]pyridine;
(4aS,9bR)-8-(2,4-dichlorophenyl)-6-propoxy-1,2,3,4,4a,9b,-hexahydro[1]benzofuro[3,2-c]pyridine;

(4aS,9bR)-8-(2,4-dichlorophenyl)-6-isopropoxy-1,2,3,4,4a,9b,-hexahydro[1]benzofuro[3,2-c]pyridine;

(4aS,9bR)-8-(2,4-dichlorophenyl)-6-butoxy-1,2,3,4,4a,9b,-hexahydro[1]benzofuro[3,2-c]pyridine;

(4aS,9bR)-8-(2,4-dichlorophenyl)-6-[(1-ethylpropyl)oxy]-1,2,3,4,4a,9b,-hexahydro[1]benzofuro[3,2-c]pyridine;

(4aS,9bR)-8-(2,4-dichlorophenyl)-6-(cyclohexyloxy)-1,2,3,4,4a,9b,-hexahydro[1]benzofuro[3,2-c]pyridine;

(4aS,9bR)-8-(2,4-dichlorophenyl)-6-phenoxy-1,2,3,4,4a,9b,-hexahydro[1]benzofuro[3,2-c]pyridine;

(4aS,9bR)-8-(2,4-dichlorophenyl)-6-(benzyloxy)-1,2,3,4,4a,9b,-hexahydro[1]benzofuro[3,2-c]pyridine;

(4aS,9bR)-8-(2,4,6-trichlorophenyl)-6-methoxy-1,2,3,4,4a,9b,-hexahydro[1]benzofuro[3,2-c]pyridine;

(4aS,9bR)-8-(2,4,6-trichlorophenyl)-6-ethoxy-1,2,3,4,4a,9b,-hexahydro[1]benzofuro[3,2-c]pyridine;

(4aS,9bR)-8-(2,4,6-trichlorophenyl)-6-propoxy-1,2,3,4,4a,9b,-hexahydro[1]benzofuro[3,2-c]pyridine;

(4aS,9bR)-8-(2,4,6-trichlorophenyl)-6-isopropoxy-1,2,3,4,4a,9b,-hexahydro[1]benzofuro[3,2-c]pyridine;

(4aS,9bR)-8-(2,4,6-trichlorophenyl)-6-butoxy-1,2,3,4,4a,9b,-hexahydro[1]benzofuro[3,2-c]pyridine;

(4aS,9bR)-8-(2,4,6-trichlorophenyl)-6-[(1-ethylpropyl)oxy]-1,2,3,4,4a,9b,-hexahydro[1]benzofuro[3,2-c]pyridine;

(4aS,9bR)-8-(2,4,6-trichlorophenyl)-6-(cyclohexyloxy)-1,2,3,4,4a,9b,-hexahydro[1]benzofuro[3,2-c]pyridine;

(4aS,9bR)-8-(2,4,6-trichlorophenyl)-6-phenoxy-1,2,3,4,4a,9b,-hexahydro[1]benzofuro[3,2-c]pyridine;

(4aS,9bR)-8-(2,4,6-trichlorophenyl)-6-(benzyloxy)-1,2,3,4,4a,9b,-hexahydro[1]benzofuro[3,2-c]pyridine;

(4aS,9bR)-8-(2,6-difluoro-4-chlorophenyl)-6-methoxy-1,2,3,4,4a,9b,-hexahydro[1]benzofuro[3,2-c]pyridine;

(4aS,9bR)-8-(2,6-difluoro-4-chlorophenyl)-6-ethoxy-1,2,3,4,4a,9b,-hexahydro[1]benzofuro[3,2-c]pyridine;

(4aS,9bR)-8-(2,6-difluoro-4-chlorophenyl)-6-propoxy-1,2,3,4,4a,9b,-hexahydro[1]benzofuro[3,2-c]pyridine;

(4aS,9bR)-8-(2,6-difluoro-4-chlorophenyl)-6-(2-propoxy)-1,2,3,4,4a,9b,-hexahydro[1]benzofuro[3,2-c]pyridine;

(4aS,9bR)-8-(2,6-difluoro-4-chlorophenyl)-6-butoxy-1,2,3,4,4a,9b,-hexahydro[1]benzofuro[3,2-c]pyridine;

(4aS,9bR)-8-(2,6-difluoro-4-chlorophenyl)-6-[(1-ethylpropyl)oxy]-1,2,3,4,4a,9b,-hexahydro[1]benzofuro[3,2-c]pyridine;

(4aS,9bR)-8-(2,6-difluoro-4-chlorophenyl)-6-(cyclohexyloxy)-1,2,3,4,4a,9b,-hexahydro[1]benzofuro[3,2-c]pyridine;

(4aS,9bR)-8-(2,6-difluoro-4-chlorophenyl)-6-phenoxy-1,2,3,4,4a,9b,-hexahydro[1]benzofuro[3,2-c]pyridine;

(4aS,9bR)-8-(2,6-difluoro-4-chlorophenyl)-6-(benzyloxy)-1,2,3,4,4a,9b,-hexahydro[1]benzofuro[3,2-c]pyridine;

(4aS,9bR)-8-(2,4-dichlorophenyl)-6-piperidin-1-yl-1,2,3,4,4a,9b-hexahydro[1]benzofuro[3,2-c]pyridine;

(4aS,9bR)-8-(2,4,6-trichlorophenyl)-6-piperidin-1-yl-1,2,3,4,4a,9b-hexahydro[1]benzofuro[3,2-c]pyridine;

(4aS,9bR)-8-(2,6-difluoro-4-chlorophenyl)-6-piperidin-1-yl-1,2,3,4,4a,9b-hexahydro[1]benzofuro[3,2-c]pyridine;

(4aS,9bR)-8-(2,4-dichlorophenyl)-6-azepan-1-yl-1,2,3,4,4a,9b-hexahydro[1]benzofuro[3,2-c]pyridine;

(4aS,9bR)-8-(2,4,6-trichlorophenyl)-6-hexahydroazepin-1-yl-1,2,3,4,4a,9b-hexahydro[1]benzofuro[3,2-c]pyridine;

(4aS,9bR)-8-(2,6-difluoro-4-chlorophenyl)-6-hexahydroazepin-1-yl-1,2,3,4,4a,9b-hexahydro[1]benzofuro[3,2-c]pyridine;

(4aS,9bR)-8-(2,4-dichlorophenyl)-6-pyrrolidin-1-yl-1,2,3,4,4a,9b-hexahydro[1]benzofuro[3,2-c]pyridine;

4aS,9bR)-8-(2,4,6-trichlorophenyl)-6-pyrrolidin-1-yl-1,2,3,4,4a,9b-hexahydro[1]benzofuro[3,2-c]pyridine;

(4aS,9bR)-8-(2,6-difluoro-4-chlorophenyl)-6-pyrrolidin-1-yl-1,2,3,4,4a,9b-hexahydro[1]benzofuro[3,2-c]pyridine;

(4aS,9bR)-8-(2,4-dichlorophenyl)-5-morpholin-4-yl-1,2,3,4,4a,9b-hexahydro-[1]benzofuro[3,2-c]pyridine;

(4aS,9bR)-8-(2,4,6-trichlorophenyl)-5-morpholin-4-yl-1,2,3,4,4a,9b-hexahydro[1]benzofuro[3,2-c]pyridine;

(4aS,9bR)-8-(2,6-difluoro-4-chlorophenyl)-5-morpholin-4-yl-1,2,3,4,4a,9b-hexahydro[1]benzofuro[3,2-c]pyridine;

(4aS,9bR)-8-(2,4-dichlorophenyl)-6-thiomorpholin-4-yl-1,2,3,4,4a,9b-hexahydro[1]benzofuro[3,2-c]pyridine;

(4aS,9bR)-8-(2,4,6-trichlorophenyl)-6-thiomorpholin-4-yl-1,2,3,4,4a,9b-hexahydro[1]benzofuro[3,2-c]pyridine;

(4aS,9bR)-8-(2,6-difluoro-4-chlorophenyl)-6-thiomorpholin-4-yl-1,2,3,4,4a,9b-hexahydro[1]benzofuro[3,2-c]pyridine;

(4aS,9bR)-8-(2,4-dichlorophenyl)-6-piperazin-1-yl-1,2,3,4,4a,9b-hexahydro[1]benzofuro[3,2-c]pyridine;

(4aS,9bR)-8-(2,4,6-trichlorophenyl)-6-piperazin-1-yl-1,2,3,4,4a,9b-hexahydro[1]benzofuro[3,2-c]pyridine;

(4aS,9bR)-8-(2,6-difluoro-4-chlorophenyl)-6-piperazin-1-yl-1,2,3,4,4a,9b-hexahydro[1]benzofuro[3,2-c]pyridine;

(4aS,9bR)-8-(2,4,6-trichlorophenyl)-N,N-dipropyl-1,2,3,4,4a,9b,-hexahydro[1]benzofuro[3,2-c]pyridin-6-amine;

(4aS,9bR)-8-(2,6-difluoro-4-chlorophenyl)-N,N-dipropyl-1,2,3,4,4a,9b,-hexahydro[1]benzofuro[3,2-c]pyridin-6-amine;

(4aS,9bR) 6-Bromo-8-(2,4-dichlorophenyl)-1,2,3,4,4a,9b-hexahydro[1]benzofuro[3,2-c]pyridine;

(4aR,9bS) 6-Bromo-8-(2,4-dichlorophenyl)-1,2,3,4,4a,9b-hexahydro[1]benzofuro[3,2-c]pyridine;

or a pharmaceutically acceptable salt thereof.

60. A compound of formula (I):

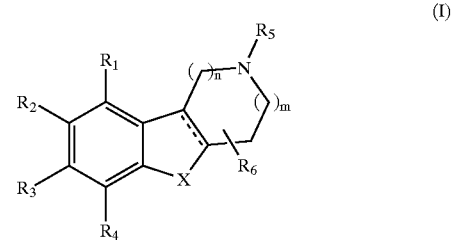

(I)

wherein:

$R_1$, $R_2$, $R_3$, and $R_4$ are independently hydrogen, halo, —$CF_3$, —$OCF_3$, —CN, —$NO_2$, —$C_{1-8}$alkyl, —$C_{3-8}$cycloalkyl, —$OR_8$, —$NR_8R_9$, —$SR_8$, —C(=O)aryl, aryl, —$C_{1-8}$alkylene(aryl), —C(=O)heteroaryl, heteroaryl, or —$C_{1-8}$alkylene(heteroaryl), provided that at least one of $R_1$, $R_2$, $R_3$, and $R_4$ is aryl optionally substituted with one or more substituents independently selected from halo, hydroxy, cyano, nitro, trifluoromethyl, trifluoromethoxy, $C_{1-6}$alkyl, —$OR_c$, —$SR_c$, phenyl, —$NR_cR_d$, or —$C(\!=\!O)NR_cR_d$;

$R_5$ is hydrogen, $C_{1-8}$alkyl, halo$C_{1-8}$alkyl, $C_{3-8}$cycloalkyl, $C_{1-8}$alkanoyl, halo$C_{1-8}$alkanoyl, —$C(\!=\!O)OR_8$, —$C(\!=\!O)$aryl, aryl, —$C_{1-8}$alkylene(aryl), —$C(\!=\!O)$heteroaryl, heteroaryl, or —$C_{1-8}$alkylene(heteroaryl);

$R_6$ is hydrogen or $C_{1-4}$alkyl;

each $R_8$ and $R_9$ is independently hydrogen, $C_{1-8}$alkyl, halo$C_{1-8}$alkyl, $C_{3-8}$cycloalkyl, —$C(\!=\!O)$aryl, aryl, —$C_{1-8}$alkylene(aryl), —$C(\!=\!O)$heteroaryl, heteroaryl, —$C_{1-8}$alkylene(heteroaryl) or $R_8$ and $R_9$ together with the nitrogen to which they are attached form a pyrrolidino, piperidino, azepano, piperazino, morpholino, or thiomorpholino ring;

m is 1;

n is 1;

X is oxy (—O—), thio (—S—) —S(=O)— or —$SO_2$—; and the bond represented by—is absent or present;

wherein any $C_{1-8}$alkyl, $C_{1-8}$alkylene, $C_{1-8}$alkoxy or $C_{3-8}$cycloalkyl of $R_1$, $R_3$, $R_4$, $R_5$, $R_6$, $R_8$ and $R_9$ is optionally partially unsaturated; and wherein any aryl or heteroaryl of $R_1$, $R_2$, $R_3$, $R_4$, $R_5$, $R_8$ or $R_9$ is optionally substituted with one or more substituents independently selected from halo, —CN, —$NO_2$, —$CF_3$, —$OCF_3$, $C_{1-8}$alkyl, $C_{2-8}$alkenyl, $C_{2-8}$alkynyl, $C_{3-8}$cycloalkyl, $C_{3-8}$cycloalkenyl, aryl, heteroaryl, —$OR_c$, —$SR_c$, —$C(\!=\!O)R_c$, —$CO_2R_c$, —$C(\!=\!O)NR_cR_d$, —$NR_cC(\!=\!O)R_d$, —$C(\!=\!O)NR_cR_d$, —$NR_cR_d$, —$NR_cC(\!=\!O)NR_cR_d$, —$SO_2NR_cR_d$ or —$SO_2R_c$;

wherein each $R_c$ and $R_d$ is independently hydrogen, $C_{1-8}$alkyl, $C_{1-8}$alkanoyl, $C_{1-8}$alkoxycarbonyl, aryl, —$C_{1-8}$alkylene(aryl), —$C(\!=\!O)$aryl, —$C(\!=\!O)$Oaryl, heteroaryl, —$C_{1-8}$alkylene(heteroaryl), —$C(\!=\!O)$heteroaryl, —$C(\!=\!O)$Oheteroaryl or $R_c$ and $R_d$ together with the nitrogen to which they are attached form a pyrrolidino, piperidino, azepano, piperazino, morpholino, or thiomorpholino ring; or a pharmaceutically acceptable salt thereof.

61. The compound of claim 60, wherein—is absent.

62. The compound of claim 60, wherein $R_2$ is phenyl optionally substituted with one or more substituents independently selected from halo, cyano, nitro, trifluoromethyl, trifluoromethoxy, $C_{1-6}$alkyl, —$OR_c$, —$SR_c$, phenyl, —$NR_cR_d$, or —$C(\!=\!O)NR_cR_d$.

63. The compound of claim 62, wherein $R_2$ is phenyl optionally substituted with one or more halo.

64. The compound of claim 63, wherein $R_2$ is phenyl substituted at the 2- or 6-position with fluoro, chloro, or bromo.

65. The compound of claim 63, wherein $R_2$ is phenyl substituted at the 2- and 6-position with halo independently selected from fluoro, chloro, and bromo.

66. The compound of claim 63, wherein $R_2$ is phenyl substituted at the 2- or 4-position with fluoro, chloro, or bromo.

67. The compound of claim 63, wherein $R_2$ is phenyl substituted at the 2- and 4-position with halo independently selected from fluoro, chloro, and bromo.

68. The compound of claim 63, wherein $R_2$ is phenyl substituted at the 2-, 4- and 6-position with halo independently selected from fluoro, chloro, and bromo.

69. The compound of claim 63, wherein $R_2$ is 2,4-dichlorophenyl, 2,4,6-trichlorophenyl or 2,6-difluoro-4-chlorophenyl.

70. The compound of claim 63, wherein $R_4$ is halo, —$CF_3$, $C_{1-8}$alkyl, —$OR_8$, —$SR_8$, —$NR_8R_9$, aryl, or —$C_{1-8}$alkylene(aryl), wherein the aryl groups are optionally substituted with one or more substituents independently selected from halo, hydroxy, cyano, nitro, trifluoromethyl, trifluoromethoxy, $C_{1-6}$alkyl, $C_{1-6}$alkoxy, phenyl, —$NR_cR_d$, and —$C(\!=\!O)NR_cR_d$.

71. The compound of claim 70, wherein $R_4$ is halo, —$CF_3$, $C_{1-8}$alkyl, —$NR_8R_9$, aryl, or —$C_{1-8}$alkylene(aryl), wherein the aryl groups are optionally substituted with one or more substituents independently selected from halo, hydroxy, cyano, nitro, trifluoromethyl, trifluoromethoxy, $C_{1-6}$alkyl, $C_{1-6}$alkoxy, phenyl, —$NR_cR_d$, and —$C(\!=\!O)NR_cR_d$.

72. The compound of claim 71, wherein $R_4$ is aryl, —$C_{1-8}$alkylene(aryl), wherein aryl is optionally substituted with one or more substituents independently selected from halo, hydroxy, cyano, nitro, trifluoromethyl, trifluoromethoxy, $C_{1-6}$alkyl, $C_{1-6}$alkoxy, phenyl, —$NR_cR_d$, and —$C(\!=\!O)NR_cR_d$, or —$NR_8R_9$, wherein $R_8$ is hydrogen, methyl, ethyl, propyl or cyclohexyl and $R_9$ is methyl, ethyl, propyl, cyclohexyl or phenyl.

73. The compound of claim 71, wherein $R_4$ is halo, —$CF_3$, or —$CH_3$.

74. The compound of claim 60, wherein the compound is:

8-(2,4-dichlorophenyl)-3,4,4a,9b-tetrahydro[1]benzofuro[3,2-c]pyridine;

8-(2,4-dichlorophenyl)-N-cyclohexyl-1,2,3,4,4a,9b,-hexahydro[1]benzofuro[3,2-c]pyridin-6-amine;

8-(2,4,6-trichlorophenyl)-N-cyclohexyl-1,2,3,4,4a,9b,-hexahydro[1]benzofuro[3,2-c]pyridin-6-amine;

8-(2,6-difluoro-4-chlorophenyl)-N-cyclohexyl-1,2,3,4,4a,9b,-hexahydro[1]benzofuro[3,2-c]pyridin-6-amine;

8-(2,4-dichlorophenyl)-N-phenyl-1,2,3,4,4a,9b,-hexahydro[1]benzofuro[3,2-c]pyridin-6-amine;

8-(2,4,6-trichlorophenyl)-N-phenyl-1,2,3,4,4a,9b,-hexahydro[1]benzofuro[3,2-c]pyridin-6-amine;

8-(2,6-difluoro-4-chlorophenyl)-N-phenyl-1,2,3,4,4a,9b,-hexahydro[1]benzofuro[3,2-c]pyridin-6-amine;

8-(2,4-dichlorophenyl)-N,N-dimethyl-1,2,3,4,4a,9b,-hexahydro[1]benzofuro[3,2-c]pyridin-6-amine;

8-(2,4,6-trichlorophenyl)-N,N-dimethyl-1,2,3,4,4a,9b,-hexahydro[1]benzofuro[3,2-c]pyridin-6-amine;

8-(2,6-difluoro-4-chlorophenyl)-N,N-dimethyl-1,2,3,4,4a,9b,-hexahydro[1]benzofuro[3,2-c]pyridin-6-amine;

8-(2,4-dichlorophenyl)-N,N-diethyl-1,2,3,4,4a,9b,-hexahydro[1]benzofuro[3,2-c]pyridin-6-amine;

8-(2,4,6-trichlorophenyl)-N,N-diethyl-1,2,3,4,4a,9b,-hexahydro[1]benzofuro[3,2-c]pyridin-6-amine;

8-(2,6-difluoro-4-chlorophenyl)-N,N-diethyl-1,2,3,4,4a,9b,-hexahydro[1]benzofuro[3,2-c]pyridin-6-amine;

8-(2,4-dichlorophenyl)-N-methyl-N-ethyl-1,2,3,4,4a,9b,-hexahydro[1]benzofuro[3,2-c]pyridin-6-amine;

8-(2,4-dichlorophenyl)-N-methyl-N-propyl-1,2,3,4,4a,9b,-hexahydro[1]benzofuro[3,2-c]pyridin-6-amine;

8-(2,4-dichlorophenyl)-N-methyl-N-cyclohexyl-1,2,3,4,4a,9b,-hexahydro[1]benzofuro[3,2-c]pyridin-6-amine;

8-(2,4-dichlorophenyl)-N-ethyl-N-propyl-1,2,3,4,4a,9b,-hexahydro[1]benzofuro[3,2-c]pyridin-6-amine;

8-(2,4-dichlorophenyl)-N-ethyl-N-cyclohexyl-1,2,3,4,4a,9b,-hexahydro[1]benzofuro[3,2-c]pyridin-6-amine;

8-(2,4-dichlorophenyl)-N,N-dipropyl-1,2,3,4,4a,9b,-hexahydro[1]benzofuro[3,2-c]pyridin-6-amine;
8-(2,4-dichlorophenyl)-N-propyl-N-cyclohexyl-1,2,3,4,4a,9b,-hexahydro[1]benzofuro[3,2-c]pyridin-6-amine;
8-(2,4-dichlorophenyl)-N,N-dicyclohexyl-1,2,3,4,4a,9b,-hexahydro[1]benzofuro[3,2-c]pyridin-6-amine;
8-(2,4-dichlorophenyl)-6-methyl-1,2,3,4,4a,9b,-hexahydro[1]benzofuro[3,2-c]-pyridine;
8-(2,4-dichlorophenyl)-6-ethyl-1,2,3,4,4a,9b,-hexahydro[1]benzofuro[3,2-c]-pyridine;
8-(2,4-dichlorophenyl)-6-propyl-1,2,3,4,4a,9b,-hexahydro[1]benzofuro[3,2-c]-pyridine;
8-(2,4-dichlorophenyl)-6-isopropyl-1,2,3,4,4a,9b,-hexahydro[1]benzofuro[3,2-c]pyridine;
8-(2,4-dichlorophenyl)-6-butyl-1,2,3,4,4a,9b,-hexahydro[1]benzofuro[3,2-c]-pyridine;
8-(2,4-dichlorophenyl)-6-(1-ethylpropyl)-1,2,3,4,4a,9b,-hexahydro[1]benzofuro[3,2-c]pyridine;
8-(2,4-dichlorophenyl)-6-cyclohexyl-1,2,3,4,4a,9b,-hexahydro[1]benzofuro[3,2-c]pyridine;
8-(2,4-dichlorophenyl)-6-phenyl-1,2,3,4,4a,9b,-hexahydro[1]benzofuro[3,2-c]-pyridine;
8-(2,4-dichlorophenyl)-6-benzyl-1,2,3,4,4a,9b,-hexahydro[1]benzofuro[3,2-c]-pyridine;
8-(2,4,6-trichlorophenyl)-6-methyl-1,2,3,4,4a,9b,-hexahydro[1]benzofuro[3,2-c]pyridine;
8-(2,4,6-trichlorophenyl)-6-ethyl-1,2,3,4,4a,9b,-hexahydro[1]benzofuro[3,2-c]pyridine;
8-(2,4,6-trichlorophenyl)-6-propyl-1,2,3,4,4a,9b,-hexahydro[1]benzofuro[3,2-c]pyridine;
8-(2,4,6-trichlorophenyl)-6-isopropyl-1,2,3,4,4a,9b,-hexahydro[1]benzofuro[3,2-c]pyridine;
8-(2,4,6-trichlorophenyl)-6-butyl-1,2,3,4,4a,9b,-hexahydro[1]benzofuro[3,2-c]pyridine;
8-(2,4,6-trichlorophenyl)-6-(1-ethylpropyl)-1,2,3,4,4a,9b,-hexahydro[1]benzofuro[3,2-c]pyridine;
8-(2,4,6-trichlorophenyl)-6-cyclohexyl-1,2,3,4,4a,9b,-hexahydro[1]benzofuro[3,2-c]pyridine;
8-(2,4,6-trichlorophenyl)-6-phenyl-1,2,3,4,4a,9b,-hexahydro[1]benzofuro[3,2-c]pyridine;
8-(2,4,6-trichlorophenyl)-6-benzyl-1,2,3,4,4a,9b,-hexahydro[1]benzofuro[3,2-c]pyridine;
8-(2,6-difluoro-4-chlorophenyl)-6-methyl-1,2,3,4,4a,9b,-hexahydro[1]benzofuro[3,2-c]pyridine;
8-(2,6-difluoro-4-chlorophenyl)-6-ethyl-1,2,3,4,4a,9b,-hexahydro[1]benzofuro[3,2-c]pyridine;
8-(2,6-difluoro-4-chlorophenyl)-6-propyl-1,2,3,4,4a,9b,-hexahydro[1]benzofuro[3,2-c]pyridine;
8-(2,6-difluoro-4-chlorophenyl)-6-isopropyl-1,2,3,4,4a,9b,-hexahydro[1]benzofuro[3,2-c]pyridine;
8-(2,6-difluoro-4-chlorophenyl)-6-butyl-1,2,3,4,4a,9b,-hexahydro[1]benzofuro[3,2-c]pyridine;
8-(2,6-difluoro-4-chlorophenyl)-6-(1-ethylpropyl)-1,2,3,4,4a,9b,-hexahydro[1]benzofuro[3,2-c]pyridine;
8-(2,6-difluoro-4-chlorophenyl)-6-cyclohexyl-1,2,3,4,4a,9b,-hexahydro[1]benzofuro[3,2-c]pyridine;
8-(2,6-difluoro-4-chlorophenyl)-6-phenyl-1,2,3,4,4a,9b,-hexahydro[1]benzofuro[3,2-c]pyridine;
8-(2,6-difluoro-4-chlorophenyl)-6-benzyl-1,2,3,4,4a,9b,-hexahydro[1]benzofuro[3,2-c]pyridine;
8-(2,4-dichlorophenyl)-6-(methylthio)-1,2,3,4,4a,9b,-hexahydro[1]benzofuro[3,2-c]pyridine;
8-(2,4-dichlorophenyl)-6-(ethylthio)-1,2,3,4,4a,9b,-hexahydro[1]benzofuro[3,2-c]pyridine;
8-(2,4-dichlorophenyl)-6-(propylthio)-1,2,3,4,4a,9b,-hexahydro[1]benzofuro[3,2-c]pyridine;
8-(2,4-dichlorophenyl)-6-(isopropylthio)-1,2,3,4,4a,9b,-hexahydro[1]benzofuro[3,2-c]pyridine;
8-(2,4-dichlorophenyl)-6-(butylthio)-1,2,3,4,4a,9b,-hexahydro[1]benzofuro[3,2-c]pyridine;
8-(2,4-dichlorophenyl)-6-[(1-ethylpropyl)thio]-1,2,3,4,4a,9b,-hexahydro[1]benzofuro[3,2-c]pyridine;
8-(2,4-dichlorophenyl)-6-(cyclohexylthio)-1,2,3,4,4a,9b,-hexahydro[1]benzofuro[3,2-c]pyridine;
8-(2,4-dichlorophenyl)-6-(phenylthio)-1,2,3,4,4a,9b,-hexahydro[1]benzofuro[3,2-c]pyridine;
8-(2,4-dichlorophenyl)-6-(benzylthio)-1,2,3,4,4a,9b,-hexahydro[1]benzofuro[3,2-c]pyridine;
8-(2,4,6-trichlorophenyl)-6-(methylthio)-1,2,3,4,4a,9b,-hexahydro[1]benzofuro[3,2-c]pyridine;
8-(2,4,6-trichlorophenyl)-6-(ethylthio)-1,2,3,4,4a,9b,-hexahydro[1]benzofuro[3,2-c]pyridine;
8-(2,4,6-trichlorophenyl)-6-(propylthio)-1,2,3,4,4a,9b,-hexahydro[1]benzofuro[3,2-c]pyridine;
8-(2,4,6-trichlorophenyl)-6-(isopropylthio)-1,2,3,4,4a,9b,-hexahydro[1]benzofuro[3,2-c]pyridine;
8-(2,4,6-trichlorophenyl)-6-(butylthio)-1,2,3,4,4a,9b,-hexahydro[1]benzofuro[3,2-c]pyridine;
8-(2,4,6-trichlorophenyl)-6-[(1-ethylpropyl)thio]-1,2,3,4,4a,9b,-hexahydro[1]benzofuro[3,2-c]pyridine;
8-(2,4,6-trichlorophenyl)-6-(cyclohexylthio)-1,2,3,4,4a,9b,-hexahydro[1]benzofuro[3,2-c]pyridine;
8-(2,4,6-trichlorophenyl)-6-(phenylthio)-1,2,3,4,4a,9b,-hexahydro[1]benzofuro[3,2-c]pyridine;
8-(2,4,6-trichlorophenyl)-6-(benzylthio)-1,2,3,4,4a,9b,-hexahydro[1]benzofuro[3,2-c]pyridine;
8-(2,6-difluoro-4-chlorophenyl)-6-(methylthio)-1,2,3,4,4a,9b,-hexahydro[1]benzofuro[3,2-c]pyridine;
8-(2,6-difluoro-4-chlorophenyl)-6-(ethylthio)-1,2,3,4,4a,9b,-hexahydro[1]benzofuro[3,2-c]pyridine;
8-(2,6-difluoro-4-chlorophenyl)-6-(propylthio)-1,2,3,4,4a,9b,-hexahydro[1]benzofuro[3,2-c]pyridine;
8-(2,6-difluoro-4-chlorophenyl)-6-(isopropylthio)-1,2,3,4,4a,9b,-hexahydro[1]benzofuro[3,2-c]pyridine;
8-(2,6-difluoro-4-chlorophenyl)-6-(butylthio)-1,2,3,4,4a,9b,-hexahydro[1]benzofuro[3,2-c]pyridine;
8-(2,6-difluoro-4-chlorophenyl)-6-[(1-ethylpropyl)thio]-1,2,3,4,4a,9b,-hexahydro[1]benzofuro[3,2-c]pyridine;
8-(2,6-difluoro-4-chlorophenyl)-6-(cyclohexylthio)-1,2,3,4,4a,9b,-hexahydro[1]benzofuro[3,2-c]pyridine;
8-(2,6-difluoro-4-chlorophenyl)-6-(phenylthio)-1,2,3,4,4a,9b,-hexahydro[1]benzofuro[3,2-c]pyridine;
8-(2,6-difluoro-4-chlorophenyl)-6-(benzylthio)-1,2,3,4,4a,9b,-hexahydro[1]benzofuro[3,2-c]pyridine;
8-(2,4-dichlorophenyl)-6-methoxy-1,2,3,4,4a,9b,-hexahydro[1]benzofuro[3,2-c]pyridine;
8-(2,4-dichlorophenyl)-6-ethoxy-1,2,3,4,4a,9b,-hexahydro[1]benzofuro[3,2-c]-pyridine;
8-(2,4-dichlorophenyl)-6-propoxy-1,2,3,4,4a,9b,-hexahydro[1]benzofuro[3,2-c]pyridine;
8-(2,4-dichlorophenyl)-6-isopropoxy-1,2,3,4,4a,9b,-hexahydro[1]benzofuro[3,2-c]pyridine;
8-(2,4-dichlorophenyl)-6-butoxy-1,2,3,4,4a,9b,-hexahydro[1]benzofuro[3,2-c]-pyridine;

8-(2,4-dichlorophenyl)-6-[(1-ethylpropyl)oxy]-1,2,3,4,4a,9b,-hexahydro[1]benzofuro[3,2-c]pyridine;

8-(2,4-dichlorophenyl)-6-(cyclohexyloxy)-1,2,3,4,4a,9b,-hexahydro[1]benzofuro[3,2-c]pyridine;

8-(2,4-dichlorophenyl)-6-phenoxy-1,2,3,4,4a,9b,-hexahydro[1]benzofuro[3,2-c]pyridine;

8-(2,4-dichlorophenyl)-6-(benzyloxy)-1,2,3,4,4a,9b,-hexahydro[1]benzofuro[3,2-c]pyridine;

8-(2,4,6-trichlorophenyl)-6-methoxy-1,2,3,4,4a,9b,-hexahydro[1]benzofuro[3,2-c]pyridine;

8-(2,4,6-trichlorophenyl)-6-ethoxy-1,2,3,4,4a,9b,-hexahydro[1]benzofuro[3,2-c]pyridine;

8-(2,4,6-trichlorophenyl)-6-propoxy-1,2,3,4,4a,9b,-hexahydro[1]benzofuro[3,2-c]pyridine;

8-(2,4,6-trichlorophenyl)-6-isopropoxy-1,2,3,4,4a,9b,-hexahydro[1]benzofuro[3,2-c]pyridine;

8-(2,4,6-trichlorophenyl)-6-butoxy-1,2,3,4,4a,9b,-hexahydro[1]benzofuro[3,2-c]pyridine;

8-(2,4,6-trichlorophenyl)-6-[(1-ethylpropyl)oxy]-1,2,3,4,4a,9b,-hexahydro[1]benzofuro[3,2-c]pyridine;

8-(2,4,6-trichlorophenyl)-6-(cyclohexyloxy)-1,2,3,4,4a,9b,-hexahydro[1]benzofuro[3,2-c]pyridine;

8-(2,4,6-trichlorophenyl)-6-phenoxy-1,2,3,4,4a,9b,-hexahydro[1]benzofuro[3,2-c]pyridine;

8-(2,4,6-trichlorophenyl)-6-(benzyloxy)-1,2,3,4,4a,9b,-hexahydro[1]benzofuro[3,2-c]pyridine;

8-(2,6-difluoro-4-chlorophenyl)-6-methoxy-1,2,3,4,4a,9b,-hexahydro[1]benzofuro[3,2-c]pyridine;

8-(2,6-difluoro-4-chlorophenyl)-6-ethoxy-1,2,3,4,4a,9b,-hexahydro[1]benzofuro[3,2-c]pyridine;

8-(2,6-difluoro-4-chlorophenyl)-6-propoxy-1,2,3,4,4a,9b,-hexahydro[1]benzofuro[3,2-c]pyridine;

8-(2,6-difluoro-4-chlorophenyl)-6-(2-propoxy)-1,2,3,4,4a,9b,-hexahydro[1]benzofuro[3,2-c]pyridine;

8-(2,6-difluoro-4-chlorophenyl)-6-butoxy-1,2,3,4,4a,9b,-hexahydro[1]benzofuro[3,2-c]pyridine;

8-(2,6-difluoro-4-chlorophenyl)-6-[(1-ethylpropyl)oxy]-1,2,3,4,4a,9b,-hexahydro[1]benzofuro[3,2-c]pyridine;

8-(2,6-difluoro-4-chlorophenyl)-6-(cyclohexyloxy)-1,2,3,4,4a,9b,-hexahydro[1]benzofuro[3,2-c]pyridine;

8-(2,6-difluoro-4-chlorophenyl)-6-phenoxy-1,2,3,4,4a,9b,-hexahydro[1]benzofuro[3,2-c]pyridine;

8-(2,6-difluoro-4-chlorophenyl)-6-(benzyloxy)-1,2,3,4,4a,9b,-hexahydro[1]benzofuro[3,2-c]pyridine;

8-(2,4-dichlorophenyl)-6-piperidin-1-yl-1,2,3,4,4a,9b-hexahydro[1]benzofuro[3,2-c]pyridine;

8-(2,4,6-trichlorophenyl)-6-piperidin-1-yl-1,2,3,4,4a,9b-hexahydro[1]benzofuro[3,2-c]pyridine;

8-(2,6-difluoro-4-chlorophenyl)-6-piperidin-1-yl-1,2,3,4,4a,9b-hexahydro[1]benzofuro[3,2-c]pyridine;

8-(2,4-dichlorophenyl)-6-azepano-1-yl-1,2,3,4,4a,9b-hexahydro[1]benzofuro[3,2-c]pyridine;

8-(2,4,6-trichlorophenyl)-6-azepano-1-yl-1,2,3,4,4a,9b-hexahydro[1]benzofuro[3,2-c]pyridine;

8-(2,6-difluoro-4-chlorophenyl)-6-azepano-1-yl-1,2,3,4,4a,9b-hexahydro-[1]benzofuro[3,2-c]pyridine;

8-(2,4-dichlorophenyl)-6-pyrrolidin-1-yl-1,2,3,4,4a,9b-hexahydro[1]benzofuro[3,2-c]pyridine;

8-(2,4,6-trichlorophenyl)-6-pyrrolidin-1-yl-1,2,3,4,4a,9b-hexahydro[1]benzofuro[3,2-c]pyridine;

8-(2,6-difluoro-4-chlorophenyl)-6-pyrrolidin-1-yl-1,2,3,4,4a,9b-hexahydro-[1]benzofuro[3,2-c]pyridine;

8-(2,4-dichlorophenyl)-5-morpholin-4-yl-1,2,3,4,4a,9b-hexahydro[1]benzofuro[3,2-c]pyridine;

8-(2,4,6-trichlorophenyl)-5-morpholin-4-yl-1,2,3,4,4a,9b-hexahydro-[1]benzofuro[3,2-c]pyridine;

8-(2,6-difluoro-4-chlorophenyl)-5-morpholin-4-yl-1,2,3,4,4a,9b-hexahydro-[1]benzofuro[3,2-c]pyridine;

8-(2,4-dichlorophenyl)-6-thiomorpholin-4-yl-1,2,3,4,4a,9b-hexahydro-[1]benzofuro[3,2-c]pyridine;

8-(2,4,6-trichlorophenyl)-6-thiomorpholin-4-yl-1,2,3,4,4a,9b-hexahydro-[1]benzofuro[3,2-c]pyridine;

8-(2,6-difluoro-4-chlorophenyl)-6-thiomorpholin-4-yl-1,2,3,4,4a,9b-hexahydro[1]benzofuro[3,2-c]pyridine;

8-(2,4-dichlorophenyl)-6-piperazin-1-yl-1,2,3,4,4a,9b-hexahydro[1]benzofuro[3,2-c]pyridine;

8-(2,4,6-trichlorophenyl)-6-piperazin-1-yl-1,2,3,4,4a,9b-hexahydro[1]benzofuro[3,2-c]pyridine;

8-(2,6-difluoro-4-chlorophenyl)-6-piperazin-1-yl-1,2,3,4,4a,9b-hexahydro[1]benzofuro[3,2-c]pyridine;

8-(2,4,6-trichlorophenyl)-N,N-dipropyl-1,2,3,4,4a,9b,-hexahydro[1]benzofuro[3,2-c]pyridin-6-amine;

8-(2,6-difluoro-4-chlorophenyl)-N,N-dipropyl-1,2,3,4,4a,9b,-hexahydro[1]benzofuro[3,2-c]pyridin-6-amine;

8-(2,4-Dichlorophenyl)-1,2,3,4,4a,9b-hexahydro[1]benzofuro[3,2-c]pyridine;

1,2,3,4,4a,9b-Hexahydro[1]benzofuro[3,2-c]pyridine;

8-[2-(Trifluoromethyl)phenyl]-1,2,3,4,4a,9b-hexahydro[1]benzofuro[3,2-c]pyridine;

8-[2-(Trifluoromethoxy)phenyl]-1,2,3,4,4a,9b-hexahydro[1]benzofuro[3,2-c]pyridine;

6-Bromo-8-(2,4-dichlorophenyl)-1,2,3,4,4a,9b-hexahydro[1]benzofuro[3,2-c]pyridine;

6-Benzyl-8-(2,4-dichlorophenyl)-1,2,3,4,4a,9b-hexahydro[1]benzofuro[3,2-c]pyridine;

6-Butyl-8-(2,4-dichlorophenyl)-1,2,3,4,4a,9b-hexahydro[1]benzofuro[3,2-c]pyridine;

8-(2,4-Dichlorophenyl)-6-(propylthio)-1,2,3,4,4a,9b-hexahydro[1]benzofuro[3,2-c]pyridine;

8-(2,4-Dichlorophenyl)-6-(isopropylthio)-1,2,3,4,4a,9b-hexahydro[1]benzofuro[3,2-c]pyridine;

8-(2,4-Dichlorophenyl)-6-(isobutylthio)-1,2,3,4,4a,9b-hexahydro[1]benzofuro[3,2-c]pyridine;

8-(2,4-Dichlorophenyl)-6-(methylthio)-1,2,3,4,4a,9b-hexahydro[1]benzofuro[3,2-c]pyridine;

6-(Cyclopentylthio)-8-(2,4-dichlorophenyl)-1,2,3,4,4a,9b-hexahydro[1]benzofuro[3,2-c]pyridine;

6-(Cyclobutylthio)-8-(2,4-dichlorophenyl)-1,2,3,4,4a,9b-hexahydro[1]benzofuro[3,2-c]pyridine;

8-(2,4-dichlorophenyl)-6-morpholin-4-yl-1,2,3,4,4a,9b-hexahydro[1]benzofuro[3,2-c]pyridine;

N-Benzyl-8-(2,4-dichlorophenyl)-1,2,3,4,4a,9b-hexahydro[1]benzofuro[3,2-c]pyridin-6-amine;

8-(2,4-Dichlorophenyl)-6-pyrrolidin-1-yl-1,2,3,4,4a,9b-hexahydro[1]benzofuro[3,2-c]pyridine;

8-(2,4-Dichlorophenyl)-6-methoxy-1,2,3,4,4a,9b-hexahydro[1]benzofuro[3,2-c]pyridine;

or a pharmaceutically acceptable salt thereof.

75. The compound of claim 60, wherein the compound is:

(4aS,9bR)-8-(2,4-dichlorophenyl)-N-cyclohexyl-1,2,3,4,4a,9b,-hexahydro[1]benzofuro[3,2-c]pyridin-6-amine;

(4aS,9bR)-8-(2,4,6-trichlorophenyl)-N-cyclohexyl-1,2,3,4,4a,9b,-hexahydro[1]benzofuro[3,2-c]pyridin-6-amine;

(4aS,9bR)-8-(2,6-difluoro-4-chlorophenyl)-N-cyclohexyl-1,2,3,4,4a,9b,-hexahydro[1]benzofuro[3,2-c]pyridin-6-amine;
(4aS,9bR)-8-(2,4-dichlorophenyl)-N-phenyl-1,2,3,4,4a,9b,-hexahydro[1]benzofuro[3,2-c]pyridin-6-amine;
(4aS,9bR)-8-(2,4,6-trichlorophenyl)-N-phenyl-1,2,3,4,4a,9b,-hexahydro[1]benzofuro[3,2-c]pyridin-6-amine;
(4aS,9bR)-8-(2,6-difluoro-4-chlorophenyl)-N-phenyl-1,2,3,4,4a,9b,-hexahydro[1]benzofuro[3,2-c]pyridin-6-amine;
(4aS,9bR)-8-(2,4-dichlorophenyl)-N,N-dimethyl-1,2,3,4,4a,9b,-hexahydro[1]benzofuro[3,2-c]pyridin-6-amine;
(4aS,9bR)-8-(2,4,6-trichlorophenyl)-N,N-dimethyl-1,2,3,4,4a,9b,-hexahydro[1]benzofuro[3,2-c]pyridin-6-amine;
(4aS,9bR)-8-(2,6-difluoro-4-chlorophenyl)-N,N-dimethyl-1,2,3,4,4a,9b,-hexahydro[1]benzofuro[3,2-c]pyridin-6-amine;
(4aS,9bR)-8-(2,4-dichlorophenyl)-N,N-diethyl-1,2,3,4,4a,9b,-hexahydro[1]benzofuro[3,2-c]pyridin-6-amine;
(4aS,9bR)-8-(2,4,6-trichlorophenyl)-N,N-diethyl-1,2,3,4,4a,9b,-hexahydro[1]benzofuro[3,2-c]pyridin-6-amine;
(4aS,9bR)-8-(2,6-difluoro-4-chlorophenyl)-N,N-diethyl-1,2,3,4,4a,9b,-hexahydro[1]benzofuro[3,2-c]pyridin-6-amine;
(4aS,9bR)-8-(2,4-dichlorophenyl)-N-methyl-N-ethyl-1,2,3,4,4a,9b,-hexahydro[1]benzofuro[3,2-c]pyridin-6-amine;
(4aS,9bR)-8-(2,4-dichlorophenyl)-N-methyl-N-propyl-1,2,3,4,4a,9b,-hexahydro[1]benzofuro[3,2-c]pyridin-6-amine;
(4aS,9bR)-8-(2,4-dichlorophenyl)-N-methyl-N-cyclohexyl-1,2,3,4,4a,9b,-hexahydro[1]benzofuro[3,2-c]pyridin-6-amine;
(4aS,9bR)-8-(2,4-dichlorophenyl)-N-ethyl-N-propyl-1,2,3,4,4a,9b,-hexahydro[1]benzofuro[3,2-c]pyridin-6-amine;
(4aS,9bR)-8-(2,4-dichlorophenyl)-N-ethyl-N-cyclohexyl-1,2,3,4,4a,9b,-hexahydro[1]benzofuro[3,2-c]pyridin-6-amine;
(4aS,9bR)-8-(2,4-dichlorophenyl)-N,N-dipropyl-1,2,3,4,4a,9b,-hexahydro[1]benzofuro[3,2-c]pyridin-6-amine;
(4aS,9bR)-8-(2,4-dichlorophenyl)-N-propyl-N-cyclohexyl-1,2,3,4,4a,9b,-hexahydro[1]benzofuro[3,2-c]pyridin-6-amine;
(4aS,9bR)-8-(2,4-dichlorophenyl)-N,N-dicyclohexyl-1,2,3,4,4a,9b,-hexahydro[1]benzofuro[3,2-c]pyridin-6-amine;
(4aS,9bR)-8-(2,4-dichlorophenyl)-6-methyl-1,2,3,4,4a,9b,-hexahydro[1]benzofuro[3,2-c]pyridine;
(4aS,9bR)-8-(2,4-dichlorophenyl)-6-ethyl-1,2,3,4,4a,9b,-hexahydro[1]benzofuro[3,2-c]pyridine;
(4aS,9bR)-8-(2,4-dichlorophenyl)-6-propyl-1,2,3,4,4a,9b,-hexahydro[1]benzofuro[3,2-c]pyridine;
(4aS,9bR)-8-(2,4-dichlorophenyl)-6-(isopropyl)-1,2,3,4,4a,9b,-hexahydro[1]benzofuro[3,2-c]pyridine;
(4aS,9bR)-8-(2,4-dichlorophenyl)-6-butyl-1,2,3,4,4a,9b,-hexahydro[1]benzofuro[3,2-c]pyridine;
(4aS,9bR)-8-(2,4-dichlorophenyl)-6-(1-ethylpropyl)-1,2,3,4,4a,9b,-hexahydro[1]benzofuro[3,2-c]pyridine;
(4aS,9bR)-8-(2,4-dichlorophenyl)-6-cyclohexyl-1,2,3,4,4a,9b,-hexahydro[1]benzofuro[3,2-c]pyridine;
(4aS,9bR)-8-(2,4-dichlorophenyl)-6-phenyl-1,2,3,4,4a,9b,-hexahydro[1]benzofuro[3,2-c]pyridine;
(4aS,9bR)-8-(2,4-dichlorophenyl)-6-benzyl-1,2,3,4,4a,9b,-hexahydro[1]benzofuro[3,2-c]pyridine;
(4aS,9bR)-8-(2,4,6-trichlorophenyl)-6-methyl-1,2,3,4,4a,9b,-hexahydro[1]benzofuro[3,2-c]pyridine;
(4aS,9bR)-8-(2,4,6-trichlorophenyl)-6-ethyl-1,2,3,4,4a,9b,-hexahydro[1]benzofuro[3,2-c]pyridine;
(4aS,9bR)-8-(2,4,6-trichlorophenyl)-6-propyl-1,2,3,4,4a,9b,-hexahydro[1]benzofuro[3,2-c]pyridine;
(4aS,9bR)-8-(2,4,6-trichlorophenyl)-6-(isopropyl)-1,2,3,4,4a,9b,-hexahydro[1]benzofuro[3,2-c]pyridine;
(4aS,9bR)-8-(2,4,6-trichlorophenyl)-6-butyl-1,2,3,4,4a,9b,-hexahydro[1]benzofuro[3,2-c]pyridine;
(4aS,9bR)-8-(2,4,6-trichlorophenyl)-6-(1-ethylpropyl)-1,2,3,4,4a,9b,-hexahydro[1]benzofuro[3,2-c]pyridine;
(4aS,9bR)-8-(2,4,6-trichlorophenyl)-6-cyclohexyl-1,2,3,4,4a,9b,-hexahydro[1]benzofuro[3,2-c]pyridine;
(4aS,9bR)-8-(2,4,6-trichlorophenyl)-6-phenyl-1,2,3,4,4a,9b,-hexahydro[1]benzofuro[3,2-c]pyridine;
(4aS,9bR)-8-(2,4,6-trichlorophenyl)-6-benzyl-1,2,3,4,4a,9b,-hexahydro[1]benzofuro[3,2-c]pyridine;
(4aS,9bR)-8-(2,6-difluoro-4-chlorophenyl)-6-methyl-1,2,3,4,4a,9b,-hexahydro[1]benzofuro[3,2-c]pyridine;
(4aS,9bR)-8-(2,6-difluoro-4-chlorophenyl)-6-ethyl-1,2,3,4,4a,9b,-hexahydro[1]benzofuro[3,2-c]pyridine;
(4aS,9bR)-8-(2,6-difluoro-4-chlorophenyl)-6-propyl-1,2,3,4,4a,9b,-hexahydro[1]benzofuro[3,2-c]pyridine;
(4aS,9bR)-8-(2,6-difluoro-4-chlorophenyl)-6-(isopropyl)-1,2,3,4,4a,9b,-hexahydro[1]benzofuro[3,2-c]pyridine;
(4aS,9bR)-8-(2,6-difluoro-4-chlorophenyl)-6-butyl-1,2,3,4,4a,9b,-hexahydro[1]benzofuro[3,2-c]pyridine;
(4aS,9bR)-8-(2,6-difluoro-4-chlorophenyl)-6-(1-ethylpropyl)-1,2,3,4,4a,9b,-hexahydro[1]benzofuro[3,2-c]pyridine;
(4aS,9bR)-8-(2,6-difluoro-4-chlorophenyl)-6-cyclohexyl-1,2,3,4,4a,9b,-hexahydro[1]benzofuro[3,2-c]pyridine;
(4aS,9bR)-8-(2,6-difluoro-4-chlorophenyl)-6-phenyl-1,2,3,4,4a,9b,-hexahydro[1]benzofuro[3,2-c]pyridine;
(4aS,9bR)-8-(2,6-difluoro-4-chlorophenyl)-6-benzyl-1,2,3,4,4a,9b,-hexahydro[1]benzofuro[3,2-c]pyridine;
(4aS,9bR)-8-(2,4-dichlorophenyl)-6-(methylthio)-1,2,3,4,4a,9b,-hexahydro[1]benzofuro[3,2-c]pyridine;
(4aS,9bR)-8-(2,4-dichlorophenyl)-6-(ethylthio)-1,2,3,4,4a,9b,-hexahydro[1]benzofuro[3,2-c]pyridine;
(4aS,9bR)-8-(2,4-dichlorophenyl)-6-(propylthio)-1,2,3,4,4a,9b,-hexahydro[1]benzofuro[3,2-c]pyridine;
(4aS,9bR)-8-(2,4-dichlorophenyl)-6-(2-propylthio)-1,2,3,4,4a,9b,-hexahydro[1]benzofuro[3,2-c]pyridine;
(4aS,9bR)-8-(2,4-dichlorophenyl)-6-(butylthio)-1,2,3,4,4a,9b,-hexahydro[1]benzofuro[3,2-c]pyridine;
(4aS,9bR)-8-(2,4-dichlorophenyl)-6-[(1-ethylpropyl)thio]-1,2,3,4,4a,9b,-hexahydro[1]benzofuro[3,2-c]pyridine;
(4aS,9bR)-8-(2,4-dichlorophenyl)-6-(cyclohexylthio)-1,2,3,4,4a,9b,-hexahydro[1]benzofuro[3,2-c]pyridine;
(4aS,9bR)-8-(2,4-dichlorophenyl)-6-(phenylthio)-1,2,3,4,4a,9b,-hexahydro[1]benzofuro[3,2-c]pyridine;
(4aS,9bR)-8-(2,4-dichlorophenyl)-6-(benzylthio)-1,2,3,4,4a,9b,-hexahydro[1]benzofuro[3,2-c]pyridine;
(4aS,9bR)-8-(2,4,6-trichlorophenyl)-6-(methylthio)-1,2,3,4,4a,9b,-hexahydro[1]benzofuro[3,2-c]pyridine;

(4aS,9bR)-8-(2,4,6-trichlorophenyl)-6-(ethylthio)-1,2,3,4,4a,9b,-hexahydro[1]benzofuro[3,2-c]pyridine;

(4aS,9bR)-8-(2,4,6-trichlorophenyl)-6-(propylthio)-1,2,3,4,4a,9b,-hexahydro[1]benzofuro[3,2-c]pyridine;

(4aS,9bR)-8-(2,4,6-trichlorophenyl)-6-(2-propylthio)-1,2,3,4,4a,9b,-hexahydro[1]benzofuro[3,2-c]pyridine;

(4aS,9bR)-8-(2,4,6-trichlorophenyl)-6-(butylthio)-1,2,3,4,4a,9b,-hexahydro[1]benzofuro[3,2-c]pyridine;

(4aS,9bR)-8-(2,4,6-trichlorophenyl)-6-[(1-ethylpropyl)thio]-1,2,3,4,4a,9b,-hexahydro[1]benzofuro[3,2-c]pyridine;

(4aS,9bR)-8-(2,4,6-trichlorophenyl)-6-(cyclohexylthio)-1,2,3,4,4a,9b,-hexahydro[1]benzofuro[3,2-c]pyridine;

(4aS,9bR)-8-(2,4,6-trichlorophenyl)-6-(phenylthio)-1,2,3,4,4a,9b,-hexahydro[1]benzofuro[3,2-c]pyridine;

(4aS,9bR)-8-(2,4,6-trichlorophenyl)-6-(benzylthio)-1,2,3,4,4a,9b,-hexahydro[1]benzofuro[3,2-c]pyridine;

(4aS,9bR)-8-(2,6-difluoro-4-chlorophenyl)-6-(methylthio)-1,2,3,4,4a,9b,-hexahydro[1]benzofuro[3,2-c]pyridine;

(4aS,9bR)-8-(2,6-difluoro-4-chlorophenyl)-6-(ethylthio)-1,2,3,4,4a,9b,-hexahydro[1]benzofuro[3,2-c]pyridine;

(4aS,9bR)-8-(2,6-difluoro-4-chlorophenyl)-6-(propylthio)-1,2,3,4,4a,9b,-hexahydro[1]benzofuro[3,2-c]pyridine;

(4aS,9bR)-8-(2,6-difluoro-4-chlorophenyl)-6-(isopropyl)-1,2,3,4,4a,9b,-hexahydro[1]benzofuro[3,2-c]pyridine;

(4aS,9bR)-8-(2,6-difluoro-4-chlorophenyl)-6-(butylthio)-1,2,3,4,4a,9b,-hexahydro[1]benzofuro[3,2-c]pyridine;

(4aS,9bR)-8-(2,6-difluoro-4-chlorophenyl)-6-[(1-ethylpropyl)thio]-1,2,3,4,4a,9b,-hexahydro[1]benzofuro[3,2-c]pyridine;

(4aS,9bR)-8-(2,6-difluoro-4-chlorophenyl)-6-(cyclohexylthio)-1,2,3,4,4a,9b,-hexahydro[1]benzofuro[3,2-c]pyridine;

(4aS,9bR)-8-(2,6-difluoro-4-chlorophenyl)-6-(phenylthio)-1,2,3,4,4a,9b,-hexahydro[1]benzofuro[3,2-c]pyridine;

(4aS,9bR)-8-(2,6-difluoro-4-chlorophenyl)-6-(benzylthio)-1,2,3,4,4a,9b,-hexahydro[1]benzofuro[3,2-c]pyridine;

(4aS,9bR)-8-(2,4-dichlorophenyl)-6-methoxy-1,2,3,4,4a,9b,-hexahydro[1]benzofuro[3,2-c]pyridine;

(4aS,9bR)-8-(2,4-dichlorophenyl)-6-ethoxy-1,2,3,4,4a,9b,-hexahydro[1]benzofuro[3,2-c]pyridine;

(4aS,9bR)-8-(2,4-dichlorophenyl)-6-propoxy-1,2,3,4,4a,9b,-hexahydro[1]benzofuro[3,2-c]pyridine;

(4aS,9bR)-8-(2,4-dichlorophenyl)-6-isopropoxy-1,2,3,4,4a,9b,-hexahydro[1]benzofuro[3,2-c]pyridine;

(4aS,9bR)-8-(2,4-dichlorophenyl)-6-butoxy-1,2,3,4,4a,9b,-hexahydro[1]benzofuro[3,2-c]pyridine;

(4aS,9bR)-8-(2,4-dichlorophenyl)-6-[(1-ethylpropyl)oxy]-1,2,3,4,4a,9b,-hexahydro[1]benzofuro[3,2-c]pyridine;

(4aS,9bR)-8-(2,4-dichlorophenyl)-6-(cyclohexyloxy)-1,2,3,4,4a,9b,-hexahydro[1]benzofuro[3,2-c]pyridine;

(4aS,9bR)-8-(2,4-dichlorophenyl)-6-phenoxy-1,2,3,4,4a,9b,-hexahydro[1]benzofuro[3,2-c]pyridine;

(4aS,9bR)-8-(2,4-dichlorophenyl)-6-(benzyloxy)-1,2,3,4,4a,9b,-hexahydro[1]benzofuro[3,2-c]pyridine;

(4aS,9bR)-8-(2,4,6-trichlorophenyl)-6-methoxy-1,2,3,4,4a,9b,-hexahydro[1]benzofuro[3,2-c]pyridine;

(4aS,9bR)-8-(2,4,6-trichlorophenyl)-6-ethoxy-1,2,3,4,4a,9b,-hexahydro[1]benzofuro[3,2-c]pyridine;

(4aS,9bR)-8-(2,4,6-trichlorophenyl)-6-propoxy-1,2,3,4,4a,9b,-hexahydro[1]benzofuro[3,2-c]pyridine;

(4aS,9bR)-8-(2,4,6-trichlorophenyl)-6-isopropoxy-1,2,3,4,4a,9b,-hexahydro[1]benzofuro[3,2-c]pyridine;

(4aS,9bR)-8-(2,4,6-trichlorophenyl)-6-butoxy-1,2,3,4,4a,9b,-hexahydro[1]benzofuro[3,2-c]pyridine;

(4aS,9bR)-8-(2,4,6-trichlorophenyl)-6-[(1-ethylpropyl)oxy]-1,2,3,4,4a,9b,-hexahydro[1]benzofuro[3,2-c]pyridine;

(4aS,9bR)-8-(2,4,6-trichlorophenyl)-6-(cyclohexyloxy)-1,2,3,4,4a,9b,-hexahydro[1]benzofuro[3,2-c]pyridine;

(4aS,9bR)-8-(2,4,6-trichlorophenyl)-6-phenoxy-1,2,3,4,4a,9b,-hexahydro[1]benzofuro[3,2-c]pyridine;

(4aS,9bR)-8-(2,4,6-trichlorophenyl)-6-(benzyloxy)-1,2,3,4,4a,9b,-hexahydro[1]benzofuro[3,2-c]pyridine;

(4aS,9bR)-8-(2,6-difluoro-4-chlorophenyl)-6-methoxy-1,2,3,4,4a,9b,-hexahydro[1]benzofuro[3,2-c]pyridine;

(4aS,9bR)-8-(2,6-difluoro-4-chlorophenyl)-6-ethoxy-1,2,3,4,4a,9b,-hexahydro[1]benzofuro[3,2-c]pyridine;

(4aS,9bR)-8-(2,6-difluoro-4-chlorophenyl)-6-propoxy-1,2,3,4,4a,9b,-hexahydro[1]benzofuro[3,2-c]pyridine;

(4aS,9bR)-8-(2,6-difluoro-4-chlorophenyl)-6-(2-propoxy)-1,2,3,4,4a,9b,-hexahydro[1]benzofuro[3,2-c]pyridine;

(4aS,9bR)-8-(2,6-difluoro-4-chlorophenyl)-6-butoxy-1,2,3,4,4a,9b,-hexahydro[1]benzofuro[3,2-c]pyridine;

(4aS,9bR)-8-(2,6-difluoro-4-chlorophenyl)-6-[(1-ethylpropyl)oxy]-1,2,3,4,4a,9b,-hexahydro[1]benzofuro[3,2-c]pyridine;

(4aS,9bR)-8-(2,6-difluoro-4-chlorophenyl)-6-(cyclohexyloxy)-1,2,3,4,4a,9b,-hexahydro[1]benzofuro[3,2-c]pyridine;

(4aS,9bR)-8-(2,6-difluoro-4-chlorophenyl)-6-phenoxy-1,2,3,4,4a,9b,-hexahydro[1]benzofuro[3,2-c]pyridine;

(4aS,9bR)-8-(2,6-difluoro-4-chlorophenyl)-6-(benzyloxy)-1,2,3,4,4a,9b,-hexahydro[1]benzofuro[3,2-c]pyridine;

(4aS,9bR)-8-(2,4-dichlorophenyl)-6-piperidin-1-yl-1,2,3,4,4a,9b-hexahydro[1]benzofuro[3,2-c]pyridine;

(4aS,9bR)-8-(2,4,6-trichlorophenyl)-6-piperidin-1-yl-1,2,3,4,4a,9b-hexahydro[1]benzofuro[3,2-c]pyridine;

(4aS,9bR)-8-(2,6-difluoro-4-chlorophenyl)-6-piperidin-1-yl-1,2,3,4,4a,9b-hexahydro[1]benzofuro[3,2-c]pyridine;

(4aS,9bR)-8-(2,4-dichlorophenyl)-6-azepan-1-yl-1,2,3,4,4a,9b-hexahydro[1]benzofuro[3,2-c]pyridine;

(4aS,9bR)-8-(2,4,6-trichlorophenyl)-6-hexahydroazepin-1-yl-1,2,3,4,4a,9b-hexahydro[1]benzofuro[3,2-c]pyridine;

(4aS,9bR)-8-(2,6-difluoro-4-chlorophenyl)-6-hexahydroazepin-1-yl-1,2,3,4,4a,9b-hexahydro[1]benzofuro[3,2-c]pyridine;

(4aS,9bR)-8-(2,4-dichlorophenyl)-6-pyrrolidin-1-yl-1,2,3,4,4a,9b-hexahydro[1]benzofuro[3,2-c]pyridine;

(4aS,9bR)-8-(2,4,6-trichlorophenyl)-6-pyrrolidin-1-yl-1,2,3,4,4a,9b-hexahydro[1]benzofuro[3,2-c]pyridine;

(4aS,9bR)-8-(2,6-difluoro-4-chlorophenyl)-6-pyrrolidin-1-yl-1,2,3,4,4a,9b-hexahydro[1]benzofuro[3,2-c]pyridine;

(4aS,9bR)-8-(2,4-dichlorophenyl)-5-morpholin-4-yl-1,2,3,4,4a,9b-hexahydro[1]benzofuro[3,2-c]pyridine;

(4aS,9bR)-8-(2,4,6-trichlorophenyl)-5-morpholin-4-yl-1,2,3,4,4a,9b-hexahydro[1]benzofuro[3,2-c]pyridine;

(4aS,9bR)-8-(2,6-difluoro-4-chlorophenyl)-5-morpholin-4-yl-1,2,3,4,4a,9b-hexahydro[1]benzofuro[3,2-c]pyridine;

(4aS,9bR)-8-(2,4-dichlorophenyl)-6-thiomorpholin-4-yl-1,2,3,4,4a,9b-hexahydro[1]benzofuro[3,2-c]pyridine;

(4aS,9bR)-8-(2,4,6-trichlorophenyl)-6-thiomorpholin-4-yl-1,2,3,4,4a,9b-hexahydro[1]benzofuro[3,2-c]pyridine;

(4aS,9bR)-8-(2,6-difluoro-4-chlorophenyl)-6-thiomorpholin-4-yl-1,2,3,4,4a,9b-hexahydro[1]benzofuro[3,2-c]pyridine;

(4aS,9bR)-8-(2,4-dichlorophenyl)-6-piperazin-1-yl-1,2,3,4,4a,9b-hexahydro[1]benzofuro[3,2-c]pyridine;

(4aS,9bR)-8-(2,4,6-trichlorophenyl)-6-piperazin-1-yl-1,2,3,4,4a,9b-hexahydro[1]benzofuro[3,2-c]pyridine;

(4aS,9bR)-8-(2,6-difluoro-4-chlorophenyl)-6-piperazin-1-yl-1,2,3,4,4a,9b-hexahydro[1]benzofuro[3,2-c]pyridine;

(4aS,9bR)-8-(2,4,6-trichlorophenyl)-N,N-dipropyl-1,2,3,4,4a,9b,-hexahydro[1]benzofuro[3,2-c]pyridin-6-amine;

(4aS,9bR)-8-(2,6-difluoro-4-chlorophenyl)-N,N-dipropyl-1,2,3,4,4a,9b,-hexahydro[1]benzofuro[3,2-c]pyridin-6-amine;

(4aS,9bR) 6-Bromo-8-(2,4-dichlorophenyl)-1,2,3,4,4a,9b-hexahydro[1]benzofuro[3,2-c]pyridine;

(4aR,9bS) 6-Bromo-8-(2,4-dichlorophenyl)-1,2,3,4,4a,9b-hexahydro[1]benzofuro[3,2-c]pyridine;

or a pharmaceutically acceptable salt thereof.

76. A compound of formula (I):

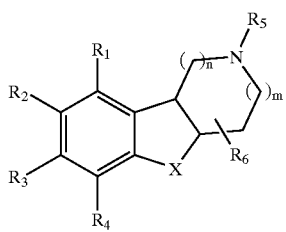

(I)

wherein:

$R_1$, $R_2$, $R_3$, and $R_4$ are independently hydrogen, halo, —$CF_3$, —$OCF_3$, —CN, —$NO_2$, —$C_{1-8}$alkyl, —$C_{3-8}$cycloalkyl, —$OR_8$, —$NR_8R_9$, —$SR_8$, —C(=O)aryl, aryl, —$C_{1-8}$alkylene(aryl), —C(=O)heteroaryl, heteroaryl, or —$C_{1-8}$alkylene(heteroaryl), provided that at least one of $R_1$, $R_2$, $R_3$, and $R_4$ is aryl optionally substituted with one or more substituents independently selected from halo, hydroxy, cyano, nitro, trifluoromethyl, trifluoromethoxy, $C_{1-6}$alkyl, —$OR_c$, —$SR_c$, phenyl, —$NR_cR_d$, or —C(=O)$NR_cR_d$, and further provided that at least two of $R_1$, $R_2$, $R_3$, and $R_4$ are other than hydrogen;

$R_5$ is hydrogen, $C_{1-8}$alkyl, halo$C_{1-8}$alkyl, $C_{3-8}$cycloalkyl, $C_{1-8}$alkanoyl, halo$C_{1-8}$alkanoyl, —C(=O)$OR_8$, —C(=O)aryl, aryl, —$C_{1-8}$alkylene(aryl), —C(=O)heteroaryl, heteroaryl, or —$C_{1-8}$alkylene(heteroaryl);

$R_6$ is hydrogen or $C_{1-4}$alkyl;

each $R_8$ and $R_9$ is independently hydrogen, $C_{1-8}$alkyl, halo$C_{1-8}$alkyl, $C_{3-8}$cycloalkyl, —C(=O)aryl, aryl, —$C_{1-8}$alkylene(aryl), —C(=O)heteroaryl, heteroaryl, or —$C_{1-8}$alkylene(heteroaryl) or $R_8$ and $R_9$ together with the nitrogen to which they are attached form a pyrrolidino, piperidino, azepano, piperazino, morpholino, or thiomorpholino ring;

m is 1;

n is 1;

X is oxy (—O—), thio (—S—) —S(=O)— or —$SO_2$—; and wherein any $C_{1-8}$alkyl, $C_{1-8}$alkylene, $C_{1-8}$alkoxy or $C_{3-8}$cycloalkyl of $R_1$, $R_3$, $R_4$, $R_5$, $R_6$, $R_8$ and $R_9$ is optionally partially unsaturated; and wherein any aryl or heteroaryl of $R_1$, $R_2$, $R_3$, $R_4$, $R_5$, $R_8$ or $R_9$ is optionally substituted with one or more substituents independently selected from halo, —CN, —$NO_2$, —$CF_3$, —$OCF_3$, $C_{1-8}$alkyl, $C_{2-8}$alkenyl, $C_{2-8}$alkynyl, $C_{3-8}$cycloalkyl, $C_{3-8}$cycloalkenyl, aryl, heteroaryl, —$OR_c$, —$SR_c$, —C(=O)$R_c$, —$CO_2R_c$, —C(=O)$NR_cR_d$, —$NR_cC$(=O)$R_d$, —C(=O)$NR_cR_d$, —$NR_cR_d$, —$NR_cC$(=O)$NR_cR_d$, —$SO_2NR_cR_d$ or —$SO_2R_c$;

wherein each $R_c$ and $R_d$ is independently hydrogen, $C_{1-8}$alkyl, $C_{1-8}$alkanoyl, $C_{1-8}$alkoxycarbonyl, aryl, —$C_{1-8}$alkylene(aryl), —C(=O)aryl, —C(=O)Oaryl, heteroaryl, —$C_{1-8}$alkylene(heteroaryl), —C(=O) heteroaryl, —C(=O)Oheteroaryl or $R_c$ and $R_d$ together with the nitrogen to which they are attached form a pyrrolidino, piperidino, azepano, piperazino, morpholino, or thiomorpholino ring; or a pharmaceutically acceptable salt thereof.

77. The compound of claim 76, wherein $R_2$ is phenyl optionally substituted with one or more substituents independently selected from halo, cyano, nitro, trifluoromethyl, trifluoromethoxy, $C_{1-6}$alkyl, —$OR_c$, —$SR_c$, phenyl, —$NR_cR_d$, or —C(=O)$NR_cR_d$.

78. The compound of claim 77, wherein $R_2$ is phenyl optionally substituted with one or more halo.

79. The compound of claim 78, wherein $R_2$ is phenyl substituted at the 2- or 6-position with fluoro, chloro, or bromo.

80. The compound of claim 78, wherein $R_2$ is phenyl substituted at the 2- and 6-position with halo independently selected from fluoro, chloro, and bromo.

81. The compound of claim 78, wherein $R_2$ is phenyl substituted at the 2- or 4-position with fluoro, chloro, or bromo.

82. The compound of claim 78, wherein $R_2$ is phenyl substituted at the 2- and 4-position with halo independently selected from fluoro, chloro, and bromo.

83. The compound of claim 78, wherein $R_2$ is phenyl substituted at the 2-, 4- and 6-position with halo independently selected from fluoro, chloro, and bromo.

84. The compound of claim 78, wherein $R_2$ is 2,4-dichlorophenyl, 2,4,6-trichlorophenyl or 2,6-difluoro-4-chlorophenyl.

85. The compound of claim 78, wherein $R_4$ is halo, —$CF_3$, $C_{1-8}$alkyl, —$OR_8$, —$SR_8$, —$NR_8R_9$, aryl or —$C_{1-8}$alkylene(aryl), wherein the aryl groups are optionally substituted with one or more substituents independently selected from halo, hydroxy, cyano, nitro, trifluoromethyl, trifluoromethoxy, $C_{1-6}$alkyl, $C_{1-6}$alkoxy, phenyl, —$NR_cR_d$, and —C(=O)$NR_cR_d$.

86. The compound of claim 85, wherein $R_4$ is halo, —$CF_3$, $C_{1-8}$alkyl, —$NR_8R_9$, aryl, or —$C_{1-8}$alkylene(aryl), wherein aryl is optionally substituted with one or more substituents independently selected from halo, hydroxy, cyano, nitro, trifluoromethyl, trifluoromethoxy, $C_{1-6}$alkyl, $C_{1-6}$alkoxy, phenyl, —$NR_cR_d$, and —C(=O)$NR_cR_d$.

87. The compound of claim 86, wherein $R_4$ is aryl, —$C_{1-8}$alkylene(aryl), wherein aryl is optionally substituted with one or more substituents independently selected from halo, hydroxy, cyano, nitro, trifluoromethyl, trifluoromethoxy, $C_{1-6}$alkyl, $C_{1-6}$alkoxy, phenyl, —$NR_cR_d$, and —$C(=O)NR_cR_d$, or —$NR_8R_9$, wherein $R_8$ is hydrogen, methyl, ethyl, propyl or cyclohexyl and $R_9$ is methyl, ethyl, propyl, cyclohexyl or phenyl.

88. The compound of claim 86, wherein $R_4$ is halo, —$CF_3$, or —$CH_3$.

89. The compound of claim 76, wherein the compound is:

8-(2,4-dichlorophenyl)-3,4,4a,9b-tetrahydro[1]benzofuro[3,2-c]pyridine;

8-(2,4-dichlorophenyl)-N-cyclohexyl-1,2,3,4,4a,9b,-hexahydro[1]benzofuro[3,2-c]pyridin-6-amine;

8-(2,4,6-trichlorophenyl)-N-cyclohexyl-1,2,3,4,4a,9b,-hexahydro[1]benzofuro[3,2-c]pyridin-6-amine;

8-(2,6-difluoro-4-chlorophenyl)-N-cyclohexyl-1,2,3,4,4a,9b,-hexahydro[1]benzofuro[3,2-c]pyridin-6-amine;

8-(2,4-dichlorophenyl)-N-phenyl-1,2,3,4,4a,9b,-hexahydro[1]benzofuro[3,2-c]pyridin-6-amine;

8-(2,4,6-trichlorophenyl)-N-phenyl-1,2,3,4,4a,9b,-hexahydro[1]benzofuro[3,2-c]pyridin-6-amine;

8-(2,6-difluoro-4-chlorophenyl)-N-phenyl-1,2,3,4,4a,9b,-hexahydro[1]benzofuro[3,2-c]pyridin-6-amine;

8-(2,4-dichlorophenyl)-N,N-dimethyl-1,2,3,4,4a,9b,-hexahydro[1]benzofuro[3,2-c]pyridin-6-amine;

8-(2,4,6-trichlorophenyl)-N,N-dimethyl-1,2,3,4,4a,9b,-hexahydro[1]benzofuro[3,2-c]pyridin-6-amine;

8-(2,6-difluoro-4-chlorophenyl)-N,N-dimethyl-1,2,3,4,4a,9b,-hexahydro[1]benzofuro[3,2-c]pyridin-6-amine;

8-(2,4-dichlorophenyl)-N,N-diethyl-1,2,3,4,4a,9b,-hexahydro[1]benzofuro[3,2-c]pyridin-6-amine;

8-(2,4,6-trichlorophenyl)-N,N-diethyl-1,2,3,4,4a,9b,-hexahydro[1]benzofuro[3,2-c]pyridin-6-amine;

8-(2,6-difluoro-4-chlorophenyl)-N,N-diethyl-1,2,3,4,4a,9b,-hexahydro[1]benzofuro[3,2-c]pyridin-6-amine;

8-(2,4-dichlorophenyl)-N-methyl-N-ethyl-1,2,3,4,4a,9b,-hexahydro[1]benzofuro[3,2-c]pyridin-6-amine;

8-(2,4-dichlorophenyl)-N-methyl-N-propyl-1,2,3,4,4a,9b,-hexahydro[1]benzofuro[3,2-c]pyridin-6-amine;

8-(2,4-dichlorophenyl)-N-methyl-N-cyclohexyl-1,2,3,4,4a,9b,-hexahydro[1]benzofuro[3,2-c]pyridin-6-amine;

8-(2,4-dichlorophenyl)-N-ethyl-N-propyl-1,2,3,4,4a,9b,-hexahydro[1]benzofuro[3,2-c]pyridin-6-amine;

8-(2,4-dichlorophenyl)-N-ethyl-N-cyclohexyl-1,2,3,4,4a,9b,-hexahydro[1]benzofuro[3,2-c]pyridin-6-amine;

8-(2,4-dichlorophenyl)-N,N-dipropyl-1,2,3,4,4a,9b,-hexahydro[1]benzofuro[3,2-c]pyridin-6-amine;

8-(2,4-dichlorophenyl)-N-propyl-N-cyclohexyl-1,2,3,4,4a,9b,-hexahydro[1]benzofuro[3,2-c]pyridin-6-amine;

8-(2,4-dichlorophenyl)-N,N-dicyclohexyl-1,2,3,4,4a,9b,-hexahydro[1]benzofuro[3,2-c]pyridin-6-amine;

8-(2,4-dichlorophenyl)-6-methyl-1,2,3,4,4a,9b,-hexahydro[1]benzofuro[3,2-c]-pyridine;

8-(2,4-dichlorophenyl)-6-ethyl-1,2,3,4,4a,9b,-hexahydro[1]benzofuro[3,2-c]-pyridine;

8-(2,4-dichlorophenyl)-6-propyl-1,2,3,4,4a,9b,-hexahydro[1]benzofuro[3,2-c]-pyridine;

8-(2,4-dichlorophenyl)-6-isopropyl-1,2,3,4,4a,9b,-hexahydro[1]benzofuro[3,2-c]pyridine;

8-(2,4-dichlorophenyl)-6-butyl-1,2,3,4,4a,9b,-hexahydro[1]benzofuro[3,2-c]pyridine;

8-(2,4-dichlorophenyl)-6-(1-ethylpropyl)-1,2,3,4,4a,9b,-hexahydro[1]benzofuro[3,2-c]pyridine;

8-(2,4-dichlorophenyl)-6-cyclohexyl-1,2,3,4,4a,9b,-hexahydro[1]benzofuro[3,2-c]pyridine;

8-(2,4-dichlorophenyl)-6-phenyl-1,2,3,4,4a,9b,-hexahydro[1]benzofuro[3,2-c]pyridine;

8-(2,4-dichlorophenyl)-6-benzyl-1,2,3,4,4a,9b,-hexahydro[1]benzofuro[3,2-c]pyridine;

8-(2,4,6-trichlorophenyl)-6-methyl-1,2,3,4,4a,9b,-hexahydro[1]benzofuro[3,2-c]pyridine;

8-(2,4,6-trichlorophenyl)-6-ethyl-1,2,3,4,4a,9b,-hexahydro[1]benzofuro[3,2-c]pyridine;

8-(2,4,6-trichlorophenyl)-6-propyl-1,2,3,4,4a,9b,-hexahydro[1]benzofuro[3,2-c]pyridine;

8-(2,4,6-trichlorophenyl)-6-isopropyl-1,2,3,4,4a,9b,-hexahydro[1]benzofuro[3,2-c]pyridine;

8-(2,4,6-trichlorophenyl)-6-butyl-1,2,3,4,4a,9b,-hexahydro[1]benzofuro[3,2-c]pyridine;

8-(2,4,6-trichlorophenyl)-6-(1-ethylpropyl)-1,2,3,4,4a,9b,-hexahydro[1]benzofuro[3,2-c]pyridine;

8-(2,4,6-trichlorophenyl)-6-cyclohexyl-1,2,3,4,4a,9b,-hexahydro[1]benzofuro[3,2-c]pyridine;

8-(2,4,6-trichlorophenyl)-6-phenyl-1,2,3,4,4a,9b,-hexahydro[1]benzofuro[3,2-c]pyridine;

8-(2,4,6-trichlorophenyl)-6-benzyl-1,2,3,4,4a,9b,-hexahydro[1]benzofuro[3,2-c]pyridine;

8-(2,6-difluoro-4-chlorophenyl)-6-methyl-1,2,3,4,4a,9b,-hexahydro[1]benzofuro[3,2-c]pyridine;

8-(2,6-difluoro-4-chlorophenyl)-6-ethyl-1,2,3,4,4a,9b,-hexahydro[1]benzofuro[3,2-c]pyridine;

8-(2,6-difluoro-4-chlorophenyl)-6-propyl-1,2,3,4,4a,9b,-hexahydro[1]benzofuro[3,2-c]pyridine;

8-(2,6-difluoro-4-chlorophenyl)-6-isopropyl-1,2,3,4,4a,9b,-hexahydro[1]benzofuro[3,2-c]pyridine;

8-(2,6-difluoro-4-chlorophenyl)-6-butyl-1,2,3,4,4a,9b,-hexahydro[1]benzofuro[3,2-c]pyridine;

8-(2,6-difluoro-4-chlorophenyl)-6-(1-ethylpropyl)-1,2,3,4,4a,9b,-hexahydro[1]benzofuro[3,2-c]pyridine;

8-(2,6-difluoro-4-chlorophenyl)-6-cyclohexyl-1,2,3,4,4a,9b,-hexahydro[1]benzofuro[3,2-c]pyridine;

8-(2,6-difluoro-4-chlorophenyl)-6-phenyl-1,2,3,4,4a,9b,-hexahydro[1]benzofuro[3,2-c]pyridine;

8-(2,6-difluoro-4-chlorophenyl)-6-benzyl-1,2,3,4,4a,9b,-hexahydro[1]benzofuro[3,2-c]pyridine;

8-(2,4-dichlorophenyl)-6-(methylthio)-1,2,3,4,4a,9b,-hexahydro[1]benzofuro[3,2-c]pyridine;

8-(2,4-dichlorophenyl)-6-(ethylthio)-1,2,3,4,4a,9b,-hexahydro[1]benzofuro[3,2-c]pyridine;

8-(2,4-dichlorophenyl)-6-(propylthio)-1,2,3,4,4a,9b,-hexahydro[1]benzofuro[3,2-c]pyridine;

8-(2,4-dichlorophenyl)-6-(isopropylthio)-1,2,3,4,4a,9b,-hexahydro[1]benzofuro[3,2-c]pyridine;

8-(2,4-dichlorophenyl)-6-(butylthio)-1,2,3,4,4a,9b,-hexahydro[1]benzofuro[3,2-c]pyridine;

8-(2,4-dichlorophenyl)-6-[(1-ethylpropyl)thio]-1,2,3,4,4a,9b,-hexahydro[1]benzofuro[3,2-c]pyridine;

8-(2,4-dichlorophenyl)-6-(cyclohexylthio)-1,2,3,4,4a,9b,-hexahydro[1]benzofuro[3,2-c]pyridine;

8-(2,4-dichlorophenyl)-6-(phenylthio)-1,2,3,4,4a,9b,-hexahydro[1]benzofuro[3,2-c]pyridine;

8-(2,4-dichlorophenyl)-6-(benzylthio)-1,2,3,4,4a,9b,-hexahydro[1]benzofuro[3,2-c]pyridine;

8-(2,4,6-trichlorophenyl)-6-(methylthio)-1,2,3,4,4a,9b,-hexahydro[1]benzofuro[3,2-c]pyridine;

8-(2,4,6-trichlorophenyl)-6-(ethylthio)-1,2,3,4,4a,9b,-hexahydro[1]benzofuro[3,2-c]pyridine;

8-(2,4,6-trichlorophenyl)-6-(propylthio)-1,2,3,4,4a,9b,-hexahydro[1]benzofuro[3,2-c]pyridine;

8-(2,4,6-trichlorophenyl)-6-(isopropylthio)-1,2,3,4,4a,9b,-hexahydro[1]benzofuro[3,2-c]pyridine;

8-(2,4,6-trichlorophenyl)-6-(butylthio)-1,2,3,4,4a,9b,-hexahydro[1]benzofuro[3,2-c]pyridine;

8-(2,4,6-trichlorophenyl)-6-[(1-ethylpropyl)thio]-1,2,3,4,4a,9b,-hexahydro[1]benzofuro[3,2-c]pyridine;

8-(2,4,6-trichlorophenyl)-6-(cyclohexylthio)-1,2,3,4,4a,9b,-hexahydro[1]benzofuro[3,2-c]pyridine;

8-(2,4,6-trichlorophenyl)-6-(phenylthio)-1,2,3,4,4a,9b,-hexahydro[1]benzofuro[3,2-c]pyridine;

8-(2,4,6-trichlorophenyl)-6-(benzylthio)-1,2,3,4,4a,9b,-hexahydro[1]benzofuro[3,2-c]pyridine;

8-(2,6-difluoro-4-chlorophenyl)-6-(methylthio)-1,2,3,4,4a,9b,-hexahydro[1]benzofuro[3,2-c]pyridine;

8-(2,6-difluoro-4-chlorophenyl)-6-(ethylthio)-1,2,3,4,4a,9b,-hexahydro[1]benzofuro[3,2-c]pyridine;

8-(2,6-difluoro-4-chlorophenyl)-6-(propylthio)-1,2,3,4,4a,9b,-hexahydro[1]benzofuro[3,2-c]pyridine;

8-(2,6-difluoro-4-chlorophenyl)-6-(isopropylthio)-1,2,3,4,4a,9b,-hexahydro[1]benzofuro[3,2-c]pyridine;

8-(2,6-difluoro-4-chlorophenyl)-6-(butylthio)-1,2,3,4,4a,9b,-hexahydro[1]benzofuro[3,2-c]pyridine;

8-(2,6-difluoro-4-chlorophenyl)-6-[(1-ethylpropyl)thio]-1,2,3,4,4a,9b,-hexahydro[1]benzofuro[3,2-c]pyridine;

8-(2,6-difluoro-4-chlorophenyl)-6-(cyclohexylthio)-1,2,3,4,4a,9b,-hexahydro[1]benzofuro[3,2-c]pyridine;

8-(2,6-difluoro-4-chlorophenyl)-6-(phenylthio)-1,2,3,4,4a,9b,-hexahydro[1]benzofuro[3,2-c]pyridine;

8-(2,6-difluoro-4-chlorophenyl)-6-(benzylthio)-1,2,3,4,4a,9b,-hexahydro[1]benzofuro[3,2-c]pyridine;

8-(2,4-dichlorophenyl)-6-methoxy-1,2,3,4,4a,9b,-hexahydro[1]benzofuro[3,2-c]pyridine;

8-(2,4-dichlorophenyl)-6-ethoxy-1,2,3,4,4a,9b,-hexahydro[1]benzofuro[3,2-c]-pyridine;

8-(2,4-dichlorophenyl)-6-propoxy-1,2,3,4,4a,9b,-hexahydro[1]benzofuro[3,2-c]pyridine;

8-(2,4-dichlorophenyl)-6-isopropoxy-1,2,3,4,4a,9b,-hexahydro[1]benzofuro[3,2-c]pyridine;

8-(2,4-dichlorophenyl)-6-butoxy-1,2,3,4,4a,9b,-hexahydro[1]benzofuro[3,2-c]-pyridine;

8-(2,4-dichlorophenyl)-6-[(1-ethylpropyl)oxy]-1,2,3,4,4a,9b,-hexahydro[1]benzofuro[3,2-c]pyridine;

8-(2,4-dichlorophenyl)-6-(cyclohexyloxy)-1,2,3,4,4a,9b,-hexahydro[1]benzofuro[3,2-c]pyridine;

8-(2,4-dichlorophenyl)-6-phenoxy-1,2,3,4,4a,9b,-hexahydro[1]benzofuro[3,2-c]pyridine;

8-(2,4-dichlorophenyl)-6-(benzyloxy)-1,2,3,4,4a,9b,-hexahydro[1]benzofuro[3,2-c]pyridine;

8-(2,4,6-trichlorophenyl)-6-methoxy-1,2,3,4,4a,9b,-hexahydro[1]benzofuro[3,2-c]pyridine;

8-(2,4,6-trichlorophenyl)-6-ethoxy-1,2,3,4,4a,9b,-hexahydro[1]benzofuro[3,2-c]pyridine;

8-(2,4,6-trichlorophenyl)-6-propoxy-1,2,3,4,4a,9b,-hexahydro[1]benzofuro[3,2-c]pyridine;

8-(2,4,6-trichlorophenyl)-6-isopropoxy-1,2,3,4,4a,9b,-hexahydro[1]benzofuro[3,2-c]pyridine;

8-(2,4,6-trichlorophenyl)-6-butoxy-1,2,3,4,4a,9b,-hexahydro[1]benzofuro[3,2-c]pyridine;

8-(2,4,6-trichlorophenyl)-6-[(1-ethylpropyl)oxy]-1,2,3,4,4a,9b,-hexahydro[1]benzofuro[3,2-c]pyridine;

8-(2,4,6-trichlorophenyl)-6-(cyclohexyloxy)-1,2,3,4,4a,9b,-hexahydro[1]benzofuro[3,2-c]pyridine;

8-(2,4,6-trichlorophenyl)-6-phenoxy-1,2,3,4,4a,9b,-hexahydro[1]benzofuro[3,2-c]pyridine;

8-(2,4,6-trichlorophenyl)-6-(benzyloxy)-1,2,3,4,4a,9b,-hexahydro[1]benzofuro[3,2-c]pyridine;

8-(2,6-difluoro-4-chlorophenyl)-6-methoxy-1,2,3,4,4a,9b,-hexahydro[1]benzofuro[3,2-c]pyridine;

8-(2,6-difluoro-4-chlorophenyl)-6-ethoxy-1,2,3,4,4a,9b,-hexahydro[1]benzofuro[3,2-c]pyridine;

8-(2,6-difluoro-4-chlorophenyl)-6-propoxy-1,2,3,4,4a,9b,-hexahydro[1]benzofuro[3,2-c]pyridine;

8-(2,6-difluoro-4-chlorophenyl)-6-(2-propoxy)-1,2,3,4,4a,9b,-hexahydro[1]benzofuro[3,2-c]pyridine;

8-(2,6-difluoro-4-chlorophenyl)-6-butoxy-1,2,3,4,4a,9b,-hexahydro[1]benzofuro[3,2-c]pyridine;

8-(2,6-difluoro-4-chlorophenyl)-6-[(1-ethylpropyl)oxy]-1,2,3,4,4a,9b,-hexahydro[1]benzofuro[3,2-c]pyridine;

8-(2,6-difluoro-4-chlorophenyl)-6-(cyclohexyloxy)-1,2,3,4,4a,9b,-hexahydro[1]benzofuro[3,2-c]pyridine;

8-(2,6-difluoro-4-chlorophenyl)-6-phenoxy-1,2,3,4,4a,9b,-hexahydro[1]benzofuro[3,2-c]pyridine;

8-(2,6-difluoro-4-chlorophenyl)-6-(benzyloxy)-1,2,3,4,4a,9b,-hexahydro[1]benzofuro[3,2-c]pyridine;

8-(2,4-dichlorophenyl)-6-piperidin-1-yl-1,2,3,4,4a,9b-hexahydro[1]benzofuro[3,2-c]pyridine;

8-(2,4,6-trichlorophenyl)-6-piperidin-1-yl-1,2,3,4,4a,9b-hexahydro[1]benzofuro[3,2-c]pyridine;

8-(2,6-difluoro-4-chlorophenyl)-6-piperidin-1-yl-1,2,3,4,4a,9b-hexahydro[1]benzofuro[3,2-c]pyridine;

8-(2,4-dichlorophenyl)-6-azepano-1-yl-1,2,3,4,4a,9b-hexahydro[1]benzofuro[3,2-c]pyridine;

8-(2,4,6-trichlorophenyl)-6-azepano-1-yl-1,2,3,4,4a,9b-hexahydro[1]benzofuro[3,2-c]pyridine;

8-(2,6-difluoro-4-chlorophenyl)-6-azepano-1-yl-1,2,3,4,4a,9b-hexahydro[1]benzofuro[3,2-c]pyridine;

8-(2,4-dichlorophenyl)-6-pyrrolidin-1-yl-1,2,3,4,4a,9b-hexahydro[1]benzofuro[3,2-c]pyridine;

8-(2,4,6-trichlorophenyl)-6-pyrrolidin-1-yl-1,2,3,4,4a,9b-hexahydro[1]benzofuro[3,2-c]pyridine;

8-(2,6-difluoro-4-chlorophenyl)-6-pyrrolidin-1-yl-1,2,3,4,4a,9b-hexahydro[1]benzofuro[3,2-c]pyridine;

8-(2,4-dichlorophenyl)-5-morpholin-4-yl-1,2,3,4,4a,9b-hexahydro[1]benzofuro[3,2-c]pyridine;

8-(2,4,6-trichlorophenyl)-5-morpholin-4-yl-1,2,3,4,4a,9b-hexahydro-[1]benzofuro[3,2-c]pyridine;

8-(2,6-difluoro-4-chlorophenyl)-5-morpholin-4-yl-1,2,3,4,4a,9b-hexahydro-[1]benzofuro[3,2-c]pyridine;

8-(2,4-dichlorophenyl)-6-thiomorpholin-4-yl-1,2,3,4,4a,9b-hexahydro[1]benzofuro[3,2-c]pyridine;

8-(2,4,6-trichlorophenyl)-6-thiomorpholin-4-yl-1,2,3,4,4a,9b-hexahydro[1]benzofuro[3,2-c]pyridine;

8-(2,6-difluoro-4-chlorophenyl)-6-thiomorpholin-4-yl-1,2,3,4,4a,9b-hexahydro[1]benzofuro[3,2-c]pyridine;

8-(2,4-dichlorophenyl)-6-piperazin-1-yl-1,2,3,4,4a,9b-hexahydro[1]benzofuro[3,2-c]pyridine;

8-(2,4,6-trichlorophenyl)-6-piperazin-1-yl-1,2,3,4,4a,9b-hexahydro[1]benzofuro[3,2-c]pyridine;

8-(2,6-difluoro-4-chlorophenyl)-6-piperazin-1-yl-1,2,3,4,
4a,9b-hexahydro-[1]benzofuro[3,2-c]pyridine;
8-(2,4,6-trichlorophenyl)-N,N-dipropyl-1,2,3,4,4a,9b,-
hexahydro[1]benzofuro[3,2-c]pyridin-6-amine;
8-(2,6-difluoro-4-chlorophenyl)-N,N-dipropyl-1,2,3,4,
4a,9b,-hexahydro[1]benzofuro[3,2-c]pyridin-6-amine;
8-(2,4-Dichlorophenyl)-1,2,3,4,4a,9b-hexahydro[1]
benzofuro[3,2-c]pyridine;
1,2,3,4,4a,9b-Hexahydro[1]benzofuro[3,2-c]pyridine;
8-[2-(Trifluoromethyl)phenyl]-1,2,3,4,4a,9b-hexahydro
[1]benzofuro[3,2-c]pyridine;
8-[2-(Trifluoromethoxy)phenyl]-1,2,3,4,4a,9b-hexahydro
[1]benzofuro[3,2-c]pyridine;
6-Bromo-8-(2,4-dichlorophenyl)-1,2,3,4,4a,9b-
hexahydro[1]benzofuro[3,2-c]pyridine;
6-Benzyl-8-(2,4-dichlorophenyl)-1,2,3,4,4a,9b-
hexahydro[1]benzofuro[3,2-c]pyridine;
6-Butyl-8-(2,4-dichlorophenyl)-1,2,3,4,4a,9b-hexahydro
[1]benzofuro[3,2-c]pyridine;
8-(2,4-Dichlorophenyl)-6-(propylthio)-1,2,3,4,4a,9b-
hexahydro[1]benzofuro[3,2-c]pyridine;
8-(2,4-Dichlorophenyl)-6-(isopropylthio)-1,2,3,4,4a,9b-
hexahydro[1]benzofuro[3,2-c]pyridine;
8-(2,4-Dichlorophenyl)-6-(isobutylthio)-1,2,3,4,4a,9b-
hexahydro[1]benzofuro[3,2-c]pyridine;
8-(2,4-Dichlorophenyl)-6-(methylthio)-1,2,3,4,4a,9b-
hexahydro[1]benzofuro[3,2-c]pyridine;
6-(Cyclopentylthio)-8-(2,4-dichlorophenyl)-1,2,3,4,4a,
9b-hexahydro[1]benzofuro[3,2-c]pyridine;
6-(Cyclobutylthio)-8-(2,4-dichlorophenyl)-1,2,3,4,4a,9b-
hexahydro[1]benzofuro[3,2-c]pyridine;
8-(2,4-dichlorophenyl)-6-morpholin-4-yl-1,2,3,4,4a,9b-
hexahydro[1]benzofuro[3,2-c]pyridine;
N-Benzyl-8-(2,4-dichlorophenyl)-1,2,3,4,4a,9b-
hexahydro[1]benzofuro[3,2-c]pyridin-6-amine;
8-(2,4-Dichlorophenyl)-6-pyrrolidin-1-yl-1,2,3,4,4a,9b-
hexahydro[1]benzofuro[3,2-c]pyridine;
8-(2,4-Dichlorophenyl)-6-methoxy-1,2,3,4,4a,9b-
hexahydro[1]benzofuro[3,2-c]pyridine;
or a pharmaceutically acceptable salt thereof.

90. The compound of claim 76, wherein the compound is:
(4aS,9bR)-8-(2,4-dichlorophenyl)-N-cyclohexyl-1,2,3,4,
4a,9b,-hexahydro[1]benzofuro[3,2-c]pyridin-6-amine;
(4aS,9bR)-8-(2,4,6-trichlorophenyl)-N-cyclohexyl-1,2,3,
4,4a,9b,-hexahydro[1]benzofuro[3,2-c]pyridin-6-
amine;
(4aS,9bR)-8-(2,6-difluoro-4-chlorophenyl)-N-
cyclohexyl-1,2,3,4,4a,9b,-hexahydro[1]benzofuro[3,2-
c]pyridin-6-amine;
(4aS,9bR)-8-(2,4-dichlorophenyl)-N-phenyl-1,2,3,4,4a,
9b,-hexahydro[1]benzofuro[3,2-c]pyridin-6-amine;
(4aS,9bR)-8-(2,4,6-trichlorophenyl)-N-phenyl-1,2,3,4,
4a,9b,-hexahydro[1]benzofuro[3,2-c]pyridin-6-amine;
(4aS,9bR)-8-(2,6-difluoro-4-chlorophenyl)-N-phenyl-1,
2,3,4,4a,9b,-hexahydro[1]benzofuro[3,2-c]pyridin-6-
amine;
(4aS,9bR)-8-(2,4-dichlorophenyl)-N,N-dimethyl-1,2,3,4,
4a,9b,-hexahydro[1]benzofuro[3,2-c]pyridin-6-amine;
(4aS,9bR)-8-(2,4,6-trichlorophenyl)-N,N-dimethyl-1,2,3,
4,4a,9b,-hexahydro[1]benzofuro[3,2-c]pyridin-6-
amine;
(4aS,9bR)-8-(2,6-difluoro-4-chlorophenyl)-N,N-
dimethyl-1,2,3,4,4a,9b,-hexahydro[1]benzofuro[3,2-c]
pyridin-6-amine;
(4aS,9bR)-8-(2,4-dichlorophenyl)-N,N-diethyl-1,2,3,4,
4a,9b,-hexahydro[1]benzofuro[3,2-c]pyridin-6-amine;
(4aS,9bR)-8-(2,4,6-trichlorophenyl)-N,N-diethyl-1,2,3,4,
4a,9b,-hexahydro[1]benzofuro[3,2-c]pyridin-6-amine;
(4aS,9bR)-8-(2,6-difluoro-4-chlorophenyl)-N,N-diethyl-
1,2,3,4,4a,9b,-hexahydro[1]benzofuro[3,2-c]pyridin-6-
amine;
(4aS,9bR)-8-(2,4-dichlorophenyl)-N-methyl-N-ethyl-1,2,
3,4,4a,9b,-hexahydro[1]benzofuro[3,2-c]pyridin-6-
amine;
(4aS,9bR)-8-(2,4-dichlorophenyl)-N-methyl-N-propyl-1,
2,3,4,4a,9b,-hexahydro[1]benzofuro[3,2-c]pyridin-6-
amine;
(4aS,9bR)-8-(2,4-dichlorophenyl)-N-methyl-N-
cyclohexyl-1,2,3,4,4a,9b,-hexahydro[1]benzofuro[3,2-
c]pyridin-6-amine;
(4aS,9bR)-8-(2,4-dichlorophenyl)-N-ethyl-N-propyl-1,2,
3,4,4a,9b,-hexahydro[1]benzofuro[3,2-c]pyridin-6-
amine;
(4aS,9bR)-8-(2,4-dichlorophenyl)-N-ethyl-N-
cyclohexyl-1,2,3,4,4a,9b,-hexahydro[1]benzofuro[3,2-
c]pyridin-6-amine;
(4aS,9bR)-8-(2,4-dichlorophenyl)-N,N-dipropyl-1,2,3,4,
4a,9b,-hexahydro[1]benzofuro[3,2-c]pyridin-6-amine;
(4aS,9bR)-8-(2,4-dichlorophenyl)-N-propyl-N-
cyclohexyl-1,2,3,4,4a,9b,-hexahydro[1]benzofuro[3,2-
c]pyridin-6-amine;
(4aS,9bR)-8-(2,4-dichlorophenyl)-N,N-dicyclohexyl-1,2,
3,4,4a,9b,-hexahydro[1]benzofuro[3,2-c]pyridin-6-
amine;
(4aS,9bR)-8-(2,4-dichlorophenyl)-6-methyl-1,2,3,4,4a,
9b,-hexahydro[1]benzofuro[3,2-c]pyridine;
(4aS,9bR)-8-(2,4-dichlorophenyl)-6-ethyl-1,2,3,4,4a,9b,-
hexahydro[1]benzofuro[3,2-c]pyridine;
(4aS,9bR)-8-(2,4-dichlorophenyl)-6-propyl-1,2,3,4,4a,
9b,-hexahydro[1]benzofuro[3,2-c]pyridine;
(4aS,9bR)-8-(2,4-dichlorophenyl)-6-(isopropyl)-1,2,3,4,
4a,9b,-hexahydro[1]benzofuro[3,2-c]pyridine;
(4aS,9bR)-8-(2,4-dichlorophenyl)-6-butyl-1,2,3,4,4a,9b,-
hexahydro[1]benzofuro[3,2-c]pyridine;
(4aS,9bR)-8-(2,4-dichlorophenyl)-6-(1-ethylpropyl)-1,2,
3,4,4a,9b,-hexahydro[1]benzofuro[3,2-c]pyridine;
(4aS,9bR)-8-(2,4-dichlorophenyl)-6-cyclohexyl-1,2,3,4,
4a,9b,-hexahydro[1]benzofuro[3,2-c]pyridine;
(4aS,9bR)-8-(2,4-dichlorophenyl)-6-phenyl-1,2,3,4,4a,
9b,-hexahydro[1]benzofuro[3,2-c]pyridine;
(4aS,9bR)-8-(2,4-dichlorophenyl)-6-benzyl-1,2,3,4,4a,
9b,-hexahydro[1]benzofuro[3,2-c]pyridine;
(4aS,9bR)-8-(2,4,6-trichlorophenyl)-6-methyl-1,2,3,4,4a,
9b,-hexahydro[1]benzofuro[3,2-c]pyridine;
(4aS,9bR)-8-(2,4,6-trichlorophenyl)-6-ethyl-1,2,3,4,4a,
9b,-hexahydro[1]benzofuro[3,2-c]pyridine;
(4aS,9bR)-8-(2,4,6-trichlorophenyl)-6-propyl-1,2,3,4,4a,
9b,-hexahydro[1]benzofuro[3,2-c]pyridine;
(4aS,9bR)-8-(2,4,6-trichlorophenyl)-6-(isopropyl)-1,2,3,
4,4a,9b,-hexahydro[1]benzofuro[3,2-c]pyridine;
(4aS,9bR)-8-(2,4,6-trichlorophenyl)-6-butyl-1,2,3,4,4a,
9b,-hexahydro[1]benzofuro[3,2-c]pyridine;
(4aS,9bR)-8-(2,4,6-trichlorophenyl)-6-(1-ethylpropyl)-1,
2,3,4,4a,9b,-hexahydro[1]benzofuro[3,2-c]pyridine;
(4aS,9bR)-8-(2,4,6-trichlorophenyl)-6-cyclohexyl-1,2,3,
4,4a,9b,-hexahydro[1]benzofuro[3,2-c]pyridine;

(4aS,9bR)-8-(2,4,6-trichlorophenyl)-6-phenyl-1,2,3,4,4a,9b,-hexahydro[1]benzofuro[3,2-c]pyridine;

(4aS,9bR)-8-(2,4,6-trichlorophenyl)-6-benzyl-1,2,3,4,4a,9b,-hexahydro[1]benzofuro[3,2-c]pyridine;

(4aS,9bR)-8-(2,6-difluoro-4-chlorophenyl)-6-methyl-1,2,3,4,4a,9b,-hexahydro[1]benzofuro[3,2-c]pyridine;

(4aS,9bR)-8-(2,6-difluoro-4-chlorophenyl)-6-ethyl-1,2,3,4,4a,9b,-hexahydro[1]benzofuro[3,2-c]pyridine;

(4aS,9bR)-8-(2,6-difluoro-4-chlorophenyl)-6-propyl-1,2,3,4,4a,9b,-hexahydro[1]benzofuro[3,2-c]pyridine;

(4aS,9bR)-8-(2,6-difluoro-4-chlorophenyl)-6-(isopropyl)-1,2,3,4,4a,9b,-hexahydro[1]benzofuro[3,2-c]pyridine;

(4aS,9bR)-8-(2,6-difluoro-4-chlorophenyl)-6-butyl-1,2,3,4,4a,9b,-hexahydro[1]benzofuro[3,2-c]pyridine;

(4aS,9bR)-8-(2,6-difluoro-4-chlorophenyl)-6-(1-ethylpropyl)-1,2,3,4,4a,9b,-hexahydro[1]benzofuro[3,2-c]pyridine;

(4aS,9bR)-8-(2,6-difluoro-4-chlorophenyl)-6-cyclohexyl-1,2,3,4,4a,9b,-hexahydro[1]benzofuro[3,2-c]pyridine;

(4aS,9bR)-8-(2,6-difluoro-4-chlorophenyl)-6-phenyl-1,2,3,4,4a,9b,-hexahydro[1]benzofuro[3,2-c]pyridine;

(4aS,9bR)-8-(2,6-difluoro-4-chlorophenyl)-6-benzyl-1,2,3,4,4a,9b,-hexahydro[1]benzofuro[3,2-c]pyridine;

(4aS,9bR)-8-(2,4-dichlorophenyl)-6-(methylthio)-1,2,3,4,4a,9b,-hexahydro[1]benzofuro[3,2-c]pyridine;

(4aS,9bR)-8-(2,4-dichlorophenyl)-6-(ethylthio)-1,2,3,4,4a,9b,-hexahydro[1]benzofuro[3,2-c]pyridine;

(4aS,9bR)-8-(2,4-dichlorophenyl)-6-(propylthio)-1,2,3,4,4a,9b,-hexahydro[1]benzofuro[3,2-c]pyridine;

(4aS,9bR)-8-(2,4-dichlorophenyl)-6-(2-propylthio)-1,2,3,4,4a,9b,-hexahydro[1]benzofuro[3,2-c]pyridine;

(4aS,9bR)-8-(2,4-dichlorophenyl)-6-(butylthio)-1,2,3,4,4a,9b,-hexahydro[1]benzofuro[3,2-c]pyridine;

(4aS,9bR)-8-(2,4-dichlorophenyl)-6-[(1-ethylpropyl)thio]-1,2,3,4,4a,9b,-hexahydro[1]benzofuro[3,2-c]pyridine;

(4aS,9bR)-8-(2,4-dichlorophenyl)-6-(cyclohexylthio)-1,2,3,4,4a,9b,-hexahydro[1]benzofuro[3,2-c]pyridine;

(4aS,9bR)-8-(2,4-dichlorophenyl)-6-(phenylthio)-1,2,3,4,4a,9b,-hexahydro[1]benzofuro[3,2-c]pyridine;

(4aS,9bR)-8-(2,4-dichlorophenyl)-6-(benzylthio)-1,2,3,4,4a,9b,-hexahydro[1]benzofuro[3,2-c]pyridine;

(4aS,9bR)-8-(2,4,6-trichlorophenyl)-6-(methylthio)-1,2,3,4,4a,9b,-hexahydro[1]benzofuro[3,2-c]pyridine;

(4aS,9bR)-8-(2,4,6-trichlorophenyl)-6-(ethylthio)-1,2,3,4,4a,9b,-hexahydro[1]benzofuro[3,2-c]pyridine;

(4aS,9bR)-8-(2,4,6-trichlorophenyl)-6-(propylthio)-1,2,3,4,4a,9b,-hexahydro[1]benzofuro[3,2-c]pyridine;

(4aS,9bR)-8-(2,4,6-trichlorophenyl)-6-(2-propylthio)-1,2,3,4,4a,9b,-hexahydro[1]benzofuro[3,2-c]pyridine;

(4aS,9bR)-8-(2,4,6-trichlorophenyl)-6-(butylthio)-1,2,3,4,4a,9b,-hexahydro[1]benzofuro[3,2-c]pyridine;

(4aS,9bR)-8-(2,4,6-trichlorophenyl)-6-[(1-ethylpropyl)thio]-1,2,3,4,4a,9b,-hexahydro[1]benzofuro[3,2-c]pyridine;

(4aS,9bR)-8-(2,4,6-trichlorophenyl)-6-(cyclohexylthio)-1,2,3,4,4a,9b,-hexahydro[1]benzofuro[3,2-c]pyridine;

(4aS,9bR)-8-(2,4,6-trichlorophenyl)-6-(phenylthio)-1,2,3,4,4a,9b,-hexahydro[1]benzofuro[3,2-c]pyridine;

(4aS,9bR)-8-(2,4,6-trichlorophenyl)-6-(benzylthio)-1,2,3,4,4a,9b,-hexahydro[1]benzofuro[3,2-c]pyridine;

(4aS,9bR)-8-(2,6-difluoro-4-chlorophenyl)-6-(methylthio)-1,2,3,4,4a,9b,-hexahydro[1]benzofuro[3,2-c]pyridine;

(4aS,9bR)-8-(2,6-difluoro-4-chlorophenyl)-6-(ethylthio)-1,2,3,4,4a,9b,-hexahydro[1]benzofuro[3,2-c]pyridine;

(4aS,9bR)-8-(2,6-difluoro-4-chlorophenyl)-6-(propylthio)-1,2,3,4,4a,9b,-hexahydro[1]benzofuro[3,2-c]pyridine;

(4aS,9bR)-8-(2,6-difluoro-4-chlorophenyl)-6-(isopropyl)-1,2,3,4,4a,9b,-hexahydro[1]benzofuro[3,2-c]pyridine;

(4aS,9bR)-8-(2,6-difluoro-4-chlorophenyl)-6-(butylthio)-1,2,3,4,4a,9b,-hexahydro[1]benzofuro[3,2-c]pyridine;

(4aS,9bR)-8-(2,6-difluoro-4-chlorophenyl)-6-[(1-ethylpropyl)thio]-1,2,3,4,4a,9b,-hexahydro[1]benzofuro[3,2-c]pyridine;

(4aS,9bR)-8-(2,6-difluoro-4-chlorophenyl)-6-(cyclohexylthio)-1,2,3,4,4a,9b,-hexahydro[1]benzofuro[3,2-c]pyridine;

(4aS,9bR)-8-(2,6-difluoro-4-chlorophenyl)-6-(phenylthio)-1,2,3,4,4a,9b,-hexahydro[1]benzofuro[3,2-c]pyridine;

(4aS,9bR)-8-(2,6-difluoro-4-chlorophenyl)-6-(benzylthio)-1,2,3,4,4a,9b,-hexahydro[1]benzofuro[3,2-c]pyridine;

(4aS,9bR)-8-(2,4-dichlorophenyl)-6-methoxy-1,2,3,4,4a,9b,-hexahydro[1]benzofuro[3,2-c]pyridine;

(4aS,9bR)-8-(2,4-dichlorophenyl)-6-ethoxy-1,2,3,4,4a,9b,-hexahydro[1]benzofuro[3,2-c]pyridine;

(4aS,9bR)-8-(2,4-dichlorophenyl)-6-propoxy-1,2,3,4,4a,9b,-hexahydro[1]benzofuro[3,2-c]pyridine;

(4aS,9bR)-8-(2,4-dichlorophenyl)-6-isopropoxy-1,2,3,4,4a,9b,-hexahydro[1]benzofuro[3,2-c]pyridine;

(4aS,9bR)-8-(2,4-dichlorophenyl)-6-butoxy-1,2,3,4,4a,9b,-hexahydro[1]benzofuro[3,2-c]pyridine;

(4aS,9bR)-8-(2,4-dichlorophenyl)-6-[(1-ethylpropyl)oxy]-1,2,3,4,4a,9b,-hexahydro[1]benzofuro[3,2-c]pyridine;

(4aS,9bR)-8-(2,4-dichlorophenyl)-6-(cyclohexyloxy)-1,2,3,4,4a,9b,-hexahydro[1]benzofuro[3,2-c]pyridine;

(4aS,9bR)-8-(2,4-dichlorophenyl)-6-phenoxy-1,2,3,4,4a,9b,-hexahydro[1]benzofuro[3,2-c]pyridine;

(4aS,9bR)-8-(2,4-dichlorophenyl)-6-(benzyloxy)-1,2,3,4,4a,9b,-hexahydro[1]benzofuro[3,2-c]pyridine;

(4aS,9bR)-8-(2,4,6-trichlorophenyl)-6-methoxy-1,2,3,4,4a,9b,-hexahydro[1]benzofuro[3,2-c]pyridine;

(4aS,9bR)-8-(2,4,6-trichlorophenyl)-6-ethoxy-1,2,3,4,4a,9b,-hexahydro[1]benzofuro[3,2-c]pyridine;

(4aS,9bR)-8-(2,4,6-trichlorophenyl)-6-propoxy-1,2,3,4,4a,9b,-hexahydro[1]benzofuro[3,2-c]pyridine;

(4aS,9bR)-8-(2,4,6-trichlorophenyl)-6-isopropoxy-1,2,3,4,4a,9b,-hexahydro[1]benzofuro[3,2-c]pyridine;

(4aS,9bR)-8-(2,4,6-trichlorophenyl)-6-butoxy-1,2,3,4,4a,9b,-hexahydro[1]benzofuro[3,2-c]pyridine;

(4aS,9bR)-8-(2,4,6-trichlorophenyl)-6-[(1-ethylpropyl)oxy]-1,2,3,4,4a,9b,-hexahydro[1]benzofuro[3,2-c]pyridine;

(4aS,9bR)-8-(2,4,6-trichlorophenyl)-6-(cyclohexyloxy)-1,2,3,4,4a,9b,-hexahydro[1]benzofuro[3,2-c]pyridine;

(4aS,9bR)-8-(2,4,6-trichlorophenyl)-6-phenoxy-1,2,3,4,4a,9b,-hexahydro[1]benzofuro[3,2-c]pyridine;

(4aS,9bR)-8-(2,4,6-trichlorophenyl)-6-(benzyloxy)-1,2,3,4,4a,9b,-hexahydro[1]benzofuro[3,2-c]pyridine;

(4aS,9bR)-8-(2,6-difluoro-4-chlorophenyl)-6-methoxy-1,2,3,4,4a,9b,-hexahydro[1]benzofuro[3,2-c]pyridine;

(4aS,9bR)-8-(2,6-difluoro-4-chlorophenyl)-6-ethoxy-1,2,3,4,4a,9b,-hexahydro[1]benzofuro[3,2-c]pyridine;

(4aS,9bR)-8-(2,6-difluoro-4-chlorophenyl)-6-propoxy-1,2,3,4,4a,9b,-hexahydro[1]benzofuro[3,2-c]pyridine;

(4aS,9bR)-8-(2,6-difluoro-4-chlorophenyl)-6-(2-propoxy)-1,2,3,4,4a,9b,-hexahydro[1]benzofuro[3,2-c]pyridine;

(4aS,9bR)-8-(2,6-difluoro-4-chlorophenyl)-6-butoxy-1,2,3,4,4a,9b,-hexahydro[1]benzofuro[3,2-c]pyridine;

(4aS,9bR)-8-(2,6-difluoro-4-chlorophenyl)-6-[(1-ethylpropyl)oxy]-1,2,3,4,4a,9b,-hexahydro[1]benzofuro[3,2-c]pyridine;

(4aS,9bR)-8-(2,6-difluoro-4-chlorophenyl)-6-(cyclohexyloxy)-1,2,3,4,4a,9b,-hexahydro[1]benzofuro[3,2-c]pyridine;

(4aS,9bR)-8-(2,6-difluoro-4-chlorophenyl)-6-phenoxy-1,2,3,4,4a,9b,-hexahydro[1]benzofuro[3,2-c]pyridine;

(4aS,9bR)-8-(2,6-difluoro-4-chlorophenyl)-6-(benzyloxy)-1,2,3,4,4a,9b,-hexahydro[1]benzofuro[3,2-c]pyridine;

(4aS,9bR)-8-(2,4-dichlorophenyl)-6-piperidin-1-yl-1,2,3,4,4a,9b-hexahydro[1]benzofuro[3,2-c]pyridine;

(4aS,9bR)-8-(2,4,6-trichlorophenyl)-6-piperidin-1-yl-1,2,3,4,4a,9b-hexahydro[1]benzofuro[3,2-c]pyridine;

(4aS,9bR)-8-(2,6-difluoro-4-chlorophenyl)-6-piperidin-1-yl-1,2,3,4,4a,9b-hexahydro[1]benzofuro[3,2-c]pyridine;

(4aS,9bR)-8-(2,4-dichlorophenyl)-6-azepan-1-yl-1,2,3,4,4a,9b-hexahydro[1]benzofuro[3,2-c]pyridine;

(4aS,9bR)-8-(2,4,6-trichlorophenyl)-6-hexahydroazepin-1-yl-1,2,3,4,4a,9b-hexahydro[1]benzofuro[3,2-c]pyridine;

(4aS,9bR)-8-(2,6-difluoro-4-chlorophenyl)-6-hexahydroazepin-1-yl-1,2,3,4,4a,9b-hexahydro[1]benzofuro[3,2-c]pyridine;

(4aS,9bR)-8-(2,4-dichlorophenyl)-6-pyrrolidin-1-yl-1,2,3,4,4a,9b-hexahydro[1]benzofuro[3,2-c]pyridine;

(4aS,9bR)-8-(2,4,6-trichlorophenyl)-6-pyrrolidin-1-yl-1,2,3,4,4a,9b-hexahydro[1]benzofuro[3,2-c]pyridine;

(4aS,9bR)-8-(2,6-difluoro-4-chlorophenyl)-6-pyrrolidin-1-yl-1,2,3,4,4a,9b-hexahydro[1]benzofuro[3,2-c]pyridine;

(4aS,9bR)-8-(2,4-dichlorophenyl)-5-morpholin-4-yl-1,2,3,4,4a,9b-hexahydro-[1]benzofuro[3,2-c]pyridine;

(4aS,9bR)-8-(2,4,6-trichlorophenyl)-5-morpholin-4-yl-1,2,3,4,4a,9b-hexahydro[1]benzofuro[3,2-c]pyridine;

(4aS,9bR)-8-(2,6-difluoro-4-chlorophenyl)-5-morpholin-4-yl-1,2,3,4,4a,9b-hexahydro[1]benzofuro[3,2-c]pyridine;

(4aS,9bR)-8-(2,4-dichlorophenyl)-6-thiomorpholin-4-yl-1,2,3,4,4a,9b-hexahydro[1]benzofuro[3,2-c]pyridine;

(4aS,9bR)-8-(2,4,6-trichlorophenyl)-6-thiomorpholin-4-yl-1,2,3,4,4a,9b-hexahydro[1]benzofuro[3,2-c]pyridine;

(4aS,9bR)-8-(2,6-difluoro-4-chlorophenyl)-6-thiomorpholin-4-yl-1,2,3,4,4a,9b-hexahydro[1]benzofuro[3,2-c]pyridine;

(4aS,9bR)-8-(2,4-dichlorophenyl)-6-piperazin-1-yl-1,2,3,4,4a,9b-hexahydro[1]benzofuro[3,2-c]pyridine;

(4aS,9bR)-8-(2,4,6-trichlorophenyl)-6-piperazin-1-yl-1,2,3,4,4a,9b-hexahydro[1]benzofuro[3,2-c]pyridine;

(4aS,9bR)-8-(2,6-difluoro-4-chlorophenyl)-6-piperazin-1-yl-1,2,3,4,4a,9b-hexahydro[1]benzofuro[3,2-c]pyridine;

(4aS,9bR)-8-(2,4,6-trichlorophenyl)-N,N-dipropyl-1,2,3,4,4a,9b,-hexahydro[1]benzofuro[3,2-c]pyridin-6-amine;

(4aS,9bR)-8-(2,6-difluoro-4-chlorophenyl)-N,N-dipropyl-1,2,3,4,4a,9b,-hexahydro[1]benzofuro[3,2-c]pyridin-6-amine;

(4aS,9bR) 6-Bromo-8-(2,4-dichlorophenyl)-1,2,3,4,4a,9b-hexahydro[1]benzofuro[3,2-c]pyridine;

(4aR,9bS) 6-Bromo-8-(2,4-dichlorophenyl)-1,2,3,4,4a,9b-hexahydro[1]benzofuro[3,2-c]pyridine;

or a pharmaceutically acceptable salt thereof.

* * * * *